(12) United States Patent
Ogita et al.

(10) Patent No.: US 11,046,667 B2
(45) Date of Patent: Jun. 29, 2021

(54) AROMATIC AMINE DERIVATIVE, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi (JP)

(72) Inventors: Kaori Ogita, Kanagawa (JP); Tsunenori Suzuki, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 97 days.

(21) Appl. No.: 16/182,690

(22) Filed: Nov. 7, 2018

(65) Prior Publication Data

US 2019/0071411 A1 Mar. 7, 2019

Related U.S. Application Data

(63) Continuation of application No. 13/078,388, filed on Apr. 1, 2011, now Pat. No. 10,570,113.

(30) Foreign Application Priority Data

Apr. 9, 2010 (JP) ................... 2010-090941

(51) Int. Cl.
*C07D 333/76* (2006.01)
*C07D 307/91* (2006.01)
(Continued)

(52) U.S. Cl.
CPC ......... *C07D 333/76* (2013.01); *C07D 307/91* (2013.01); *C09K 11/06* (2013.01);
(Continued)

(58) Field of Classification Search
CPC .... C07D 307/91; C07D 333/76; C09K 11/06; C09K 2211/1088; C09K 2211/1092;
(Continued)

(56) References Cited

U.S. PATENT DOCUMENTS 6,748,024 B2 6/2004 Kuchi et al.
6,816,557 B2 11/2004 Kuchi et al.
(Continued)

FOREIGN PATENT DOCUMENTS

CN 101910147 A 12/2010
CN 102232068 A 11/2011
(Continued)

OTHER PUBLICATIONS

Goldsmith.C et al., "C—H Bond Activation by a Ferric Methoxide Complex: Modeling the Rate-Determining Step in the Mechanism of Lipoxygenase", J. Am. Chem. Soc. (Journal of the American Chemical Society), 2002, vol. 124, No. 1, pp. 83-96.
(Continued)

*Primary Examiner* — Dawn L Garrett
(74) *Attorney, Agent, or Firm* — Fish & Richardson P.C.

(57) ABSTRACT

Provided is a novel aromatic amine derivative represented by General Formula (G1) below. (In the formula, A represents oxygen or sulfur, and $R^1$ to $R^7$ individually represent any of a hydrogen atom, an alkyl group having 1 to 6 carbon atoms, a substituted or unsubstituted phenyl group, and a substituted or unsubstituted biphenyl group. In addition, $\alpha^1$ and $\alpha^2$ individually represent a substituted or unsubstituted phenylene group. Further, $Ar^1$ represents a substituted or unsubstituted condensed aromatic hydrocarbon having 14 to 18 carbon atoms included in a ring. Further, $Ar^2$ represents a substituted or unsubstituted aryl group having 6 to 13 carbon atoms included in a ring. Further, j and n are individually 0 or 1, and p is 1 or 2.)
(Continued)

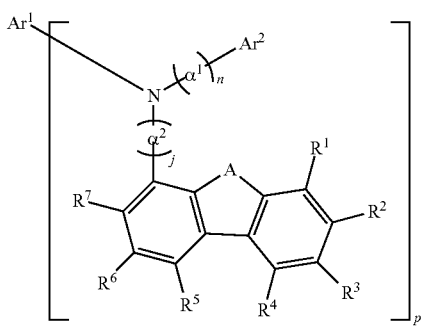

(G1)

14 Claims, 37 Drawing Sheets

(51) Int. Cl.
  *C09K 11/06* (2006.01)
  *H01L 51/00* (2006.01)
  *H01L 51/50* (2006.01)
  *H05B 33/14* (2006.01)
  *H05B 33/28* (2006.01)
(52) U.S. Cl.
  CPC ........ *H01L 51/006* (2013.01); *H01L 51/0054* (2013.01); *H01L 51/0061* (2013.01); *H01L 51/0073* (2013.01); *H01L 51/0074* (2013.01); *H05B 33/14* (2013.01); *H05B 33/28* (2013.01); *C09K 2211/1088* (2013.01); *C09K 2211/1092* (2013.01); *H01L 51/5012* (2013.01)
(58) Field of Classification Search
  CPC ............... H01L 51/0054; H01L 51/006; H01L 51/0061; H01L 51/0073; H01L 51/0074; H01L 51/5012
  See application file for complete search history.

(56) References Cited

U.S. PATENT DOCUMENTS

| | | |
|---|---|---|
| 6,905,788 B2 | 6/2005 | Tyan et al. |
| 7,504,163 B2 | 3/2009 | Jarikov |
| 7,649,211 B2 | 1/2010 | Ohsawa |
| 7,651,786 B2 | 1/2010 | Matsuura et al. |
| 7,700,201 B2 | 4/2010 | Seo et al. |
| 7,732,063 B2 | 6/2010 | Matsuura et al. |
| 7,927,716 B2 | 4/2011 | Matsuura et al. |
| 8,076,676 B2 | 12/2011 | Ohsawa |
| 8,231,942 B2 | 7/2012 | Shitagaki et al. |
| 8,283,052 B2 | 10/2012 | Egawa et al. |
| 8,324,802 B2 | 12/2012 | Matsuura et al. |
| 8,334,648 B2 | 12/2012 | Matsuura et al. |
| 8,410,492 B2 | 4/2013 | Ohsawa |
| 8,431,250 B2 | 4/2013 | Mizuki et al. |
| 8,518,492 B2 | 8/2013 | Shitagaki et al. |
| 8,653,537 B2 | 2/2014 | He et al. |
| 8,703,304 B2 | 4/2014 | Yabunouchi |
| 8,785,001 B2 | 7/2014 | Vestweber et al. |
| 8,795,847 B2 | 8/2014 | Heil et al. |
| 8,803,420 B2 | 8/2014 | Kawamura et al. |
| 8,845,926 B2 | 9/2014 | Shitagaki et al. |
| 8,860,019 B2 | 10/2014 | Ohsawa |
| 8,999,521 B2 | 4/2015 | Stoessel et al. |
| 9,017,825 B2 | 4/2015 | Heil et al. |
| 9,095,033 B2 | 7/2015 | Naraoka et al. |
| 9,153,790 B2 | 10/2015 | Kuma et al. |
| 9,343,682 B2 | 5/2016 | Matsuura et al. |
| 9,728,727 B2 | 8/2017 | Matsuura et al. |
| 9,960,358 B2 | 5/2018 | Matsuura et al. |
| 10,243,145 B2 | 3/2019 | Matsuura et al. |
| 10,570,113 B2 * | 2/2020 | Ogita .................. H01L 51/0074 |
| 2003/0118866 A1 | 6/2003 | Oh et al. |
| 2004/0110958 A1 | 6/2004 | Nishiyama et al. |
| 2004/0124766 A1* | 7/2004 | Nakagawa .......... H01L 51/0073 313/504 |
| 2005/0221124 A1 | 10/2005 | Hwang et al. |
| 2006/0029828 A1 | 2/2006 | Kanno et al. |
| 2006/0040132 A1 | 2/2006 | Liao et al. |
| 2006/0051615 A1 | 3/2006 | Kanno et al. |
| 2006/0180812 A1 | 8/2006 | Sakata et al. |
| 2007/0009758 A1 | 1/2007 | Funahashi |
| 2007/0215867 A1 | 9/2007 | Kawakami et al. |
| 2007/0215889 A1 | 9/2007 | Kawakami et al. |
| 2007/0252511 A1 | 11/2007 | Funahashi |
| 2007/0278938 A1 | 12/2007 | Yabunouchi et al. |
| 2008/0015399 A1 | 1/2008 | Funahashi |
| 2008/0122345 A1 | 5/2008 | Sakata et al. |
| 2008/0124572 A1 | 5/2008 | Mizuki et al. |
| 2008/0193794 A1 | 8/2008 | Egawa et al. |
| 2008/0203406 A1 | 8/2008 | He et al. |
| 2008/0206598 A1 | 8/2008 | Ohsawa et al. |
| 2008/0246395 A1 | 10/2008 | Nakai et al. |
| 2009/0159877 A1 | 6/2009 | Meng |
| 2009/0317539 A1 | 12/2009 | Shitagaki et al. |
| 2010/0001636 A1 | 1/2010 | Yabunouchi |
| 2010/0155714 A1 | 6/2010 | Seo et al. |
| 2010/0295445 A1 | 11/2010 | Kuma et al. |
| 2010/0314615 A1 | 12/2010 | Mizuki et al. |
| 2011/0095270 A1 | 4/2011 | Meng |
| 2011/0095678 A1 | 4/2011 | Ogita et al. |
| 2011/0156016 A1 | 6/2011 | Kawamura et al. |
| 2012/0112169 A1 | 5/2012 | Mizuki et al. |
| 2012/0146014 A1 | 6/2012 | Kato |
| 2012/0299473 A1 | 11/2012 | Mizutani et al. |
| 2013/0069523 A1 | 3/2013 | Matsuura et al. |
| 2013/0153878 A1 | 6/2013 | Mizuki et al. |
| 2014/0061630 A1 | 3/2014 | Yabunouchi |

FOREIGN PATENT DOCUMENTS

| | | |
|---|---|---|
| CN | 102725280 A | 10/2012 |
| EP | 1541657 A | 6/2005 |
| EP | 1978574 A | 10/2008 |
| EP | 2199361 A | 6/2010 |
| EP | 2239259 A | 10/2010 |
| EP | 2295421 A | 3/2011 |
| EP | 2295519 A | 3/2011 |
| EP | 2423206 A | 2/2012 |
| EP | 2434559 A | 3/2012 |
| EP | 2468725 A | 6/2012 |
| EP | 2487991 A | 8/2012 |
| EP | 2525425 A | 11/2012 |
| EP | 2532655 A | 12/2012 |
| JP | 2004-204238 A | 7/2004 |
| JP | 2005-112765 A | 4/2005 |
| JP | 2005-285618 A | 10/2005 |
| JP | 2006-066872 A | 3/2006 |
| JP | 3926791 | 6/2007 |
| JP | 2008-509565 | 3/2008 |
| JP | 2008-106042 A | 5/2008 |
| JP | 2008-258396 A | 10/2008 |
| JP | 4188401 | 11/2008 |
| JP | 2008-291263 A | 12/2008 |
| JP | 2009-105963 A | 5/2009 |
| JP | 2009-518328 | 5/2009 |
| JP | 2009-531341 | 9/2009 |
| JP | 2009-299049 A | 12/2009 |
| JP | 2011-173973 A | 9/2011 |
| JP | 2011-231108 A | 11/2011 |
| JP | 5690636 | 3/2015 |
| JP | 2018-188444 A | 11/2018 |
| KR | 2007-0056061 A | 5/2007 |
| KR | 2008-0029811 A | 4/2008 |
| KR | 2010-0017799 A | 2/2010 |
| KR | 2010-0097181 A | 9/2010 |
| KR | 2011-0043625 A | 4/2011 |

(56) References Cited

FOREIGN PATENT DOCUMENTS

| | | |
|---|---|---|
| KR | 2011-0071127 A | 6/2011 |
| KR | 2012-0124429 A | 11/2012 |
| TW | I285441 | 8/2007 |
| TW | 201012898 | 4/2010 |
| TW | 201012899 | 4/2010 |
| TW | 201100396 | 1/2011 |
| TW | 201136910 | 11/2011 |
| WO | WO-2002/080375 | 10/2002 |
| WO | WO-2005/108348 | 11/2005 |
| WO | WO-2006/015567 | 2/2006 |
| WO | WO-2007/139124 | 12/2007 |
| WO | WO-2009/084512 | 7/2009 |
| WO | WO-2009/145016 | 12/2009 |
| WO | WO-2010/013675 | 2/2010 |
| WO | WO-2010/013676 | 2/2010 |
| WO | WO-2010/122810 | 10/2010 |
| WO | WO-2010/134352 | 11/2010 |
| WO | WO-2011/021520 | 2/2011 |
| WO | WO-2011/043083 | 4/2011 |
| WO | WO-2011/086941 | 7/2011 |
| WO | WO-2011/096506 | 8/2011 |

OTHER PUBLICATIONS

Onishi.T et al., "A Method of Measuring an Energy Level", High Molecular EL Materials—Development of Light-Emitting High Molecular Compounds, Dec. 25, 2004, pp. 64-67, Kyoritsu Shuppan.

Yu.Y et al., "Cu(I)-Mediated Reductive Amination of Boronic Acids with Nitroso Aromatics", Organic Letters, 2004, vol. 6, No. 15, pp. 2631-2634.

Chinese Office Action (Application No. 201110095493.8) dated Jul. 31, 2014.

Korean Office Action (Application No. 2016-0155907) dated Apr. 27, 2018.

Qiu.F et al., "Anthracene derivatives as highly efficient deep-blue emitters with extremely low driving voltages, Von≤ 2.7 V", Dyes and Pigments, Sep. 1, 2020, vol. 180, p. 108458, Elsevier.

* cited by examiner

AROMATIC AMINE DERIVATIVE, LIGHT-EMITTING ELEMENT, LIGHT-EMITTING DEVICE, ELECTRONIC DEVICE, AND LIGHTING DEVICE

CROSS-REFERENCE TO RELATED APPLICATIONS

This application is a continuation of U.S. application Ser. No. 13/078,388, filed Apr. 1, 2011, which claims the benefit of a foreign priority application filed in Japan as Serial No. 2010-090941 on Apr. 9, 2010, both of which are incorporated by reference.

BACKGROUND OF THE INVENTION

1. Field of the Invention

The present invention relates to novel organic compounds that emit light by application of voltage and that can be at least partly used in light-emitting elements. The invention further relates to light-emitting elements, light-emitting devices, electronic devices, and lighting devices including the organic compounds.

2. Description of the Related Art

In recent years, research and development have been extensively conducted on light-emitting elements using electroluminescence (EL). In a basic structure of such light-emitting elements, a layer containing a light-emitting substance is interposed between a pair of electrodes. By applying voltage to the light-emitting elements, the light-emitting substance can emit light.

Such light-emitting elements are of a self-luminous type, and thus have advantages over liquid crystal displays, such as higher visibility of a pixel, no need of a backlight, very short response time of the light-emitting elements, and the like. Thus, the light-emitting elements are suitable for flat panel display elements. The light-emitting elements have another great advantage that they can be manufactured to be thin and light.

Further, since these light-emitting elements can be formed in a film form, they make it easy to provide planar light emission, thereby achieving large-area elements utilizing the planar light emission. This feature is difficult to obtain with point light sources typified by an incandescent lamp and an LED or linear light sources typified by a fluorescent lamp. Accordingly, the light-emitting element is extremely effective for use as a surface light source applicable to illumination and the like.

Light-emitting elements utilizing electroluminescence are broadly classified according to whether they use an organic compound or an inorganic compound as a light-emitting substance. In an organic EL element using an organic compound as a light-emitting substance, by voltage application to the light-emitting element, electrons from one electrode and holes from the other electrode are injected into a layer containing the light-emitting organic compound, and current flows. Recombination of the electrons and the holes in the light-emitting organic compound generates an excited state of the light-emitting organic compound. When the excited state relaxes to a ground state, the light-emitting organic compound releases the relaxation energy as light emission.

Having such a mechanism, the above light-emitting element is called a current-excitation light-emitting element. Note that the excited state generated in an organic compound can be a singlet excited state or a triplet excited state. Light emission from the singlet excited state is referred to as fluorescence, and luminescence from the triplet excited state is referred to as phosphorescence.

There is another method of light emission instead of the light emission in accordance with the excitation generated by recombination of electrons and holes and the relaxation from the excitation state. In that method, excitation energy is transferred from an organic compound that is excited by current to another organic compound, and the newly excited organic compound emits light in relaxing. This method is effective when the concentration of organic compound molecules for light emission is high, for example, when the emission efficiency is decreased by stacking interaction (concentration quenching).

Specifically, in this method, a light-emitting material is dispersed (doped) in a light-emitting layer in an organic EL element. Doping organic compound molecules for light emission into a host material suppresses the stacking interaction, whereby efficiency of a light-emitting element can be increased. In the light-emitting element, excitation energy is transferred from the host material excited by current to a dopant material, which makes the dopant material emit light. Note that when Substance A is dispersed in a matrix formed of Substance B, which is another substance, Substance B forming the matrix is called a host material while Substance A dispersed in the matrix is called a dopant material (also called a guest material).

Light emitted by a light-emitting material is unique to the material, and development of a material that emits light of a favorable color is difficult. In addition, fabrication of a light-emitting element that achieves significant characteristics of a long lifetime, low power consumption, and the like is very difficult. This is because the significant performances of light-emitting elements, such as the lifetime or power consumption, depend not only on light-emitting substances but also largely on element structures, compatibility between a light-emitting substance and a host material, and the like.

In particular, the lifetime of a blue light-emitting element is shorter than that of light-emitting elements of the other colors, and thus development of a material that can achieve both a long lifetime and favorable color purity is desired. For example, in order to use organic EL elements as display elements or the like in flat panel displays that are commercially available, further improvement of the blue light-emitting element is required so that significant objects of an increase in lifetime and improvement of color purity can be realized. Thus, light-emitting element materials having a variety of molecular structures have been proposed (see Patent Documents 1 and 2, for example).

REFERENCE

Patent Document

[Patent Document 1] Japanese Published Patent Application No. 2004-204238
[Patent Document 2] PCT International Publication No. 2005/108348

SUMMARY OF THE INVENTION

The present invention is made for providing a blue light-emitting element having high color purity and a long lifetime. An object of one embodiment of the present invention is to provide a novel aromatic amine derivative that has high color purity and is favorable as a blue light-emitting material for an organic EL element.

Another object is to provide a light-emitting element, a light-emitting device, a lighting device, and an electronic device using the novel aromatic amine derivative.

One embodiment of the present invention is an aromatic amine derivative represented by General Formula (G1) below.

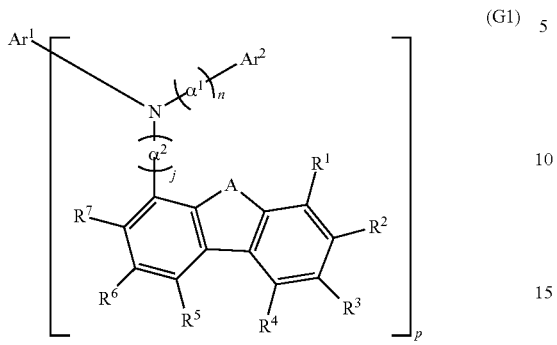

(G1)

$R^1$ to $R^7$ individually represent any of a hydrogen atom, an alkyl group having 1 to 6 carbon atoms, a substituted or unsubstituted phenyl group, and a substituted or unsubstituted biphenyl group. In addition, □$α^1$ and $α^2$ individually represent a substituted or unsubstituted phenylene group. Further, $Ar^1$ represents a substituted or unsubstituted condensed aromatic hydrocarbon having 14 to 18 carbon atoms included in a ring. Further, $Ar^2$ represents a substituted or unsubstituted aryl group having 6 to 13 carbon atoms included in a ring. Further, j and n are individually 0 or 1, and p is 1 or 2. In addition, A represents O (oxygen) or S (sulfur).

Another embodiment of the present invention is an aromatic amine derivative represented by General Formula (G2) below.

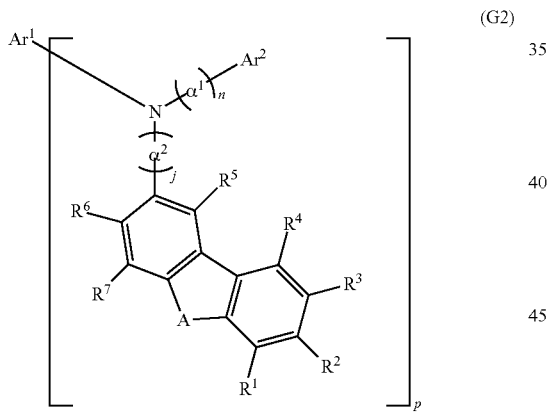

(G2)

$R^1$ to $R^7$ individually represent any of a hydrogen atom, an alkyl group having 1 to 6 carbon atoms, a substituted or unsubstituted phenyl group, and a substituted or unsubstituted biphenyl group. In addition, $α^1$ and $α^2$ individually represent a substituted or unsubstituted phenylene group. Further, $Ar^1$ represents a substituted or unsubstituted condensed aromatic hydrocarbon having 14 to 18 carbon atoms included in a ring. Further, $Ar^2$ represents a substituted or unsubstituted aryl group having 6 to 13 carbon atoms included in a ring. Further, j and n are individually 0 or 1, and p is 1 or 2. In addition, A represents O (oxygen) or S (sulfur).

$Ar^1$ in General Formula (G1) and General Formula (G2) can be General Formula (Ar1-1) or General Formula (Ar1-2). $R^8$ to $R^{10}$ in General Formula (Ar1-1) and $R^8$ and $R^{10}$ in General Formula (Ar1-2) individually represent any of a hydrogen atom, an alkyl group having 1 to 6 carbon atoms, a substituted or unsubstituted phenyl group, and a substituted or unsubstituted biphenyl group. Note that when $Ar^1$ in General Formula (G1) and General Formula (G2) is General Formula (Ar1-1), p is 1. When $Ar^1$ in General Formula (G1) and General Formula (G2) is General Formula (Ar1-2), p is 2.

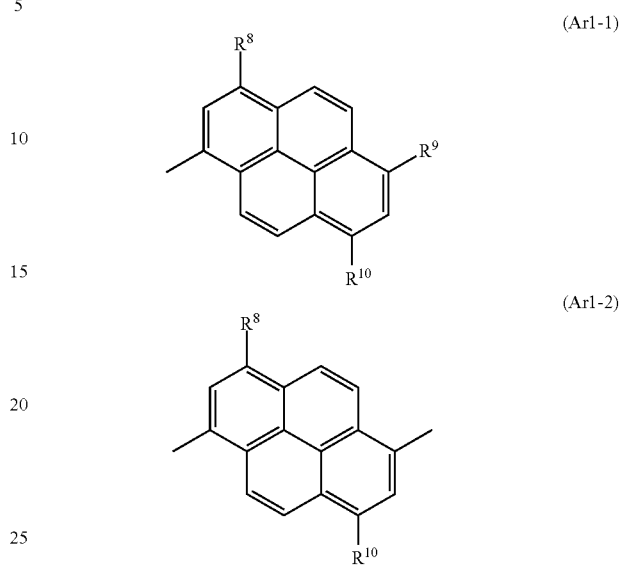

(Ar1-1)

(Ar1-2)

Another embodiment of the present invention is an aromatic amine derivative represented by General Formula (G3) below. General Formula (G3) represents an aromatic amine derivative in which $Ar^1$ is General Formula (Ar1-2), j is 0, and p is 2 in a compound represented by General Formula (G1).

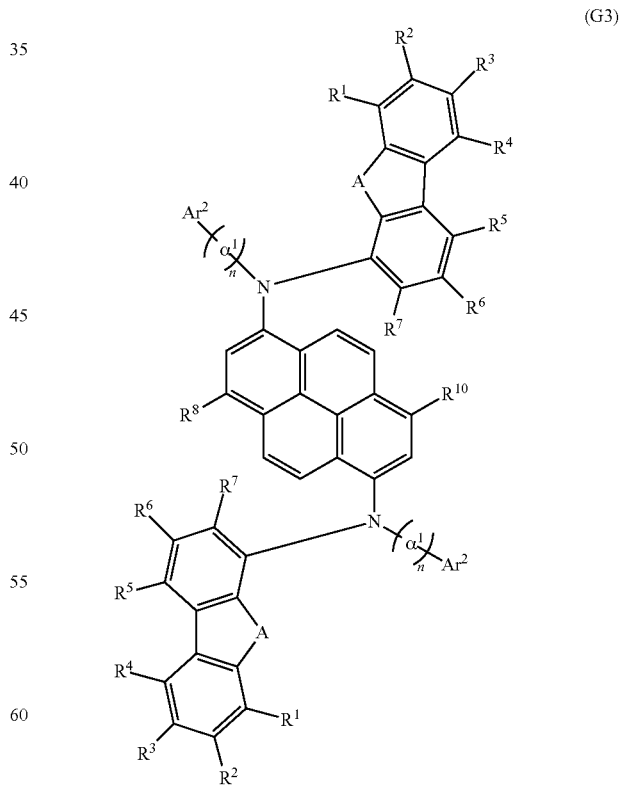

(G3)

In General Formula (G3), $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group. In addition, α¹ represents a substituted or unsubstituted phenylene group. Further, Ar² represents a substituted or unsubstituted aryl group having 6 to 13 carbon atoms included in a ring. Further, n is 0 or 1. In addition, A represents O (oxygen) or S (sulfur).

Another embodiment of the present invention is an aromatic amine derivative represented by General Formula (G4) below. General Formula (G4) represents an aromatic amine derivative in which Ar¹ is General Formula (Ar1-2), j is 1, and p is 2 in a compound represented by General Formula (G1).

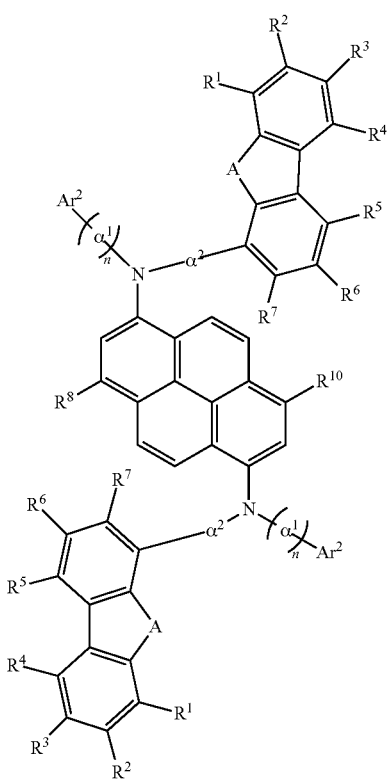
(G4)

In General Formula (G4), $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group. In addition, $α^1$ and $α^2$ individually represent a substituted or unsubstituted phenylene group. Further, Ar² represents a substituted or unsubstituted aryl group having 6 to 13 carbon atoms included in a ring. Further, n is 0 or 1. In addition, A represents O (oxygen) or S (sulfur).

In General Formula (G1) to General Formula (G4), it is preferable that $α^1$ and $α^2$ be individually any of Structural Formulae (α-1) to (α-3) below.

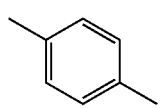
(α-1)

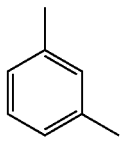
(α-2)

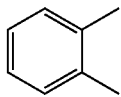
(α-3)

Another embodiment of the present invention is an aromatic amine derivative represented by General Formula (G5) below. General Formula (G5) represents an aromatic amine derivative in which $α^2$ in General Formula (G4) is Structural Formula (α-2).

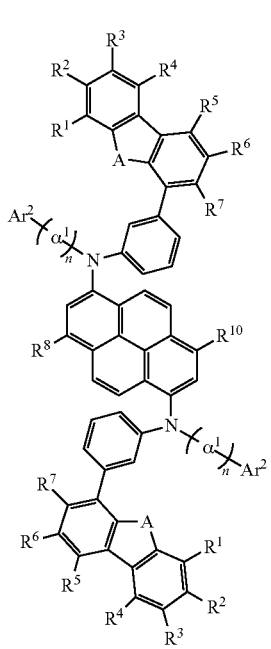
(G5)

In General Formula (G5), $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group. In addition, α¹ represents a substituted or unsubstituted phenylene group. Further, Ar² represents a substituted or unsubstituted aryl group having 6 to 13 carbon atoms included in a ring. Further, n is 0 or 1. In addition, A represents O (oxygen) or S (sulfur).

In General Formula (G5), as in General Formula (G1) to General Formula (G4), n is 0 or 1. When n is 1, $α^1$ is preferably any of Structural Formulae (α-1) to (α-3) above.

In General Formula (G1) to General Formula (G5), Ar² is preferably any of Structural Formulae (Ar2-1) to (Ar2-6) below.

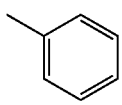
(Ar2-1)

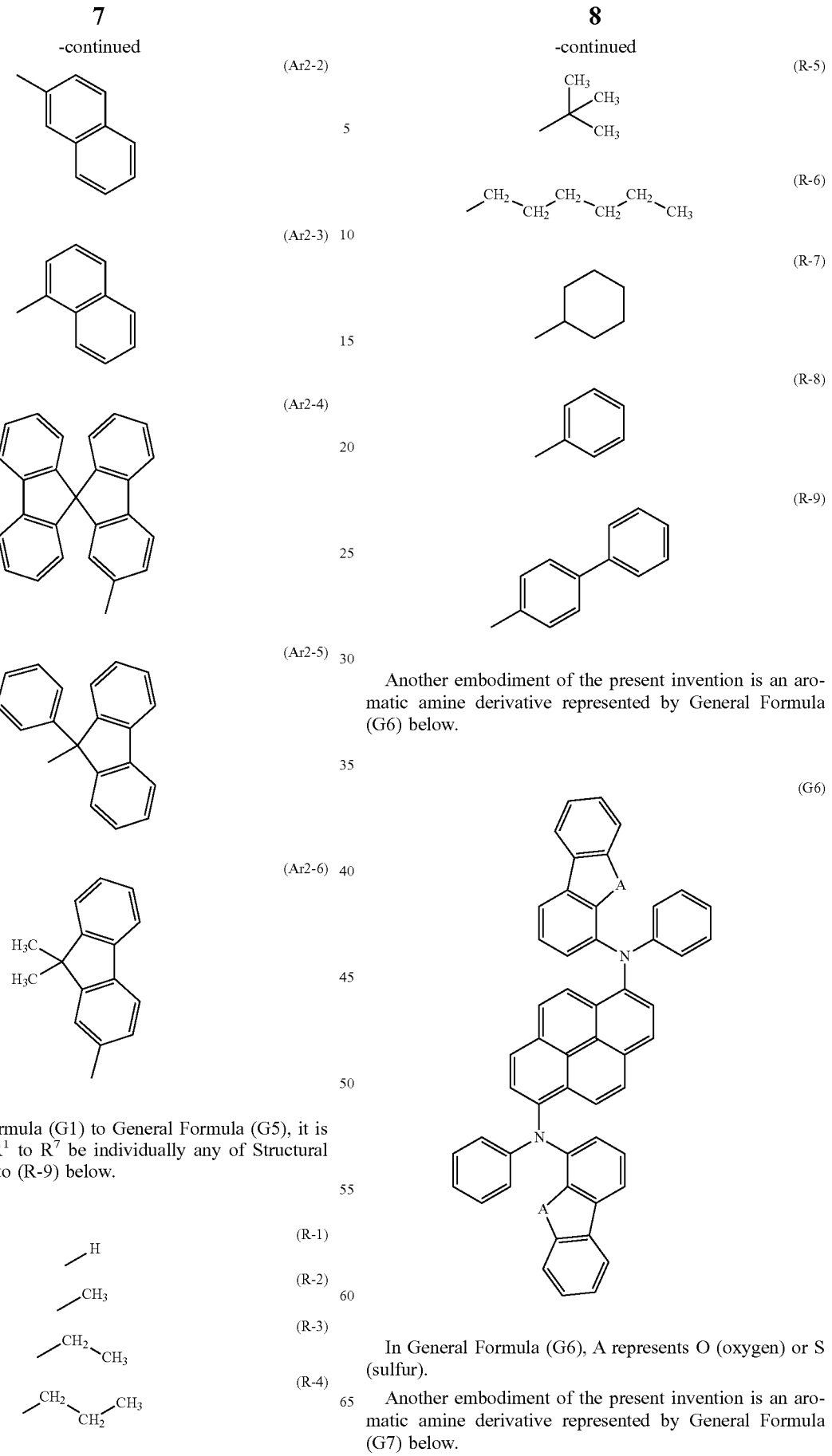

In General Formula (G1) to General Formula (G5), it is preferable that $R^1$ to $R^7$ be individually any of Structural Formulae (R-1) to (R-9) below.

Another embodiment of the present invention is an aromatic amine derivative represented by General Formula (G6) below.

In General Formula (G6), A represents O (oxygen) or S (sulfur).

Another embodiment of the present invention is an aromatic amine derivative represented by General Formula (G7) below.

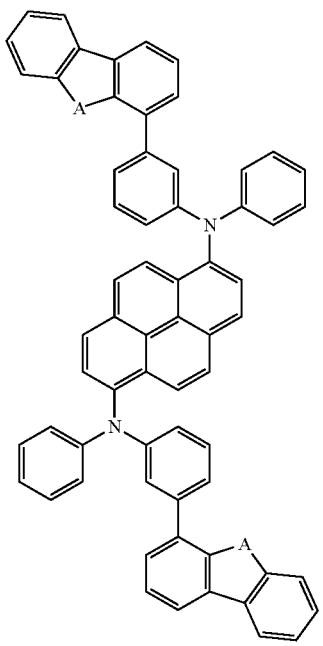

(G7)

In General Formula (G7), A represents O (oxygen) or S (sulfur).

Another embodiment of the present invention is an aromatic amine derivative represented by General Formula (G8) below.

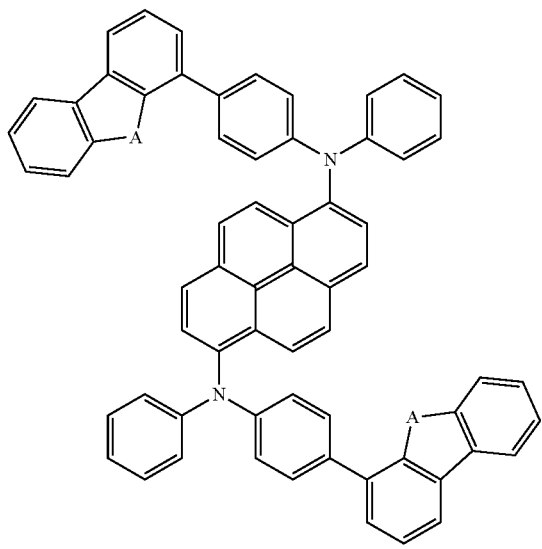

(G8)

In General Formula (G8), A represents O (oxygen) or S (sulfur).

Another embodiment of the present invention is a light-emitting element including an EL layer between a pair of electrodes, the EL layer includes a light-emitting layer, and the light-emitting layer contains any of the above aromatic amine derivatives (General Formula (G1) to General Formula (G8)).

Another embodiment of the present invention is a light-emitting device formed using the above light-emitting element, and an electronic device formed using the light-emitting device. Another embodiment of the present invention is a lighting device formed using the light-emitting device.

The light-emitting device which is one embodiment of the present invention includes the above light-emitting element and a control means which controls light emission from the light-emitting element. Note that the light-emitting device in this specification includes image display devices, light-emitting devices, or light sources (including lighting device). The light-emitting device also includes all types of modules such as a module in which a connector such as an flexible printed circuit (FPC), a tape automated bonding (TAB) tape, or a tape carrier package (TCP) is attached to a panel; a module in which a printed wiring board is provided on the tip of a TAB tape or a TCP; and a module in which an IC (integrated circuit) is directly mounted on a light-emitting element by the COG (chip on glass) technique.

An aromatic amine derivative which is one embodiment of the present invention can emit visible light having a short wavelength, and can emit blue light with favorable color purity.

In addition, by using the aromatic amine derivative which is one embodiment of the present invention, a light-emitting element having high emission efficiency and high reliability can be obtained.

Further, by using this light-emitting element, a light-emitting device, an electronic device, and a lighting device with high reliability can be obtained.

DETAILED DESCRIPTION OF THE INVENTION

Figure 1A:
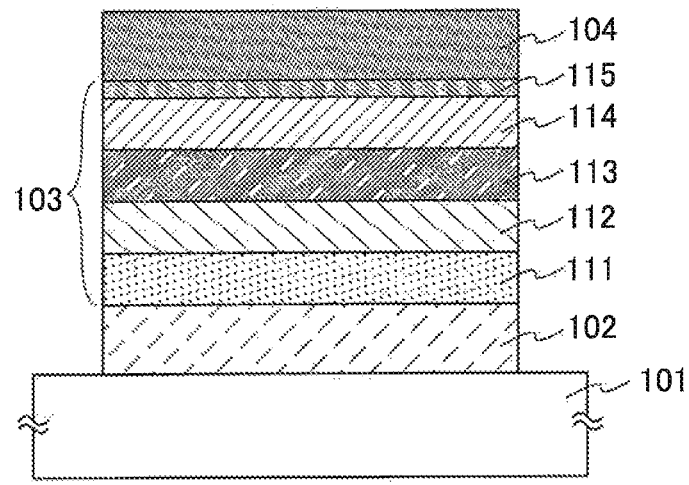
FIGS. 1A and 1B illustrate light emitting elements.

Hereinafter, embodiments and examples of the present invention will be described in detail with reference to the accompanying drawings. However, the invention is not limited to the description below, and those skilled in the art will appreciate that a variety of modifications can be made to the modes and details without departing from the spirit and scope of the invention. Therefore, the invention should not be construed as being limited to the description in the following embodiments and examples.

Embodiment 1

In this embodiment, an aromatic amine derivative which is one embodiment of the present invention is described.

The aromatic amine derivative of this embodiment is an aromatic amine derivative represented by General Formula (G1) or General Formula (G2) below.

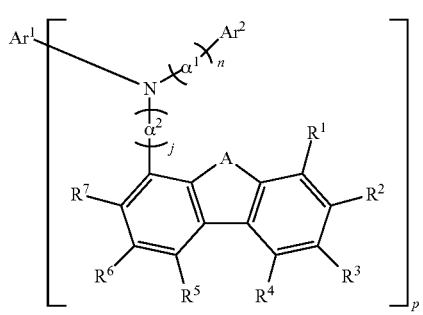

(G1)

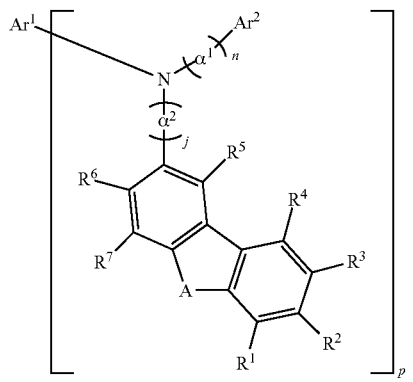

(G2)

$R^1$ to $R^7$ individually represent any of a hydrogen atom, an alkyl group having 1 to 6 carbon atoms, a substituted or unsubstituted phenyl group, and a substituted or unsubstituted biphenyl group. In addition, $\alpha^1$ and $\alpha^2$ individually represent a substituted or unsubstituted phenylene group. Further, $Ar^1$ represents a substituted or unsubstituted condensed aromatic hydrocarbon having 14 to 18 carbon atoms included in a ring. Further, $Ar^2$ represents a substituted or unsubstituted aryl group having 6 to 13 carbon atoms included in a ring. Further, j and n are individually 0 or 1, and p is 1 or 2. In addition, A represents O (oxygen) or S (sulfur).

An alkyl group is preferably used as the substituents $R^1$ to $R^7$ in General Formula (G1) and General Formula (G2) because the solubility in an organic solvent is improved and purification becomes easy. With the improvement of the solubility, a more uniform film can be formed in wet process manufacture of an organic EL element.

Since the molecule includes a sterically bulky structure, such as a dibenzofuranyl group or a dibenzothiophenyl group, interaction between molecules is suppressed and morphology (the form of molecules) is improved. Thus, a film quality is improved, and concentration quenching and excimer formation can be suppressed more easily.

Further, a dibenzofuranyl group and a dibenzothiophenyl group are electrochemically stable. Therefore, a compound including a dibenzofuranyl group or a dibenzothiophenyl group in a molecule that can be represented by General Formula (G1) or General Formula (G2) has high efficiency and a long lifetime, and thus is suitable for a light-emitting material.

$Ar^1$ in General Formula (G1) and General Formula (G2) can be General Formula (Ar1-1) or General Formula (Ar1-2) below. $R^8$ to $R^{10}$ in General Formula (Ar1-1) and $R^8$ and $R^{10}$ in General Formula (Ar1-2) individually represent any of a hydrogen atom, an alkyl group having 1 to 6 carbon atoms, a substituted or unsubstituted phenyl group, and a substituted or unsubstituted biphenyl group. Note that when $Ar^1$ in General Formula (G1) and General Formula (G2) is General Formula (Ar1-1), p is 1. When $Ar^1$ in General Formula (G1) and General Formula (G2) is General Formula (Ar1-2), p is 2.

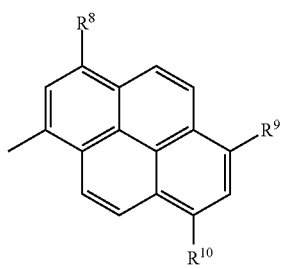

(Ar1-1)

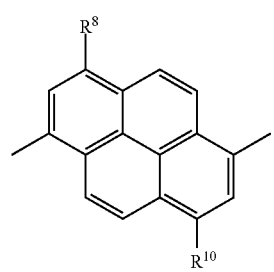

(Ar1-2)

Aromatic amine derivatives represented by General Formula (G1) and General Formula (G2) including a substituent represented by General Formula (Ar1-1) and General Formula (Ar1-2) in a molecule are preferable because quantum yield and emission efficiency are high.

In addition, an alkyl group is also preferably used as the substituents $R^8$ to $R^{10}$ in General Formula (Ar1-1) and the substituents $R^8$ and $R^{10}$ in General Formula (Ar1-2) because the solubility in an organic solvent is improved and purification becomes easy. With the improvement of the solubility, a more uniform film can be formed in wet process manufacture of an organic EL element. Moreover, the molecule forms a more steric structure, so that a film quality is improved, and concentration quenching and excimer formation can be suppressed more easily.

Note that when $R^1$ to $R^7$, $\alpha^1$ and $\alpha^2$, and $Ar^2$ individually have a substituent, the substituent may be an alkyl group such as a methyl group, an ethyl group, a propyl group, a pentyl group, or a hexyl group; or an aryl group such as a phenyl group or a biphenyl group. Such alkyl groups may be connected to each other to form a ring.

In order to achieve an object, an aromatic amine derivative represented by General Formula (G3) below is preferably used, in which $Ar^1$ is General Formula (Ar1-2), j is 0, and p is 2 in a compound represented by General Formula (G1). $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group. In addition, $\alpha^1$ represents a substituted or unsubstituted phenylene group. Further, $Ar^2$ represents a substituted or unsubstituted aryl group having 6 to 13 carbon atoms included in a ring. Further, n is 0 or 1, and A represents O (oxygen) or S (sulfur).

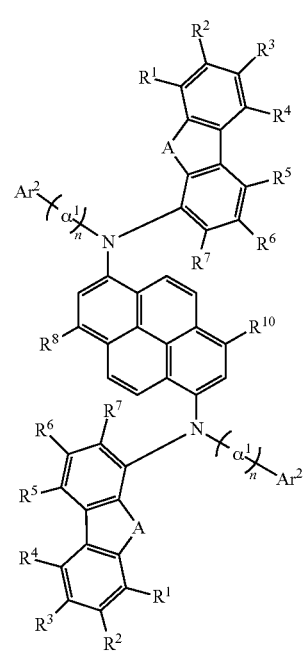

(G3)

In order to achieve an object, an aromatic amine derivative represented by General Formula (G9) below may also be used, in which $Ar^1$ is General Formula (Ar1-2), j is 0, and p is 2 in a compound represented by General Formula (G2). $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group. In addition, $\alpha^1$ represents a substituted or unsubstituted phenylene group. Further, $Ar^2$ represents a substituted or unsubstituted aryl group having 6 to 13 carbon atoms included in a ring. Further, n is 0 or 1, and A represents O (oxygen) or S (sulfur).

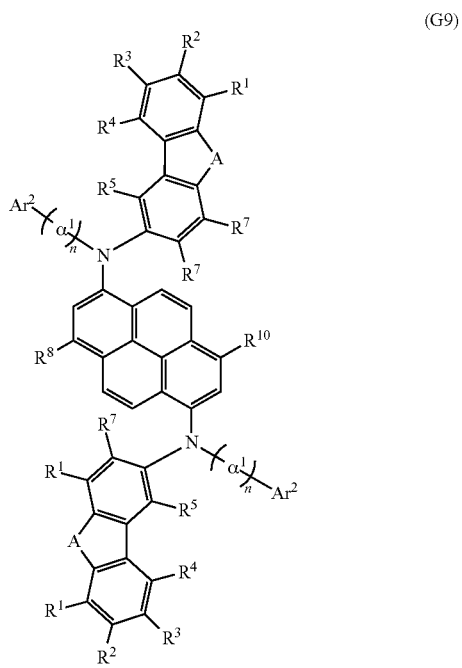

(G9)

In addition, an aromatic amine derivative represented by General Formula (G4) below is also preferable, in which Ar¹ is General Formula (Ar1-2), j is 1, and p is 2 in a compound represented by General Formula (G1). $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group. In addition, $\alpha^1$ and $\alpha^2$ individually represent a substituted or unsubstituted phenylene group. Further, Ar² represents a substituted or unsubstituted aryl group having 6 to 13 carbon atoms included in a ring. Further, n is 0 or 1, and A represents O (oxygen) or S (sulfur).

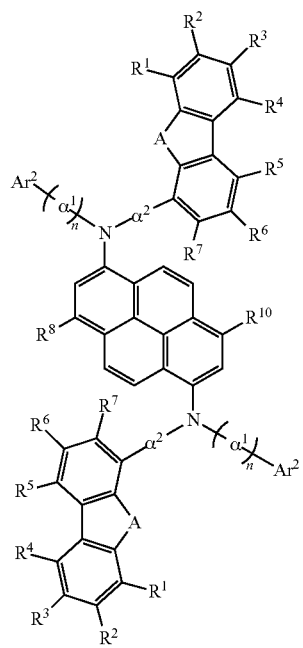

(G4)

The aromatic amine derivatives represented by General Formula (G3), General Formula (G4), and General Formula (G9) have narrow half-widths of emission spectra, so that emission colors with high color purity are easily obtained. In particular, blue emission with high color purity is easily obtained. In addition, because the Stokes shift is small, when this material is doped as a light-emitting material in an organic EL element, energy transfer efficiently occurs from a host material and high emission efficiency is easily obtained.

Further, as in General Formula (G3), General Formula (G4), and General Formula (G9), when p in General Formula (G1) or General Formula (G2) is 2, the molecular weight is increased and the thermophysical property is improved. Therefore, when such an aromatic amine derivative is used as a light-emitting material in an organic EL element, deposition stability is increased.

It is preferable that $\alpha^1$ and $\alpha^2$ in General Formula (G1) to General Formula (G4) and General Formula (G9) be individually any of Structural Formulae (α-1) to (α-3) below.

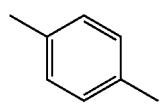

(α-1)

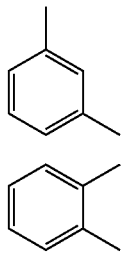

(α-2)

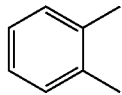

(α-3)

As in General Formula (G5), when $\alpha^2$ in General Formula (G4) is Structural Formula (α-2) above, the molecular structure can be more bulky and the thermophysical property can be more improved with interaction between molecules suppressed. $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group. In addition, $\alpha^1$ represents a substituted or unsubstituted phenylene group. Further, Ar² represents a substituted or unsubstituted aryl group having 6 to 13 carbon atoms included in a ring. Further, n is 0 or 1, and A represents O (oxygen) or S (sulfur).

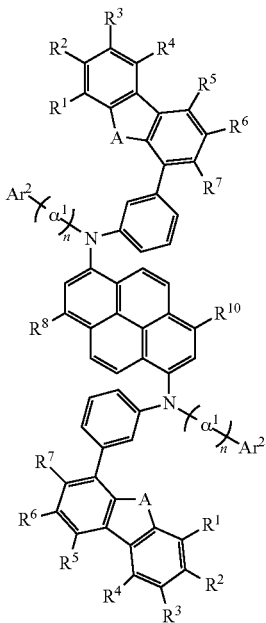

(G5)

In General Formula (G5), as in General Formula (G1) to General Formula (G4), n is 0 or 1. When n is 1, $\alpha^1$ is preferably any of Structural Formulae (α-1) to (α-3) above.

In General Formula (G1) to General Formula (G5) and General Formula (G9), Ar² is preferably any of Structural Formulae (Ar2-1) to (Ar2-6) below.

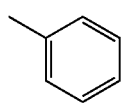

(Ar2-1)

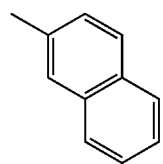 (Ar2-2)

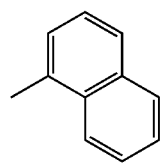 (Ar2-3)

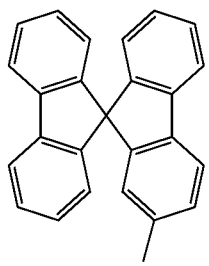 (Ar2-4)

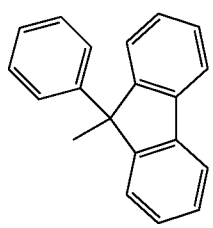 (Ar2-5)

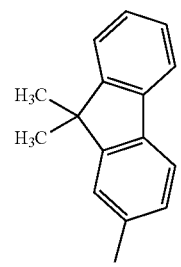 (Ar2-6)

In General Formula (G1) to General Formula (G5) and General Formula (G9), it is preferable that $R^1$ to $R^7$ be individually any of Structural Formulae (R-1) to (R-9) below.

(R-1) —H (R-2) —CH$_3$

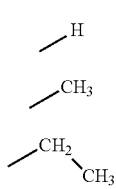 (R-3)

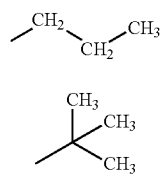 (R-4)

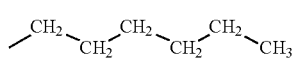 (R-5)

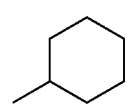 (R-6)

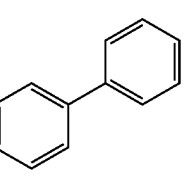 (R-7)

(R-8)

(R-9)

Specific examples of the aromatic amine derivatives represented by General Formula (G1) to General Formula (G5) and General Formula (G9) include aromatic amine derivatives represented by Structural Formula (100) to Structural Formula (380). However, the present invention is not limited to the following structural formulae.

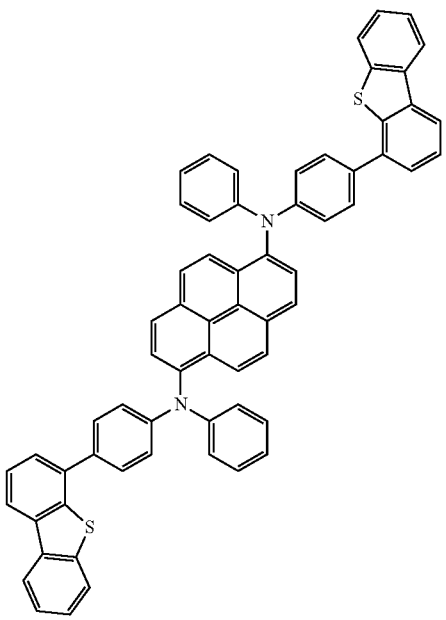 (100)

(101)
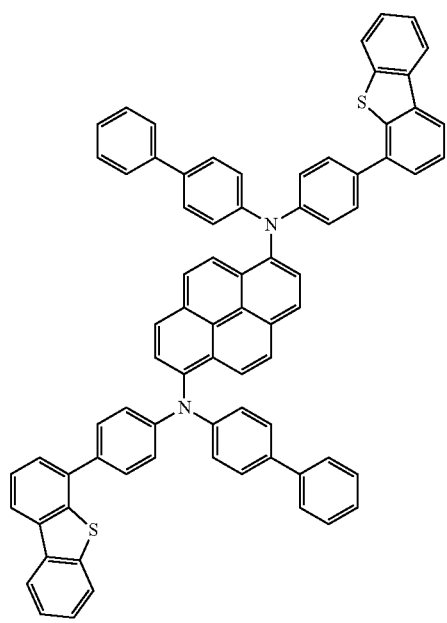
(102)
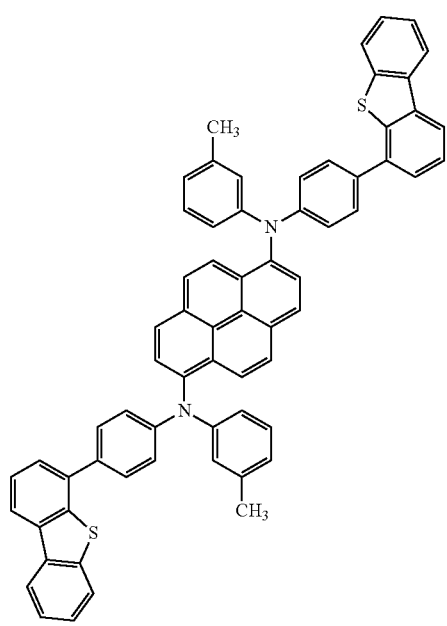
(103)
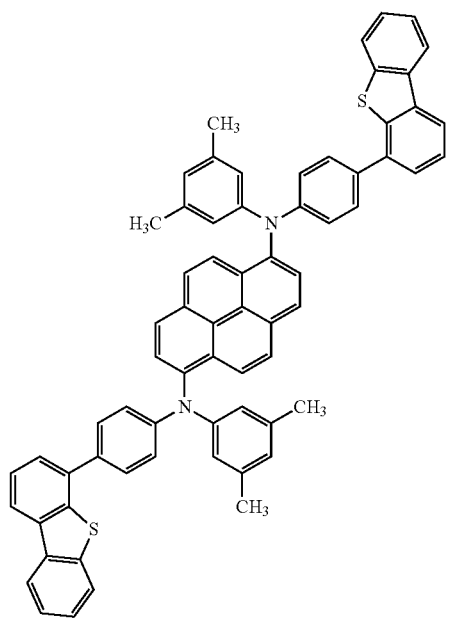
(104)
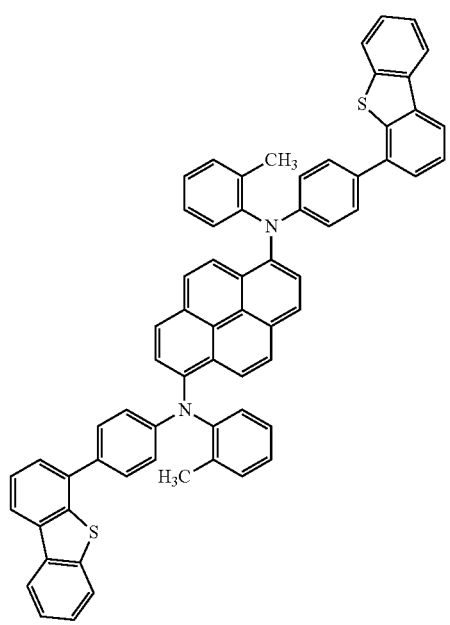

(105)
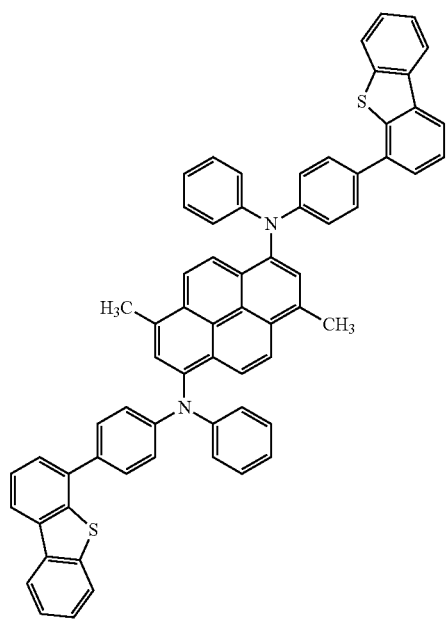
(107)
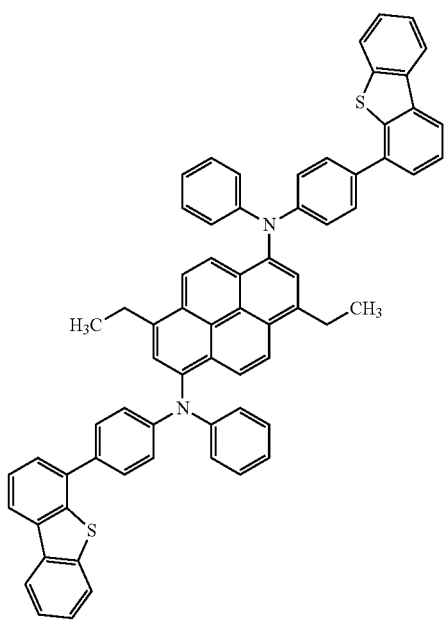
(106)
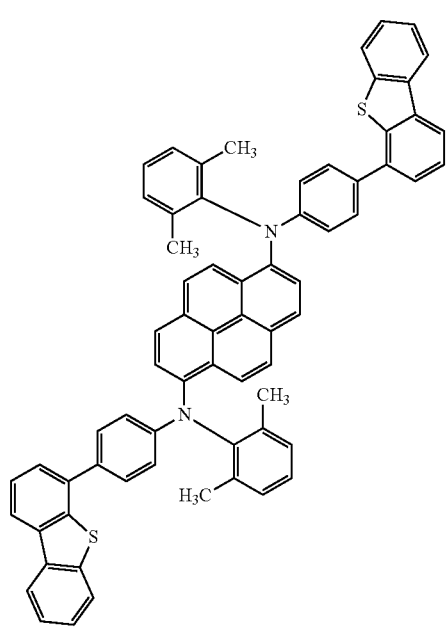
(108)
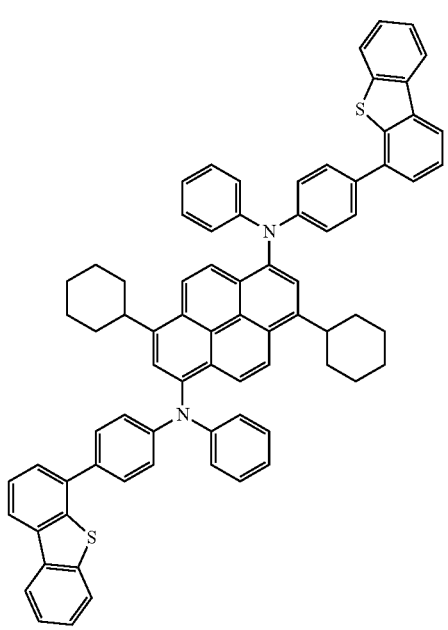

-continued
(109)
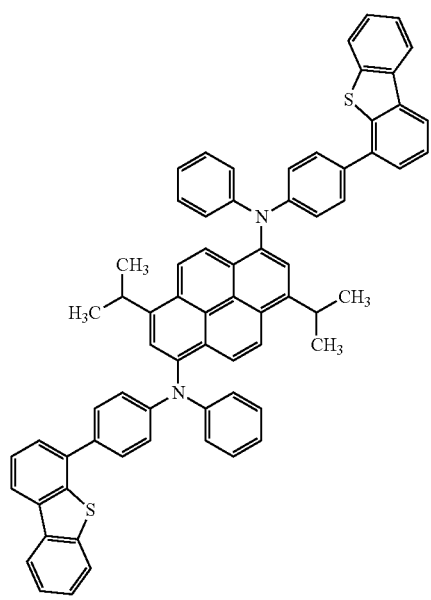
(110)
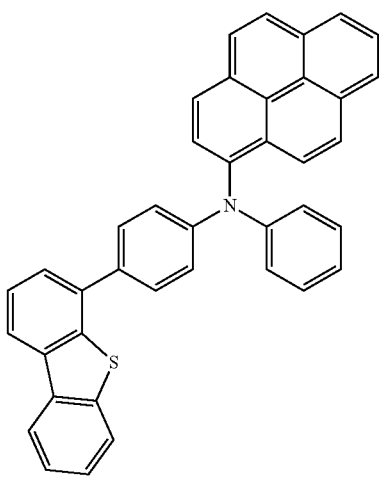
(111)
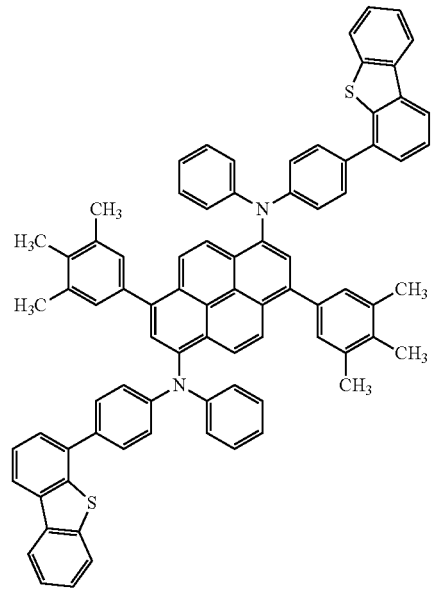
(112)
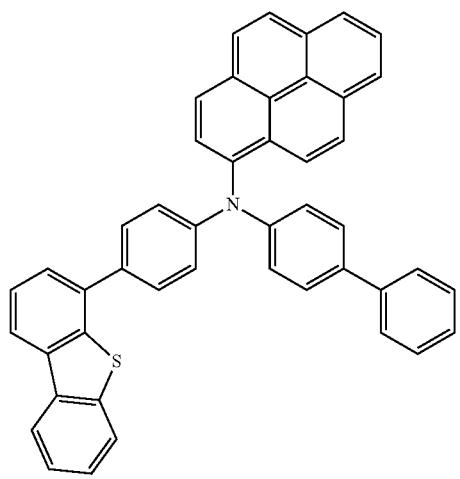
(113)

(114)
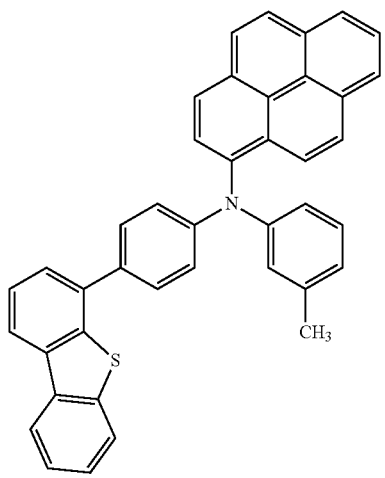
(115)
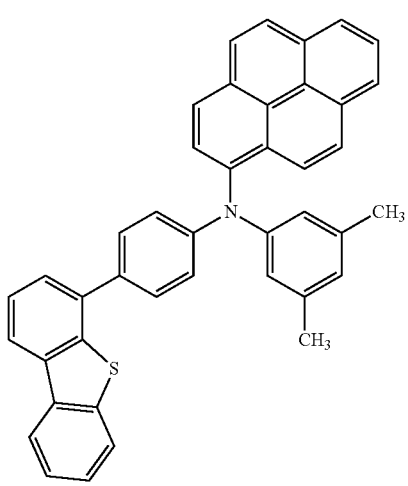
(116)
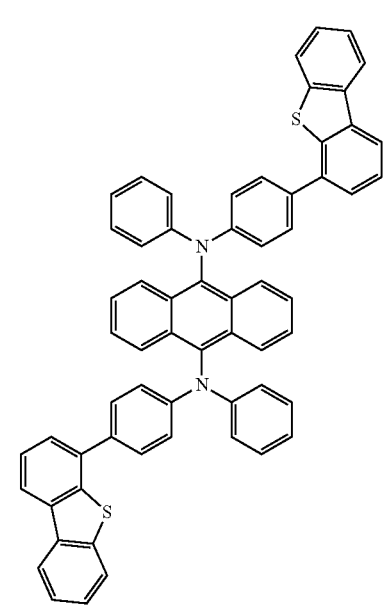
(117)
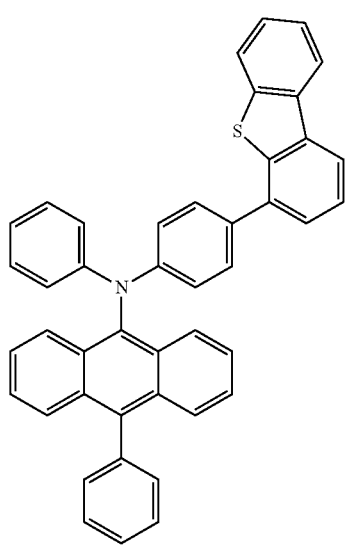
(118)
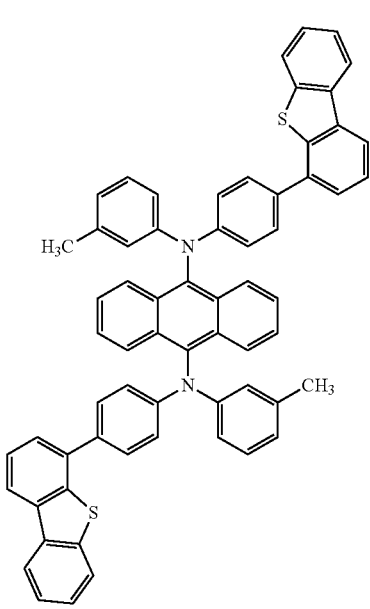

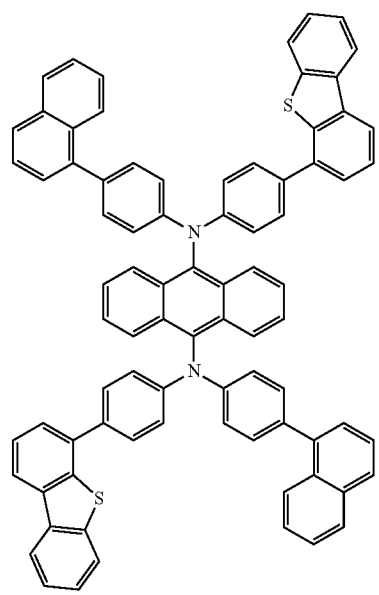
(119)
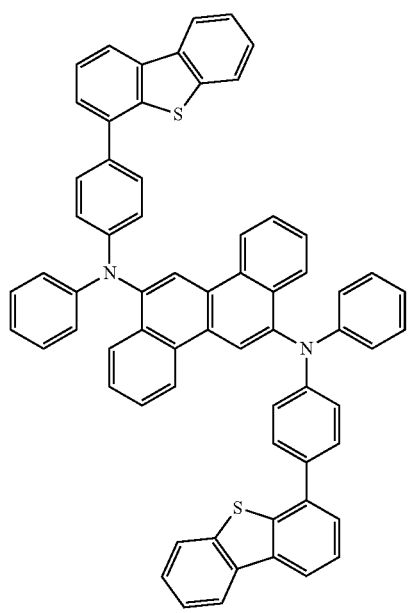
(121)
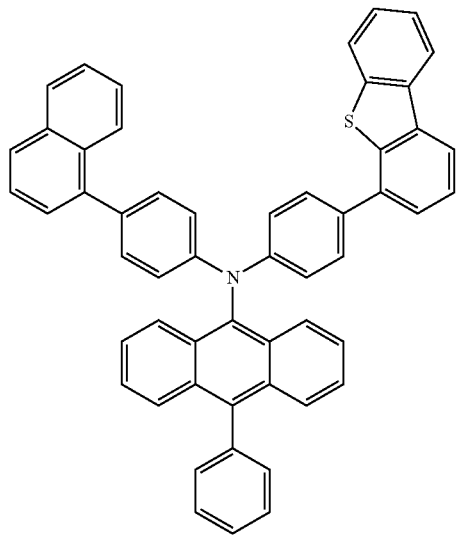
(120)
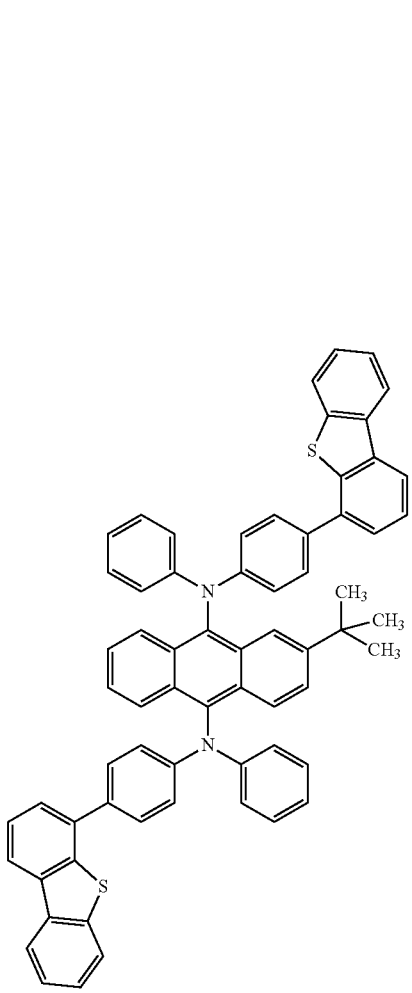
(122)

(123)
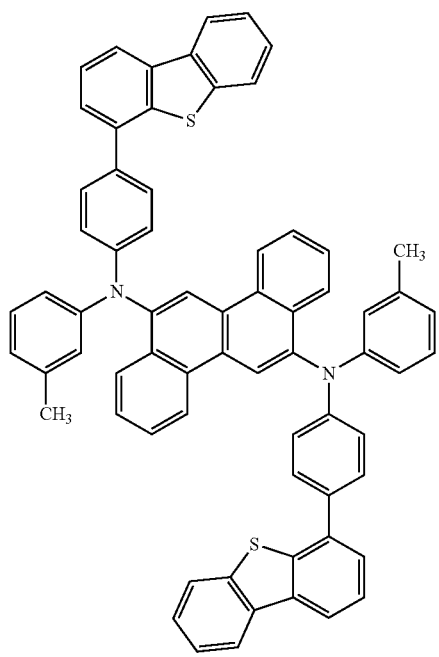
(124)
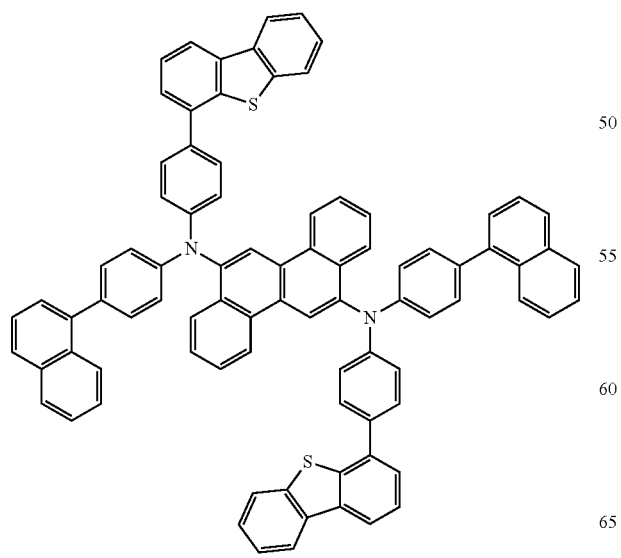
(125)
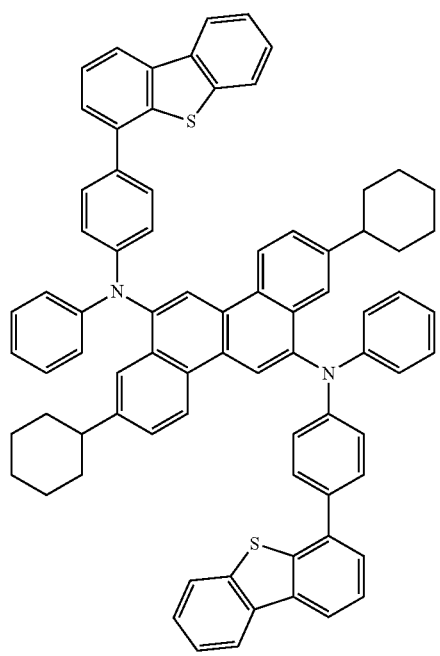
(126)
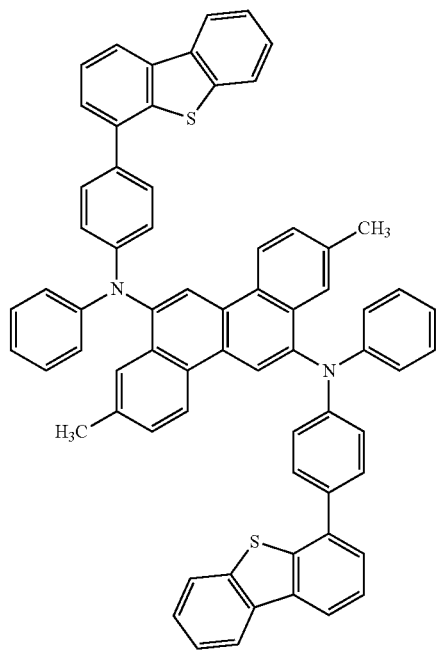

(127)
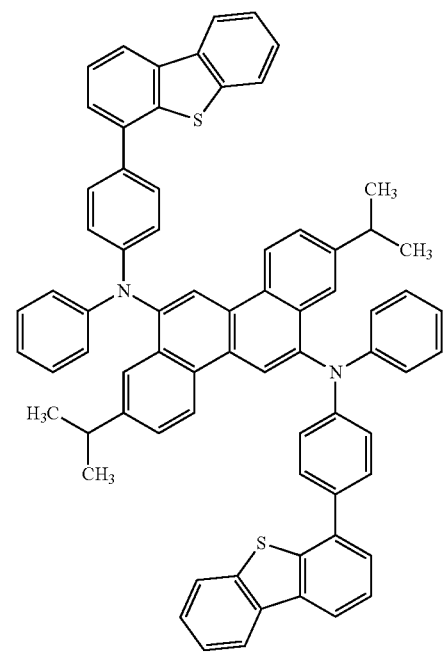
(128)
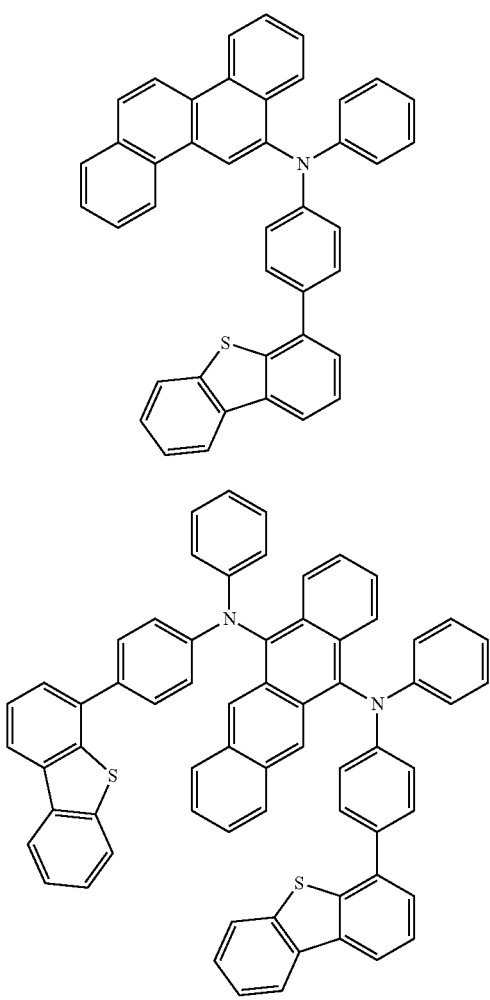
(129)
(130)
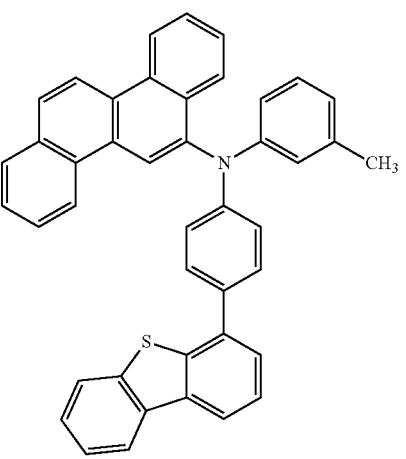
(131)
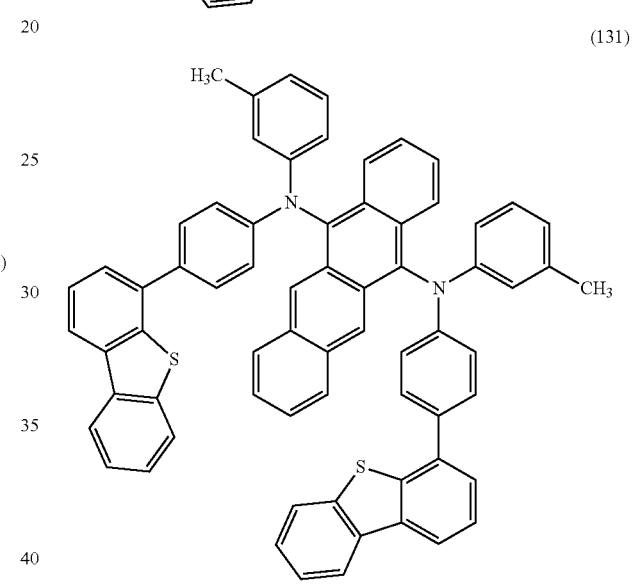
(132)
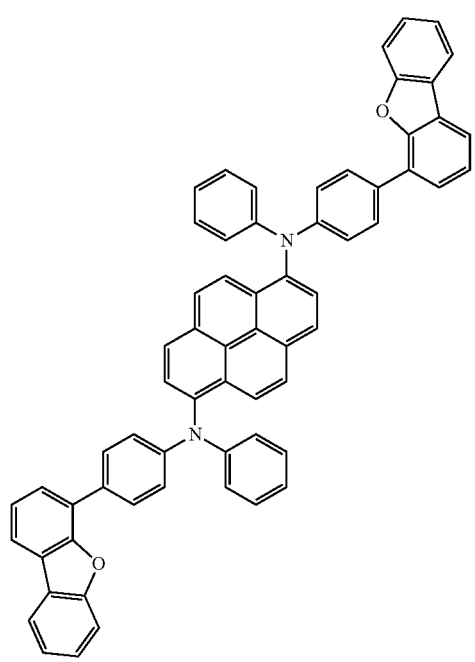

(133)
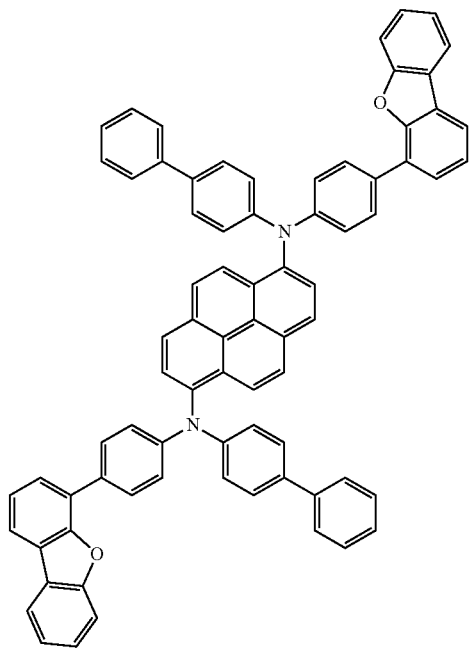
(135)
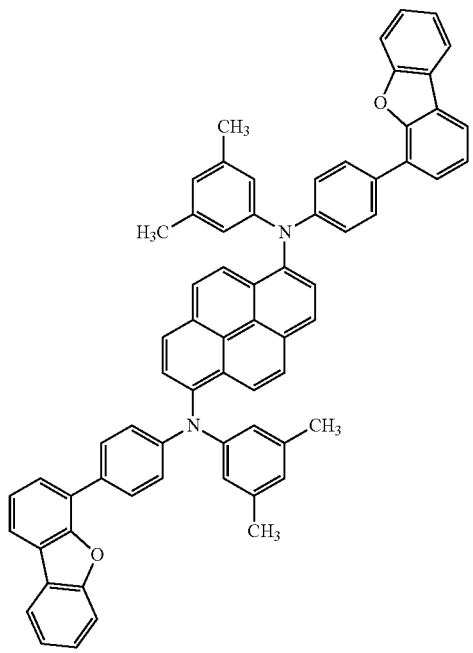
(134)
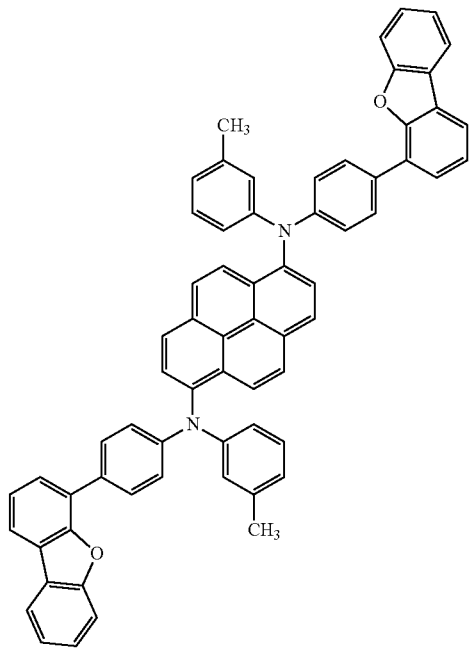
(136)
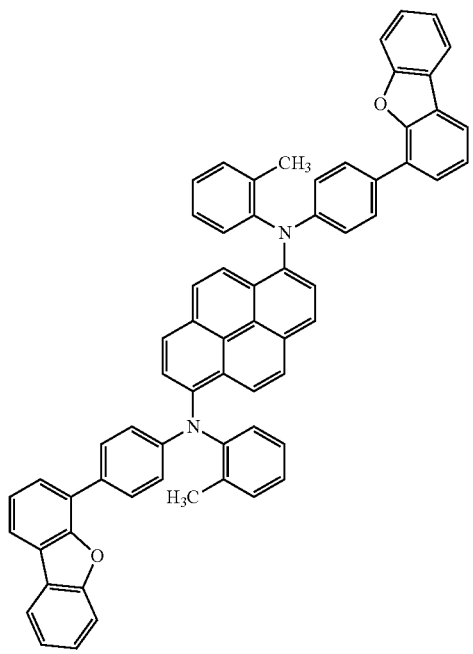

(137)
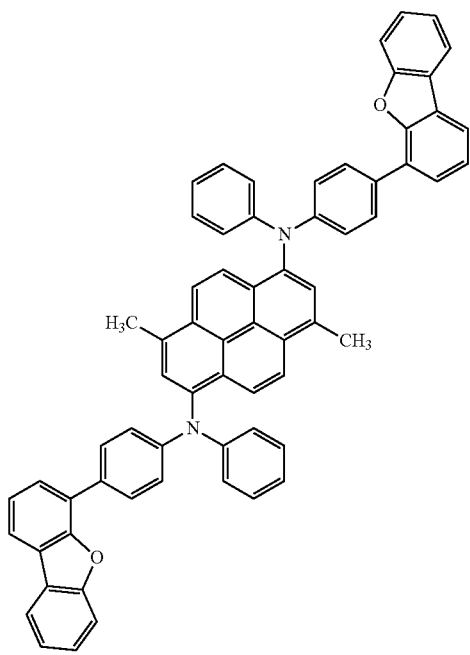
(139)
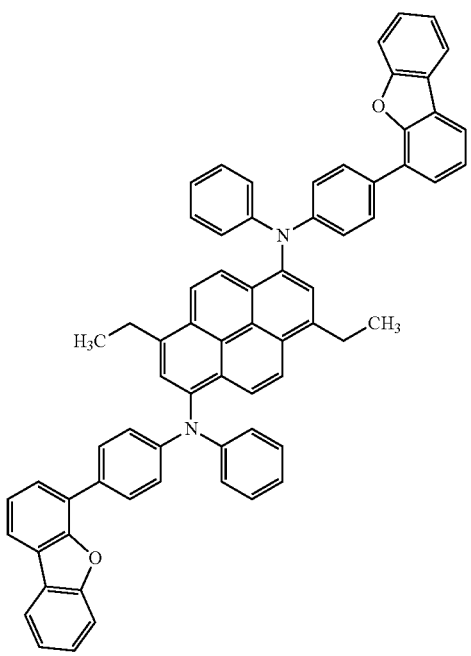
(138)
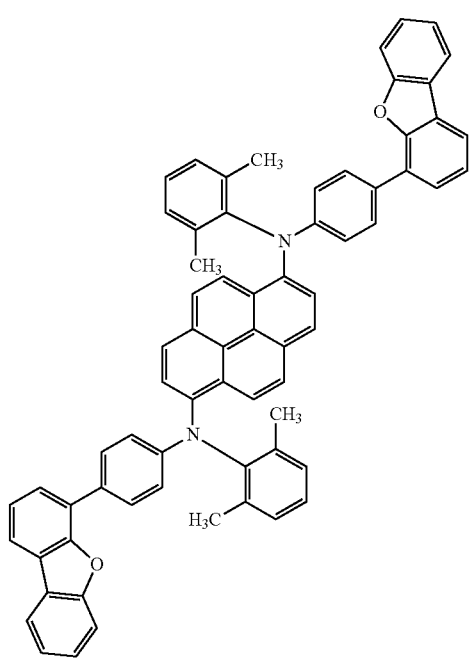
(140)
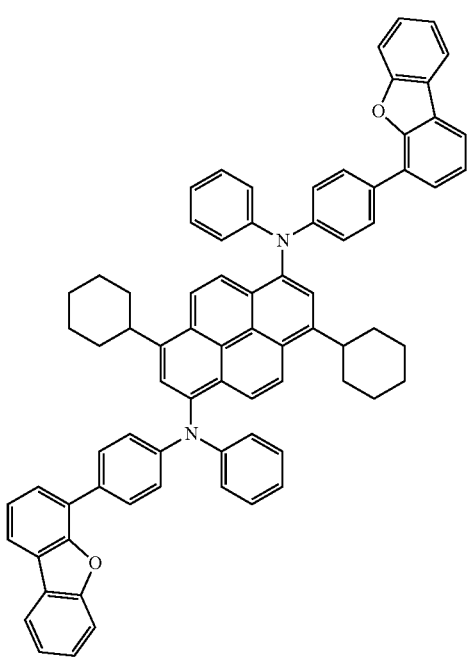

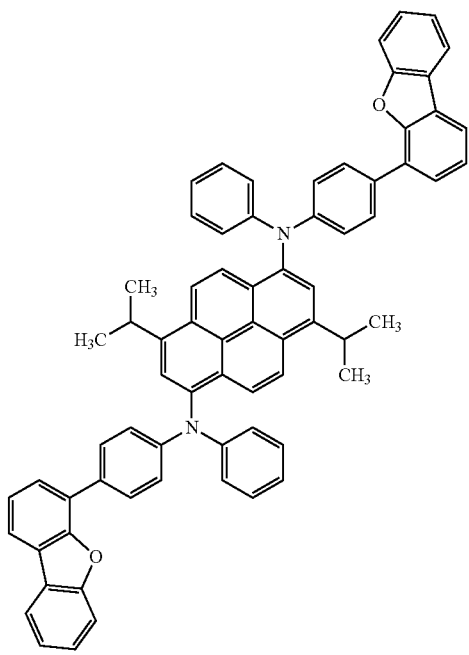
(141)
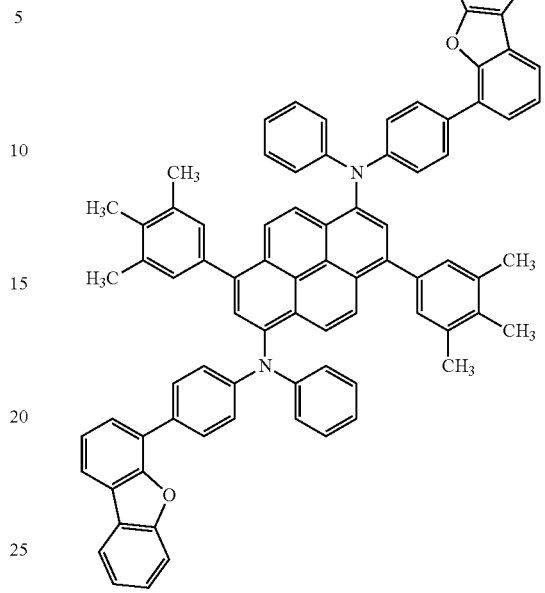
(143)
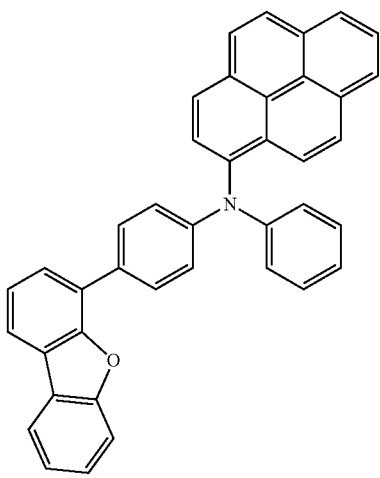
(144)
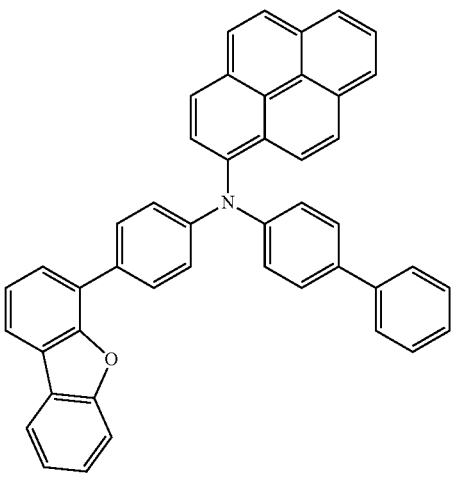
(142)
(145)

(146)
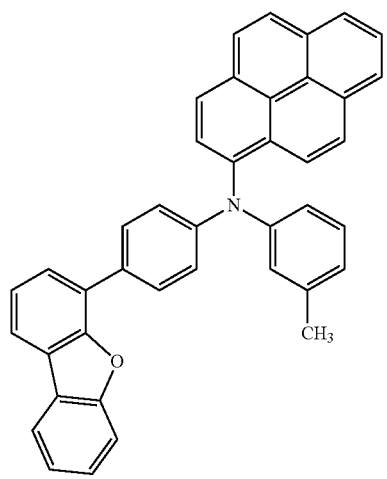
(147)
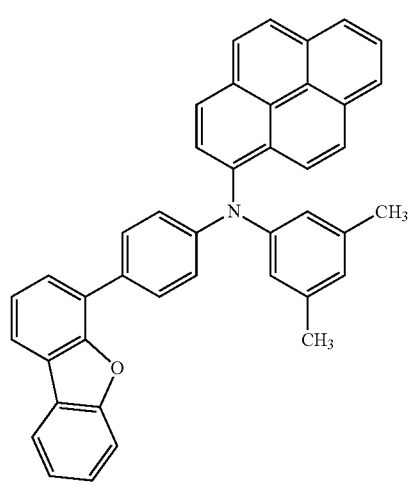
(148)
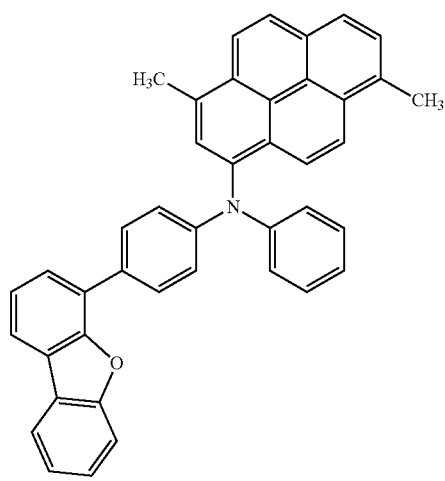
(149)
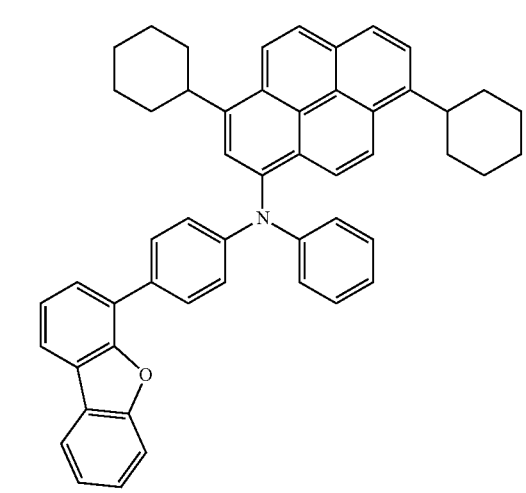
(150)
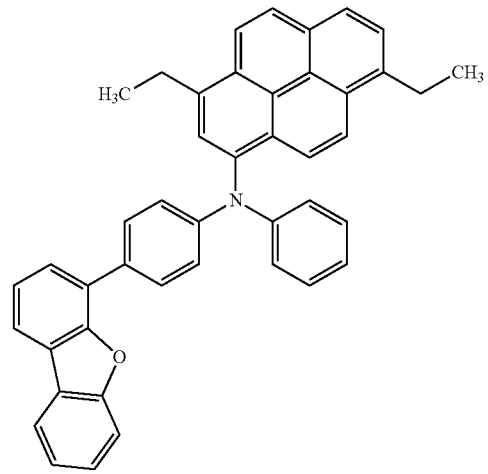
(151)
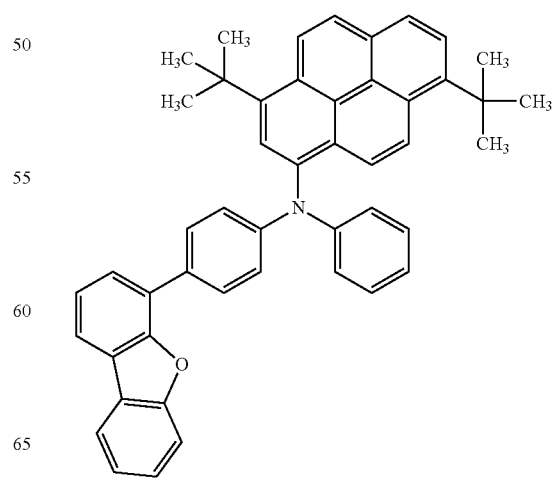

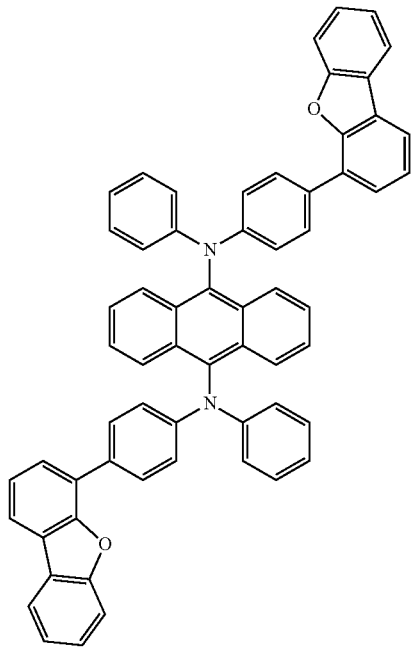
(152)
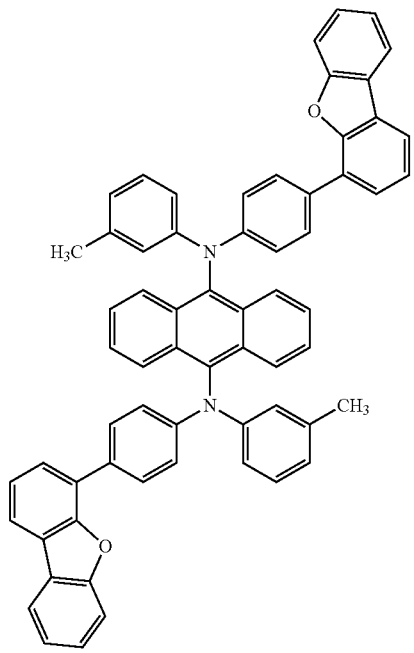
(154)
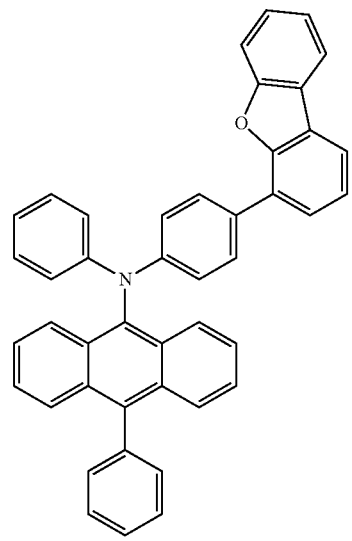
(153)
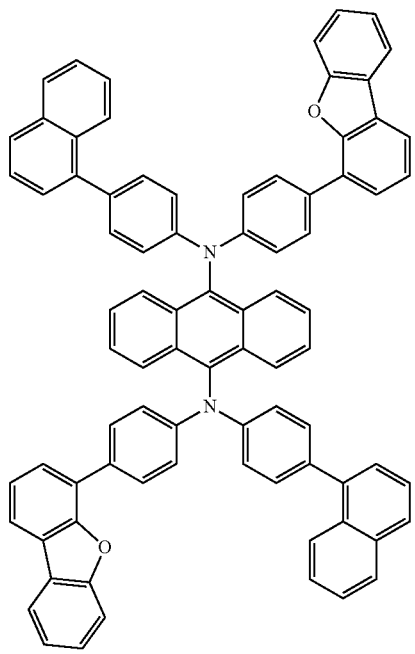
(155)

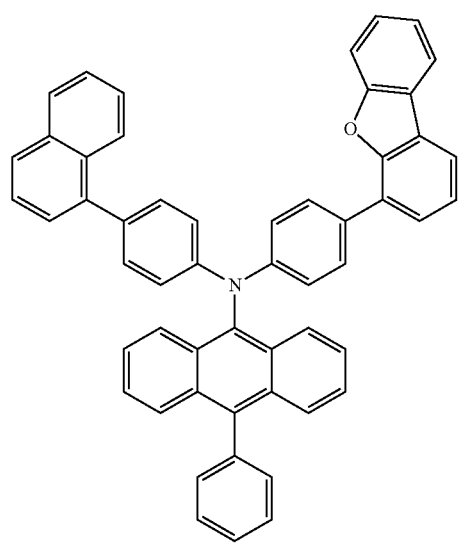
(156)
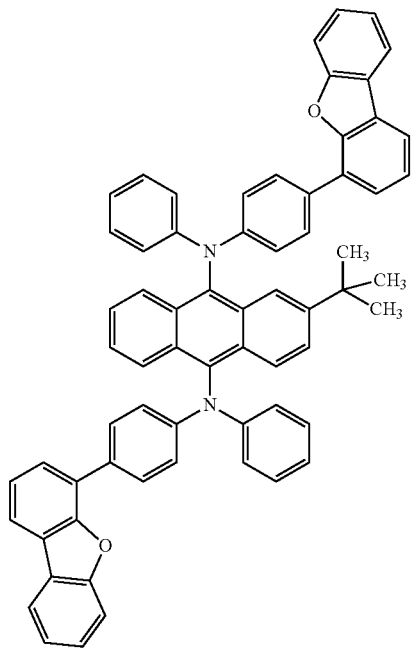
(158)
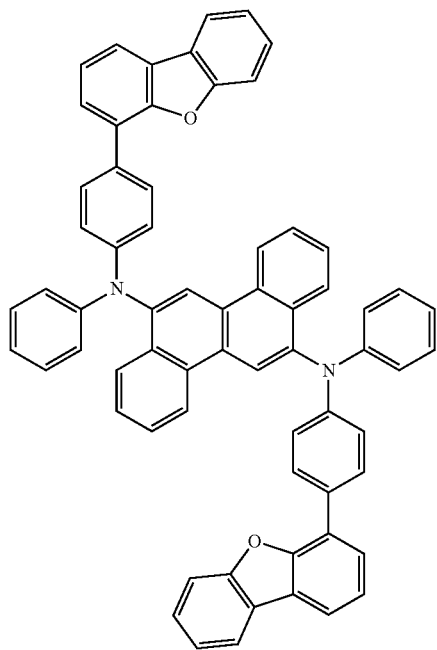
(157)
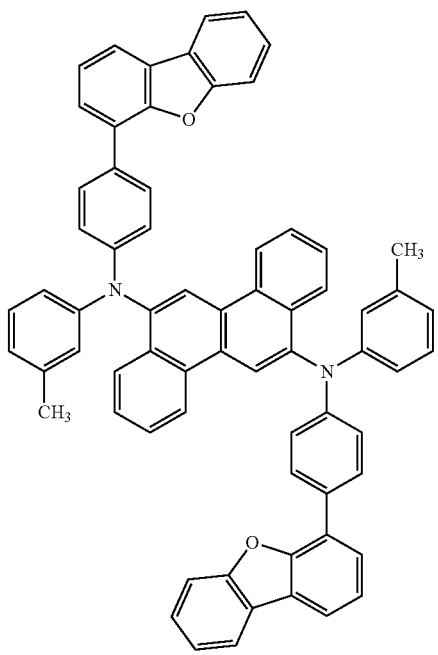
(159)

(160)
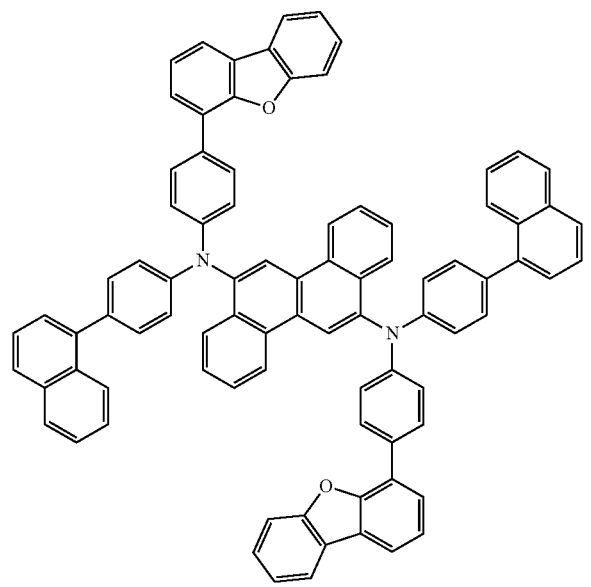
(162)
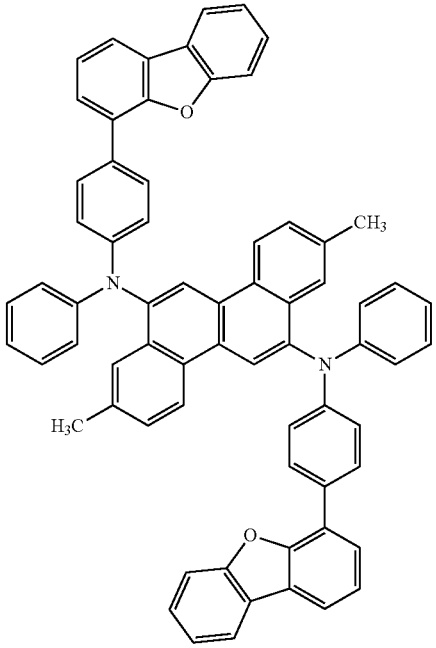
(161)
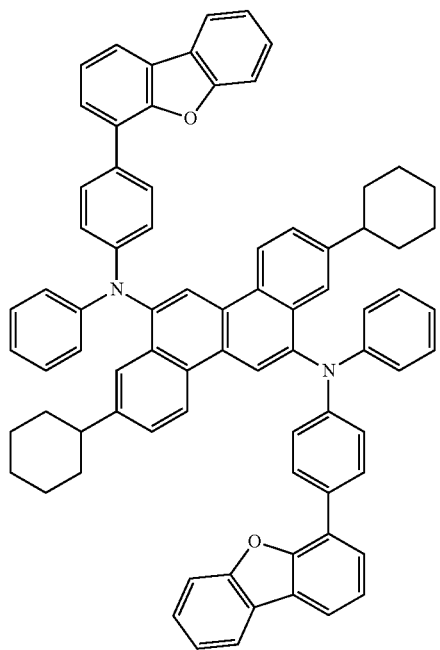
(163)
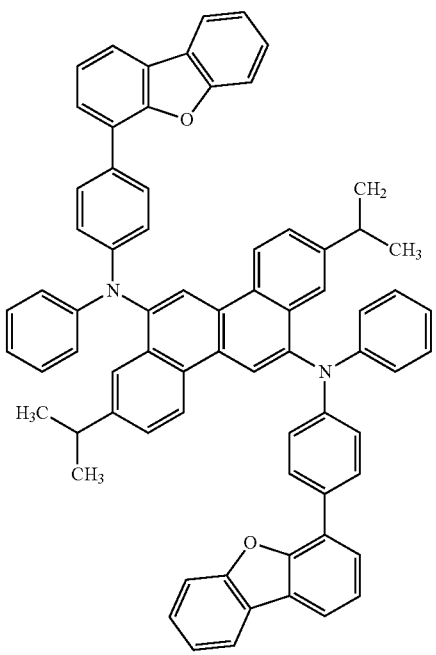

(165)
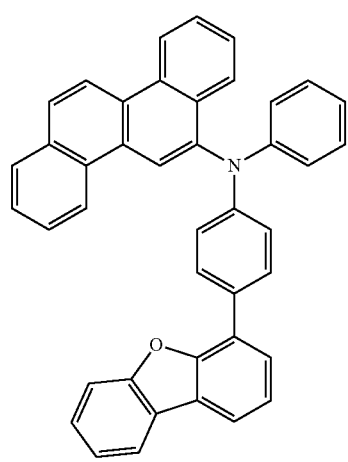
(166)
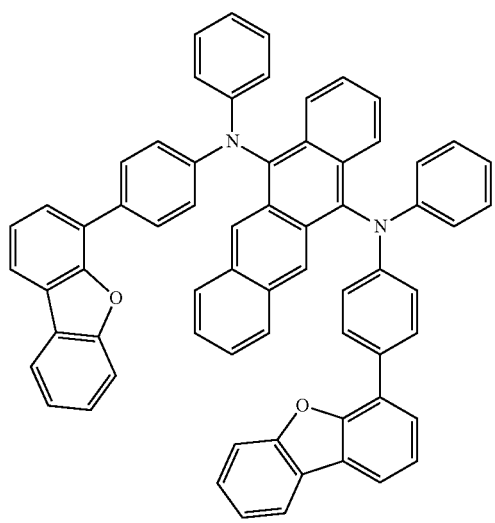
(167)
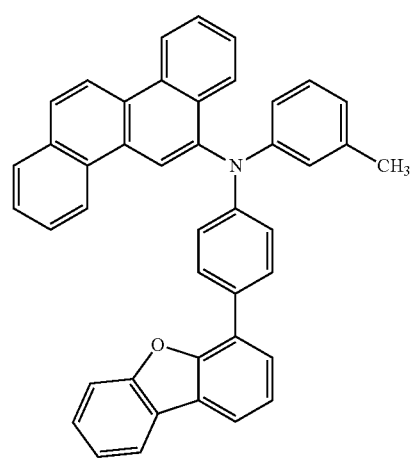
(168)
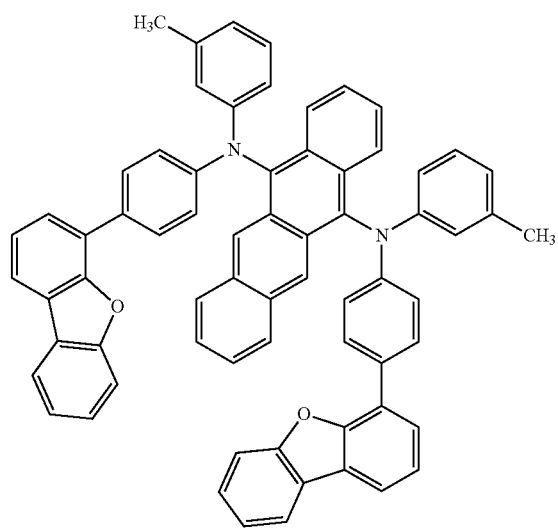
(169)
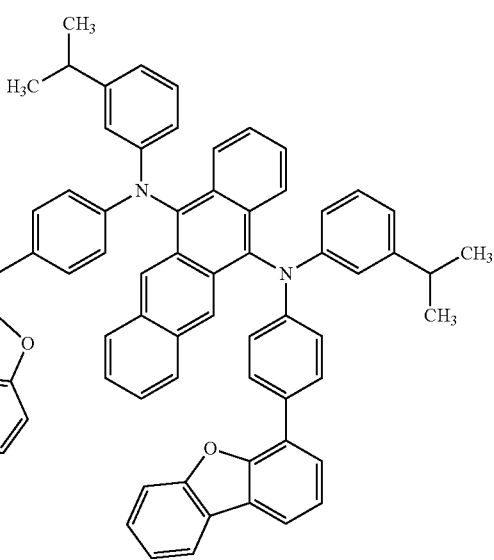

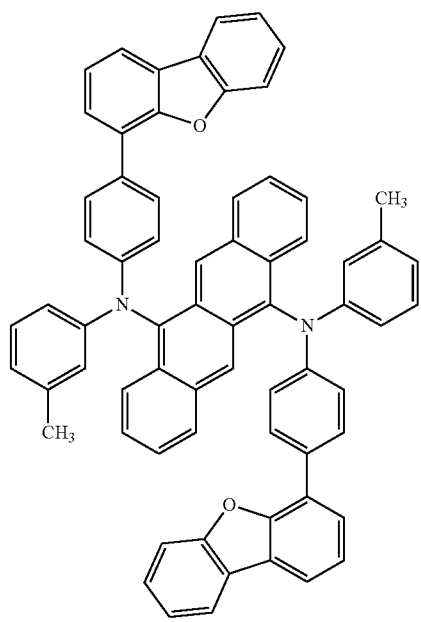
(170)
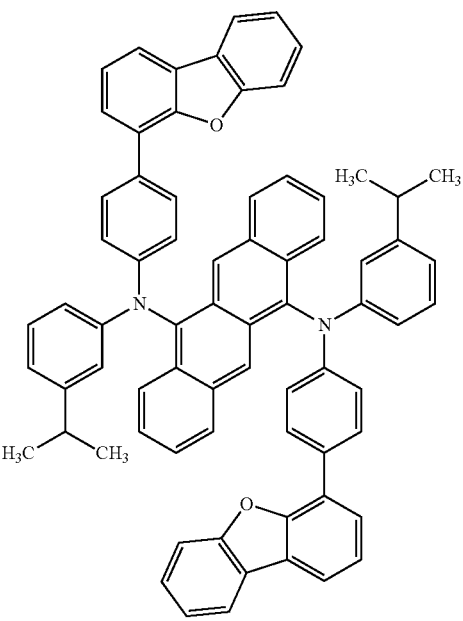
(172)
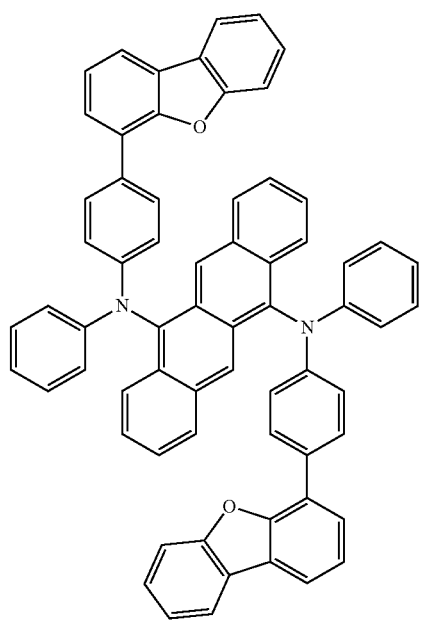
(171)
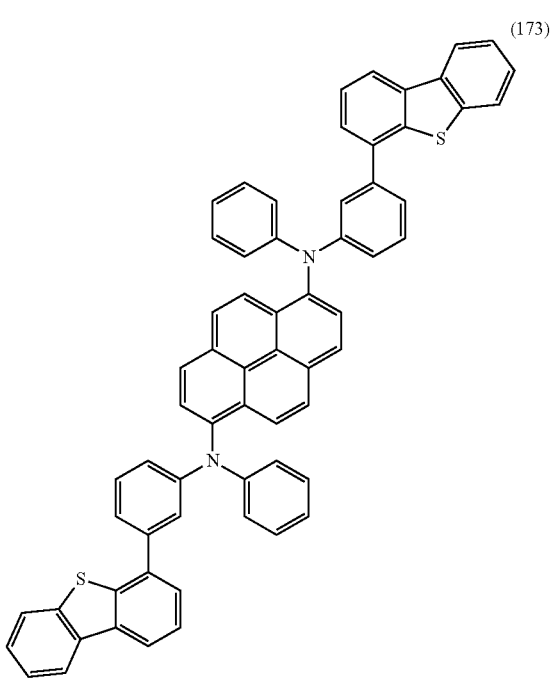
(173)

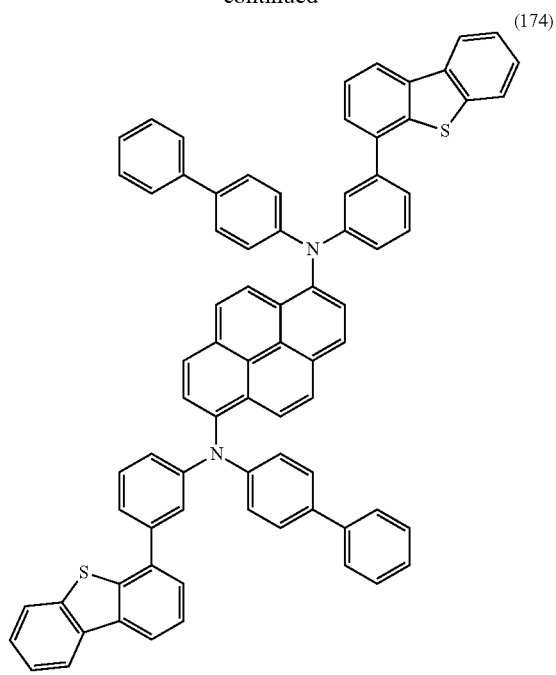
(174)
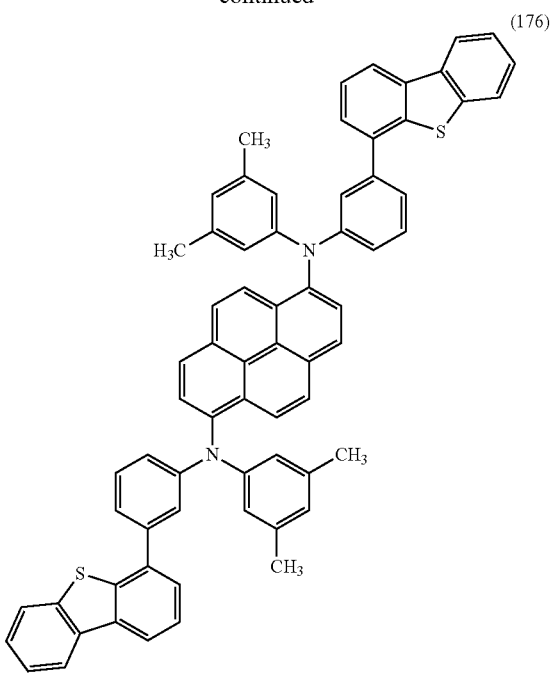
(176)
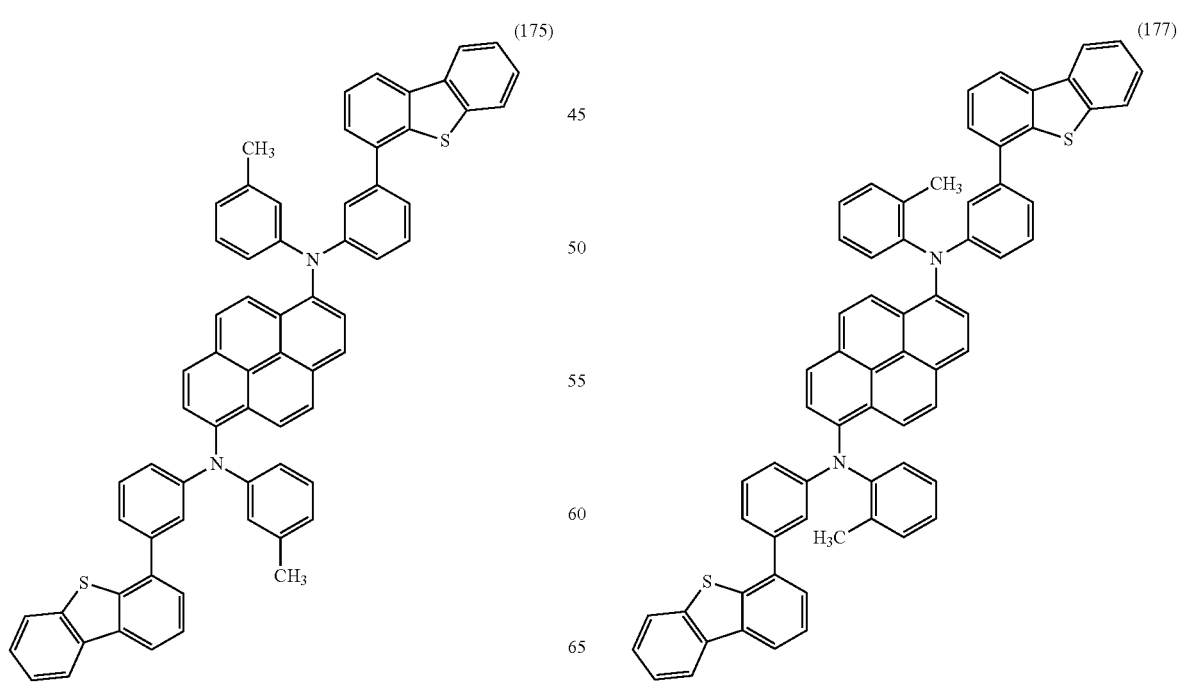
(175)
(177)

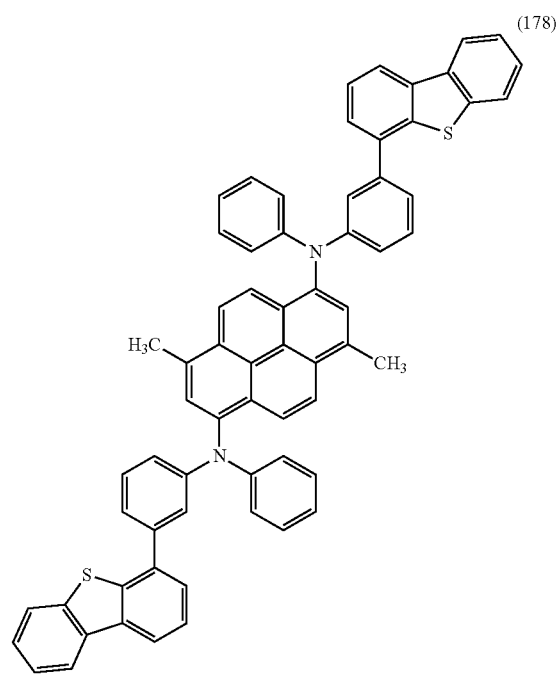
(178)
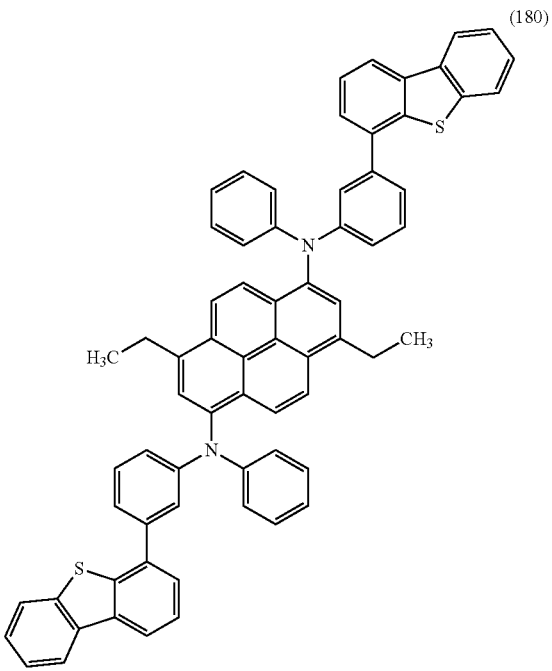
(180)
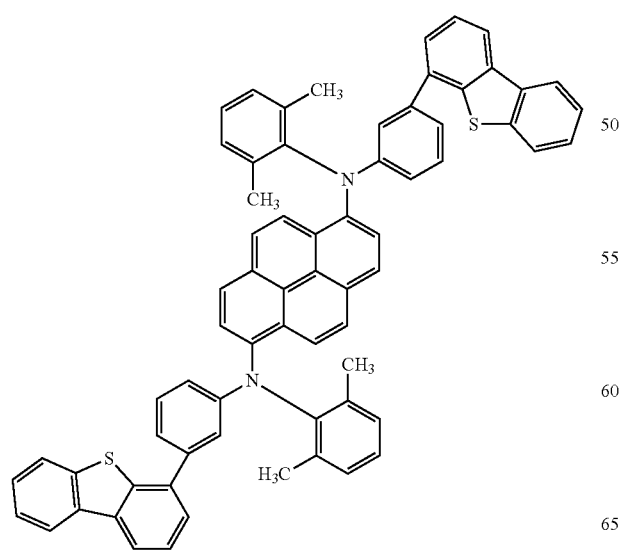
(179)
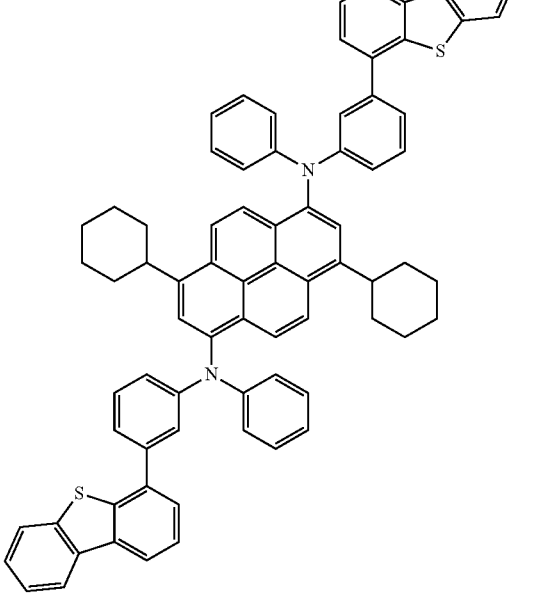
(181)

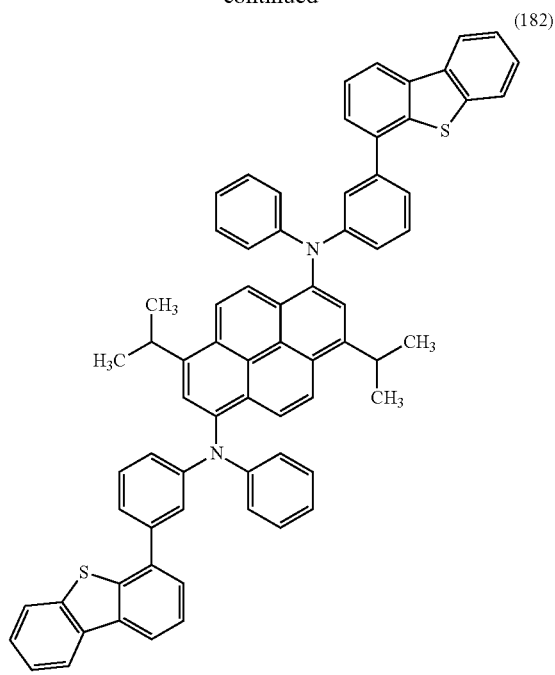
(182)
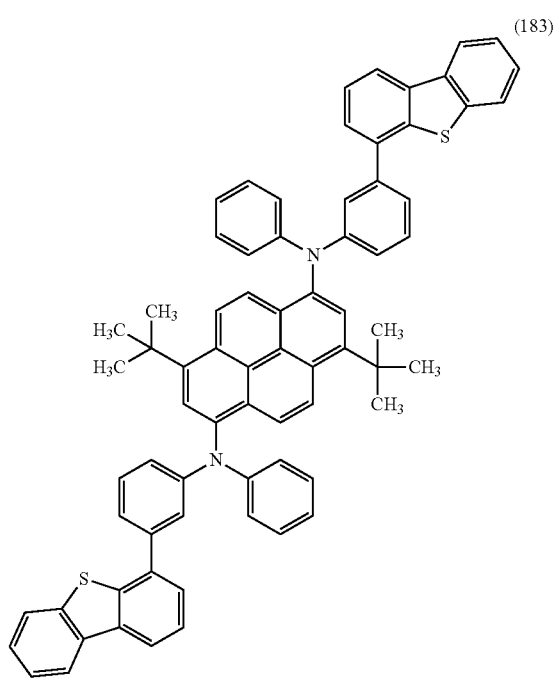
(183)
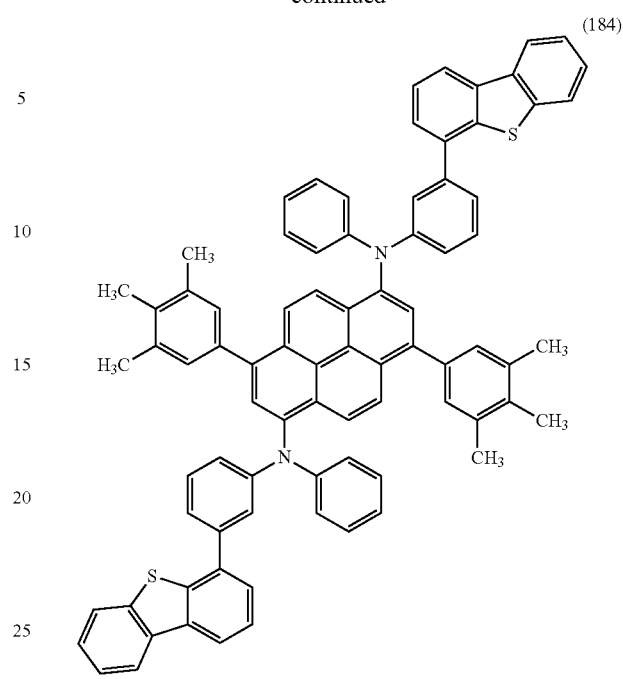
(184)
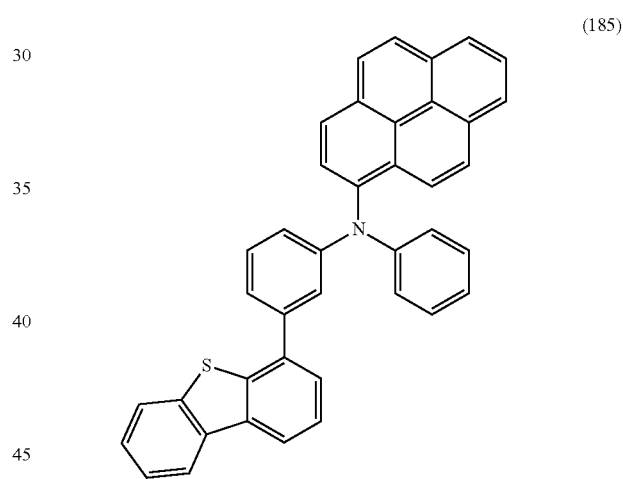
(185)
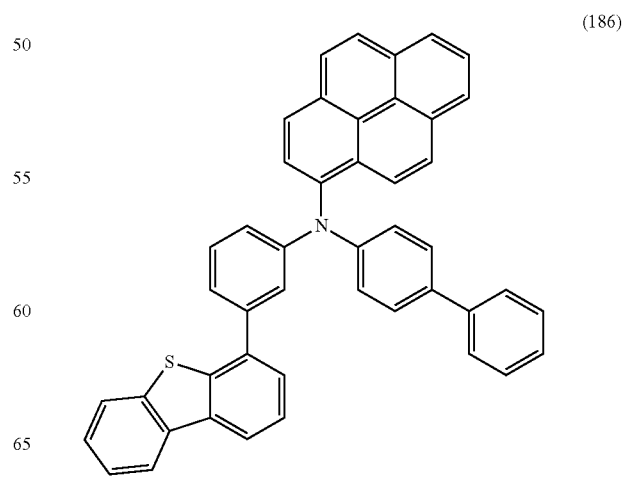
(186)

-continued
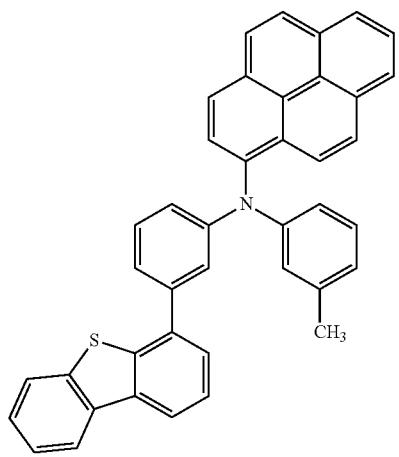
(187)
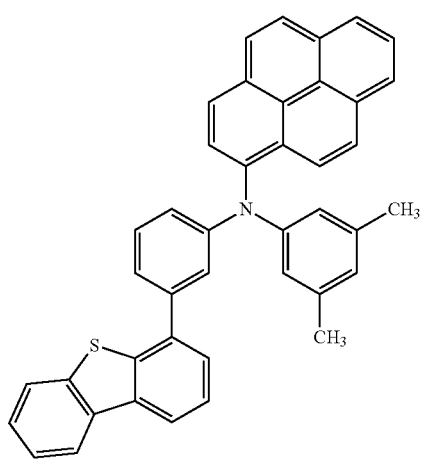
(188)
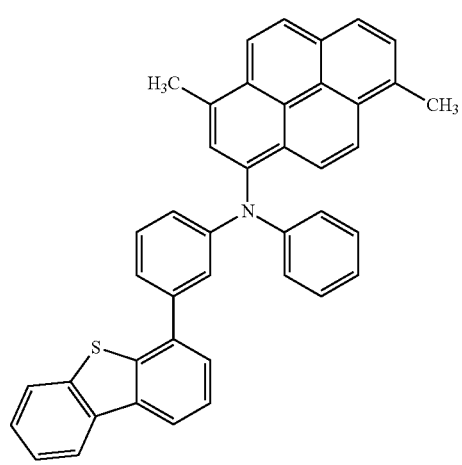
(189)
-continued
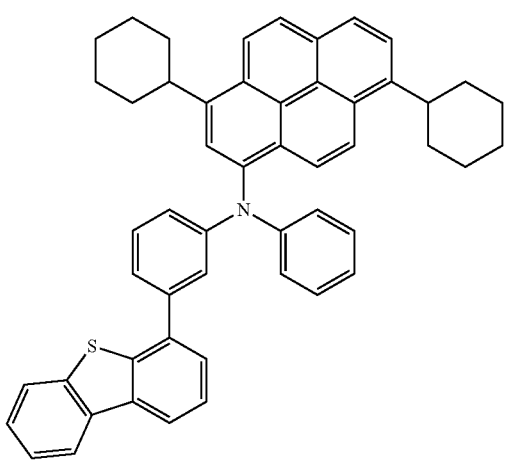
(190)
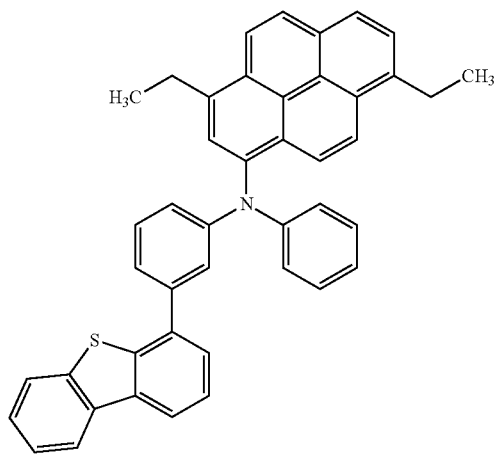
(191)
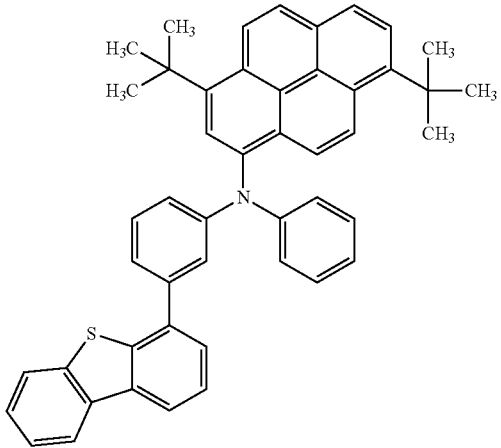
(192)

(193)
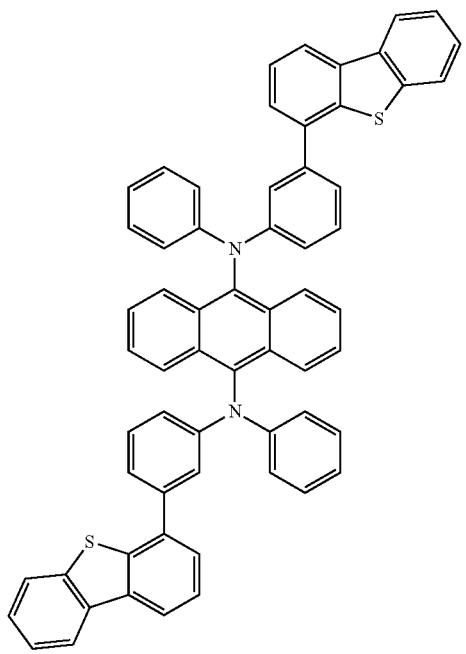
(194)
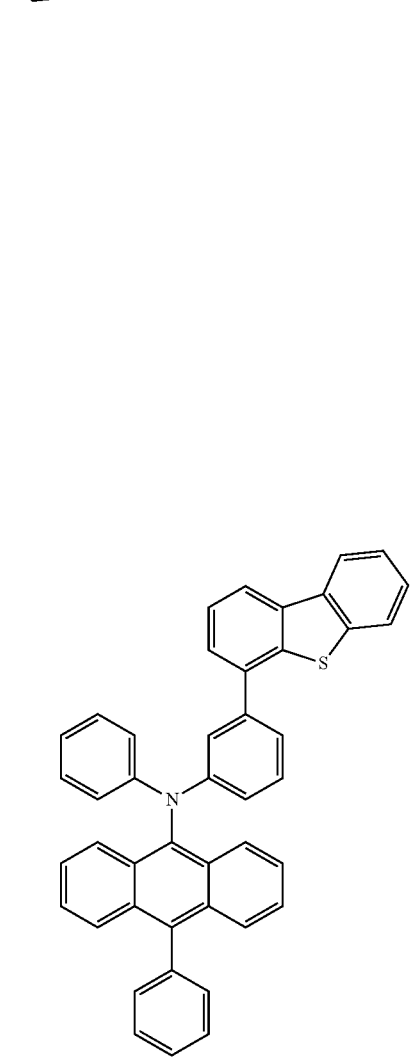
(195)
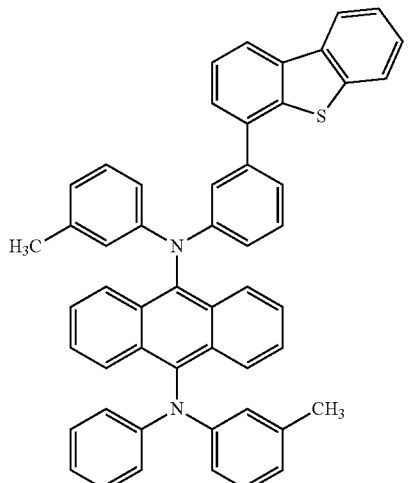
(196)
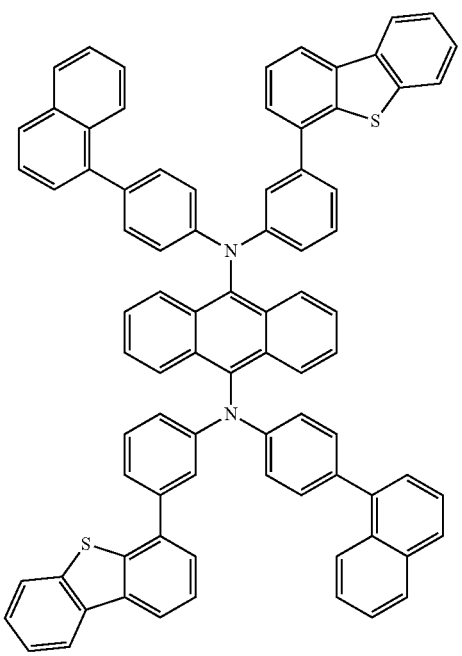

(197)
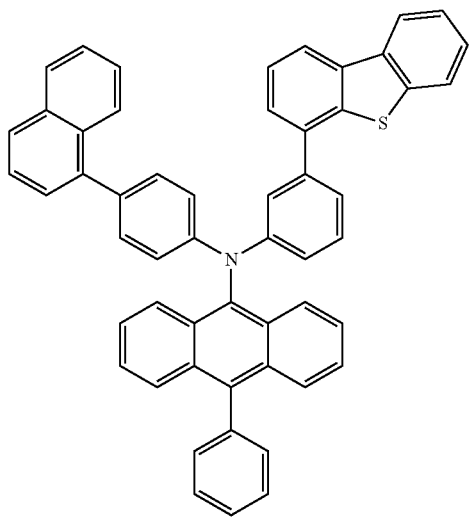
(198)
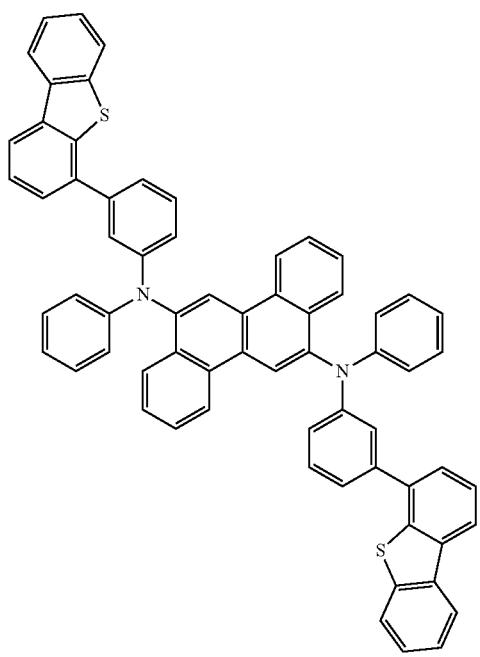
(199)
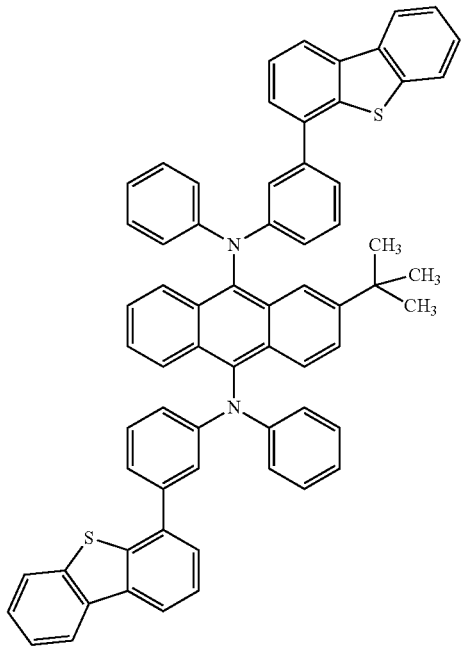
(200)
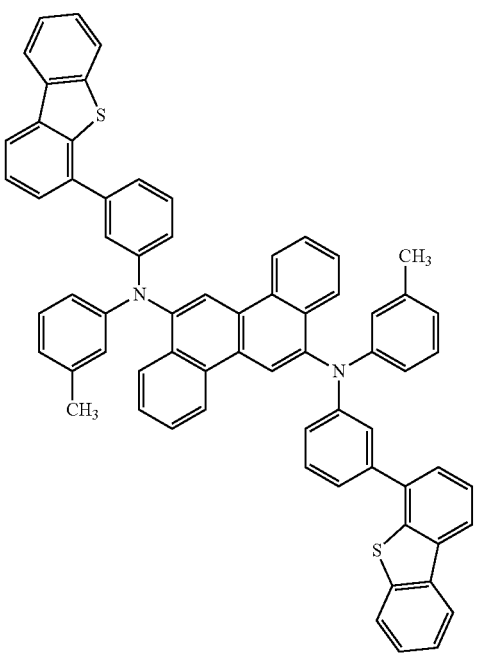

(201)
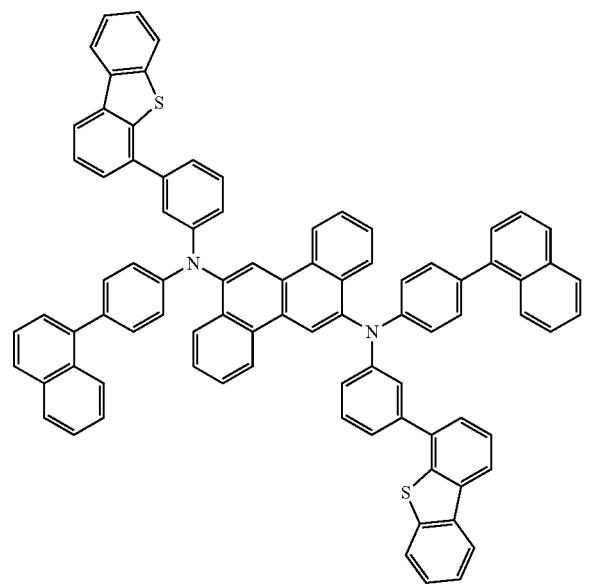
(203)
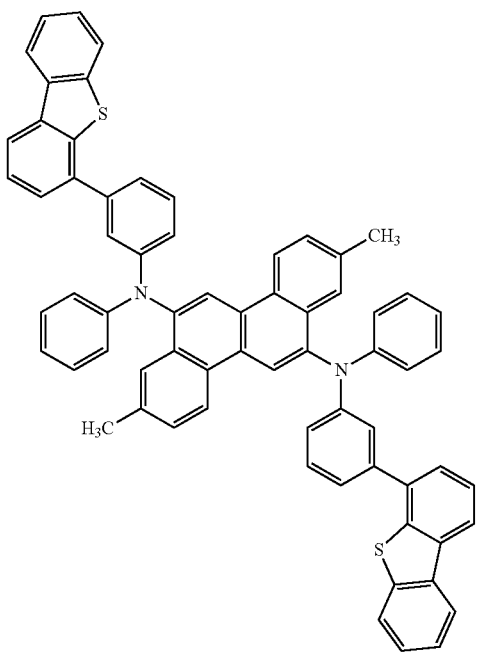
(202)
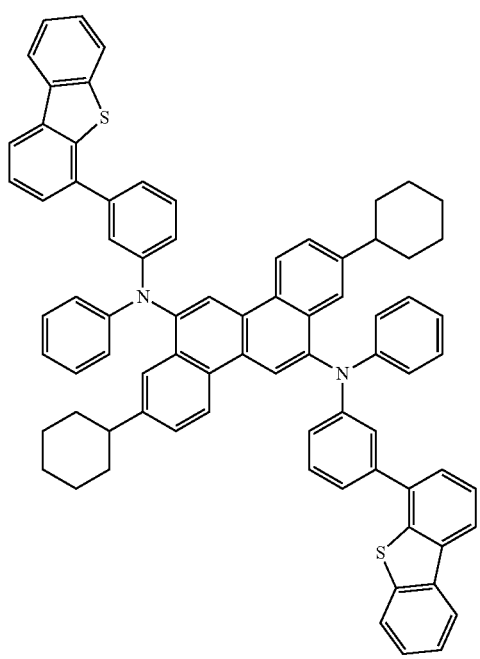
(204)
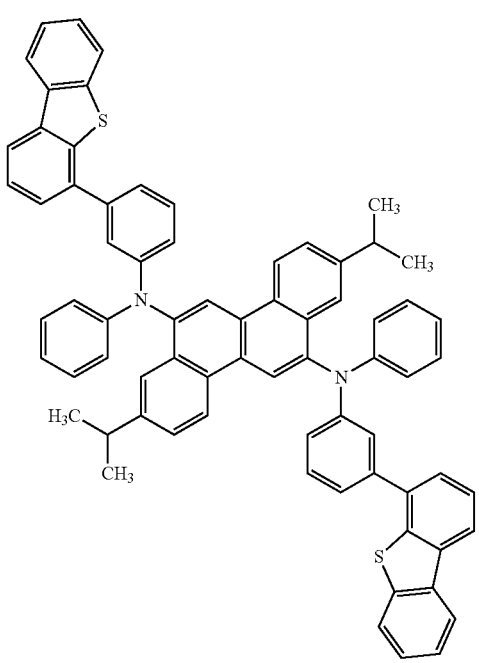

(205)
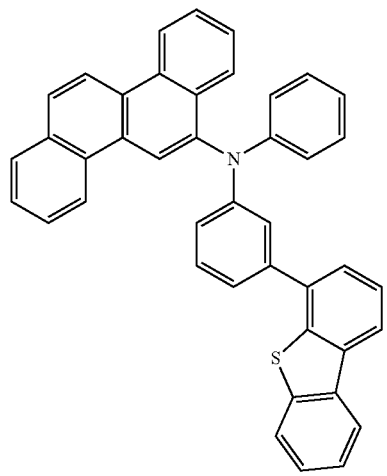
(206)
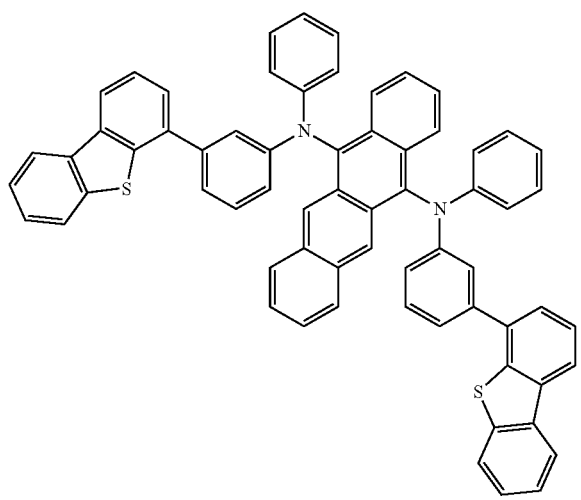
(207)
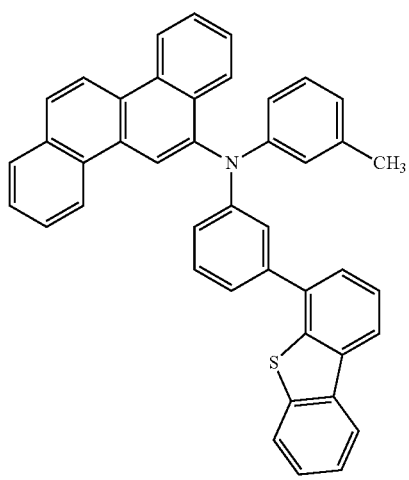
(208)
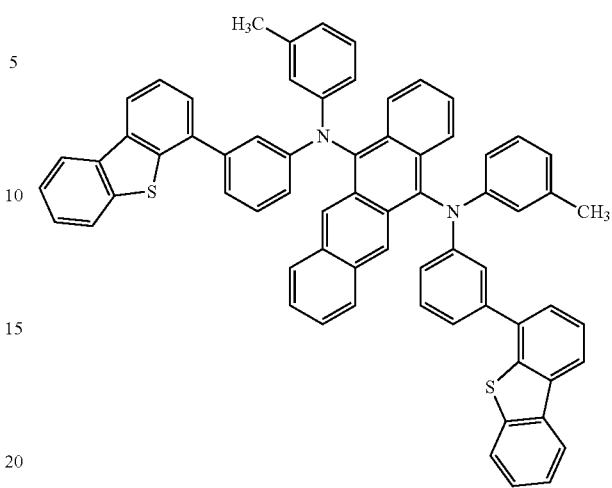
(209)
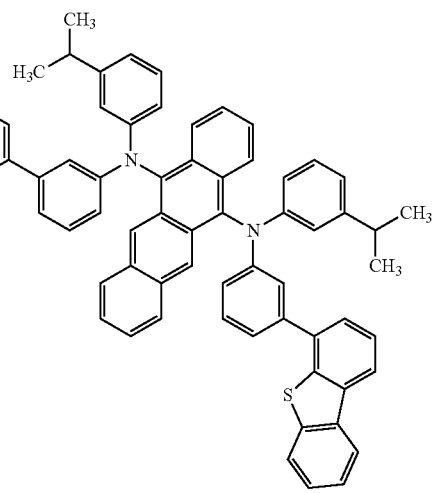
(210)
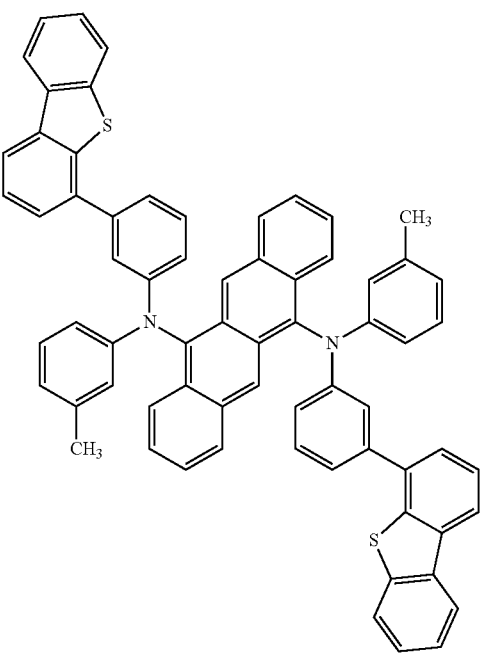

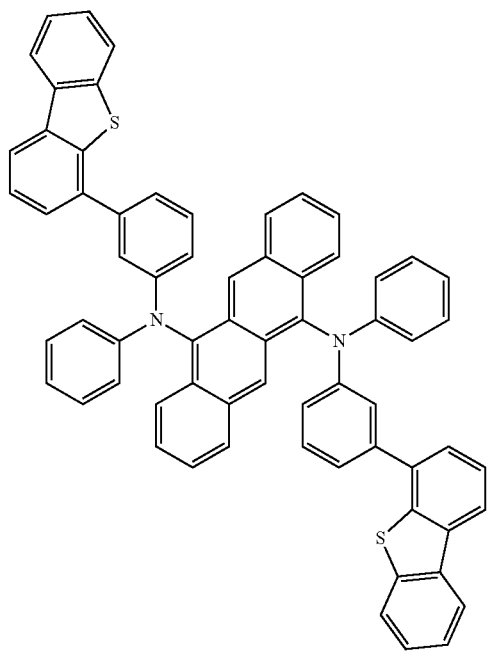
(211)
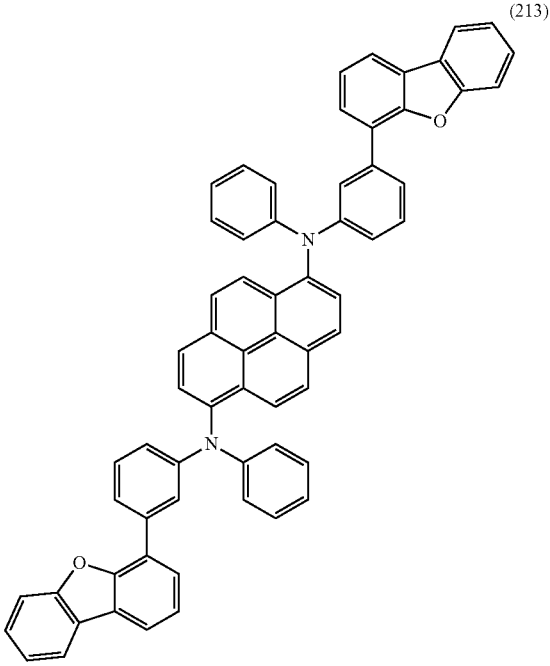
(213)
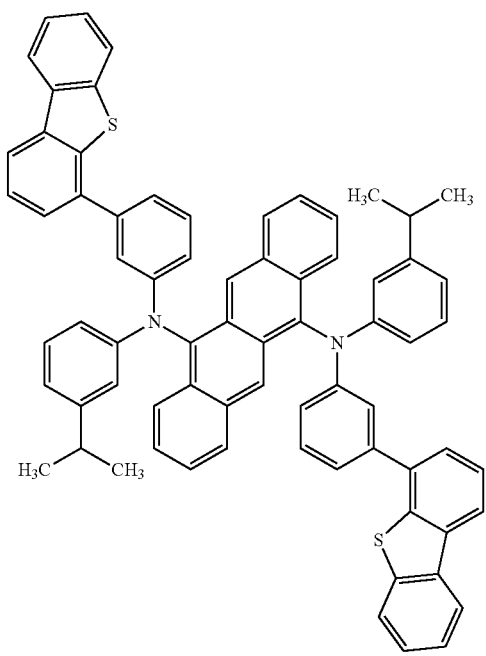
(212)
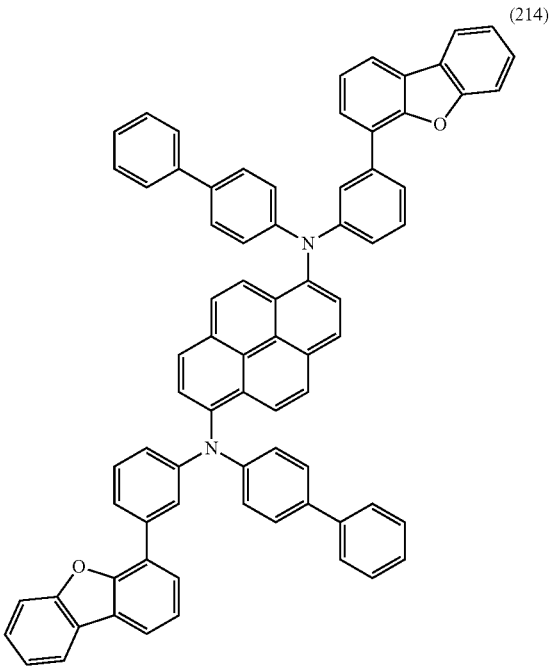
(214)

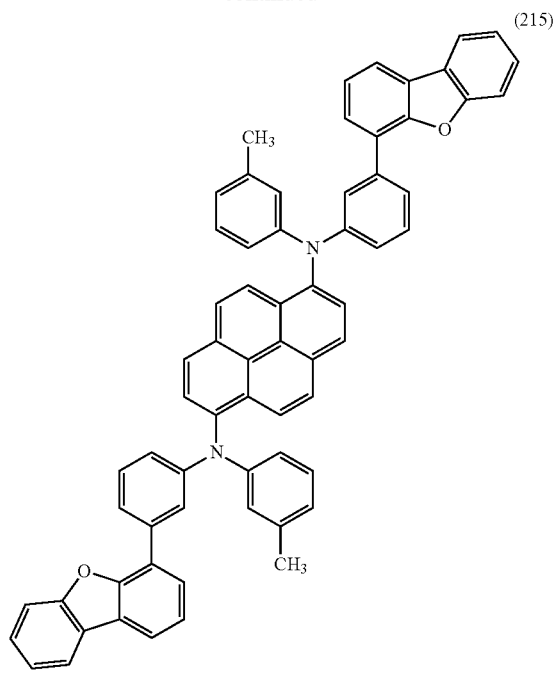
(215)
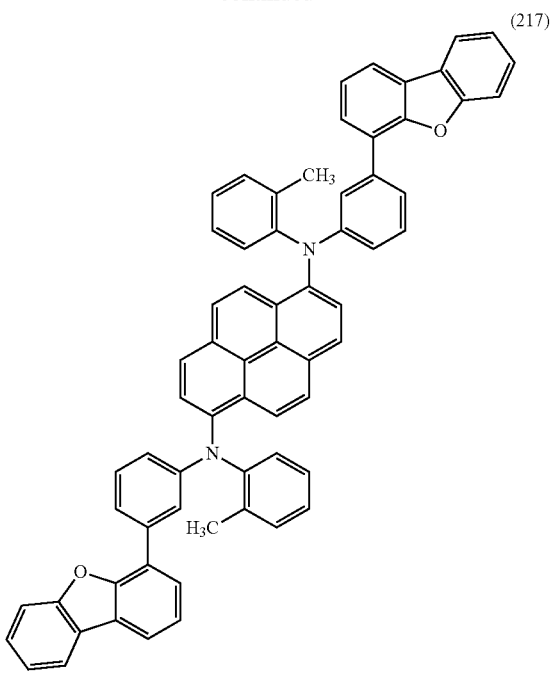
(217)
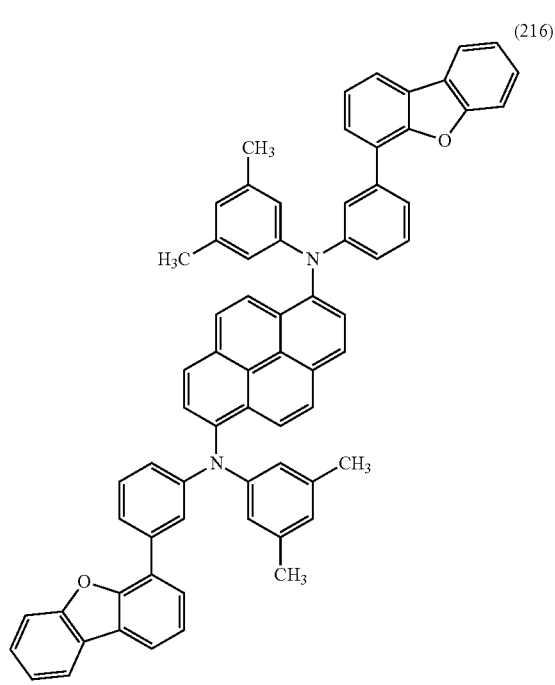
(216)
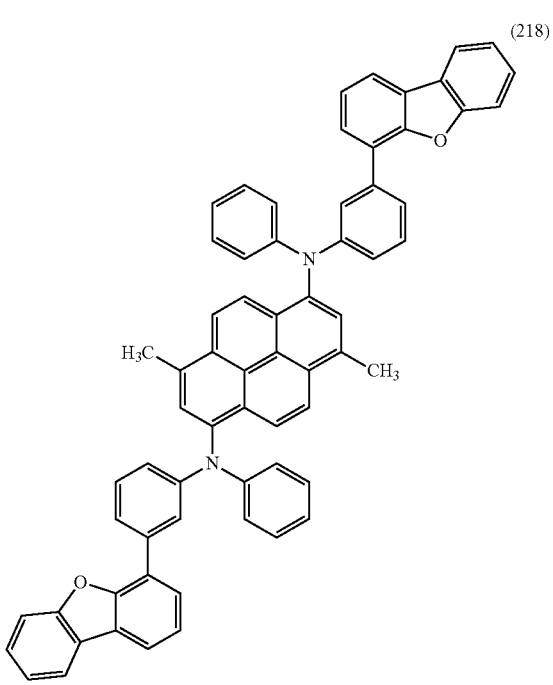
(218)

(219)
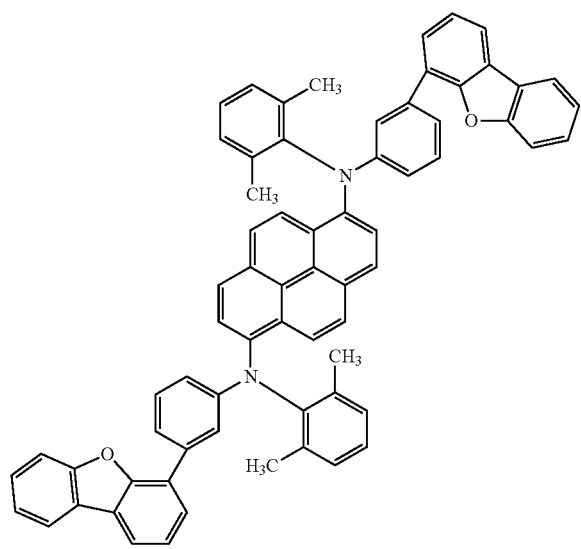
(221)
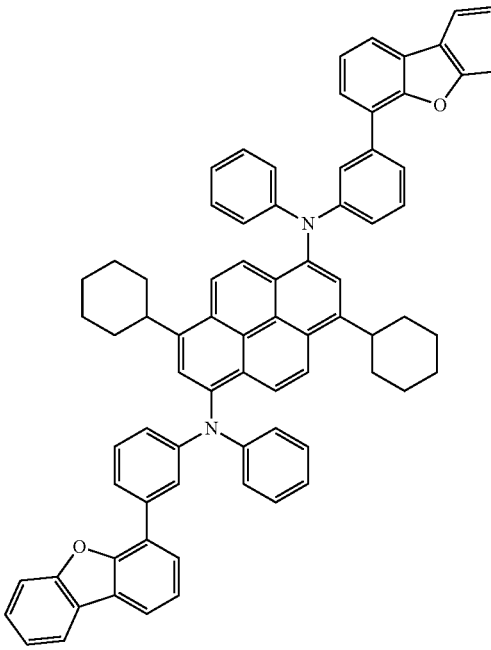
(220)
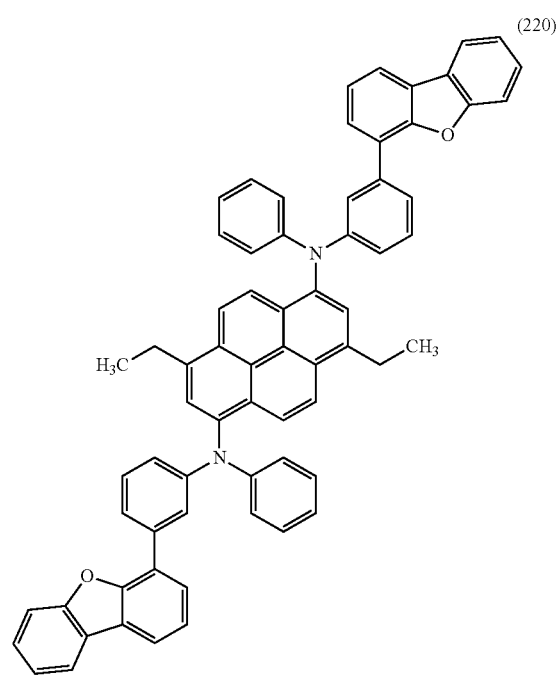
(222)
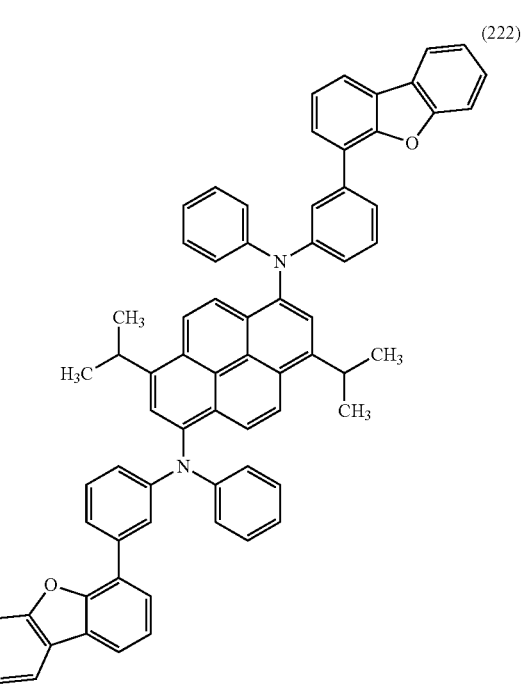

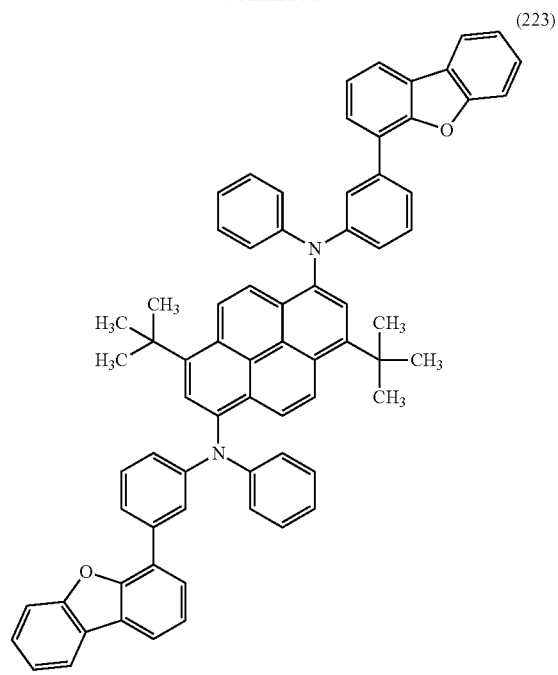
(223)
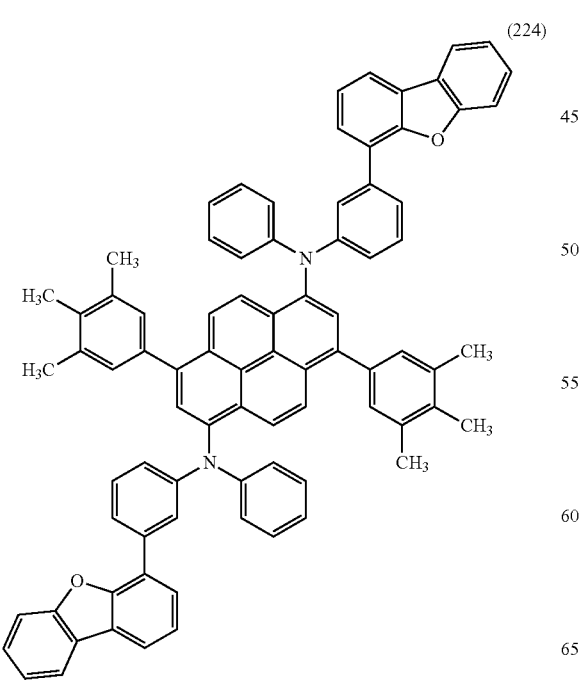
(224)
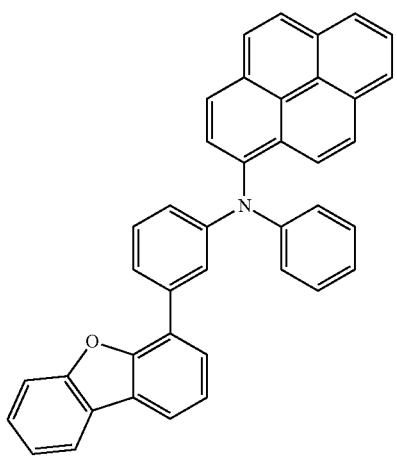
(225)
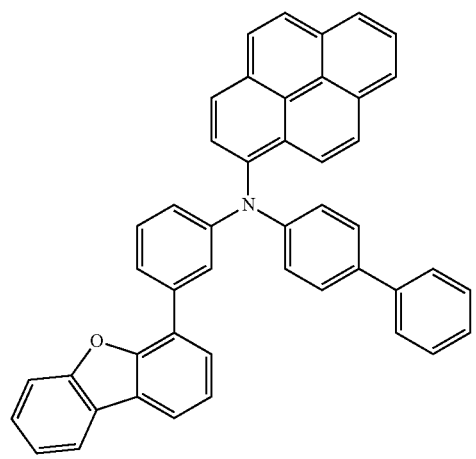
(226)
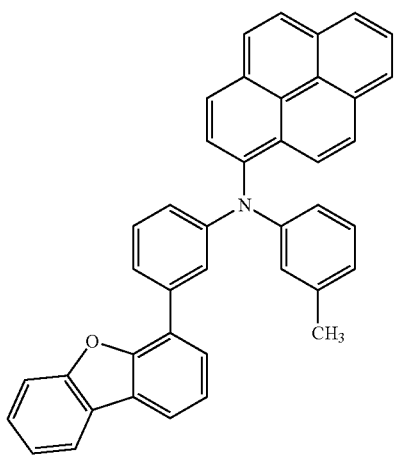
(227)

(228)
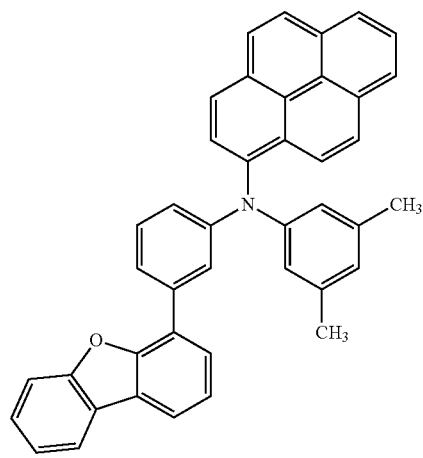
(229)
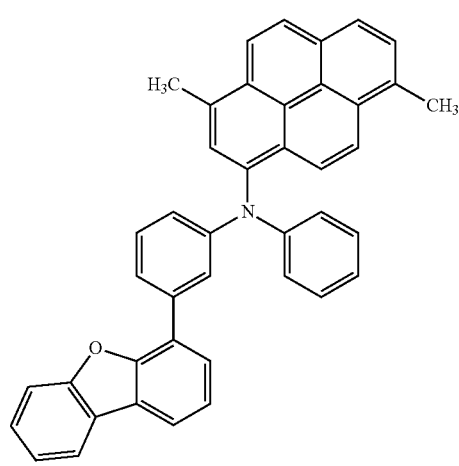
(230)
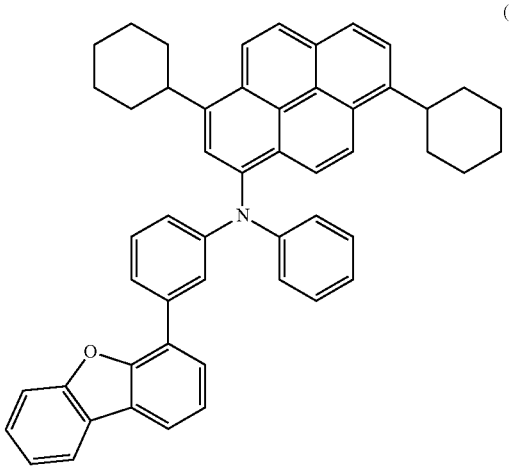
(231)
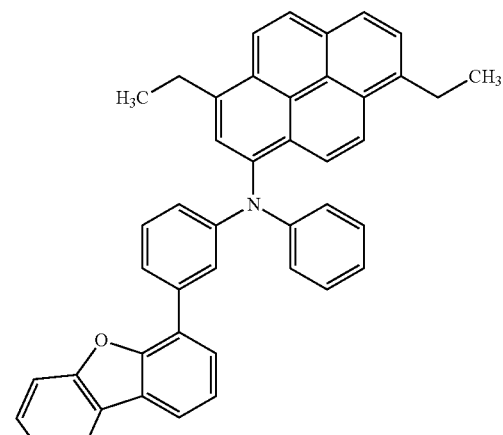
(232)
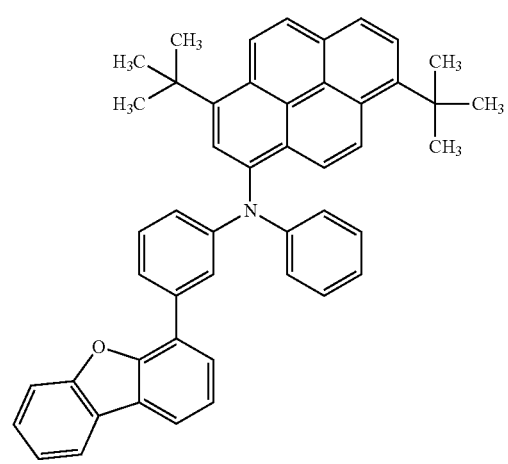
(233)
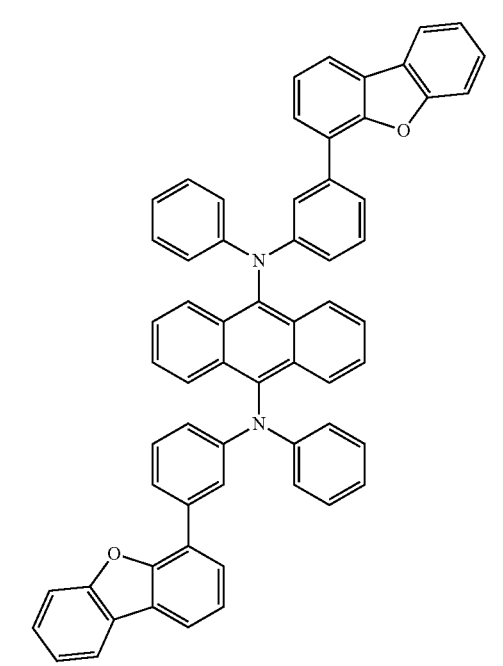

(234)
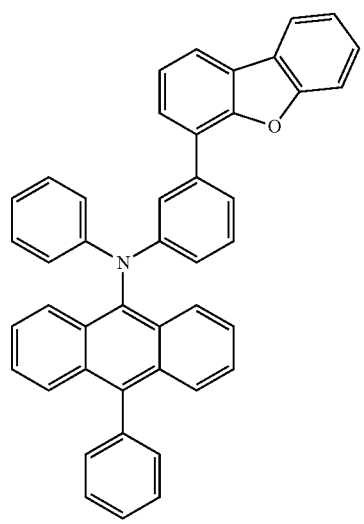
(235)
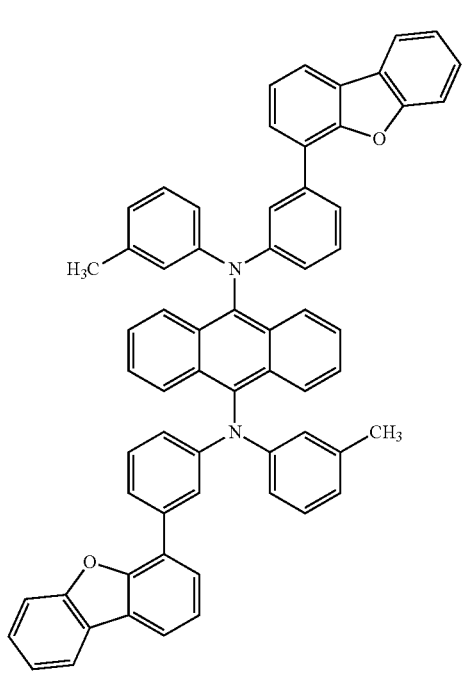
(236)
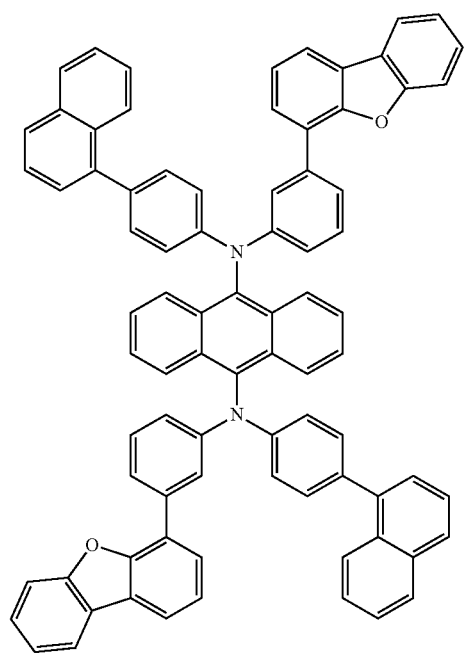
(237)
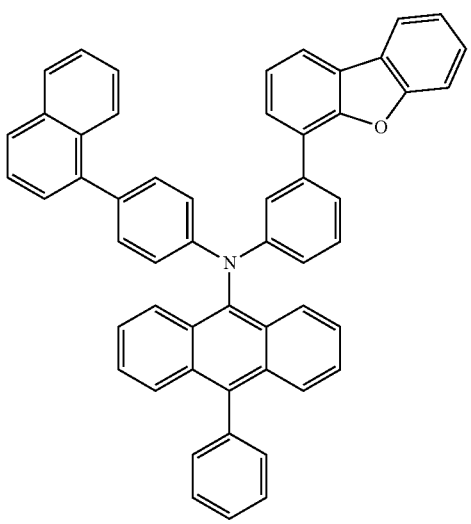

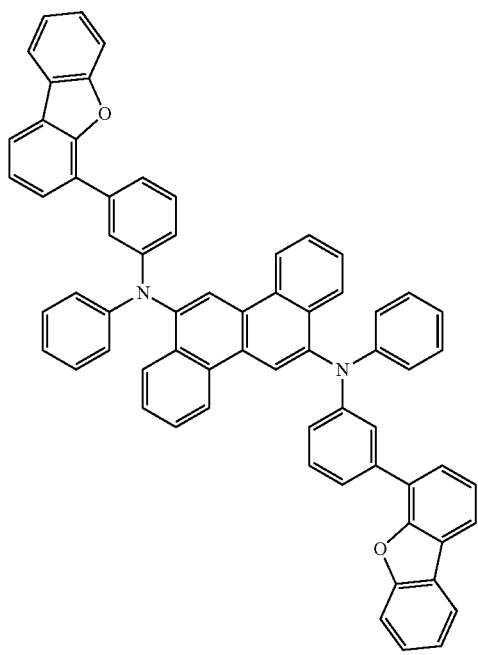
(238)
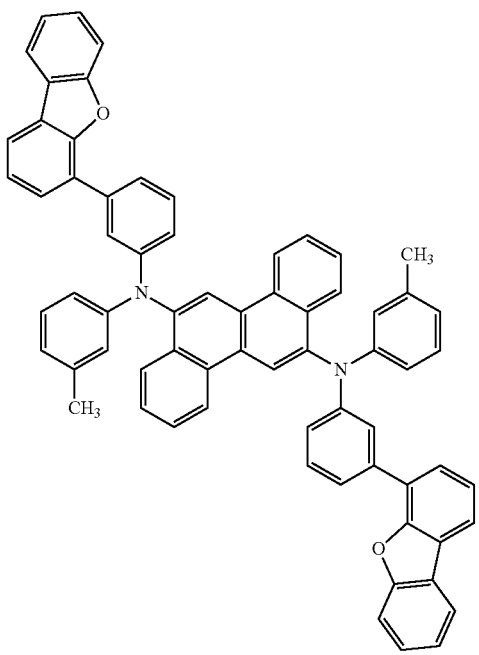
(240)
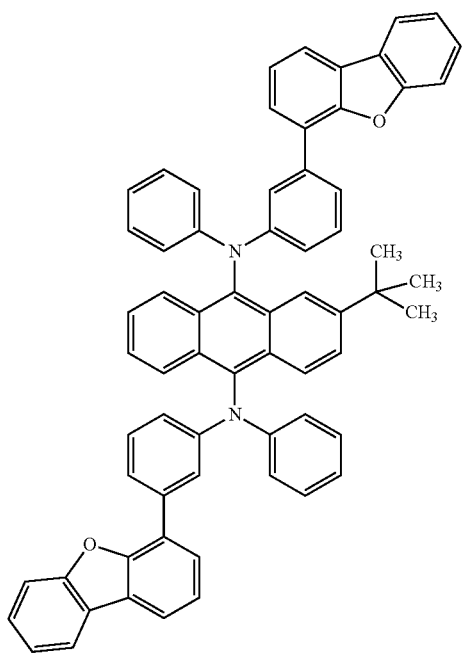
(239)
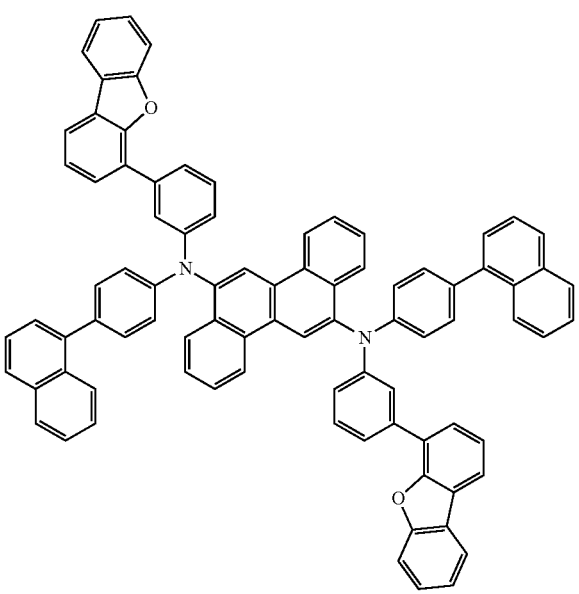
(241)

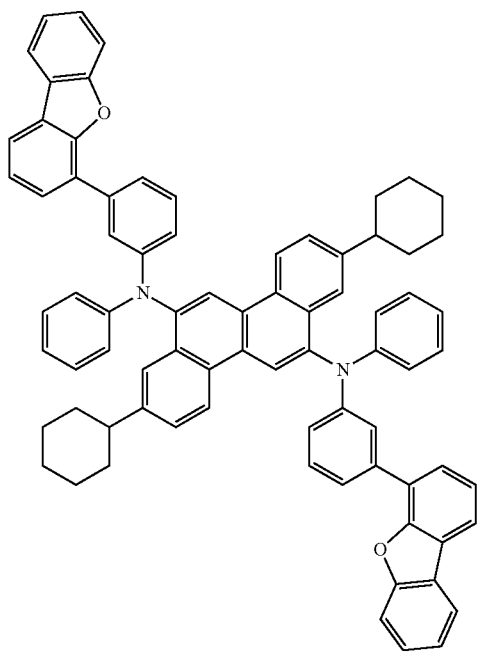
(242)
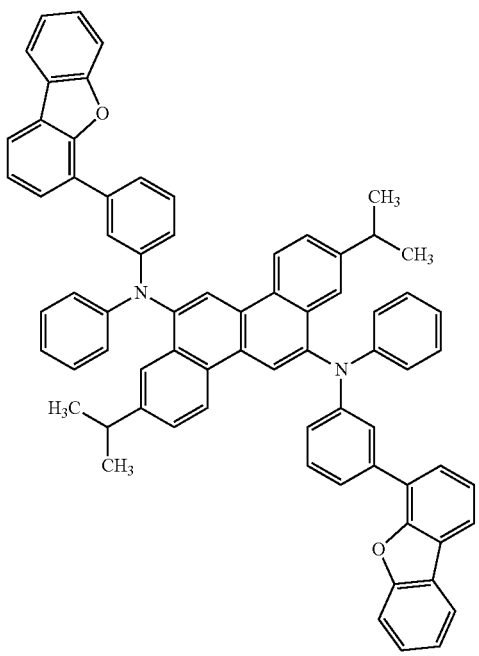
(244)
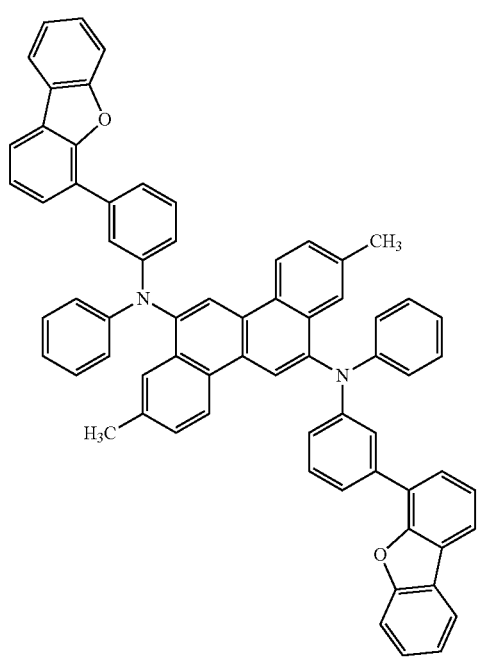
(243)
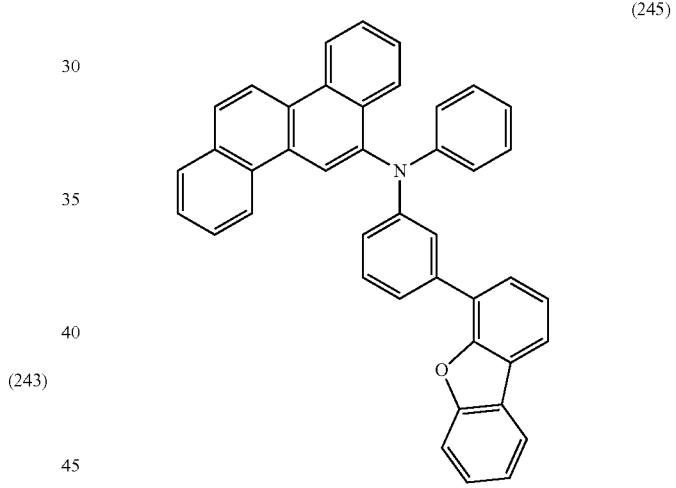
(245)
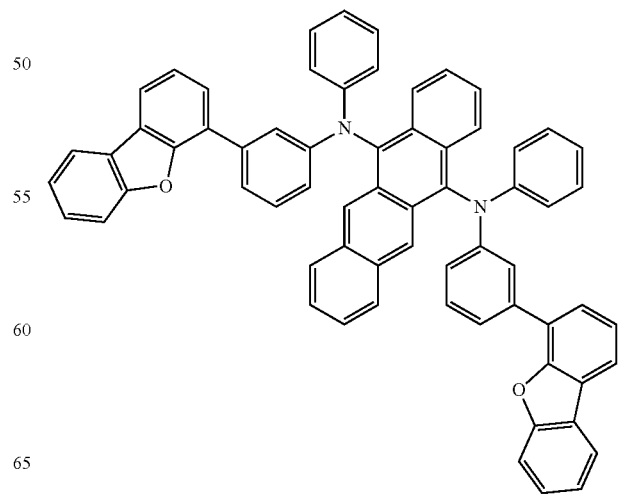
(246)

-continued
(247)
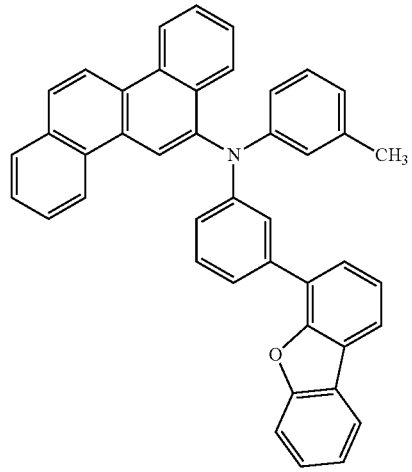
(248)
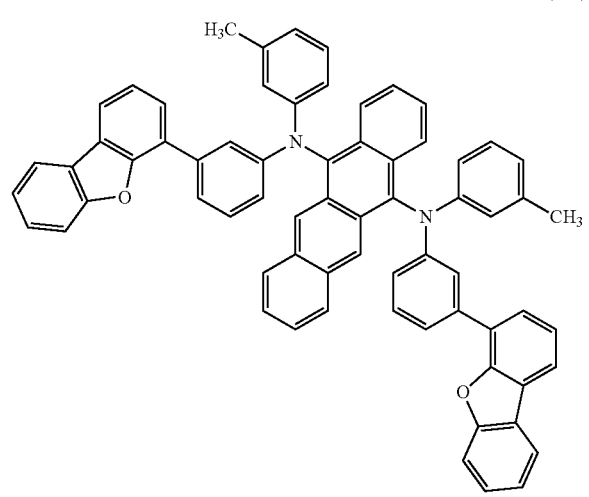
(249)
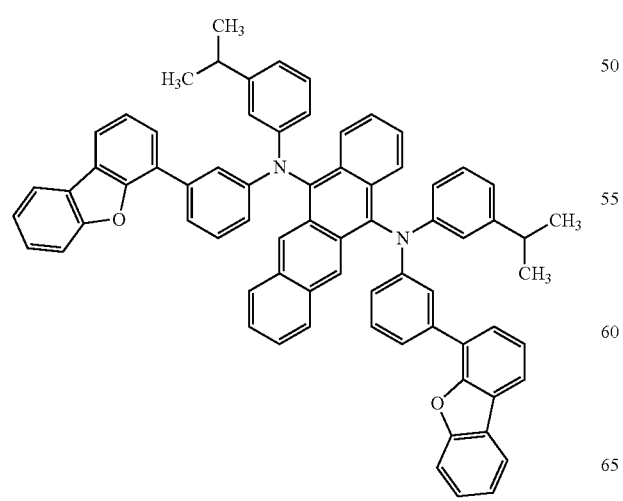
-continued
(250)
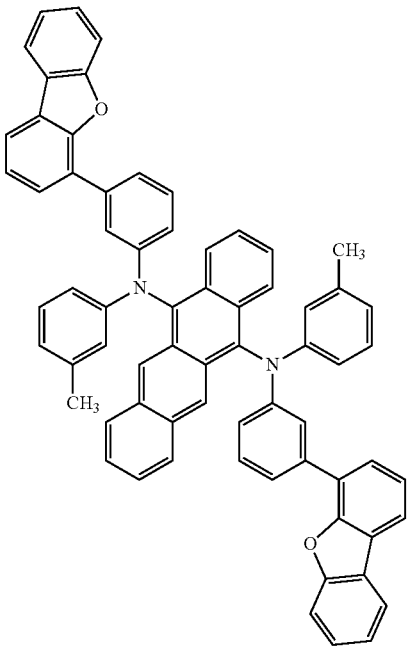
(251)
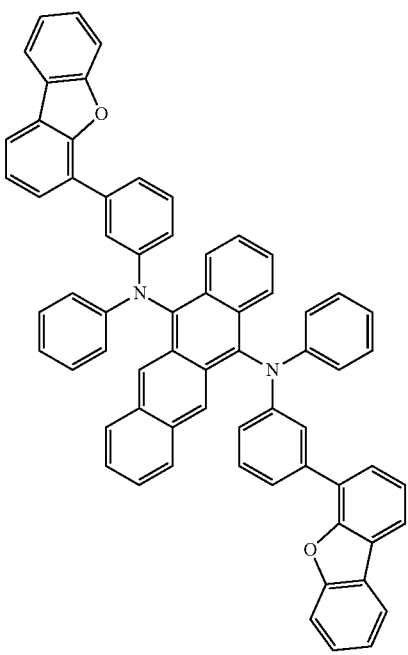

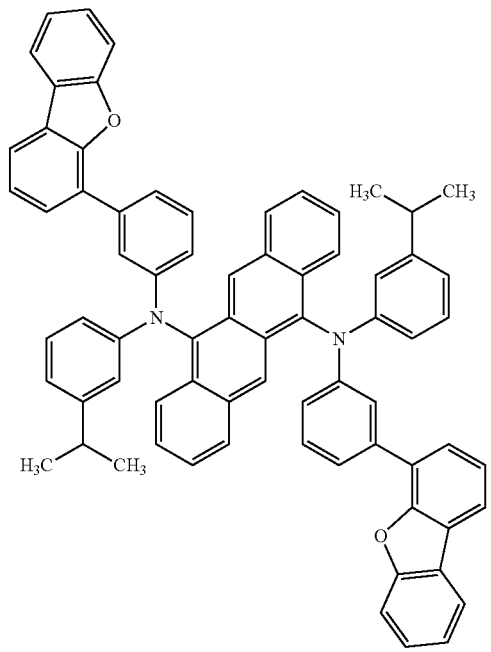
(252)
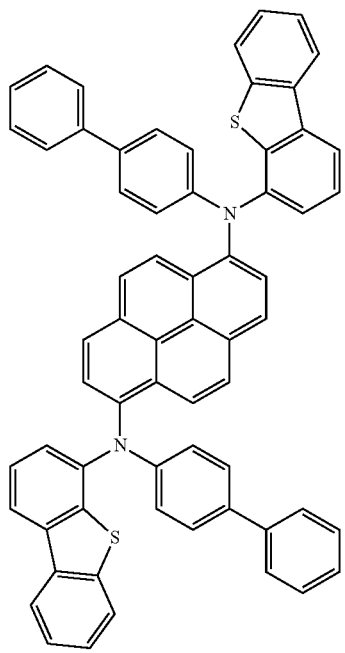
(254)
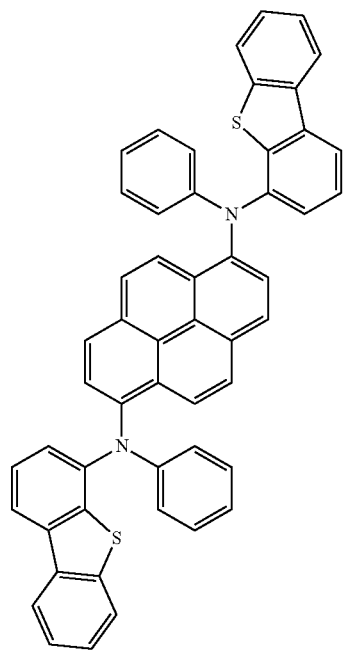
(253)
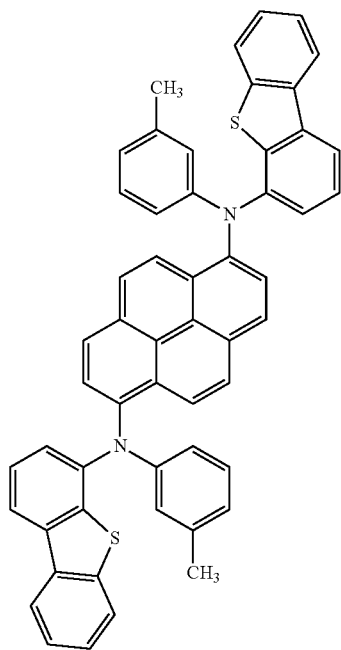
(255)

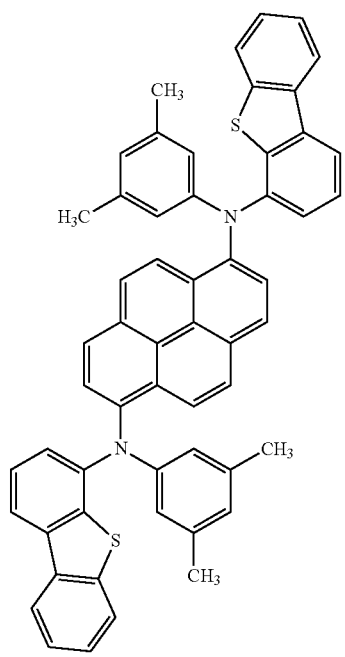
(256)
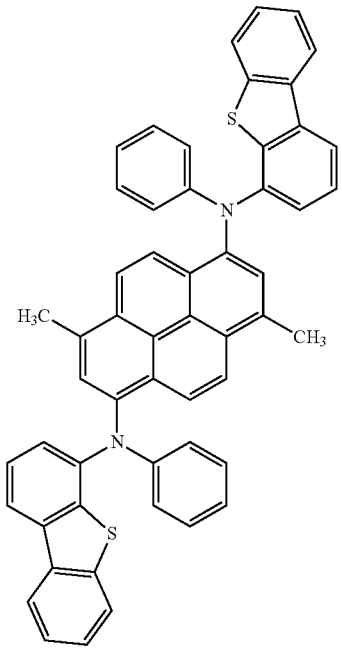
(258)
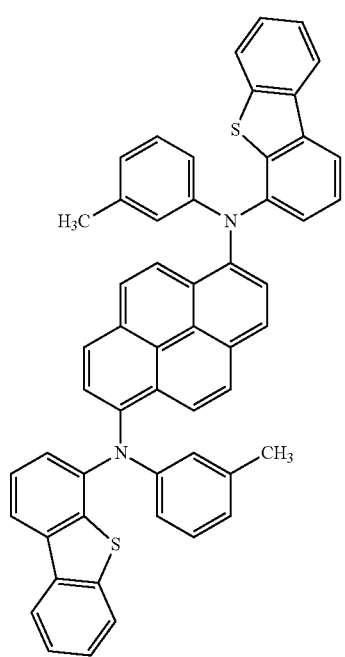
(257)
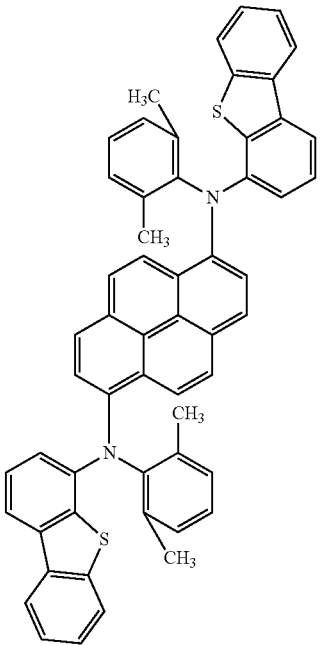
(259)

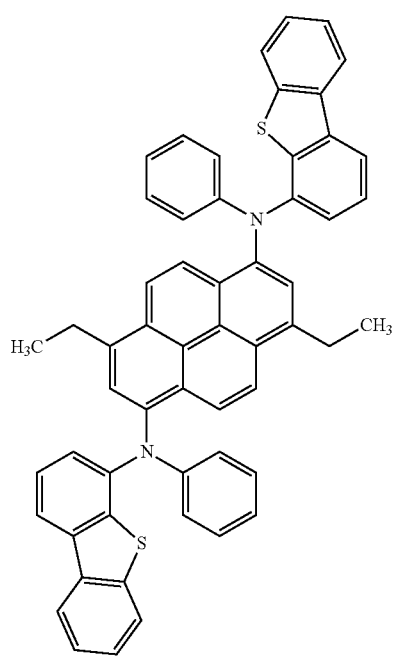
(260)
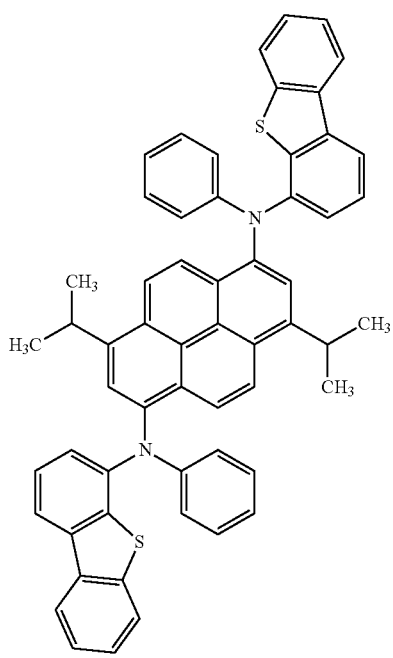
(262)
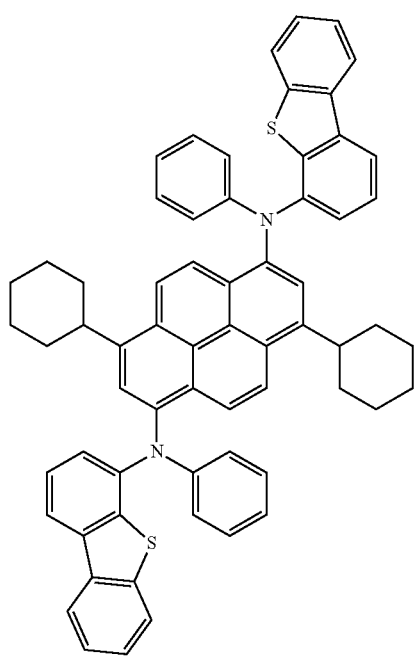
(261)
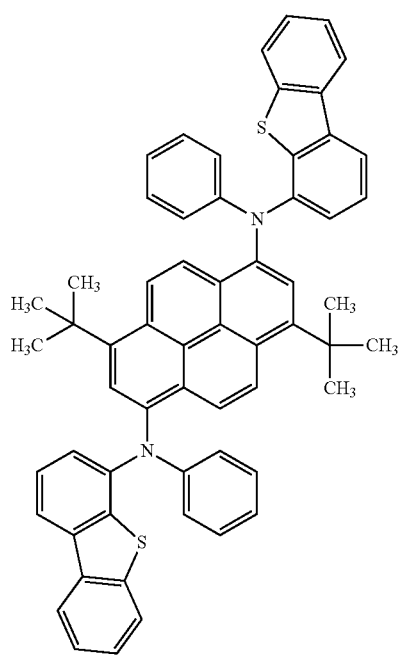
(263)

US 11,046,667 B2
(264)
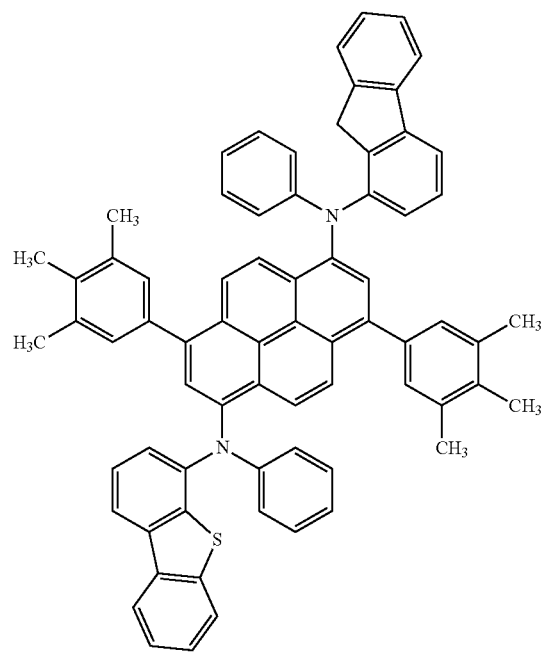
(265)
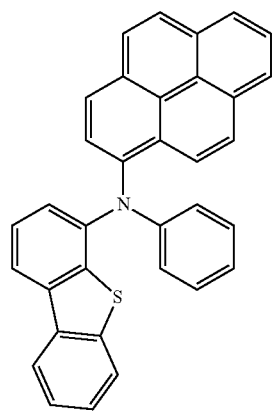
(266)
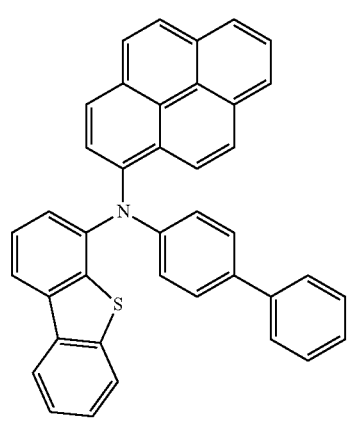
(267)
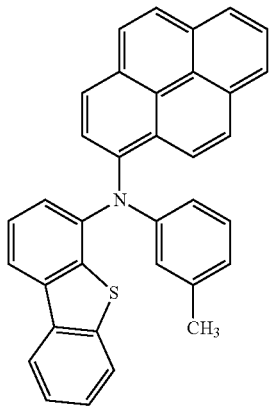
(268)
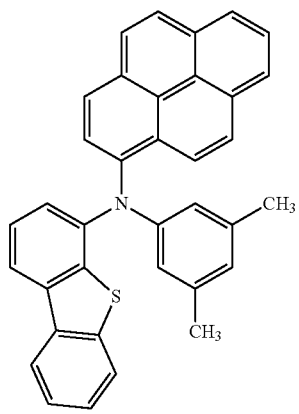
(269)
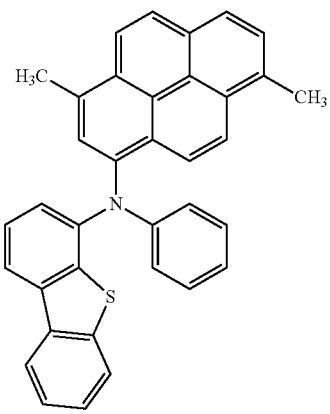
(270)
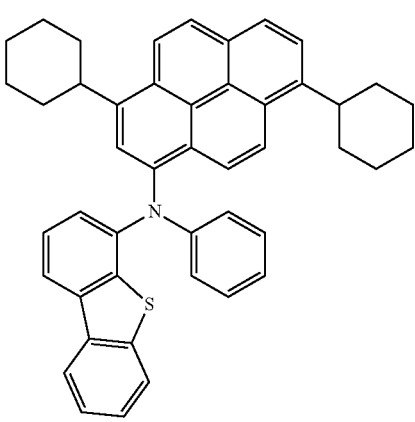

(271)
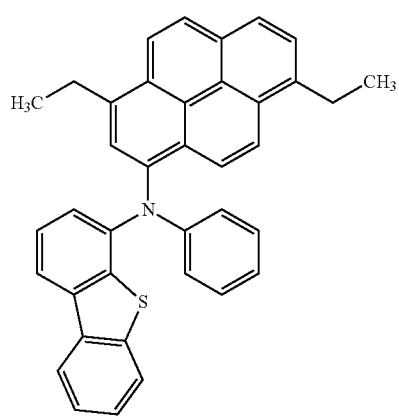
(272)
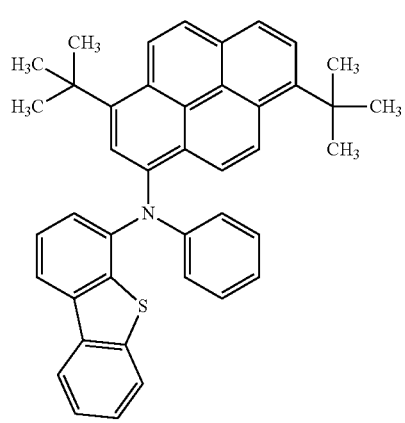
(273)
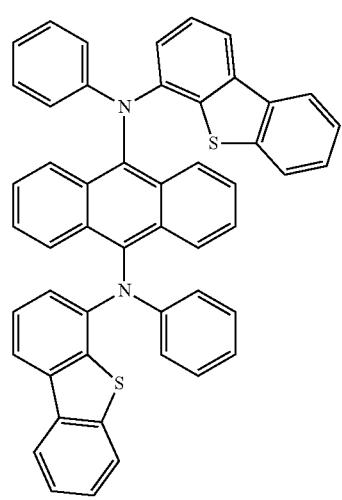
(274)
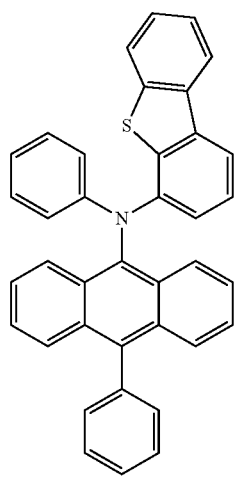
(275)
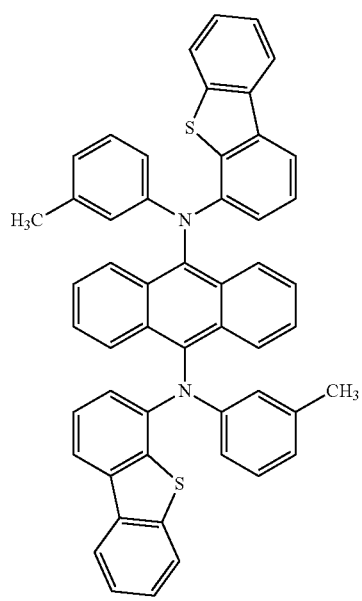

(276)
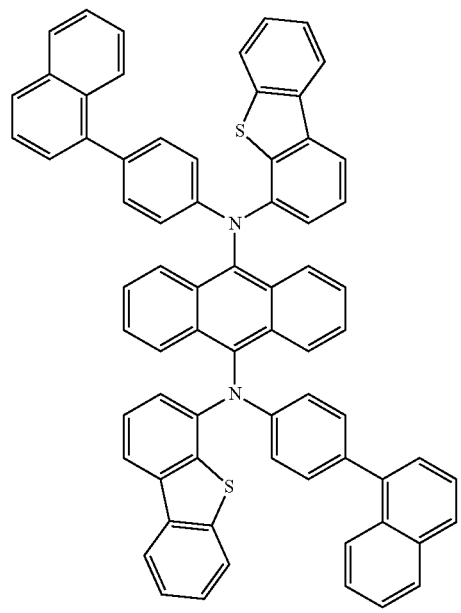
(277)
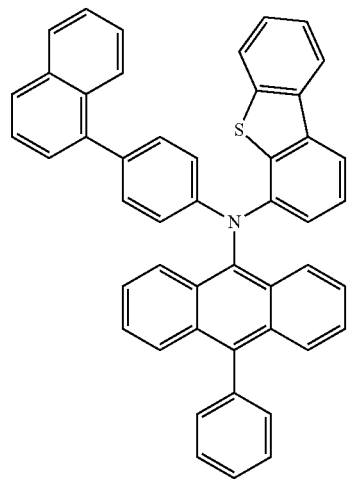
(278)
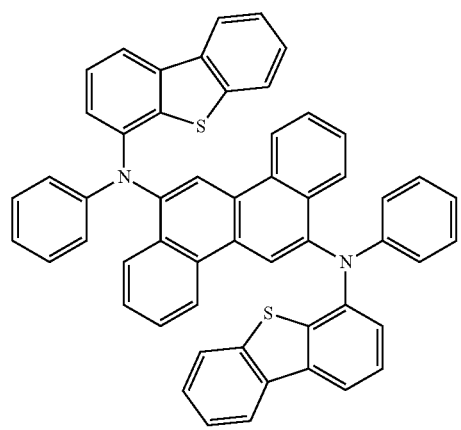
(279)
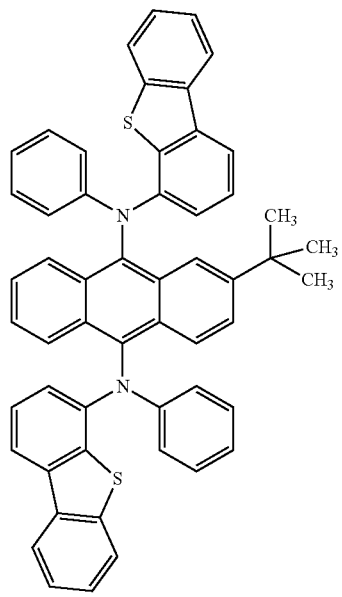
(280)
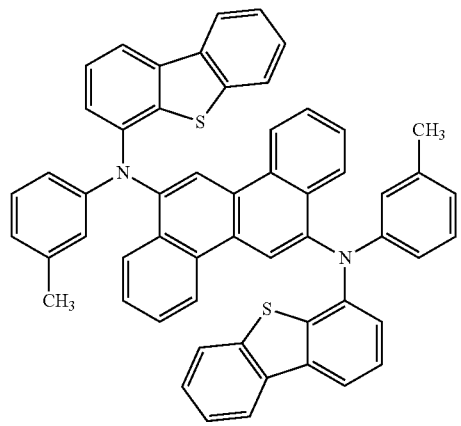
(281)
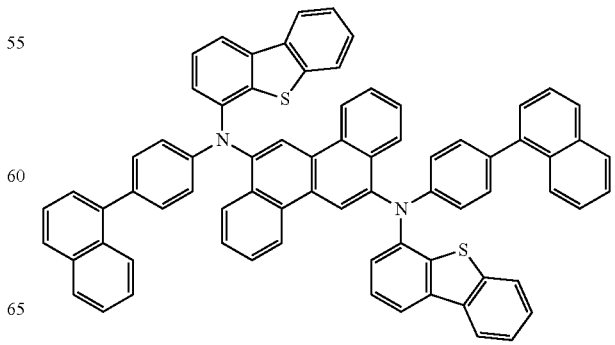

(282)
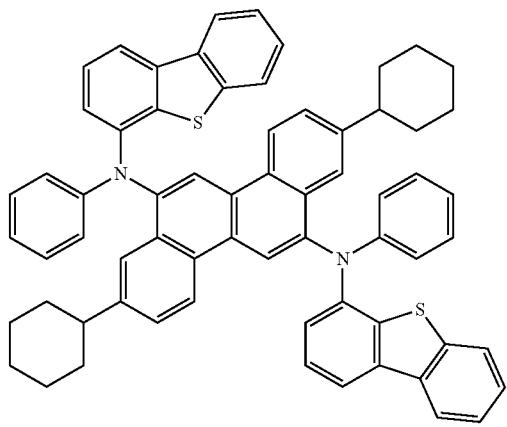
(283)
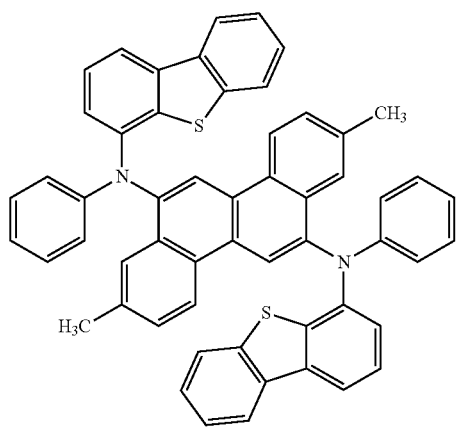
(284)
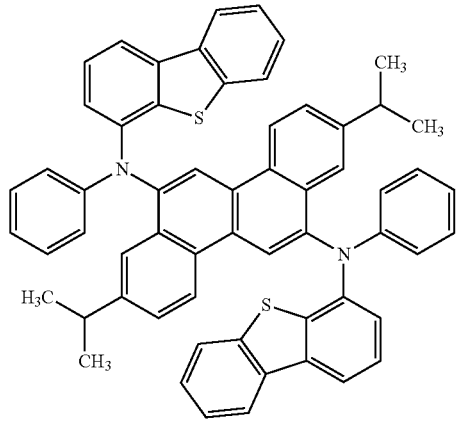
(285)
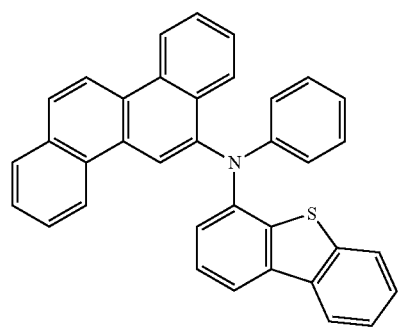
(286)
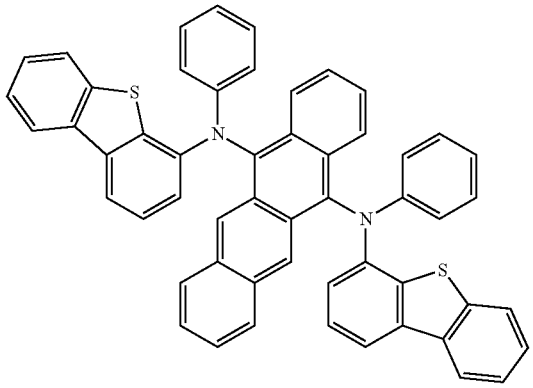
(287)
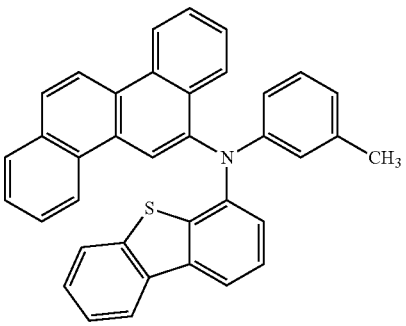
(288)
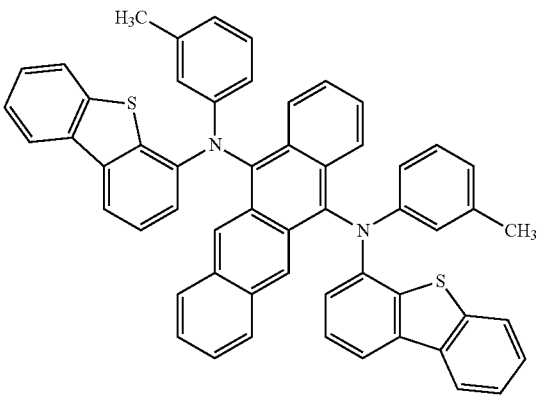
(289)
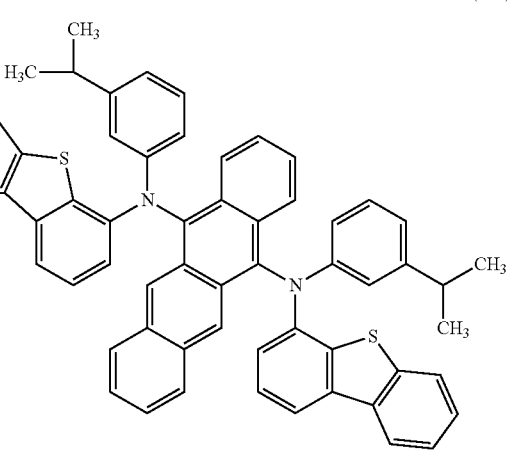

(290)
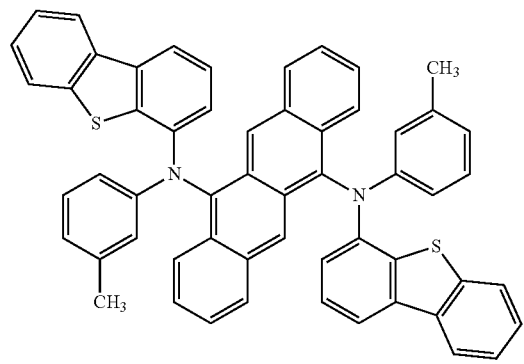
(291)
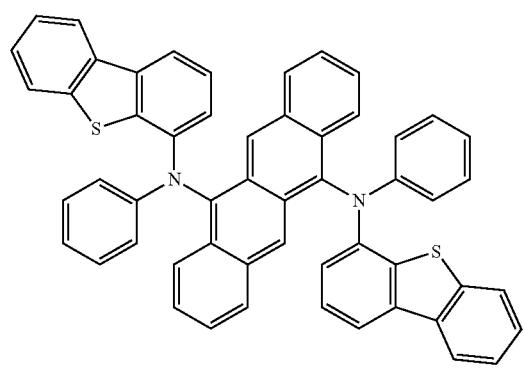
(292)
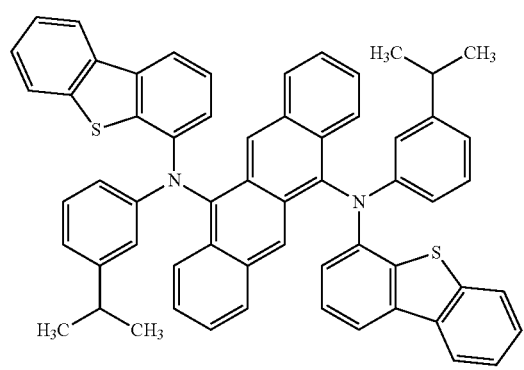
(293)
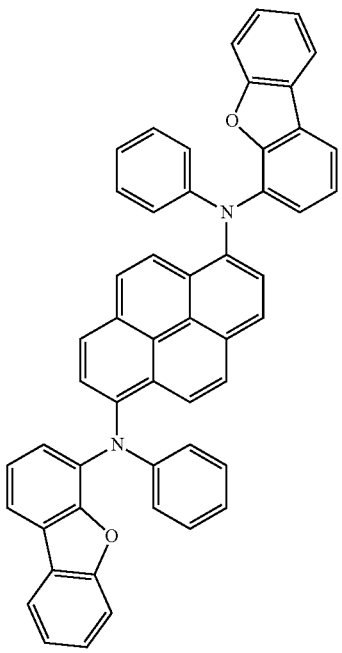
(294)
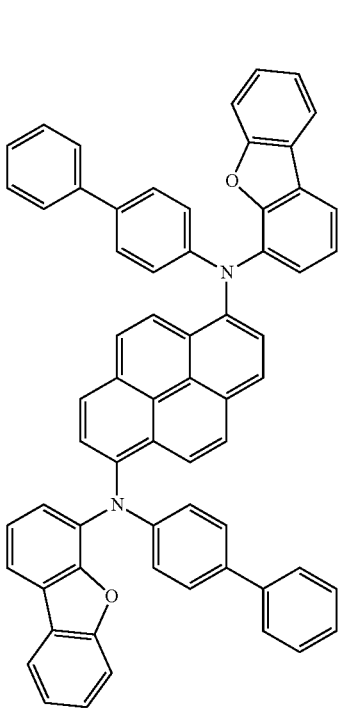

(295)
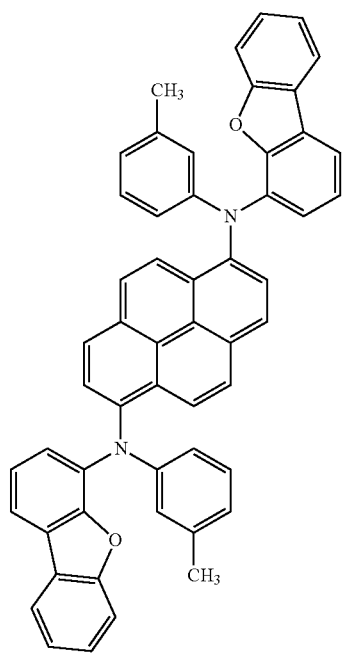
(296)
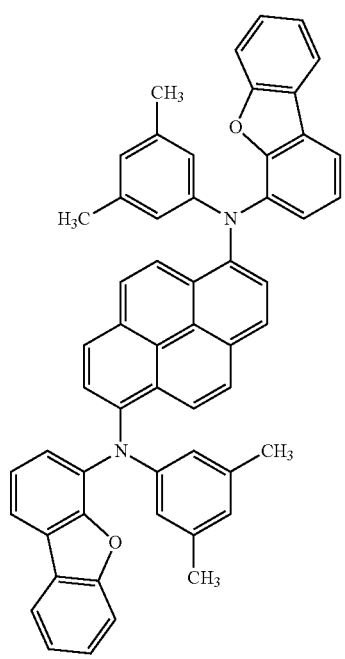
(297)
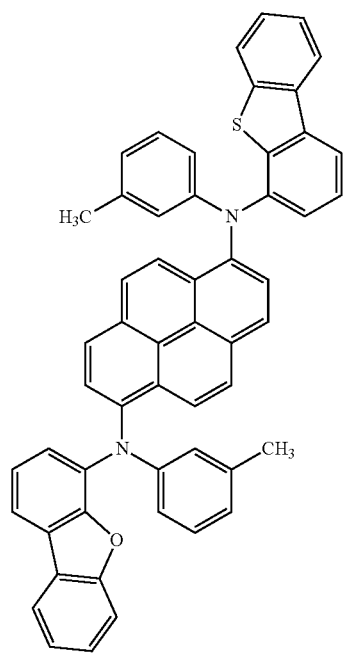
(298)
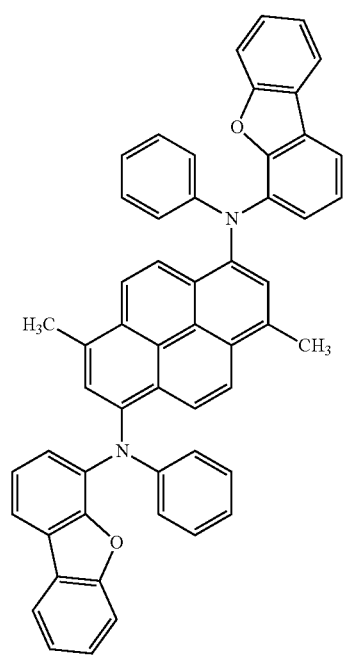

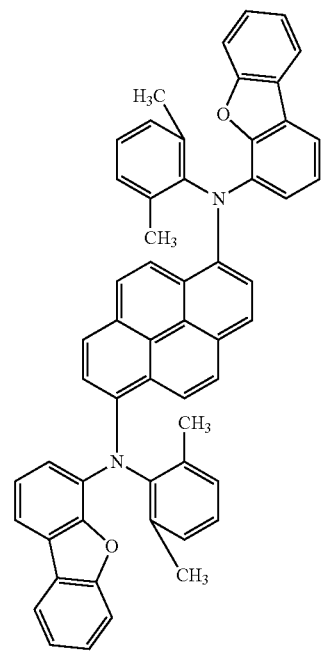
(299)
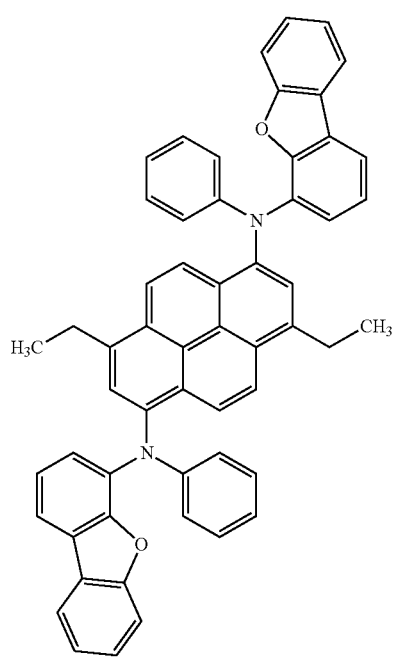
(300)
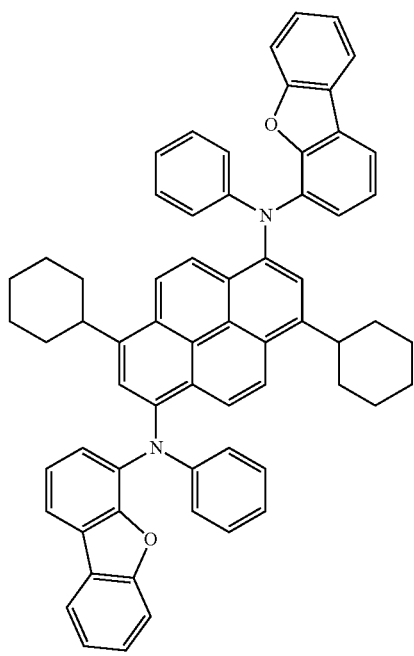
(301)
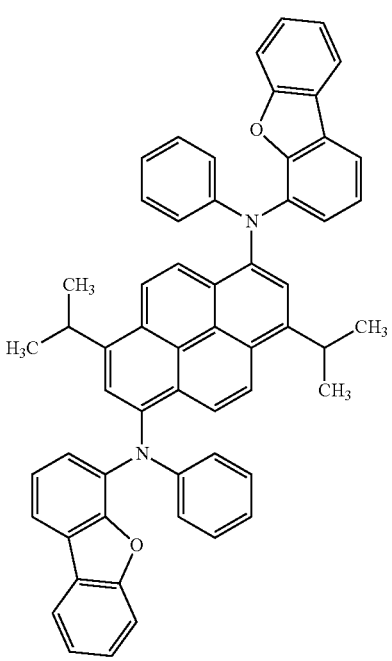
(302)

(303)
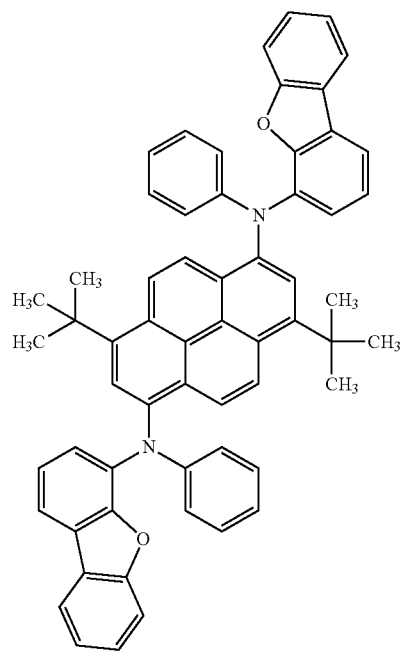
(304)
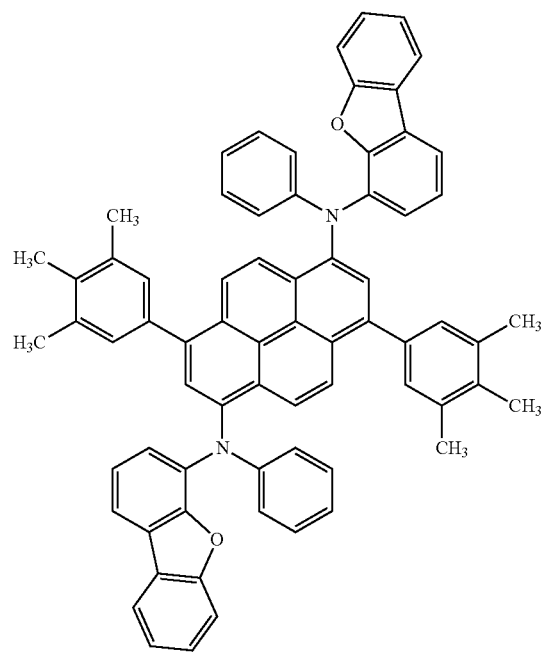
(305)
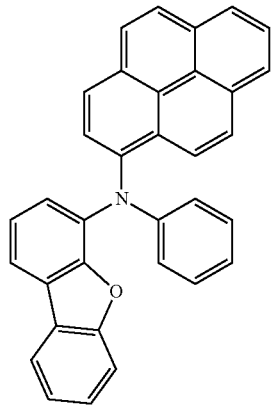
(306)
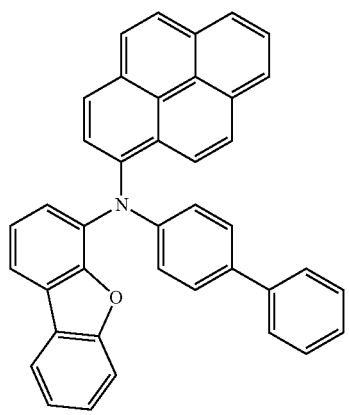
(307)
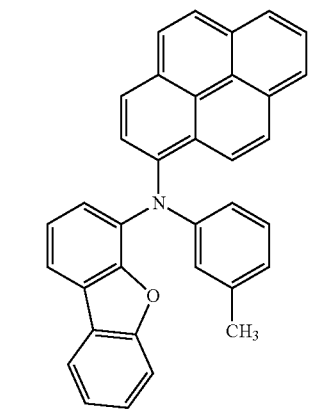
(308)
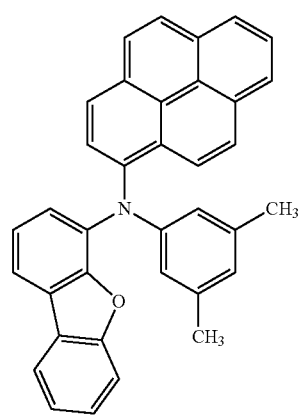

(309) 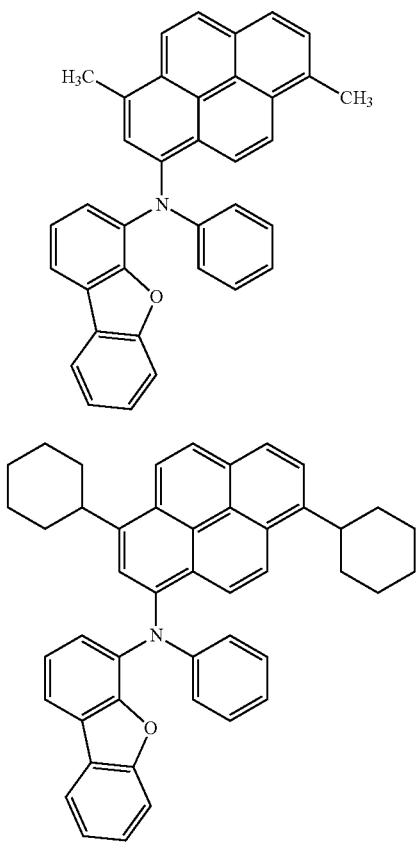
(310)
(311) 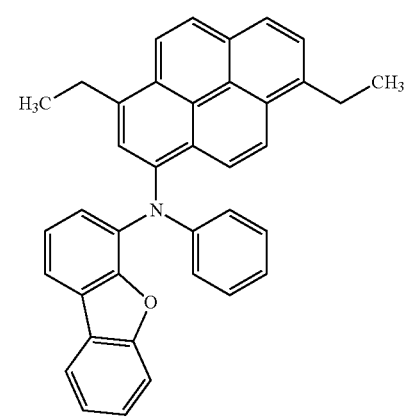
(312) 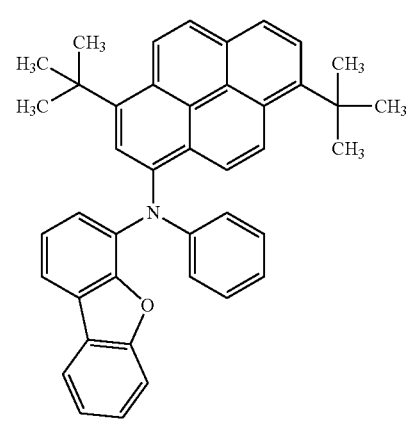
(313) 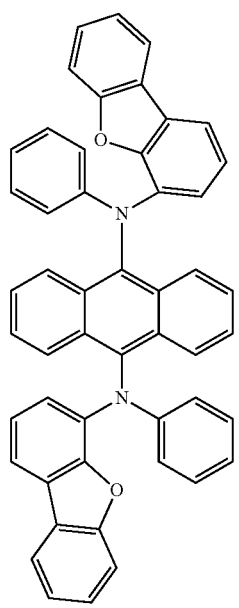
(314) 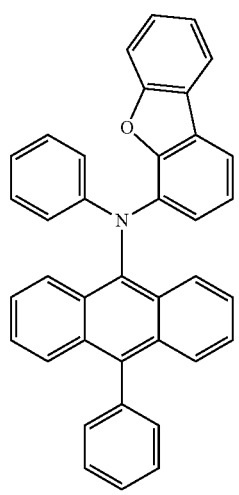

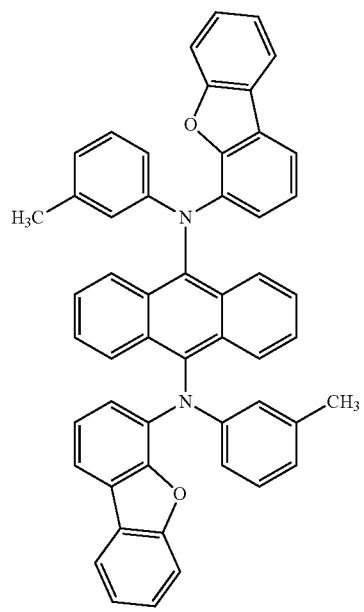
(315)
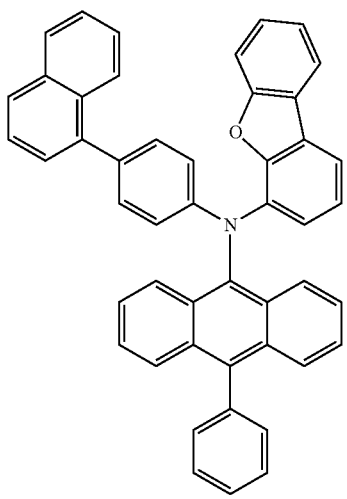
(317)
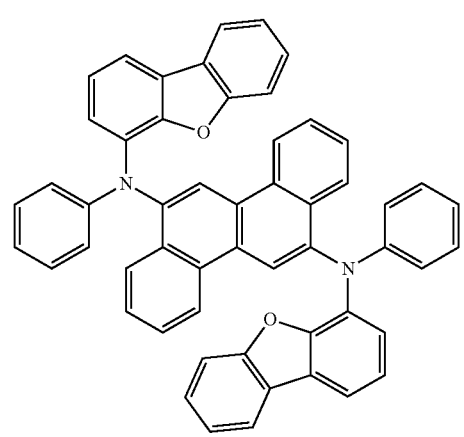
(318)
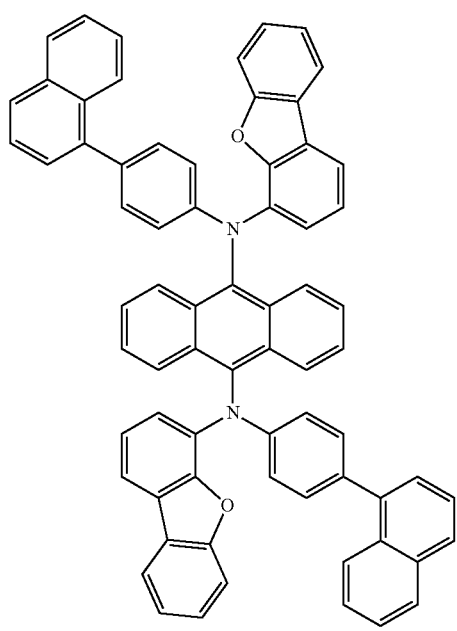
(316)
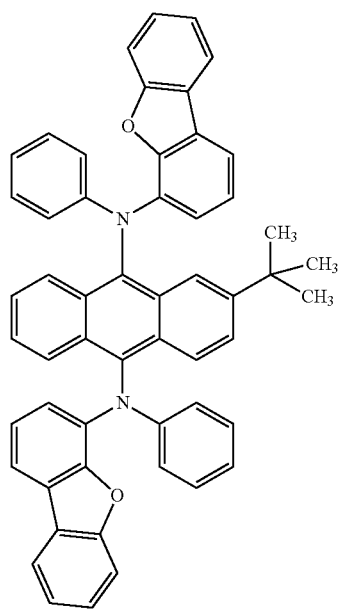
(319)

(320)
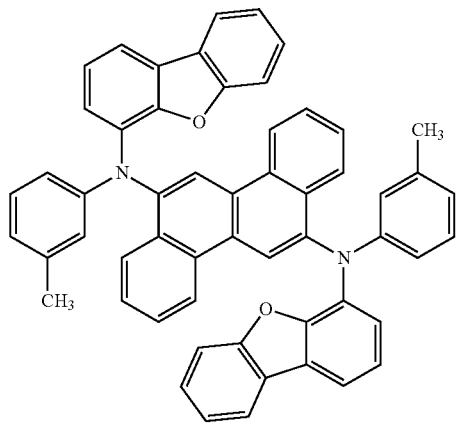
(324)
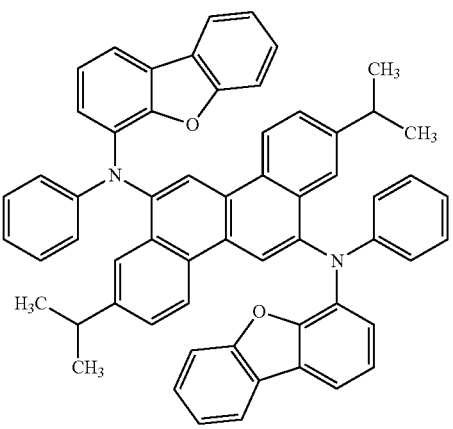
(321)
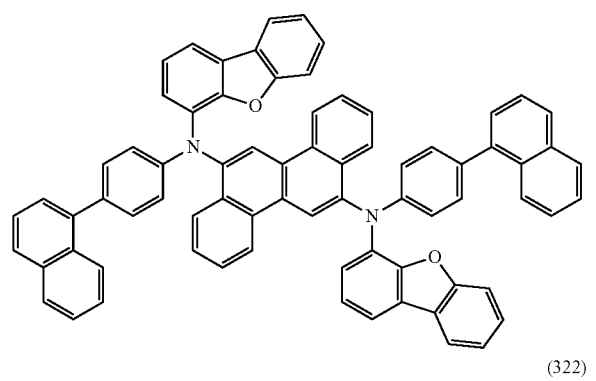
(325)
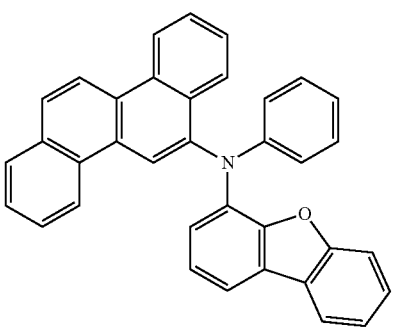
(322)
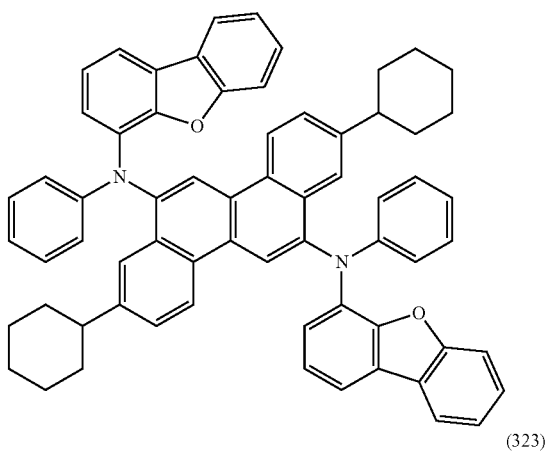
(326)
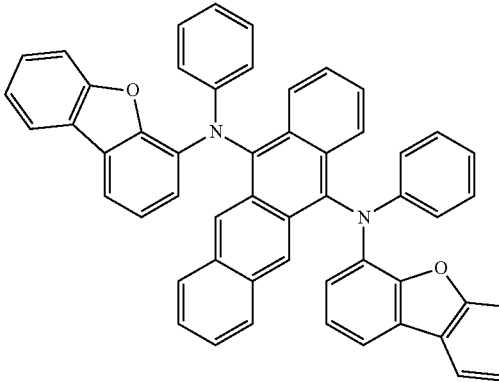
(323)
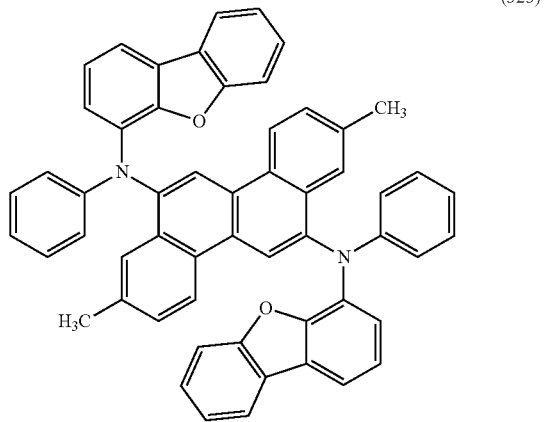
(327)
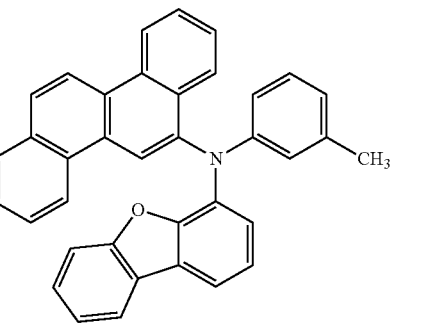

(328)
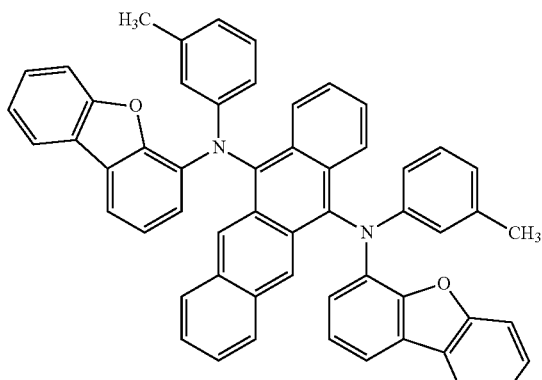
(331)
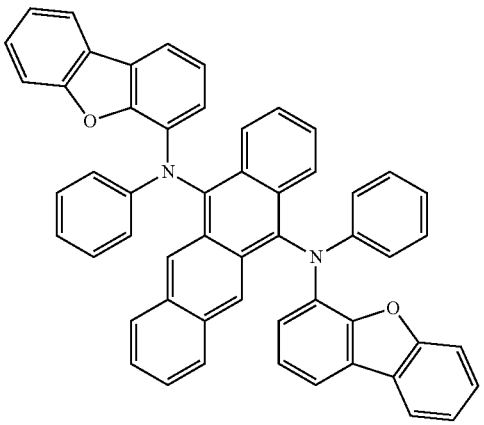
(329)
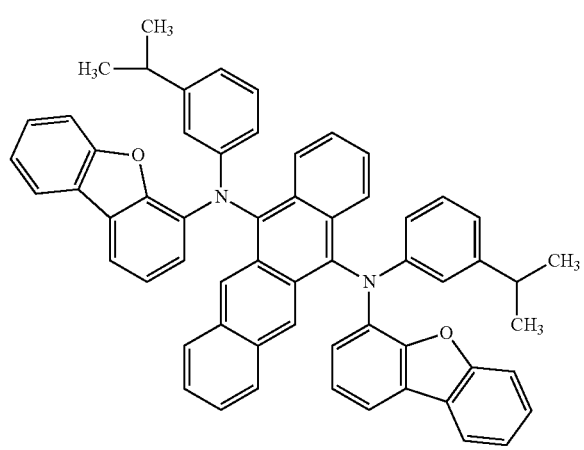
(332)
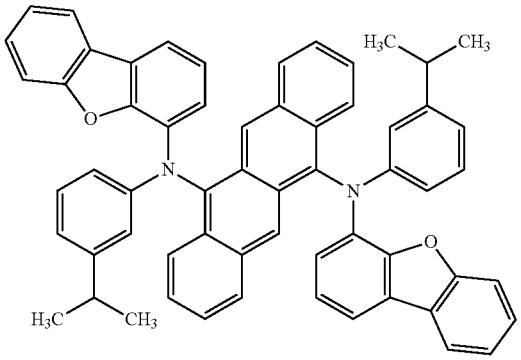
(330)
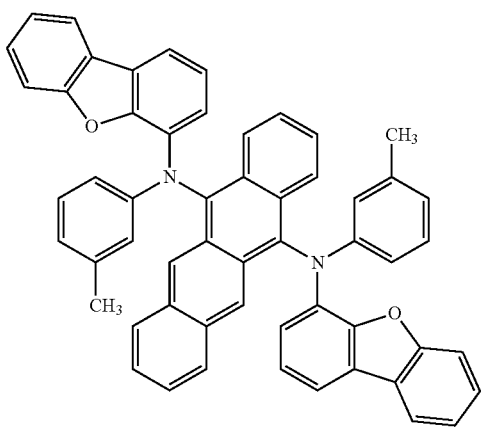
(333)
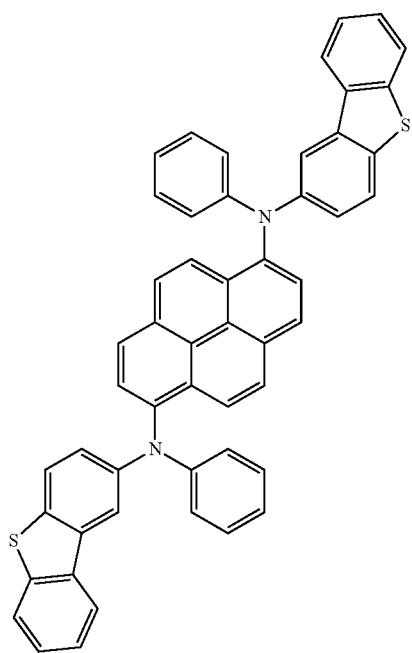

(334)
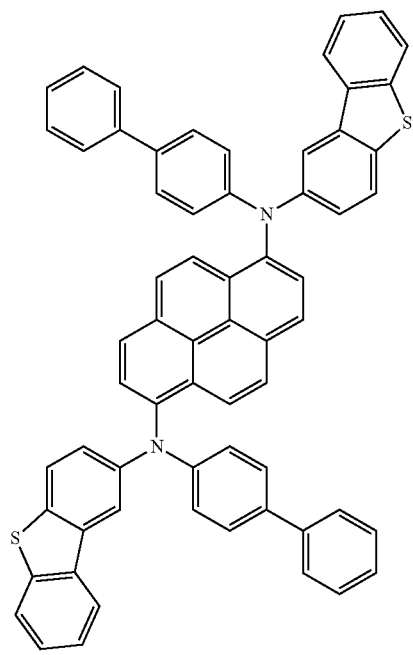
(336)
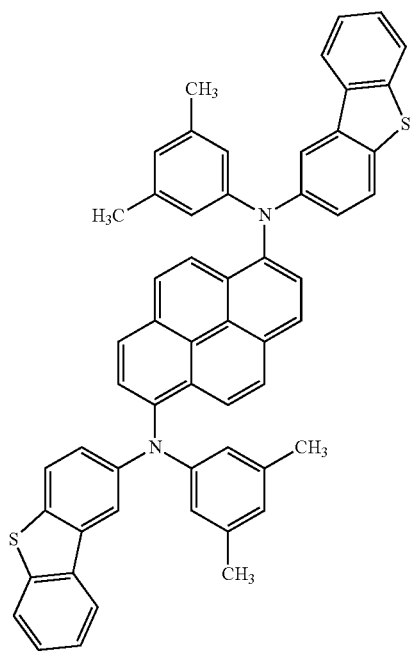
(335)
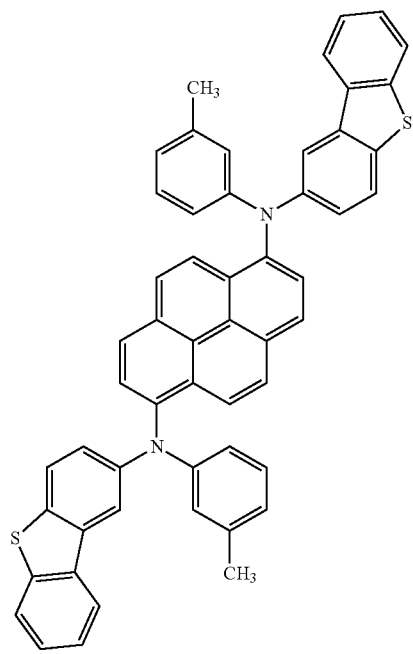
(337)
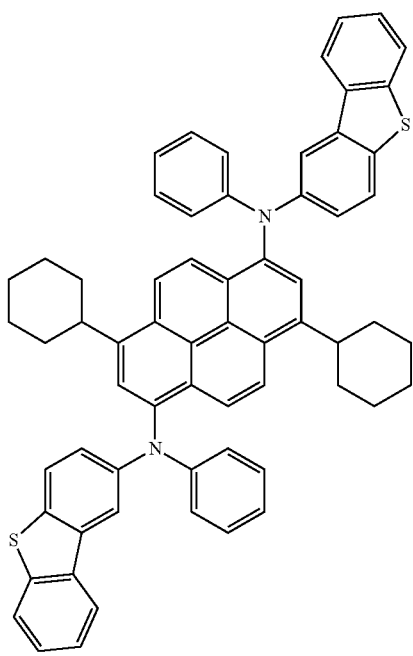

(338)
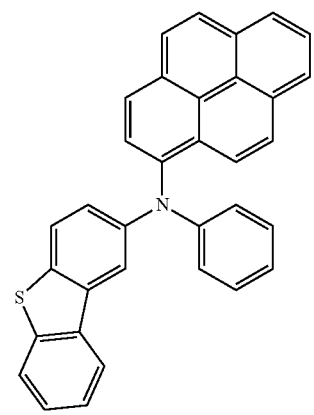
(339)
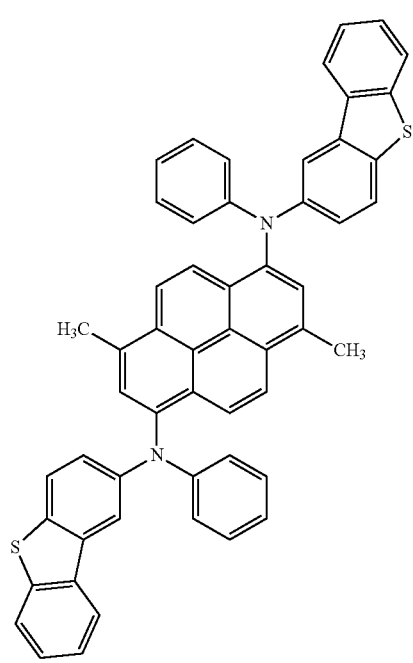
(340)
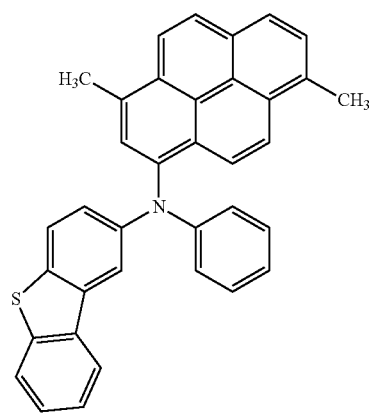
(341)
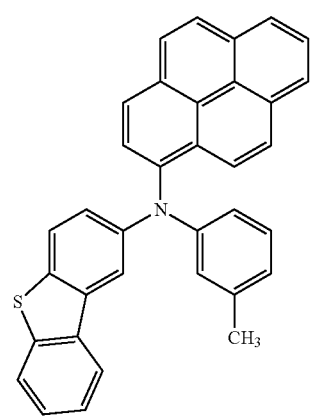
(342)
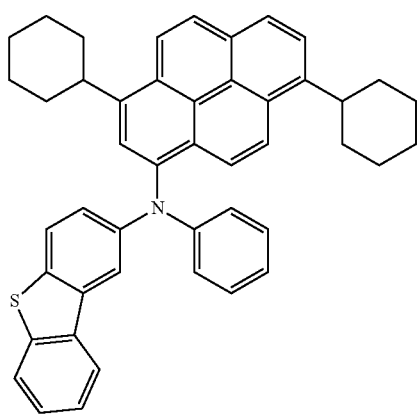
(343)
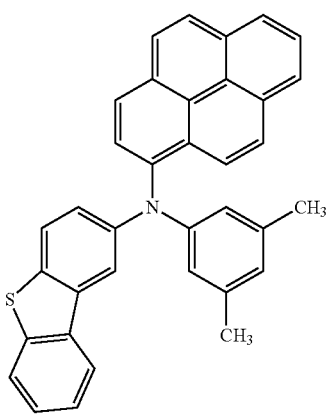

(344)
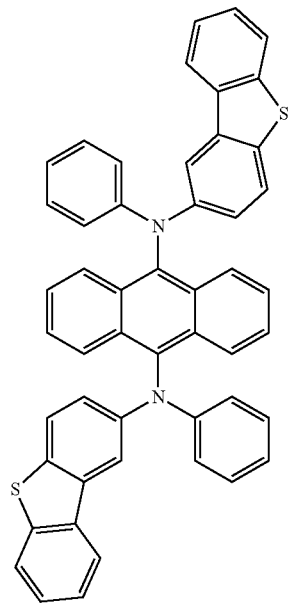
(345)
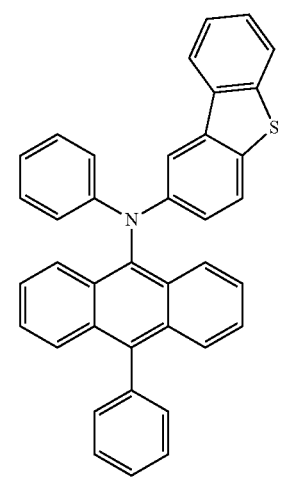
(346)
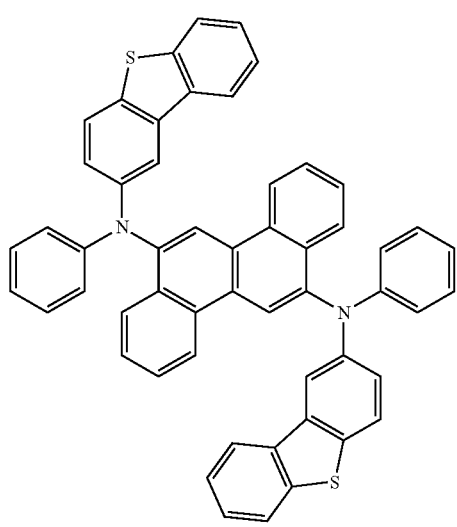
(347)
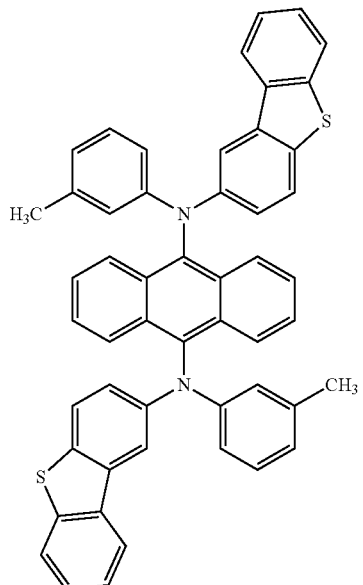
(348)
(349)
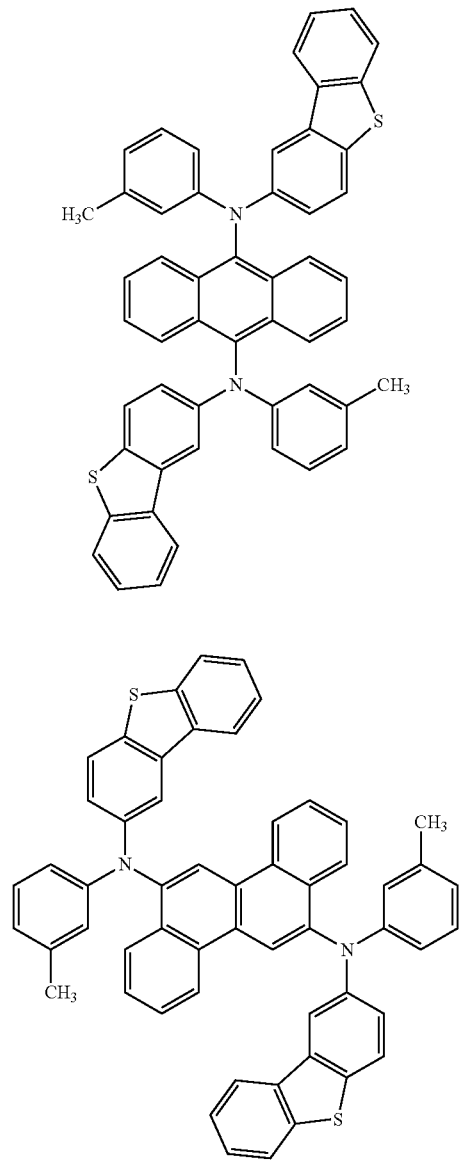

-continued
(350)
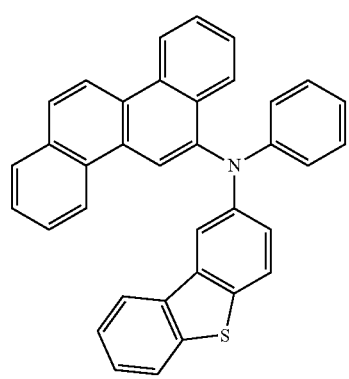
(351)
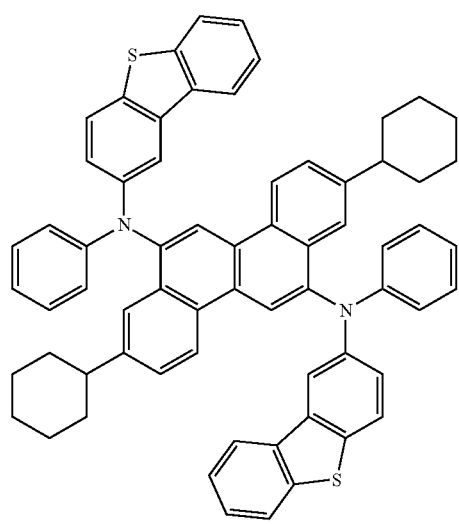
(352)
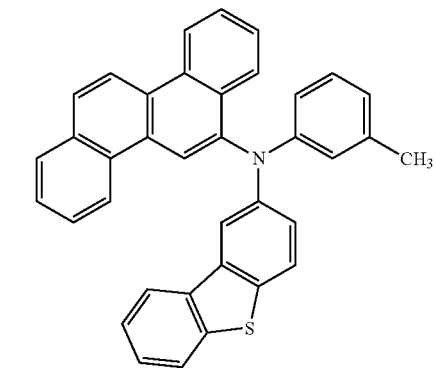
-continued
(353)
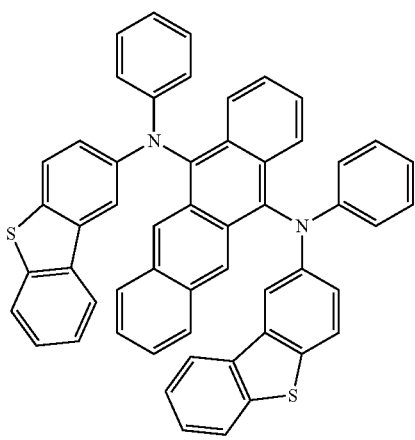
(354)
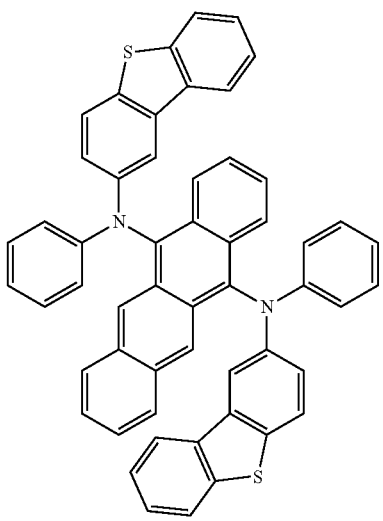
(355)
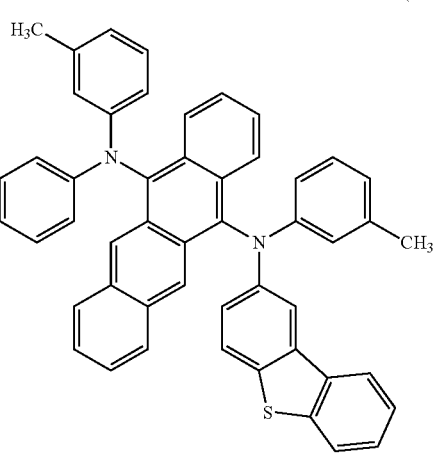

(356)
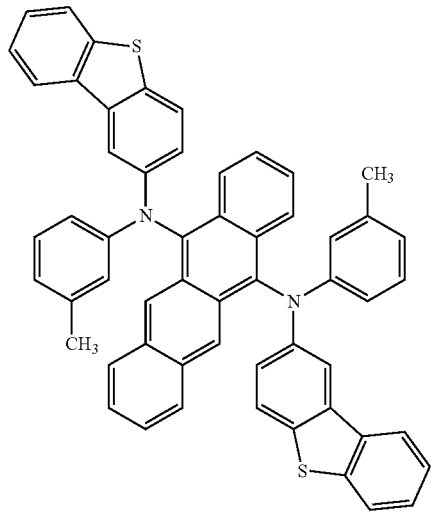
(357)
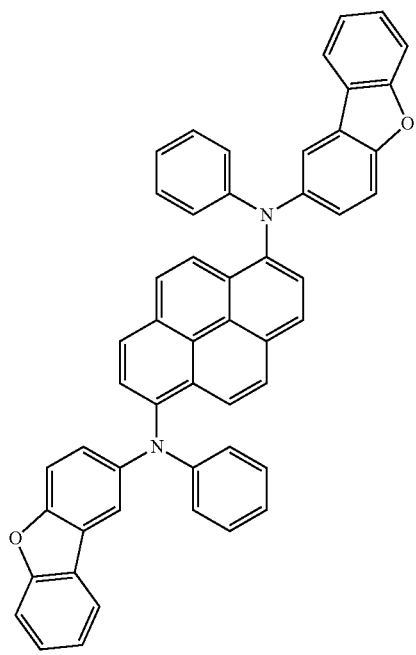
(358)
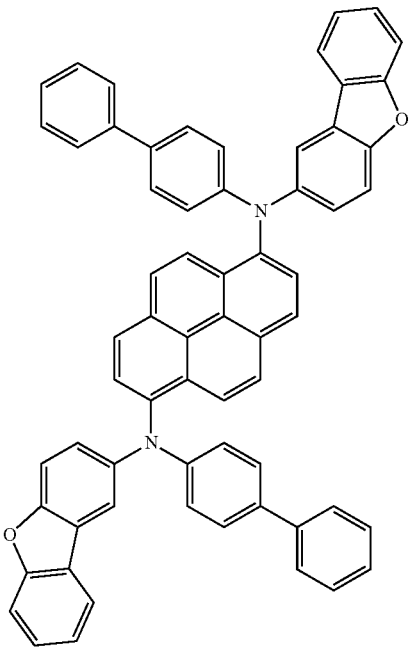
(359)
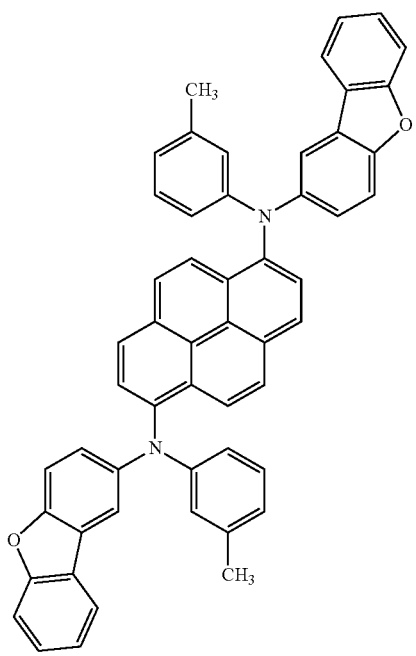

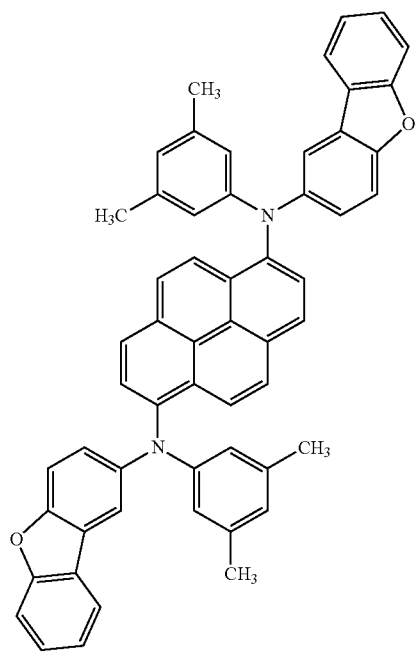
(360)
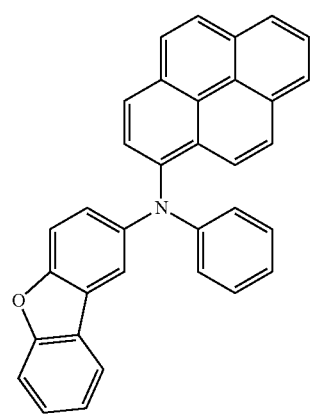
(362)
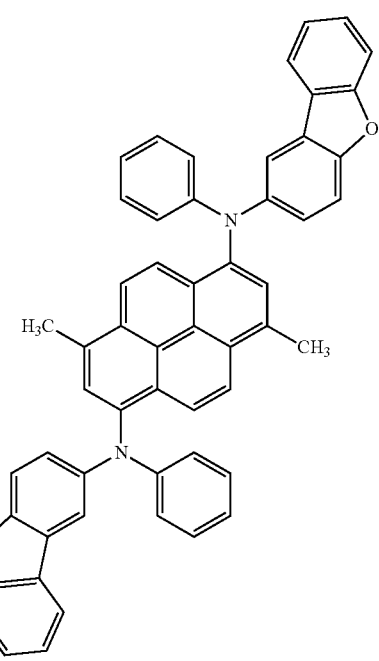
(363)
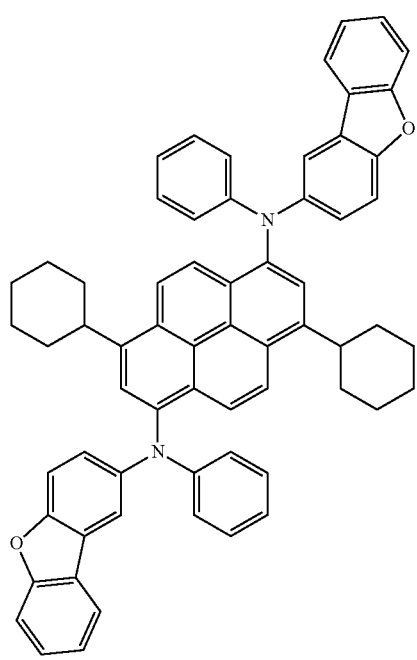
(361)
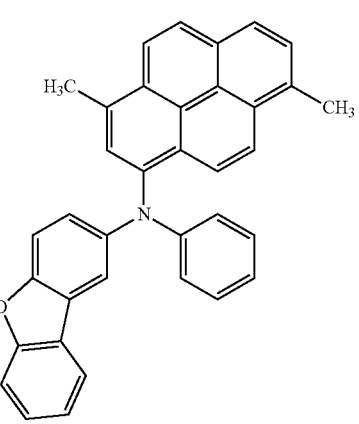
(364)

(365)
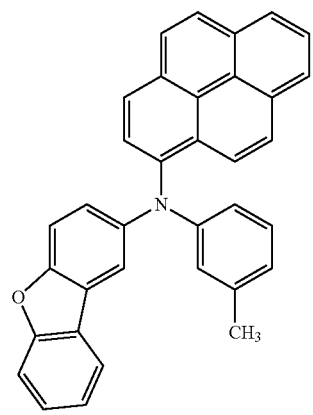
(366)
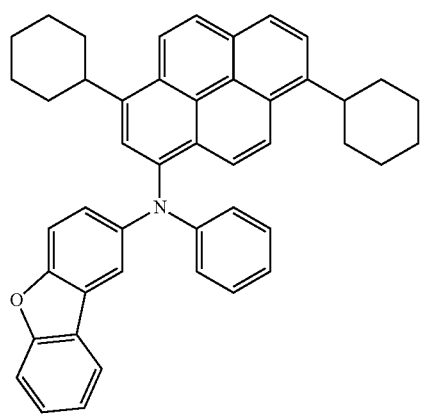
(367)
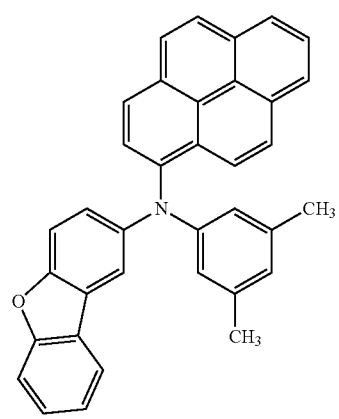
(368)
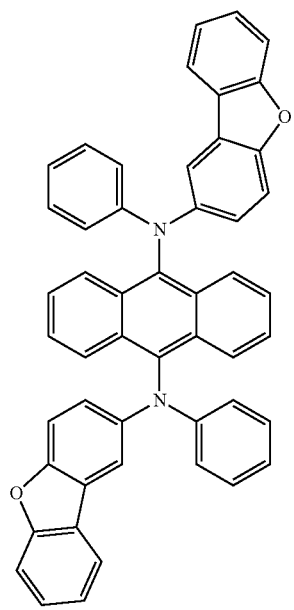
(369)
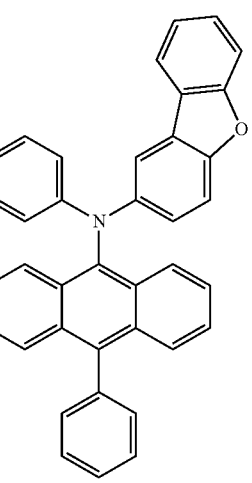
(370)
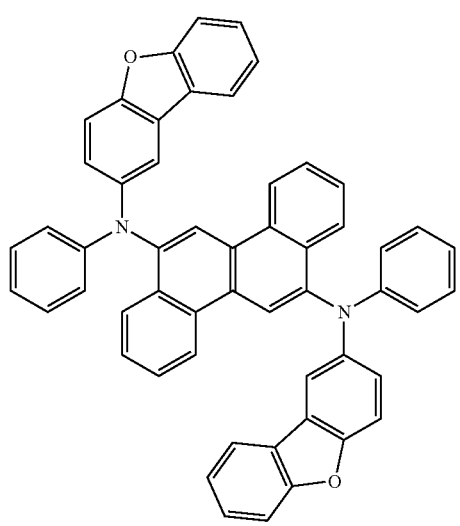

(371)
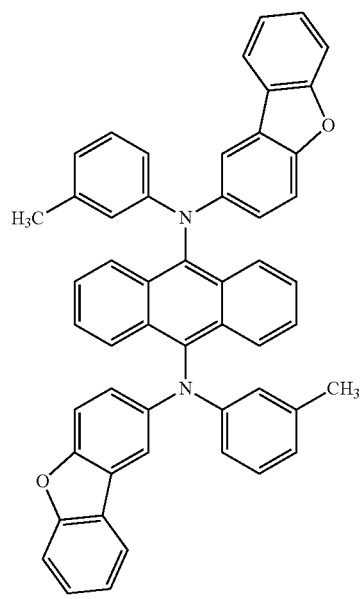
(372)
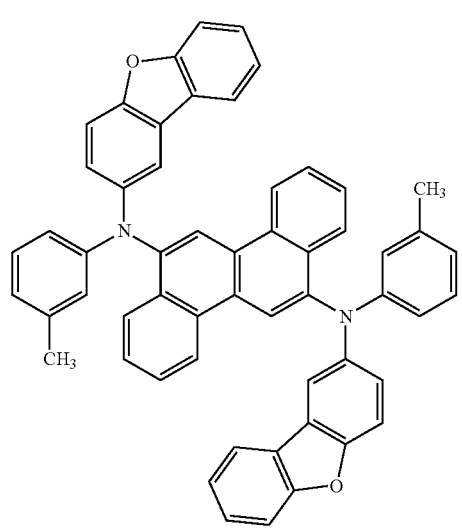
(373)
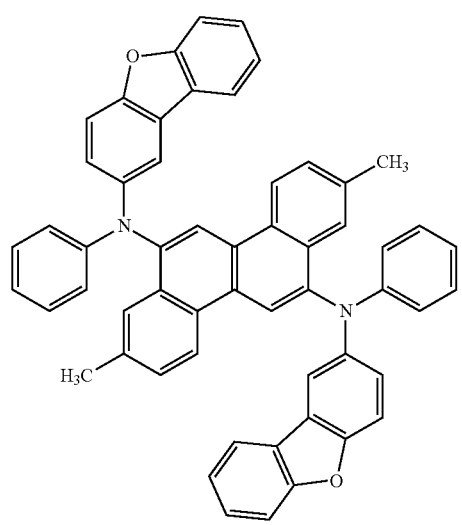
(374)
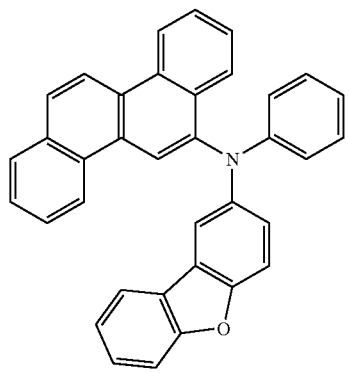
(375)
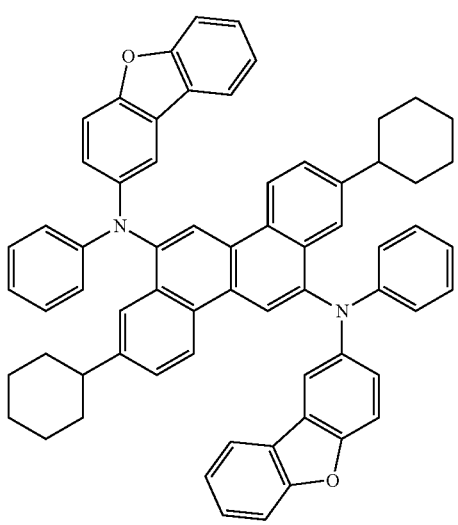
(376)
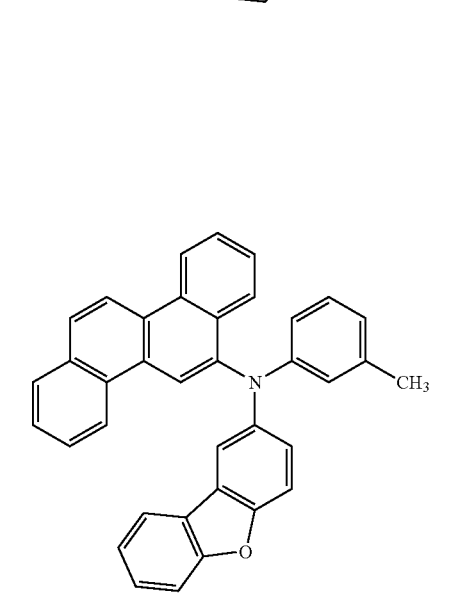

(377)

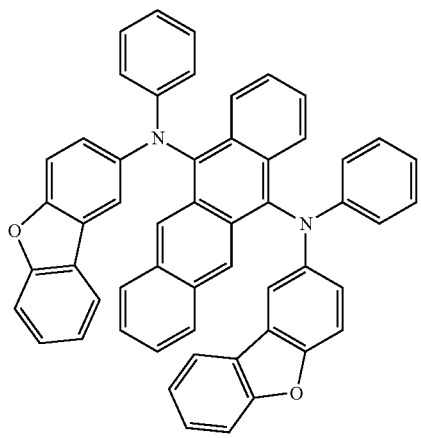

(378)

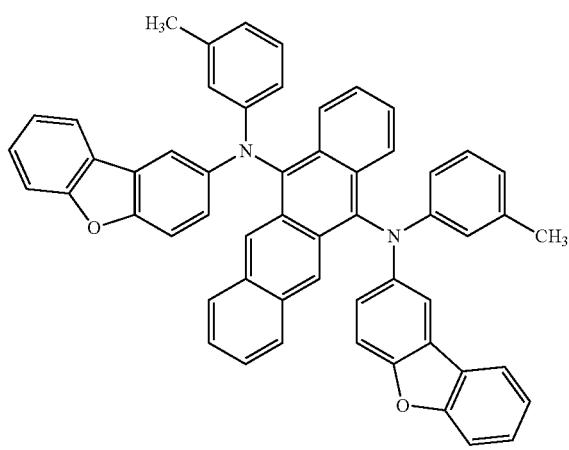

(379)

(380)

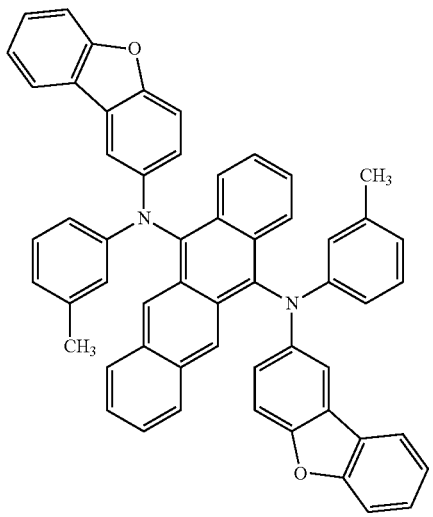

A variety of reactions can be applied to a method for synthesizing an aromatic amine derivative of this embodiment. For example, the aromatic amine derivative of this embodiment represented by General Formula (G1) can be synthesized by synthesis methods described below. Note that the method for synthesizing the aromatic amine derivative which is one embodiment of the present invention is not limited to the following synthesis methods.

Synthesis Method of Aromatic Amine Derivative Represented by General Formula (G1)

First, as shown in Synthesis Scheme (A-1), a halide of a dibenzofuran derivative or a dibenzothiophene derivative (a1) and an aryl compound having amine (a2) are coupled, so that an amine derivative (a3) can be obtained.

(A-1)

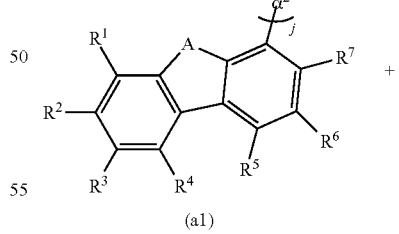

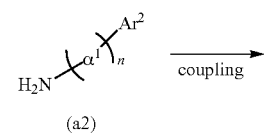

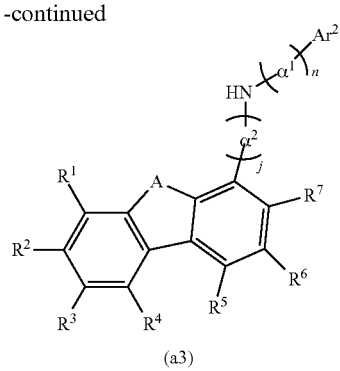

(a3)

Note that in Synthesis Scheme (A-1), A represents O (oxygen) or S (sulfur), and $R^1$ to $R^7$ individually represent any of a hydrogen atom, an alkyl group having 1 to 6 carbon atoms, a substituted or unsubstituted phenyl group, and a substituted or unsubstituted biphenyl group. In addition, $\alpha^1$ and $\alpha^2$ individually represent a substituted or unsubstituted phenylene group. Further, $Ar^2$ represents a substituted or unsubstituted aryl group having 6 to 13 carbon atoms included in a ring. Further, j and n are individually 0 or 1. In addition, $X^1$ represents a halogen, preferably bromine or iodine, which has high reactivity, more preferably iodine.

In Synthesis Scheme (A-1), a variety of reaction conditions can be employed in the coupling reaction of a halide of a dibenzofuran derivative or a dibenzothiophene derivative and an aryl compound having amine (a primary arylamine compound or a secondary arylamine compound); for example, a synthesis method using a metal catalyst in the presence of a base can be employed.

The case where a Hartwig-Buchwald reaction is performed in Synthesis Scheme (A-1) is shown. A palladium catalyst can be used as the metal catalyst, and a mixture of a palladium complex and a ligand thereof can be used as the palladium catalyst. As a specific palladium complex, bis(dibenzylideneacetone)palladium(0), palladium(II) acetate, and the like are given.

As a ligand, tri(tert-butyl)phosphine, tri(n-hexyl)phosphine, tricyclohexylphosphine, 1,1-bis(diphenylphosphino)ferrocene (abbreviation: DPPF), and the like can be given.

As a substance which can be used as the base, an organic base such as sodium tert-butoxide, an inorganic base such as potassium carbonate, and the like can be given.

This reaction is preferably performed in a solution, and toluene, xylene, benzene, or the like can be used as a solvent. However, the catalyst, ligand, base, and solvent which can be used are not limited thereto. In addition, this reaction is preferably performed in an inert atmosphere of nitrogen, argon, or the like.

The case where an Ullmann reaction is performed in Synthesis Scheme (A-1) is also shown. A copper catalyst can be used as the metal catalyst, and specifically, copper(I) iodide or copper(II) acetate can be given as the copper catalyst. As an example of a substance that can be used as the base, an inorganic base such as potassium carbonate can be given.

The above reaction is preferably performed in a solution, and 1,3-dimethyl-3,4,5,6-tetrahydro-2(1H)-pyrimidinone (abbreviation: DMPU), toluene, xylene, benzene, and the like can be given as a solvent that can be used in this reaction. However, the catalyst, base, and solvent which can be used are not limited thereto. In addition, this reaction is preferably performed in an inert atmosphere of nitrogen, argon, or the like.

Note that when the reaction temperature is higher than or equal to 100° C., the objective substance can be obtained in a shorter time and in a higher yield in an Ullmann reaction; therefore, a solvent having a high boiling point, such as DMPU or xylene, is preferably used. Further, when the reaction temperature is higher than or equal to 150° C., the objective substance can be more preferably obtained; therefore, a solvent such as DMPU whose boiling point is higher is more preferably used.

Next, as shown in Synthesis Scheme (A-2), the amine derivative (a3) and a halogenated arene (a4) are coupled, so that an aromatic amine derivative represented by General Formula (G1) can be obtained.

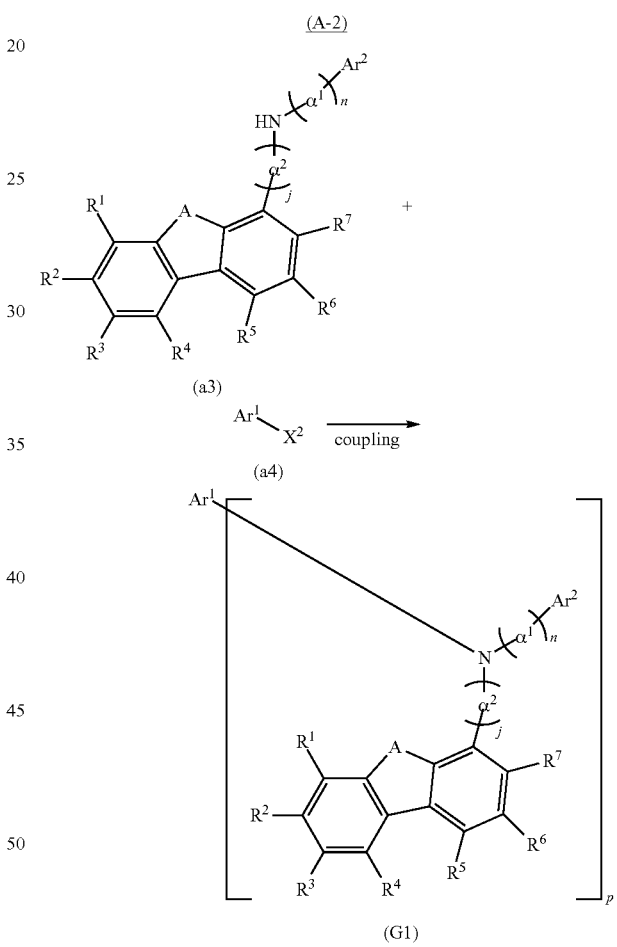

Note that in Synthesis Scheme (A-2), A represents O (oxygen) or S (sulfur), and $R^1$ to $R^7$ individually represent any of a hydrogen atom, an alkyl group having 1 to 6 carbon atoms, a substituted or unsubstituted phenyl group, and a substituted or unsubstituted biphenyl group. In addition, $\alpha^1$ and $\alpha^2$ individually represent a substituted or unsubstituted phenylene group. Further, $Ar^1$ represents a substituted or unsubstituted condensed aromatic hydrocarbon having 14 to 18 carbon atoms included in a ring. Further, $Ar^2$ represents a substituted or unsubstituted aryl group having 6 to 13 carbon atoms included in a ring. Further, j and n are individually 0 or 1, and p is 1 or 2. In addition, $X^2$ represents a halogen, preferably bromine or iodine, which has high reactivity, more preferably iodine.

At this step, in the case where p is 1, one equivalent of the amine derivative (a3) is reacted with the halogenated arene (a4). In the case where p is 2, two equivalents of the amine derivative (a3) are reacted with the halogenated arene (a4).

In Synthesis Scheme (A-2), a variety of reaction conditions can be employed in the coupling reaction of an aryl compound having a halogen group and an aryl compound (a primary arylamine compound or a secondary arylamine compound) having amine; for example, a synthesis method using a metal catalyst in the presence of a base can be employed. Note that a Hartwig-Buchwald reaction or an Ullmann reaction may be employed in Synthesis Scheme (A-2) as in Synthesis Scheme (A-1).

In the above manner, the aromatic amine derivative represented by General Formula (G1) of this embodiment can be synthesized.

Synthesis Method of Aromatic Amine Derivative Represented by General Formula (G2)

First, as shown in Synthesis Scheme (A-3), a halide of a dibenzofuran derivative or a dibenzothiophene derivative (a5) and an aryl compound having amine (a6) are coupled, so that an amine derivative (a7) can be obtained.

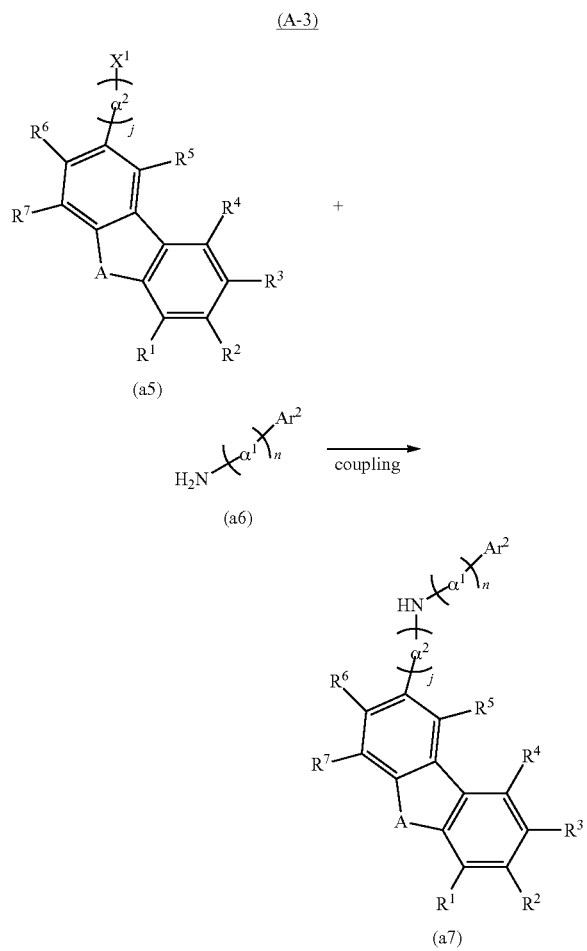

Note that in Synthesis Scheme (A-3), A represents O (oxygen) or S (sulfur), and $R^1$ to $R^7$ individually represent any of a hydrogen atom, an alkyl group having 1 to 6 carbon atoms, a substituted or unsubstituted phenyl group, and a substituted or unsubstituted biphenyl group. In addition, $\alpha^1$ and $\alpha^2$ individually represent a substituted or unsubstituted phenylene group. Further, $Ar^2$ represents a substituted or unsubstituted aryl group having 6 to 13 carbon atoms included in a ring. Further, j and n are individually 0 or 1. In addition, $X^1$ represents a halogen, preferably bromine or iodine, which has high reactivity, more preferably iodine.

In Synthesis Scheme (A-3), a variety of reaction conditions can be employed in the coupling reaction of a halide of a dibenzofuran derivative or a dibenzothiophene derivative and an aryl compound (a primary arylamine compound or a secondary arylamine compound) having amine; for example, a synthesis method using a metal catalyst in the presence of a base can be employed.

The case where a Hartwig-Buchwald reaction is performed in Synthesis Scheme (A-3) is shown. A palladium catalyst can be used as the metal catalyst, and a mixture of a palladium complex and a ligand thereof can be used as the palladium catalyst. As a specific palladium complex, bis(dibenzylideneacetone)palladium(0), palladium(II) acetate, and the like are given.

As a ligand, tri(tert-butyl)phosphine, tri(n-hexyl)phosphine, tricyclohexylphosphine, 1,1-bis(diphenylphosphino)ferrocene (abbreviation: DPPF), and the like can be given.

As a substance which can be used as the base, an organic base such as sodium tert-butoxide, an inorganic base such as potassium carbonate, and the like can be given. This reaction is preferably performed in a solution, and toluene, xylene, benzene, or the like can be used as a solvent. However, the catalyst, ligand, base, and solvent which can be used are not limited thereto. In addition, this reaction is preferably performed in an inert atmosphere of nitrogen, argon, or the like.

The case where an Ullmann reaction is performed in Synthesis Scheme (A-3) is also shown. A copper catalyst can be used as the metal catalyst, and specifically, copper(I) iodide or copper(II) acetate can be given as the copper catalyst. As an example of a substance that can be used as the base, an inorganic base such as potassium carbonate can be given.

The above reaction is preferably performed in a solution, and 1,3-dimethyl-3,4,5,6-tetrahydro-2(1H)-pyrimidinone (abbreviation: DMPU), toluene, xylene, benzene, and the like can be given as a solvent that can be used in this reaction. However, the catalyst, base, and solvent which can be used are not limited thereto. In addition, this reaction is preferably performed in an inert atmosphere of nitrogen, argon, or the like.

Note that when the reaction temperature is higher than or equal to 100° C., the objective substance can be obtained in a shorter time and in a higher yield in an Ullmann reaction; therefore, a solvent having a high boiling point, such as DMPU or xylene, is preferably used. Further, when the reaction temperature is higher than or equal to 150° C., the objective substance can be more preferably obtained; therefore, a solvent such as DMPU whose boiling point is higher is more preferably used.

Next, as shown in Synthesis Scheme (A-4), the amine derivative (a7) and a halogenated arene (a8) are coupled, so that an aromatic amine derivative represented by General Formula (G2) can be obtained.

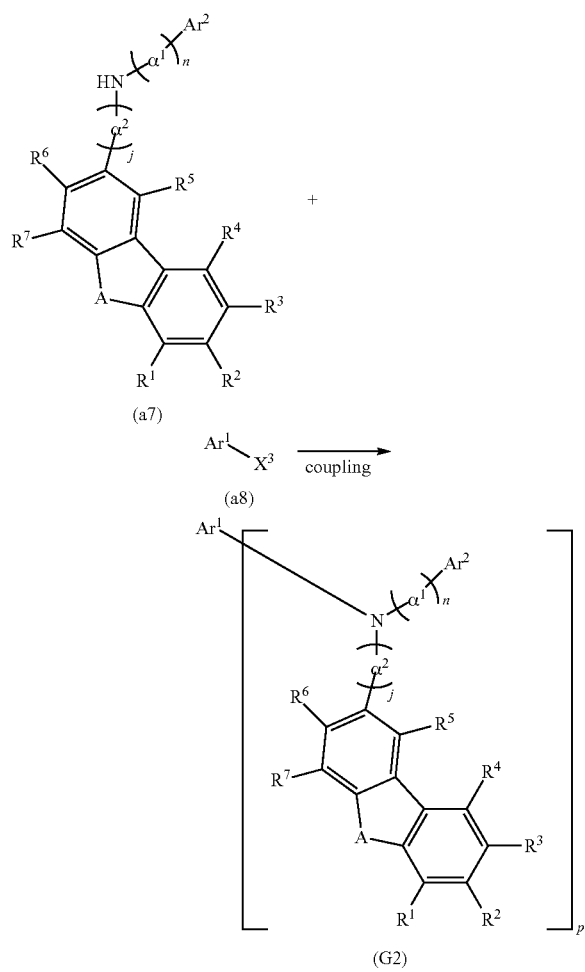

(A-4)

(a7)

(a8)

coupling (G2)

Note that in Synthesis Scheme (A-4), A represents O (oxygen) or S (sulfur), and $R^1$ to $R^7$ individually represent any of a hydrogen atom, an alkyl group having 1 to 6 carbon atoms, a substituted or unsubstituted phenyl group, and a substituted or unsubstituted biphenyl group. In addition, $\alpha^1$ and $\alpha^2$ individually represent a substituted or unsubstituted phenylene group. Further, $Ar^1$ represents a substituted or unsubstituted condensed aromatic hydrocarbon having 14 to 18 carbon atoms included in a ring. Further, $Ar^2$ represents a substituted or unsubstituted aryl group having 6 to 13 carbon atoms included in a ring. Further, j and n are individually 0 or 1, and p is 1 or 2. In addition, $X^3$ represents a halogen, preferably bromine or iodine, which has high reactivity, more preferably iodine.

At this step, in the case where p is 1, one equivalent of the amine derivative (a7) is reacted with the halogenated arene (a8). In the case where p is 2, two equivalents of the amine derivative (a7) are reacted with the halogenated arene (a8).

In Synthesis Scheme (A-4), a variety of reaction conditions can be employed in the coupling reaction of an aryl compound having a halogen group and an aryl compound (a primary arylamine compound or a secondary arylamine compound) having amine; for example, a synthesis method using a metal catalyst in the presence of a base can be employed.

Note that a Hartwig-Buchwald reaction or an Ullmann reaction may be employed in Synthesis Scheme (A-4) as in Synthesis Scheme (A-3).

In the above manner, the aromatic amine derivative represented by General Formula (G2) of this embodiment can be synthesized.

The aromatic amine derivative represented by General Formula (G1) or the aromatic amine derivative represented by General Formula (G2) of this embodiment can emit visible light having a short wavelength, and can emit blue light with favorable color purity.

Further, by using the aromatic amine derivative represented by General Formula (G1) or the aromatic amine derivative represented by General Formula (G2) of this embodiment to form a light-emitting element, the light-emitting element can have improved characteristics.

Note that this embodiment can be freely combined with any of the other embodiments.

Embodiment 2

In this embodiment, the aromatic amine derivatives represented by General Formula (G3) and General Formula (G9), which are described in Embodiment 1, and aromatic amine derivatives represented by General Formula (G6) and General Formula (G10) are described.

In the aromatic amine derivative represented by General Formula (G6) below, $R^1$ to $R^7$, $R^8$, and $R^{10}$ are hydrogen atoms, $Ar^2$ is Structural Formula (Ar2-1) shown in Embodiment 1, n is 0, and A is O (oxygen) or S (sulfur) in a compound represented by General Formula (G3). In addition, a characteristic of the aromatic amine derivative represented by General Formula (G6) is that a tertiary amine is formed at the fourth position of a dibenzofuranyl group or a dibenzothiophenyl group in General Formula (G3).

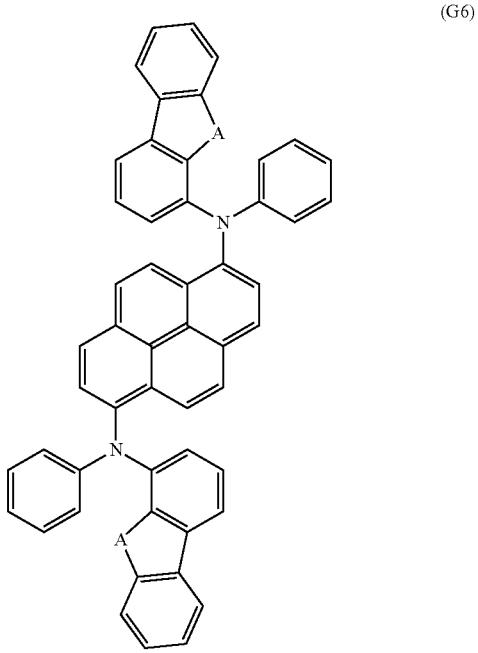

(G6)

In the aromatic amine derivative represented by General Formula (G10) below, $R^1$ to $R^7$, $R^8$, and $R^{10}$ are hydrogen atoms, $Ar^2$ is Structural Formula (Ar2-1) shown in Embodiment 1, n is 0, and A is O (oxygen) or S (sulfur) in a compound represented by General Formula (G9). In addition, a characteristic of the aromatic amine derivative represented by General Formula (G10) is that a tertiary amine is formed at the second position of a dibenzofuranyl group or a dibenzothiophenyl group in General Formula (G9).

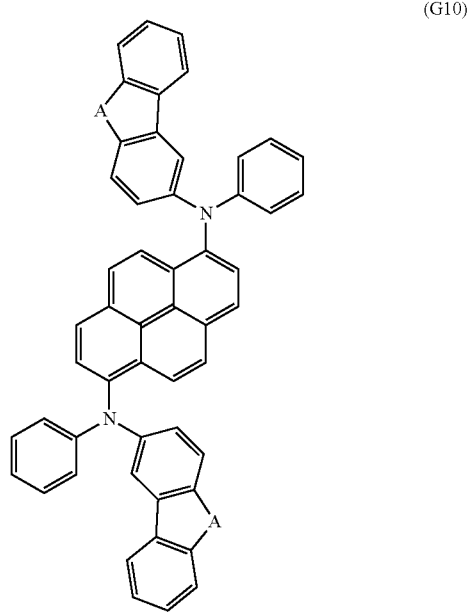

(G10)

The aromatic amine derivatives represented by General Formula (G6) and General Formula (G10) are both light-emitting materials having high emission efficiency and a long lifetime; however, the aromatic amine derivative represented by General Formula (G6), in which a tertiary amine is formed at the fourth position of a dibenzofuranyl group or a dibenzothiophenyl group, emits blue light with more favorable color purity and thus is more preferable than the aromatic amine derivative represented by General Formula (G10), in which a tertiary amine is formed at the second position of a dibenzofuranyl group or a dibenzothiophenyl group. This is because difference in conjugation of molecules of light-emitting materials is generated depending on the bonding position of a dibenzofuranyl group or a dibenzothiophenyl group for forming a tertiary amine. Further, owing to the difference in conjugation of molecules of light-emitting materials, a peak of an emission spectrum of the aromatic amine derivative represented by General Formula (G6) shifts to short-wavelength side.

When a dibenzofuranyl group in which A is O (oxygen) is included in the aromatic amine derivative represented by General Formula (G6) or General Formula (G10), the peak of an emission spectrum is in a shorter wavelength side than when a dibenzothiophenyl group in which A is S (sulfur) is included; thus, blue light with favorable color purity is emitted.

That is, among aromatic amine derivatives represented by General Formula (G6) or aromatic amine derivatives represented by General Formula (G10), a compound represented by Structural Formula (G6-1) in which A is O (oxygen) and a tertiary amine is formed at the fourth position of a dibenzofuranyl group emits blue light with the highest color purity.

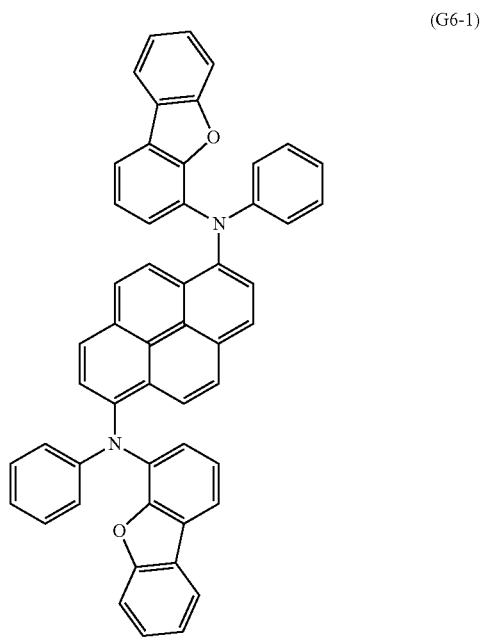

(G6-1)

Synthesis Method of Aromatic Amine Derivative Represented by General Formula (G6)

A variety of reactions can be applied to a method for synthesizing the aromatic amine derivative represented by General Formula (G6), which has high efficiency and a long lifetime and emits blue light with high color purity. As an example, Synthesis Scheme (A-5) can be employed.

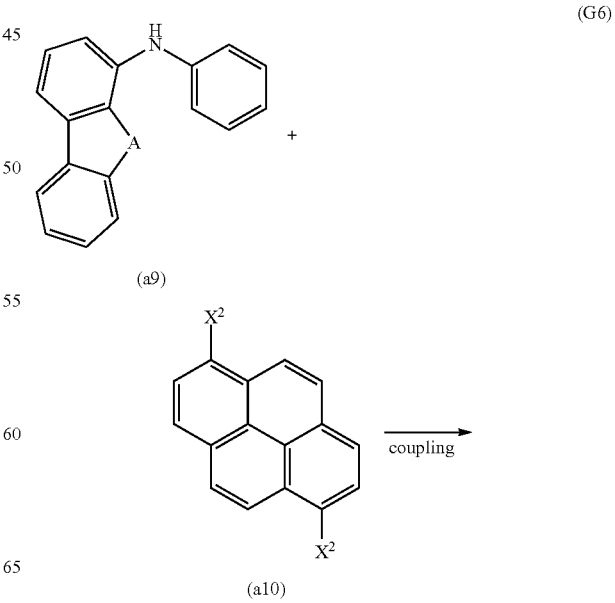

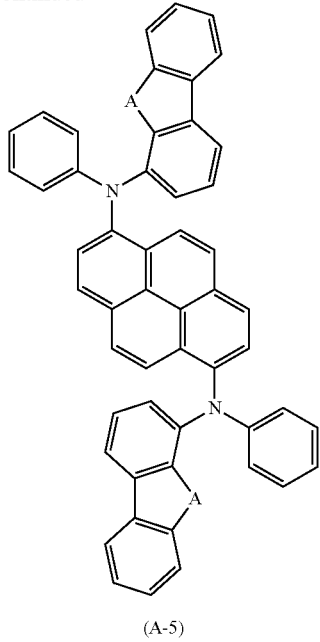

(A-5)

As shown in Synthesis Scheme (A-5), a secondary aromatic amine derivative (a9) and a halogenated pyrene (a10) are coupled, so that the aromatic amine derivative represented by General Formula (G6) can be obtained. Note that in Synthesis Scheme (A-5), A represents O (oxygen) or S (sulfur). $X^2$ represents a halogen, preferably bromine or iodine, which has high reactivity, more preferably iodine.

In Synthesis Scheme (A-5), a variety of reaction conditions can be employed in the coupling reaction of a pyrene compound having a halogen group and an aryl compound having amine (a primary arylamine compound or a secondary arylamine compound). As in Embodiment 1, a synthesis method using a metal catalyst in the presence of a base can be employed, such as a Hartwig-Buchwald reaction or an Ullmann reaction. At this time, two equivalents of the amine derivative (a9) are reacted with the halogenated pyrene (a10), so that the aromatic amine derivative represented by General Formula (G6) can be obtained.

Synthesis Method of Secondary Aromatic Amine Derivative (a9) Represented by General Formula (G11)

Here, a synthesis method of the secondary aromatic amine derivative (a9) shown in Synthesis Scheme (A-5) is described with reference to General Formula (G11). As an example, Synthesis Scheme (A-6) can be employed.

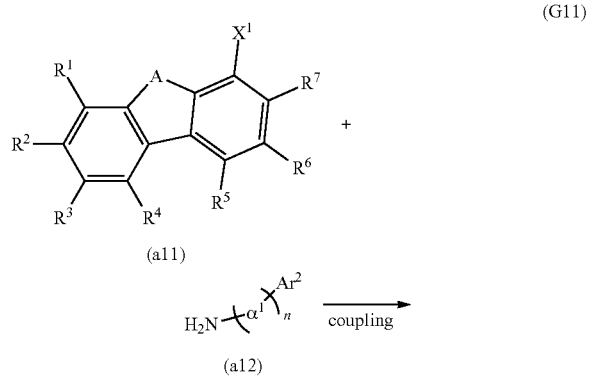

(G11)

(a11)

(a12) coupling

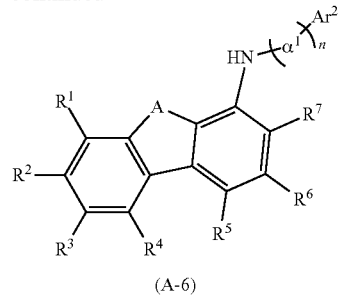

(A-6)

Note that in Synthesis Scheme (A-6), A represents O (oxygen) or S (sulfur), and $R^1$ to $R^7$ individually represent any of a hydrogen atom, an alkyl group having 1 to 6 carbon atoms, a substituted or unsubstituted phenyl group, and a substituted or unsubstituted biphenyl group. In addition, $\alpha^1$ represents a substituted or unsubstituted phenylene group. Further, $Ar^2$ represents a substituted or unsubstituted aryl group having 6 to 13 carbon atoms included in a ring. Further, n is 0 or 1. Specifically, the structures of $R^1$ to $R^7$, $\alpha^1$, and $Ar^2$ described in Embodiment 1 are given. In addition, $X^1$ represents a halogen, preferably bromine or iodine, which has high reactivity, more preferably iodine.

The reaction shown in Synthesis Scheme (A-6) is a coupling reaction of a halide of a dibenzofuran derivative or a dibenzothiophene derivative and an aryl compound having amine (a primary arylamine compound or a secondary arylamine compound). A variety of reaction conditions can be employed in this coupling reaction. For example, a synthesis method using a metal catalyst in the presence of a base can be employed, such as a Hartwig-Buchwald reaction or an Ullmann reaction described in Embodiment 1.

As shown in Synthesis Scheme (A-5) above, in the process of obtaining an aromatic amine derivative that is represented by General Formula (G6), which has high efficiency and a long lifetime and emits blue light with high color purity, a secondary aromatic amine derivative represented by General Formula (G11) is needed. Further, the secondary aromatic amine derivative represented by General Formula (G11) is a novel substance and a very valuable compound.

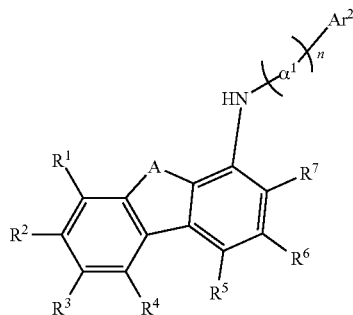

(G11)

In the above manner, by using a compound described in this embodiment, a novel aromatic amine derivative that is favorable as a blue light-emitting material for an organic EL element can be provided, which is one of the objects of the present invention. Further, by including a novel aromatic amine derivative described in this embodiment, a light-emitting element can have improved characteristics.

Note that this embodiment can be freely combined with any of the other embodiments.

Embodiment 3

In this embodiment, the aromatic amine derivative represented by General Formula (G4), which is described in Embodiment 1, is described. In particular, described is an aromatic amine derivative represented by General Formula (G7) in which $R^1$ to $R^7$, $R^8$, and $R^{10}$ are hydrogen atoms, $Ar^2$ is Structural Formula (Ar2-1), and n is 0 in General Formula (G5) in which $\alpha^2$ in General Formula (G4) is Structural Formula ($\alpha$-2). Further, also described is an aromatic amine derivative represented by General Formula (G8) in which $\alpha^2$ is Structural Formula ($\alpha$-1), $R^1$ to $R^7$, $R^8$, and $R^{10}$ are hydrogen atoms, $Ar^2$ is Structural Formula (Ar2-1), and n is 0 in General Formula (G4).

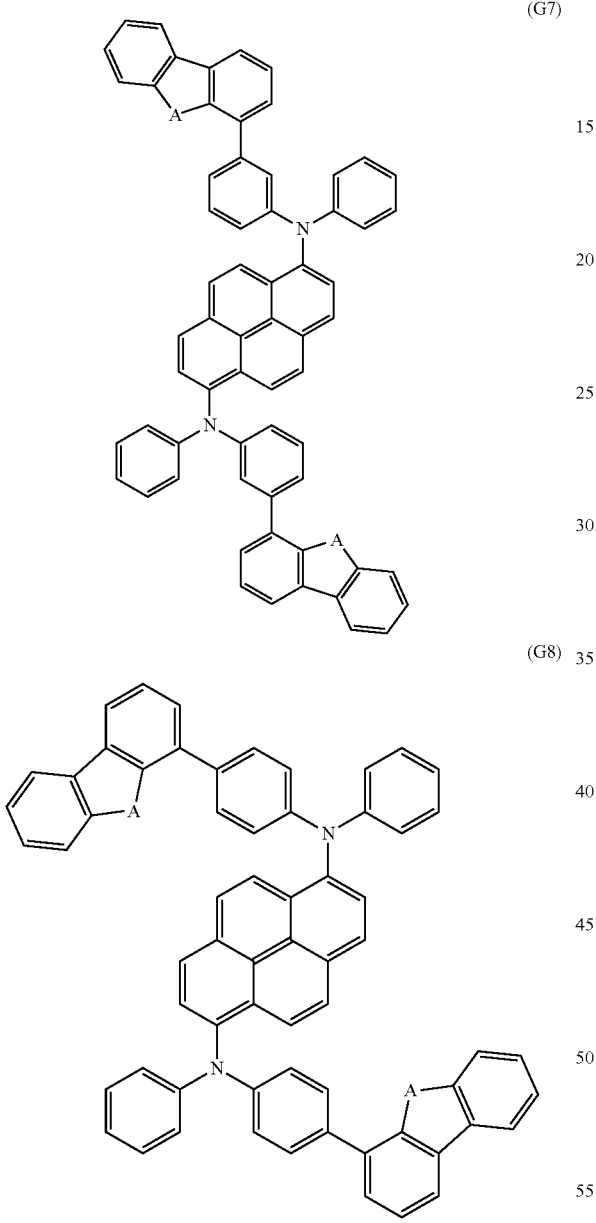

A characteristic of the aromatic amine derivative represented by General Formula (G7) is that a dibenzofuranyl group or a dibenzothiophenyl group is bonded at a meta position of a phenylene group that is bonded to an amino group. A characteristic of the aromatic amine derivative represented by General Formula (G8) is that a dibenzofuranyl group or a dibenzothiophenyl group is bonded at a para position of a phenylene group that is bonded to an amino group. Note that A in General Formula (G7) and General Formula (G8) represents O (oxygen) or S (sulfur).

The aromatic amine derivatives represented by General Formula (G7) and General Formula (G8) are both light-emitting materials having high efficiency and a long lifetime; however, the aromatic amine derivative represented by General Formula (G7), in which a dibenzofuranyl group or a dibenzothiophenyl group is bonded at a meta position of a phenylene group, can emit blue light with higher color purity than the aromatic amine derivative represented by General Formula (G8), in which a dibenzofuranyl group or a dibenzothiophenyl group is bonded at a para position of a phenylene group. This is because an emission spectrum of the aromatic amine derivative represented by General Formula (G7) shifts to short-wavelength side.

Synthesis Method of Aromatic Amine Derivative Represented by General Formula (G7)

A variety of reactions can be applied to a method for synthesizing the aromatic amine derivative represented by General Formula (G7). As an example, Synthesis Scheme (A-7) can be employed.

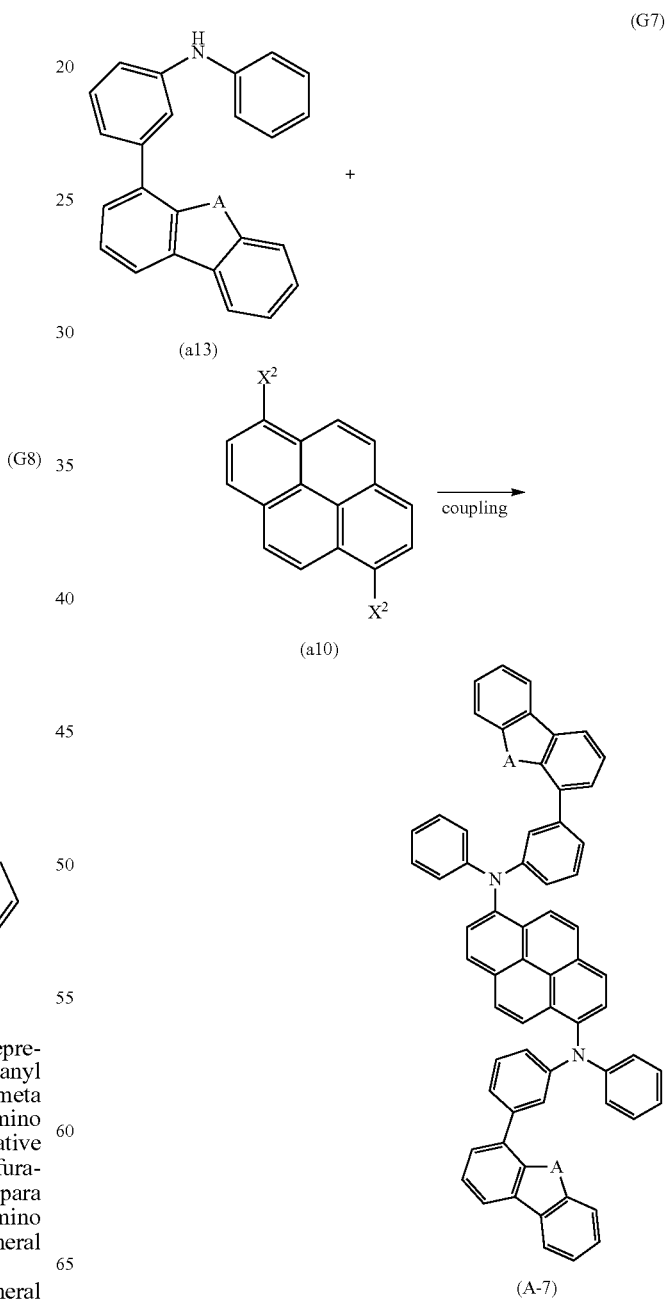

The reaction shown in Synthesis Scheme (A-7) is a coupling reaction of a pyrene compound having a halogen group and an aryl compound having amine (a primary arylamine compound or a secondary arylamine compound), as described in Embodiment 1. A variety of reaction conditions can be employed in this coupling reaction. As an example, a synthesis method using a metal catalyst in the presence of a base can be employed, such as a Hartwig-Buchwald reaction or an Ullmann reaction described in Embodiment 1.

As shown in Synthesis Scheme (A-7), a secondary aromatic amine derivative (a13) and a halogenated pyrene (a10) are coupled, so that the aromatic amine derivative represented by General Formula (G7) can be obtained. At this time, two equivalents of the amine derivative (a13) are reacted with the halogenated pyrene (a10), so that the aromatic amine derivative represented by General Formula (G7) can be obtained. This reaction is preferably performed in a solution, and any of the solvents described in Embodiment 1 can be used. In addition, this reaction is preferably performed in an inert atmosphere of nitrogen, argon, or the like. $X^2$ represents a halogen, preferably bromine or iodine, which has high reactivity, more preferably iodine. Note that in Synthesis Scheme (A-7), A represents O (oxygen) or S (sulfur).

Embodiment 4

In this embodiment, a light-emitting element formed using any of the aromatic amine derivatives described in Embodiments 1 to 3 is described.

The light-emitting element in this embodiment includes a first electrode which functions as an anode, a second electrode which functions as a cathode, and an EL layer interposed between the first electrode and the second electrode. Note that the light-emitting element in this embodiment can emit light when voltage is applied to each electrode such that the potential of the first electrode is higher than that of the second electrode.

In addition, the EL layer of the light-emitting element in this embodiment includes, over the first electrode functioning as an anode, a first layer (hole-injection layer), a second layer (hole-transport layer), a third layer (light-emitting layer), a fourth layer (electron-transport layer), and a fifth layer (electron-injection layer).

A structure of the light-emitting element in this embodiment is described with reference to FIGS. 1A and 1B. A substrate 101 is used as a support of the light-emitting element. For the substrate 101, glass, quartz, plastics, or the like can be used, for example. Further, a flexible substrate may be used. The flexible substrate is a substrate that can be bent, such as a plastic substrate made of polycarbonate, polyarylate, or polyether sulfone, for example. Alternatively, a film (made of polypropylene, polyester, vinyl, polyvinyl fluoride, vinyl chloride, or the like), an inorganic film formed by evaporation, or the like can be used.

The above substrate 101 may remain in a light-emitting device or an electronic device which is a product utilizing the light-emitting element of this embodiment. Alternatively, the substrate 101 may only function as the support of the light-emitting element in its manufacturing process without remaining in an end product.

For a first electrode 102 formed over the substrate 101, a metal, an alloy, an electrically conductive compound, a mixture thereof, or the like which has a high work function (specifically, a work function of 4.0 eV or more) is preferably used. Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide, or the like can be used. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), nitride of metal materials (for example, titanium nitride), and the like can be given. Note that in this embodiment, since a first layer 111 in an EL layer 103 which is formed in contact with the first electrode 102 includes a composite material which facilitates hole injection regardless of the work function of the first electrode 102, any known material can be used as long as the material can be used as an electrode material (e.g., a metal, an alloy, an electrically conductive compound, a mixture thereof, and an element belonging to Group 1 or Group 2 of the periodic table).

Such a material can be deposited by a sputtering method. For example, indium oxide-zinc oxide (IZO) can be deposited by a sputtering method using a target in which 1 wt % to 10 wt % zinc oxide is added to indium oxide, and indium oxide containing tungsten oxide and zinc oxide can be deposited by a sputtering method using a target in which 0.5 wt % to 5 wt % tungsten oxide and 0.1 wt % to 1 wt % zinc oxide are added to indium oxide. Alternatively, a vacuum evaporation method, a coating method, an inkjet method, a spin coating method, or the like may be used.

Further, in the EL layer 103 formed over the first electrode 102, when a composite material described below is used as a material for the first layer 111 formed in contact with the first electrode 102, any of a variety of metals, alloys, electrically conductive compounds, and a mixture thereof can be used as a material used for the first electrode 102 regardless of whether the work function is high or low. For example, aluminum (Al), silver (Ag), an alloy containing aluminum (e.g., AlSi), or the like can also be used.

Alternatively, it is possible to use any of elements belonging to Group 1 or Group 2 of the periodic table, that is, alkali metals such as lithium (Li) and cesium (Cs), alkaline earth metals such as magnesium (Mg), calcium (Ca), and strontium (Sr), alloys containing them (e.g., MgAg and AlLi), rare earth metals such as europium (Eu) and ytterbium (Yb), alloys containing them, and the like which are materials with a low work function.

Note that in the case where the first electrode 102 is formed using an alkali metal, an alkaline-earth metal, or an alloy thereof, a vacuum evaporation method or a sputtering method can be used. Alternatively, in the case where a silver paste or the like is used, a coating method, an inkjet method, or the like can be used.

The EL layer 103 formed over the first electrode 102 can be formed using a known material instead of the aromatic amine derivatives described in Embodiments 1 to 3, and either a low molecular compound or a high molecular compound can be used. Note that the substance contained in the EL layer 103 is not limited to an organic compound and may partly contain an inorganic compound.

The EL layer 103 is formed by, for example, stacking a hole-injection layer containing a substance having a high hole-injection property, a hole-transport layer containing a substance having a high hole-transport property, a light-emitting layer containing a light-emitting substance, an electron-transport layer containing a substance having a high electron-transport property, and an electron-injection layer containing a substance having a high electron-injection property, in an appropriate combination.

Note that the EL layer 103 illustrated in FIG. 1A includes the first layer (hole-injection layer) 111, a second layer (hole-transport layer) 112, a third layer (light-emitting layer) 113, a fourth layer (electron-transport layer) 114, and a fifth layer (electron-injection layer) 115 which are stacked in that order from the first electrode 102 side.

The first layer 111 contains a substance having a high hole-injection property. As the substance having a high hole-injection property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, or the like can be used. Alternatively, a low molecular organic compound can also be used; for example, a phthalocyanine-based compound such as phthalocyanine (abbreviation: $H_2Pc$), copper(II) phthalocyanine (abbreviation: CuPc) can be used.

Examples of the low molecular organic compound also include aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like. In addition, the aromatic amine derivatives described in Embodiments 1 to 3 may also be used.

Further alternatively, any of high molecular compounds (e.g., oligomers, dendrimers, or polymers) can be used. Examples of the high molecular compounds include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N'-bis(4-butylphenyl)-N,N'-bis(phenyl)benzidine (abbreviation: Poly-TPD). Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Alternatively, for the first layer 111, a composite material in which an acceptor substance is mixed into a substance having a high hole-transport property can be used. Note that, by using such a substance with a high hole-transport property containing an acceptor substance, a material used to form an electrode may be selected regardless of its work function. In other words, instead of a material with a high work function, a material with a low work function may also be used for the first electrode 102. Such a composite material can be formed by co-evaporation of a substance having a high hole-transport property and a substance having an acceptor property. Note that in this specification, the word "composite" means not only a state in which two materials are simply mixed but also a state in which a plurality of materials are mixed and charges are transferred between the materials.

As the organic compound for the composite material, various compounds such as an aromatic amine compound, a carbazole derivative, aromatic hydrocarbon, or a high molecular compound (such as oligomer, dendrimer, or polymer) can be used. The organic compound used for the composite material is preferably an organic compound having a high hole-transport property. Specifically, a substance having a hole mobility of $10^{-6}$ cm$^2$/Vs or higher is preferably used. However, materials other than these may also be used as long as the hole-transport property is higher than the electron-transport property. Examples of the organic compound which can be used for the composite material are specifically listed below.

Examples of the organic compound that can be used for the composite material include aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Further, aromatic hydrocarbon compounds can also be used such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, and 2,3,6,7-tetramethyl-9,10-di(1-naphthyl)anthracene.

Further, another aromatic hydrocarbon compound can also be used such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, or coronene; and an aromatic hydrocarbon compound having a vinyl group can also be used such as 4,4'-bis(2,2-diphenylvinyl)biphenyl (abbreviation: DPVBi) or 9,10-bis[4-(2,2-diphenylvinyl)phenyl]anthracene (abbreviation: DPVPA). In addition, the aromatic amine derivatives described in Embodiments 1 to 3 may also be used.

As the acceptor substance that can be used in the composite material, organic compounds such as 7,7,8,8-tetracyano-2,3,5,6-tetrafluoroquinodimethane (abbreviation: $F_4$-TCNQ) and chloranil, and a transition metal oxide can be given. Oxides of metals belonging to Group 4 to Group 8 in the periodic table can also be used. Specifically, the following are preferable owing to a high electron-accepting property: vanadium oxide, niobium oxide, tantalum oxide, chromium oxide, molybdenum oxide, tungsten oxide, manganese oxide, and rhenium oxide. Among these, molybdenum oxide is especially preferable since it is stable in the air and its hygroscopicity is low and is easily treated.

Note that for the first layer 111, a composite material formed using any of the above high molecular compounds such as PVK, PVTPA, PTPDMA, and Poly-TPD and any of the above acceptor substances may be used. Note also that a composite material in which the aromatic amine derivative described in any of Embodiments 1 to 3 and the above acceptor substance are combined can be used for the first layer 111.

The second layer 112 contains a substance having a high hole-transport property. Examples of the substance having a high hole-transport property include aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ cm$^2$/Vs or higher. However, materials other than these may also be used as long as the hole-transport property is higher than the electron-transport property. In addition, the aromatic amine derivatives described in Embodiment 1 to Embodiment 3 may also be used. The layer containing a substance with a high hole-transport property is not limited to a single layer, and two or more layers containing the above substances may be stacked.

For the second layer 112, a carbazole derivative such as CBP, CzPA, or PCzPA or an anthracene derivative such as t-BuDNA, DNA, or DPAnth may also be used.

Note that a high molecular compound such as poly(N-vinylcarbazole) (abbreviation: PVK) or poly(4-vinyltriphenylamine) (abbreviation: PVTPA) can also be used for the second layer 112.

The third layer 113 is a light-emitting layer containing a substance having a high light-emitting property. In the light-emitting layer, a substance having a high light-emitting property can be contained as a main component, or a substance having a high light-emitting property can be dispersed in another substance. In this embodiment, the aromatic amine derivative described in any of Embodiments 1 to 3 is used as the substance having a high light-emitting property.

When the aromatic amine derivative described in any of Embodiments 1 to 3 is dispersed in another substance, the mass ratio of the aromatic amine compound described in any of Embodiments 1 to 3 to the total is preferably 10% or less. A known substance can be used as a substance in which a substance having a light-emitting property is dispersed. It is preferable to use a substance whose lowest unoccupied molecular orbital level (LUMO level) is shallower (the absolute value is smaller) and highest occupied molecular orbital level (HOMO level) is deeper (the absolute value is larger) than those of the substance having a light-emitting property (the aromatic amine derivative described in any of Embodiments 1 to 3).

Specifically, a metal complex can be used such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ).

Alternatively, a heterocyclic compound can be used such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(biphenyl-4-yl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), or bathocuproine (abbreviation: BCP).

Alternatively, a condensed aromatic compound can be used such as 9-[4-(N-carbazolyl)phenyl]-10-phenylanthracene (abbreviation: CzPA), 9-[4-(3,6-diphenyl-N-carbazolyl)phenyl]-10-phenylanthracene (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), or 3,3',3"-(benzene-1,3,5-triyl)tripyrene (abbreviation: TPB3).

As a substance in which the light-emitting substance is dispersed, plural kinds of substances can be used. For example, in order to suppress crystallization, a substance such as rubrene which suppresses crystallization may be further added. In addition, NPB, Alq, or the like can be further added in order to efficiently transfer energy to the light-emitting substance. With a structure in which a light-emitting substance is thus dispersed in another substance, crystallization of the third layer 113 can be suppressed. Further, concentration quenching which results from the high concentration of the substance having a high light-emitting property can also be suppressed.

Further, in particular, among the above substances, a substance having an electron-transport property is preferably used so that a light-emitting substance is dispersed therein to form the third layer 113. Specifically, among the above metal complexes, heterocyclic compounds, and condensed aromatic compounds, CzPA, DNA, or t-BuDNA can be used. Further, a high molecular compound to be given below as a substance which can be used for the fourth layer 114 can also be used.

Note that the third layer 113 may be formed using two or more layers. For example, in the case where the third layer 113 is formed by stacking a first light-emitting layer and a second light-emitting layer in that order from the hole-transport layer side, the first light-emitting layer can be formed using a substance having a hole-transport property as a host material and the second light-emitting layer can be formed using a substance having an electron-transport property as a host material. It is more preferable that a material in which the hole-transport property is higher than the electron-transport property be used for the host material of the first light-emitting layer and a material in which the electron-transport property is higher than the hole-transport property be used for the host material of the second light-emitting layer. With the above structure, a light emission region is formed between the first light-emitting layer and the second light-emitting layer, whereby an element having higher efficiency can be obtained.

When the above-described third layer 113 is formed using a plurality of materials, it is possible to employ co-evaporation using a vacuum evaporation method, or an ink-jet method, a spin coating method, a dip coating method, or the like using a mixed solution.

The fourth layer 114 is an electron-transport layer containing a substance having a high electron-transport property. For the fourth layer 114, a low molecular organic compound can be used; for example, a metal complex such as Alq, Almq₃, BeBq₂, BAlq, Znq, ZnPBO, or ZnBTZ, or the like can be used. Alternatively, instead of the metal complex, a heterocyclic compound such as PBD, OXD-7, TAZ, TPBI, BPhen, or BCP can be used. The substances mentioned here are mainly ones that have an electron mobility of $10^{-6}$ cm$^2$/Vs or higher. Note that any substance other than the above substances may be used for the electron-transport layer as long as it is a substance in which the electron-transport property is higher than the hole-transport property. In addition, the electron-transport layer is not limited to a single layer, but may be a stack of two or more layers that contain the above substances.

For the fourth layer 114, a high molecular compound can also be used. For example, poly[(9,9-dihexylfluorene-2,7-diyl)-co-(pyridine-3,5-diyl)] (abbreviation: PF-Py), poly[(9, 9-dioctylfluorene-2,7-diyl)-co-(2,2'-bipyridine-6,6'-diyl)] (abbreviation: PF-BPy), or the like can be used.

The fifth layer 115 is an electron-injection layer containing a substance having a high electron-injection property. For the fifth layer 115, an alkali metal, an alkaline earth metal, or a compound thereof, such as lithium fluoride (LiF), cesium fluoride (CsF), or calcium fluoride (CaF$_2$), can be used. Alternatively, a layer containing a substance having an electron-transport property and an alkali metal, an alkaline earth metal, or a compound thereof may be used; specifically, a layer containing Alq and magnesium (Mg), or the like may be used. Note that in this case, electrons can be more efficiently injected from a second electrode 104.

The second electrode 104 is preferably formed using a metal, an alloy, an electrically conductive compound, or a mixture of these, having a low work function (specifically, a work function of 3.8 eV or lower is preferable). Specific examples of such a cathode material include an element that belongs to Group 1 or Group 2 of the periodic table, that is, alkali metals such as lithium (Li) and cesium (Cs), alkaline earth metals such as magnesium (Mg), calcium (Ca), and strontium (Sr), alloys containing these (e.g., MgAg and AlLi), rare earth metals such as europium (Eu) and ytterbium (Yb), alloys containing these, and the like.

Note that in the case where the second electrode 104 is formed using an alkali metal, an alkaline-earth metal, or an alloy thereof, a vacuum evaporation method or a sputtering method can be used. Alternatively, in the case of using a silver paste or the like, a coating method, an inkjet method, or the like can be used.

Note that by proving the fifth layer 115, the second electrode 104 can be formed using any of a variety of conductive materials such as Al, Ag, ITO, and indium oxide-tin oxide containing silicon or silicon oxide regardless of the work functions. A film of such a conductive material can be formed by a sputtering method, an inkjet method, a spin coating method, or the like.

Further, as a formation method of the EL layer 103 in which the first layer (hole-injection layer) 111, the second layer (hole-transport layer) 112, the third layer (light-emitting layer) 113, the fourth layer (electron-transport layer) 114, and the fifth layer (electron-injection layer) 115 are stacked in that order, any of a variety of methods can be employed regardless of whether the method is a dry process or a wet process. For example, a vacuum evaporation method, an inkjet method, a spin coating method, or the like can be used. Note that a different formation method may be employed for each layer.

The second electrode 104 can also be formed by a wet process using a paste of a metal material instead of a dry process such as a sputtering method or a vacuum evaporation method.

Since holes mainly flow between the first electrode 102 and the first layer (hole-injection layer) 111, between the first layer (hole-injection layer) 111 and the second layer (hole-transport layer) 112, and between the second layer (hole-transport layer) 112 and the third layer (light-emitting layer) 113, the HOMO levels (work function in a case of metal) thereof are preferably the same or almost the same to reduce the carrier injection barrier between the adjacent layers. Similarly, electrons mainly flow between the third layer (light-emitting layer) 113 and the fourth layer (electron-transport layer) 114, between the fourth layer (electron-transport layer) 114 and the fifth layer (electron-injection layer) 115, and between the fifth layer (electron-injection layer) 115 and the second electrode 104, the LUMO levels (work function in a case of metal) thereof are preferably the same or almost the same to reduce the carrier injection barrier between the adjacent layers. The difference is preferably less than or equal to 0.2 eV, more preferably less than or equal to 0.1 eV.

It is preferable that a difference between the HOMO levels in the second layer (hole-transport layer) 112 and the third layer (light-emitting layer) 113 and a difference between the LUMO levels in the third layer (light-emitting layer) 113 and the fourth layer (electron-transport layer) 114 be large because carriers are confined in the light-emitting layer and a light-emitting element with higher efficiency can be obtained. Note that in this case, when a barrier is too high, a driving voltage is high, which becomes a burden on the element. Therefore, each of the differences is preferably less than or equal to 0.4 eV, more preferably less than or equal to 0.2 eV.

In the light-emitting element of this embodiment, current flows by potential difference between the first electrode 102 and the second electrode 104, holes and electrons are recombined in the EL layer 103, an organic compound having a light-emitting property is brought into an excited state, and when the excited state relaxes to a ground state, the light-emitting organic compound releases the relaxation energy as light emission. The emitted light is extracted out through one or both of the first electrode 102 and the second electrode 104. Accordingly, one or both of the first electrode 102 and the second electrode 104 needs/need to be an electrode having a light-transmitting property.

Figure 2A:
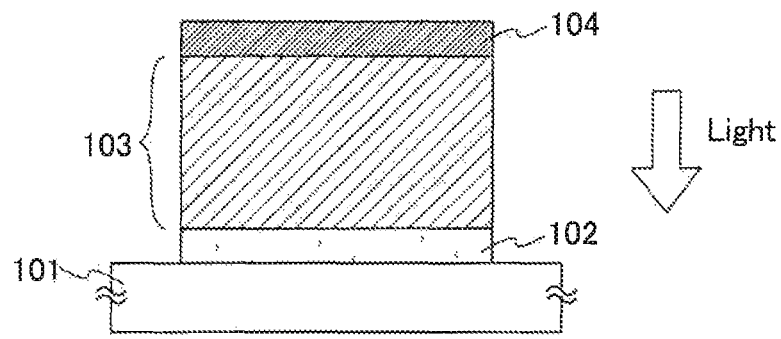
FIGS. 2A to 2C illustrate light-emitting elements.
Figure 2B:
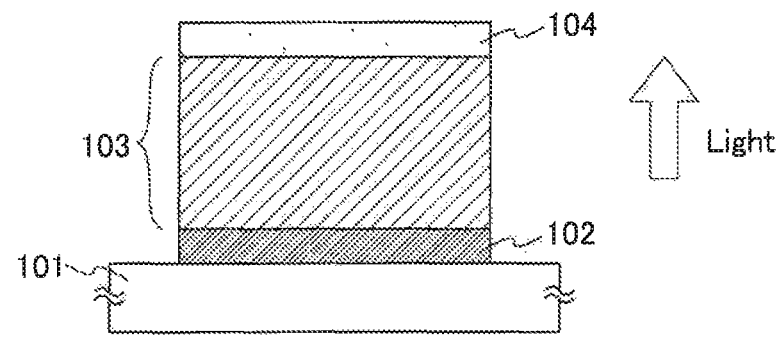
Figure 2C:
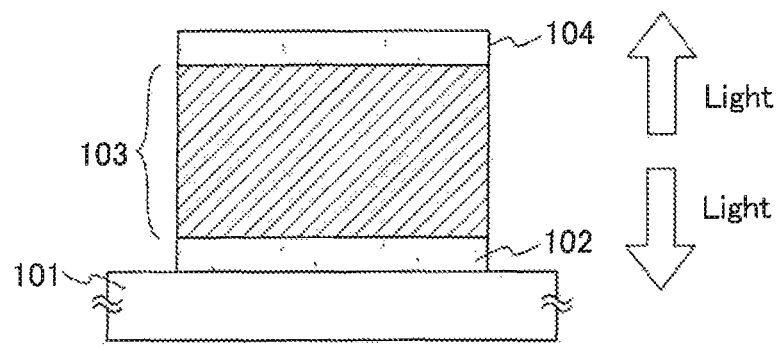

As illustrated in FIG. 2A, when only the first electrode 102 has a light-transmitting property, light emitted by the EL layer 103 is extracted from the substrate 101 side through the first electrode 102. Alternatively, as illustrated in FIG. 2B, when only the second electrode 104 has a light-transmitting property, light emitted by the EL layer 103 is extracted from the side opposite to the substrate 101 through the second electrode 104. As illustrated in FIG. 2C, when each of the first electrode 102 and the second electrode 104 has a light-transmitting property, light emitted by the EL layer 103 is extracted from both the substrate 101 side and the side opposite to the substrate 101 side through the first electrode 102 and the second electrode 104.

Note that the structure of the layers provided between the first electrode 102 and the second electrode 104 is not limited to the above structure. Structures other than the above may be employed as long as at least the second layer 112 which is a hole-transport layer and the third layer 113 which is a light-emitting layer are included.

Figure 1B:
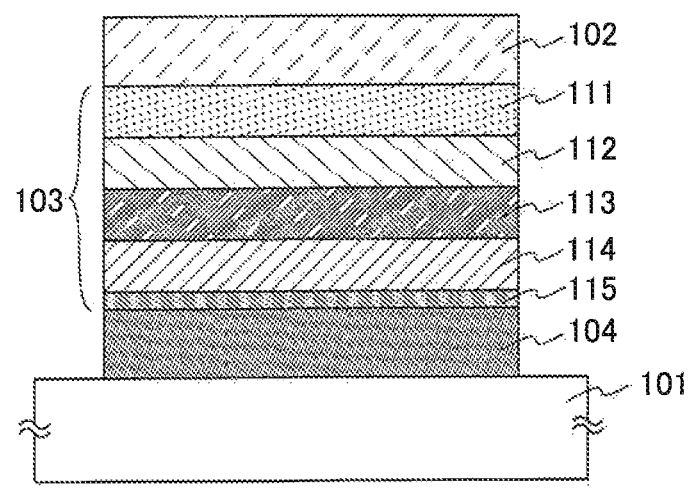

Alternatively, as illustrated in FIG. 1B, a structure may be employed in which the second electrode 104 functioning as a cathode, the EL layer 103, and the first electrode 102 functioning as an anode are stacked in that order over the substrate 101. Note that the EL layer 103 in this case has a structure in which the fifth layer 115, the fourth layer 114, the third layer 113, the second layer 112, the first layer 111, and the first electrode 102 are stacked in that order over the second electrode 104.

Note that by use of the light-emitting element of this embodiment, a passive matrix light-emitting device or an active matrix light-emitting device in which drive of the light-emitting element is controlled by a thin film transistor (TFT) can be fabricated.

Note that there is no particular limitation on the structure of the TFT in the case of fabricating an active matrix light-emitting device. For example, a staggered TFT or an inverted staggered TFT can be used as appropriate. Further, a driver circuit formed over a TFT substrate may be formed using both of an n-type TFT and a p-type TFT or only either an n-type TFT or a p-type TFT. Furthermore, there is no particular limitation on the crystallinity of a semiconductor film used for the TFT. An amorphous semiconductor film may be used, or a crystalline semiconductor film may be used.

In the above-described manner, the light-emitting element described in this embodiment contains the aromatic amine derivative which is described in any of Embodiments 1 to 3 as a light-emitting substance; therefore, element efficiency can be improved and a long lifetime can be achieved.

Embodiment 5

In this embodiment, a mode of a light-emitting element (hereinafter also referred to as a stacked-type element) having a plurality of stacked light-emitting units (also referred to as EL layers) is described with reference to FIGS. 3A and 3B. The light-emitting element is a stacked-type light-emitting element including a plurality of light-emitting units between a first electrode and a second electrode. A structure of each of the light-emitting units can be similar to the structure described in Embodiment 4. In other words, the light-emitting element described in Embodiment 4 is a light-emitting element having one light-emitting unit. In this embodiment, a light-emitting element having a plurality of light-emitting units is described.

Figure 3A:
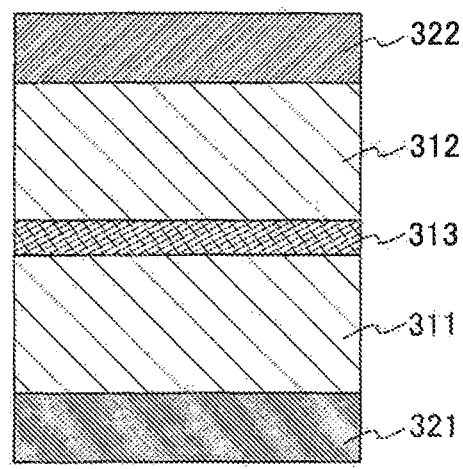
FIGS. 3A and 3B illustrate light emitting elements.

In FIG. 3A, a first light-emitting unit 311 and a second light-emitting unit 312 are stacked between a first electrode 321 and a second electrode 322. The electrodes described in Embodiment 4 can be used as the first electrode 321 and the second electrode 322. Structures of the first light-emitting unit 311 and the second light-emitting unit 312 may be the same or different from each other, and can be the same as those described in Embodiment 4.

A charge generation layer 313 functions such that electrons are injected into one light-emitting unit and holes are injected into the other light-emitting unit by application of voltage between the first electrode 321 and the second electrode 322. That is, the charge generation layer 313 may have either a structure including an organic compound having a high hole-transport property and an electron acceptor (an acceptor) or a structure including an organic compound having a high electron-transport property and an electron donor (a donor). The charge generation layer 313 may have a single layer structure or a stack structure of a plurality of layers. As the stack structure of a plurality of layers, a structure in which a hole-injection layer and an electron-injection layer are stacked is preferable.

For the hole-injection layer, a semiconductor or an insulator, such as molybdenum oxide, vanadium oxide, rhenium oxide, or ruthenium oxide, can be used. Alternatively, the hole-injection layer may have a structure in which an acceptor substance is added to a substance having a high hole-transport property. A layer containing a substance having a high hole-transport property and an acceptor substance contains, as an acceptor substance, 7,7,8,8-tetracyano-2,3,5,6-tetrafluoroquinodimethane (abbreviation: $F_4$-TCNQ) or metal oxide such as vanadium oxide, molybdenum oxide, or tungsten oxide. As the substance having a high hole-transport property, various compounds such as an aromatic amine compound, a carbazole derivative, aromatic hydrocarbon, a high-molecular compound, oligomer, dendrimer, polymer, and the like can be used. Note that the aromatic amine derivative of the present invention described in any of Embodiments 1 to 3 can also be used. Note that a substance having a hole mobility of $10^{-6}$ cm$^2$/Vs or higher is preferably employed as the substance having a high hole-transport property. Note that any other substance may also be used as long as it is a substance in which the hole-transport property is higher than the electron-transport property. Since a composite material of the substance having a high hole-transport property and the acceptor substance has an excellent carrier-injection property and an excellent carrier-transport property, low-voltage driving and low-current driving can be realized.

For the electron-injection layer, an insulator or a semiconductor such as lithium oxide, lithium fluoride, or cesium carbonate, can be used. Alternatively, the electron-injection layer may have a structure in which a donor substance is added to a substance having a high electron-transport property. As the donor substance, an alkali metal, an alkaline-earth metal, a rare-earth metal, a metal that belongs to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transport property, the materials described in Embodiment 1 to Embodiment 3 can be used. Note that a substance having an electron mobility of $10^{-6}$ cm$^2$/Vs or higher is preferably employed as the substance having a high electron-transport property. Note that any other substance may also be used as long as it is a substance in which the electron-transport property is higher than the hole-transport property. Since a composite material of the substance having a high electron-transport property and the donor substance has an excellent carrier-injection property and an excellent carrier-transport property, low-voltage driving and low-current driving can be realized.

Further, the electrode materials described in Embodiment 4 can be used for the charge generation layer 313. For example, the charge generation layer 313 may be formed by combining a layer containing a substance having a high hole-transport property and metal oxide with a transparent conductive film. Note that the charge generation layer 313 is preferably a highly light-transmitting layer in view of light extraction efficiency.

In any case, any structure for the charge generation layer 313 interposed between the first light-emitting unit 311 and the second light-emitting unit 312 is acceptable as long as it is one by which electrons are injected into one of the light-emitting units and holes are injected into the other of the light-emitting units by application of voltage between the first electrode 321 and the second electrode 322. An acceptable structure is one in which, for example, the charge generation layer 313 injects electrons into the first light-emitting unit 311 and injects holes into the second light-emitting unit 312 when voltage is applied such that the potential of the first electrode is higher than that of the second electrode.

Figure 3B:
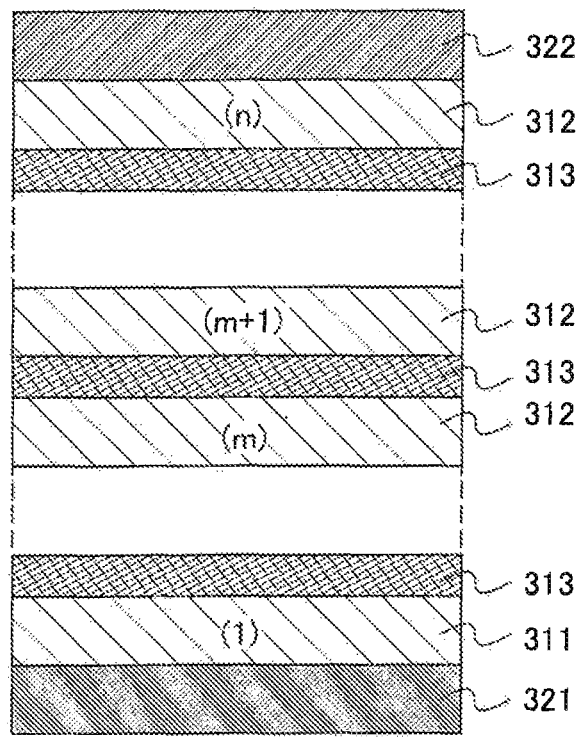

In this embodiment, the light-emitting element having two light-emitting units is described; however, an embodiment of the present invention can be similarly applied to a light-emitting element in which three or more light-emitting units are stacked as illustrated in FIG. 3B. A plurality of light-emitting units which are partitioned by the charge generation layer are arranged between a pair of electrodes, as in the light-emitting element of this embodiment, whereby the element can emit light in a high luminance region while current density is kept low. Since current density can be kept low, the element can have a long lifetime. When the light-emitting element is applied for illumination, voltage drop due to resistance of an electrode material can be reduced, thereby achieving homogeneous light emission in a large area. Moreover, a light-emitting device of low power consumption, which can be driven at a low voltage, can be achieved.

The light-emitting units emit light having different colors from each other, thereby obtaining light emission of a desired color in the whole light-emitting element. For example, in the light-emitting element having two light-emitting units, when emission color of the first light-emitting unit and emission color of the second light-emitting unit are complementary colors, a light-emitting element emitting white light as a whole light-emitting element can be obtained. Note that the word "complementary" means color relationship in which an achromatic color is obtained when colors are mixed. That is, white light emission can be obtained by mixture of light obtained from substances emitting light with complementary colors. The same can be applied to a light-emitting element which has three light-emitting units. For example, when the first light-emitting unit emits red light, the second light-emitting unit emits green light, and the third light-emitting unit emits blue light, white light can be emitted from the whole light-emitting element.

Note that this embodiment can be combined with another embodiment as appropriate.

Embodiment 6

Figure 4A:
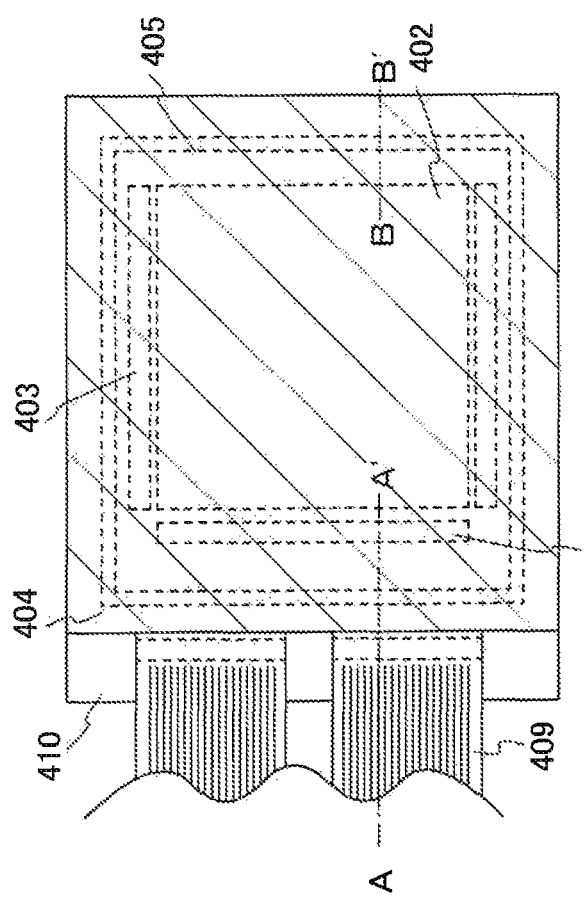
FIGS. 4A and 4B illustrate a light-emitting device.
Figure 4B:
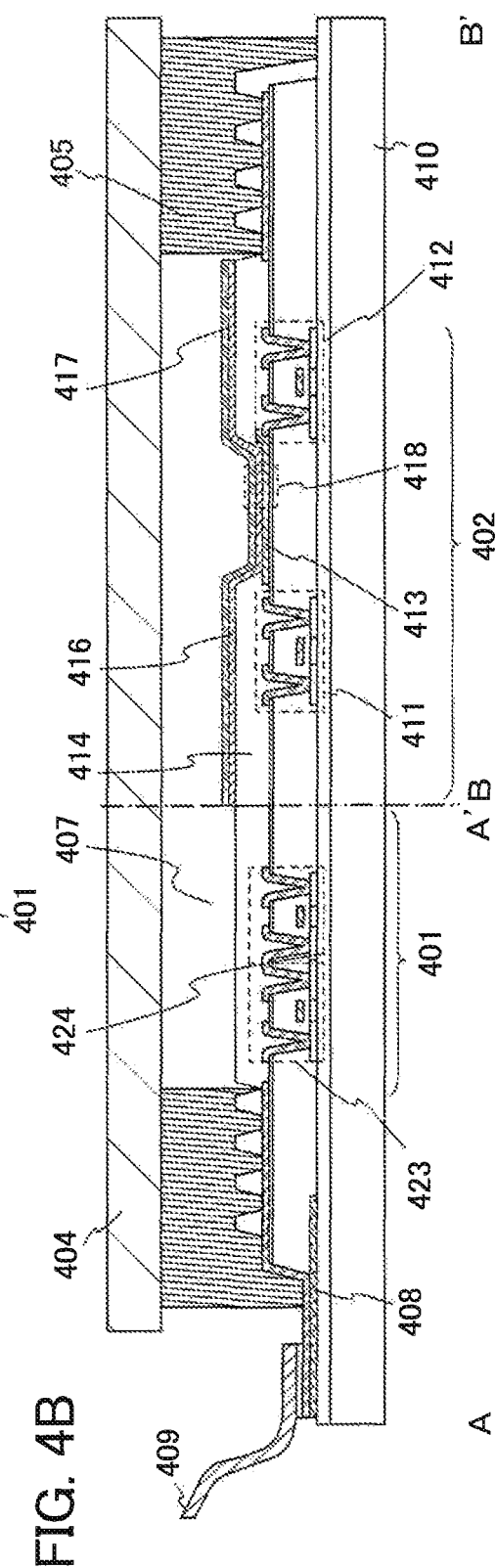

In this embodiment, a light-emitting device having a light-emitting element of Embodiment 4 or Embodiment 5 in a pixel portion is described with reference to FIGS. 4A and 4B. FIG. 4A is a top view illustrating a light-emitting device while FIG. 4B is a cross-sectional view along lines A-A' and B-B' of FIG. 4A.

In FIG. 4A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Reference numeral 404 denotes a sealing substrate, reference numeral 405 denotes a sealant, and an inner side region enclosed by the sealant 405 is a space 407 as shown in FIG. 4B.

A lead wiring 408 is a wiring to transmit a signal that is to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure is described with reference to FIG. 4B. The driver circuit portion and the pixel portion are formed over an element substrate 410. In this case, one pixel in the pixel portion 402 and the source side driver circuit 401 which is the driver circuit portion are illustrated. A CMOS circuit, which is a combination of an n-channel TFT 423 and a p-channel TFT 424, is formed as the source side driver circuit 401. Such a driver circuit may be formed by using various circuits such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413.

Further, either a negative-type photosensitive material which becomes insoluble in an etchant by light irradiation or a positive-type photosensitive material which becomes soluble in an etchant by light irradiation can be used as the insulator 414. In order to improve the coverage, the insulator 414 is preferably provided such that either an upper end portion or a lower end portion of the insulator 414 has a curved surface. For example, when positive photosensitive acrylic is used as a material for the insulator 414, only an upper end portion of the insulator 414 can have a curved surface with a radius of curvature (0.2 μm to 3 μm).

Over the first electrode 413, an EL layer 416 and a second electrode 417 are formed. In this case, the first electrode 413 can be formed using any of a variety of materials such as metals, alloys, and electrically conductive compounds or a mixture thereof. Note that, as a specific material, the material described in Embodiment 4 as the material which can be used for the first electrode can be used.

The EL layer 416 is formed by any of a variety of methods such as an evaporation method using an evaporation mask, an inkjet method, and a spin coating method. The EL layer 416 has the structure described in Embodiment 4 or Embodiment 5. Further, as another material included in the EL layer 416, any of low molecular compounds, high molecular compounds (including oligomers and dendrimers) may be used. As the material for the EL layer, an organic compound or an inorganic compound may be used.

The second electrode 417 can be formed using any of a variety of metals, alloys, and electrically conductive compounds, or a mixture thereof. Among such materials, a metal, an alloy, an electrically conductive compound, a mixture thereof, or the like having a low work function (a work function of 3.8 eV or less) is preferably used when the second electrode 417 is used as a cathode. As an example, an element belonging to Group 1 or Group 2 in the periodic table, i.e., an alkali metal such as lithium (Li) or cesium (Cs), an alkaline earth metal such as magnesium (Mg), calcium (Ca), or strontium (Sr), or an alloy containing any of these (e.g., MgAg or AlLi), and the like can be given.

Note that in the case where light generated in the EL layer 416 is transmitted through the second electrode 417, for the second electrode 417, a stack of a metal thin film with a reduced thickness and a transparent conductive film (indium oxide-tin oxide (ITO), indium oxide-tin oxide containing silicon or silicon oxide, indium oxide-zinc oxide (IZO), or indium oxide containing tungsten oxide and zinc oxide, or the like) can also be used.

By joining the sealing substrate 404 and the element substrate 410 with the sealant 405, a structure where the light-emitting element 418 is provided in the space 407 surrounded by the element substrate 410, the sealing substrate 404, and the sealant 405 is formed. Note that the space 407 is filled with a filler such as an inert gas (e.g., nitrogen or argon) or the sealant 405.

Note that as the sealant 405, an epoxy-based resin is preferably used. A material used for these is desirably a material which does not transmit moisture or oxygen as much as possible. The sealing substrate 404 can be formed of a glass substrate; a quartz substrate; or a plastic substrate including fiberglass-reinforced plastics (FRP), polyvinyl fluoride (PVF), polyester, acrylic, or the like.

In the above manner, the active matrix light-emitting device having the light-emitting element described in Embodiment 4 or Embodiment 5 can be obtained.

Figure 5A:
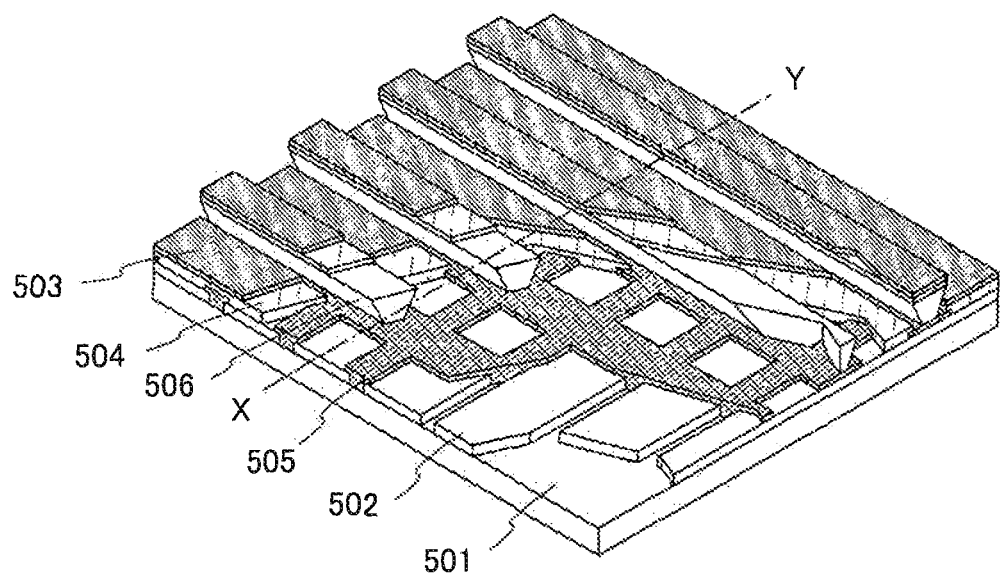
FIGS. 5A and 5B illustrate a light-emitting device.
Figure 5B:
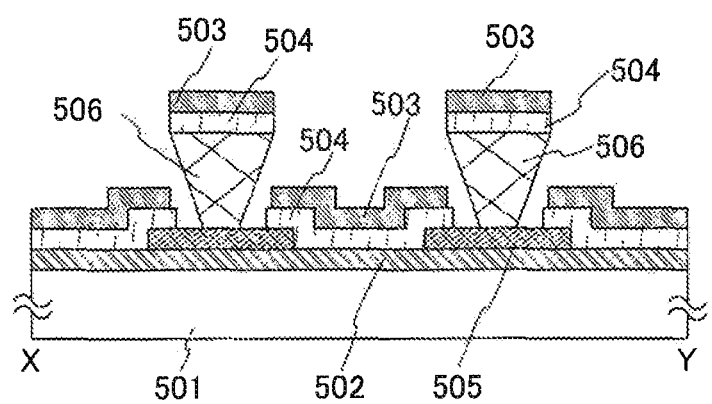

Further, the light-emitting element described in Embodiment 4 or Embodiment 5 can be used for a passive matrix light-emitting device instead of the above active matrix light-emitting device. FIGS. 5A and 5B illustrate a perspective view and a cross-sectional view of a passive matrix light-emitting device using the light-emitting element described in the above embodiment. Note that FIG. 5A is a perspective view of the light-emitting device, and FIG. 5B is a cross-sectional view taken along line X-Y of FIG. 5A.

In FIGS. 5A and 5B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The side surfaces of the partition layer 506 slope so that the distance between one side surface and the other side surface gradually decreases toward the surface of the substrate. In other words, a cross section taken along the direction of the short side of the partition layer 506 is trapezoidal, and the lower side (which is in contact with the insulating layer 505 in FIG. 5B) of the trapezoid is shorter than the upper side (which is not in contact with the insulating layer 505 in FIG. 5B). By providing the partition layer 506 in such a manner, a defect of the light-emitting element due to static electricity or the like can be prevented.

Accordingly, the passive matrix light-emitting device having the light-emitting element of Embodiment 4 or 5 can be obtained.

Note that any of the light-emitting devices described in this embodiment (the active matrix light-emitting device and the passive matrix light-emitting device) are formed using the light-emitting element described in the above embodiment, which has high emission efficiency and a long lifetime, and accordingly a light-emitting device with low power consumption and high reliability can be obtained.

Note that this embodiment can be used in appropriate combination with a structure described in another embodiment.

Embodiment 7

In this embodiment, electronic devices and lighting devices, each of which includes the light-emitting device described in Embodiment 6 as a part, are described. Examples of the electronic devices include cameras such as video cameras and digital cameras, goggle type displays, navigation systems, audio replay devices (e.g., car audio systems and audio systems), computers, game machines, portable information terminals (e.g., mobile computers, mobile phones, portable game machines, and electronic book readers), image replay devices in which a recording medium is provided (specifically, devices that are capable of replaying recording media such as digital versatile discs (DVDs) and equipped with a display device that can display an image), and the like. Specific examples of these electronic devices are illustrated in FIGS. 6A to 6D.

Figure 6A:
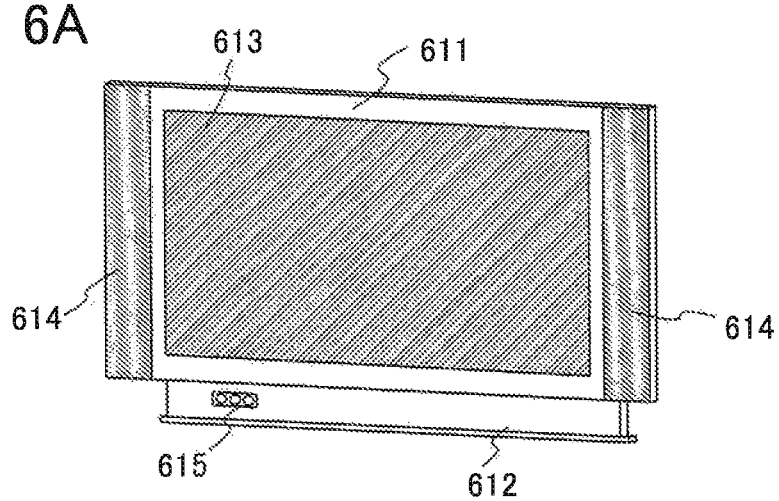
FIGS. 6A to 6D illustrate electronic devices.

FIG. 6A illustrates a television set according to an embodiment of the present invention, which includes a housing 611, a supporting base 612, a display portion 613, speaker portions 614, video input terminals 615, and the like. In this television set, the light-emitting device of the present invention can be applied to the display portion 613. Since the light-emitting device of the present invention has a feature of high emission efficiency, a television set having reduced power consumption can be obtained by application of the light-emitting device of the present invention.

Figure 6B:
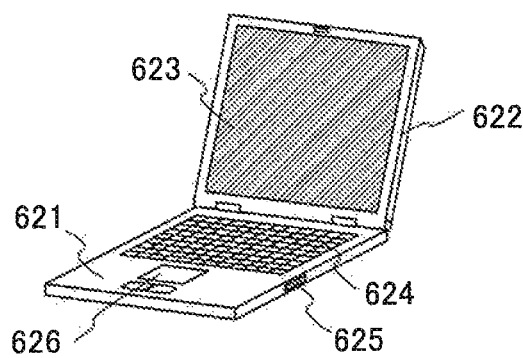

FIG. 6B illustrates a computer according to an embodiment of the present invention, which includes a main body 621, a housing 622, a display portion 623, a keyboard 624, an external connection port 625, a pointing device 626, and the like. In this computer, the light-emitting device of the present invention can be applied to the display portion 623. Since the light-emitting device of the present invention has a feature of high emission efficiency, a computer having reduced power consumption can be obtained by application of the light-emitting device of the present invention.

Figure 6C:
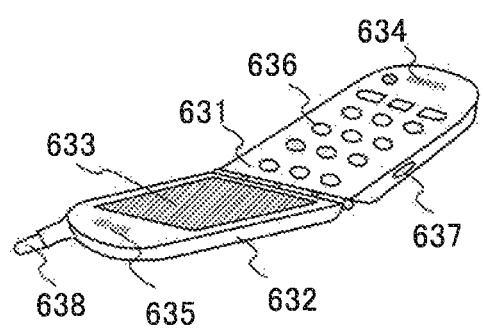

FIG. 6C illustrates a mobile phone according to an embodiment of the present invention, which includes a main body 631, a housing 632, a display portion 633, an audio input portion 634, an audio output portion 635, operation keys 636, an external connection port 637, an antenna 638, and the like. In this mobile phone, the light-emitting device of the present invention can be applied to the display portion 633. Since the light-emitting device of the present invention has a feature of high emission efficiency, a mobile phone having reduced power consumption can be obtained by application of the light-emitting device of the present invention.

Figure 6D:
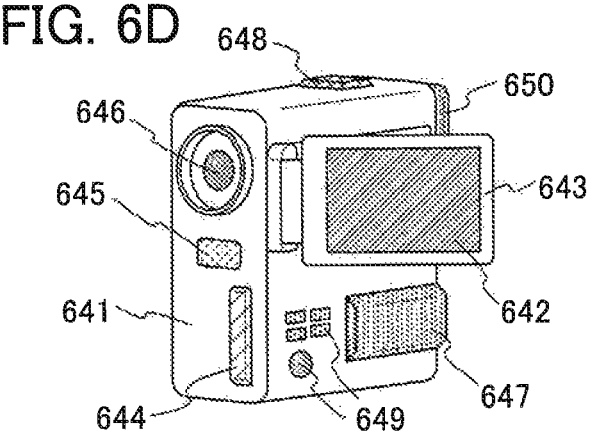

FIG. 6D illustrates a camera according to an embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of the present invention can be applied to the display portion 642. Since the light-emitting device of the present invention has a feature of high emission efficiency, a camera having reduced power consumption can be obtained by application of the light-emitting device of the present invention.

As thus described, application range of the light-emitting device of one embodiment of the present invention is quite wide, and this light-emitting device can be applied to electronic devices of a variety of fields. By applying the light-emitting device of the present invention, an electronic device having reduced power consumption can be obtained.

Figure 7:
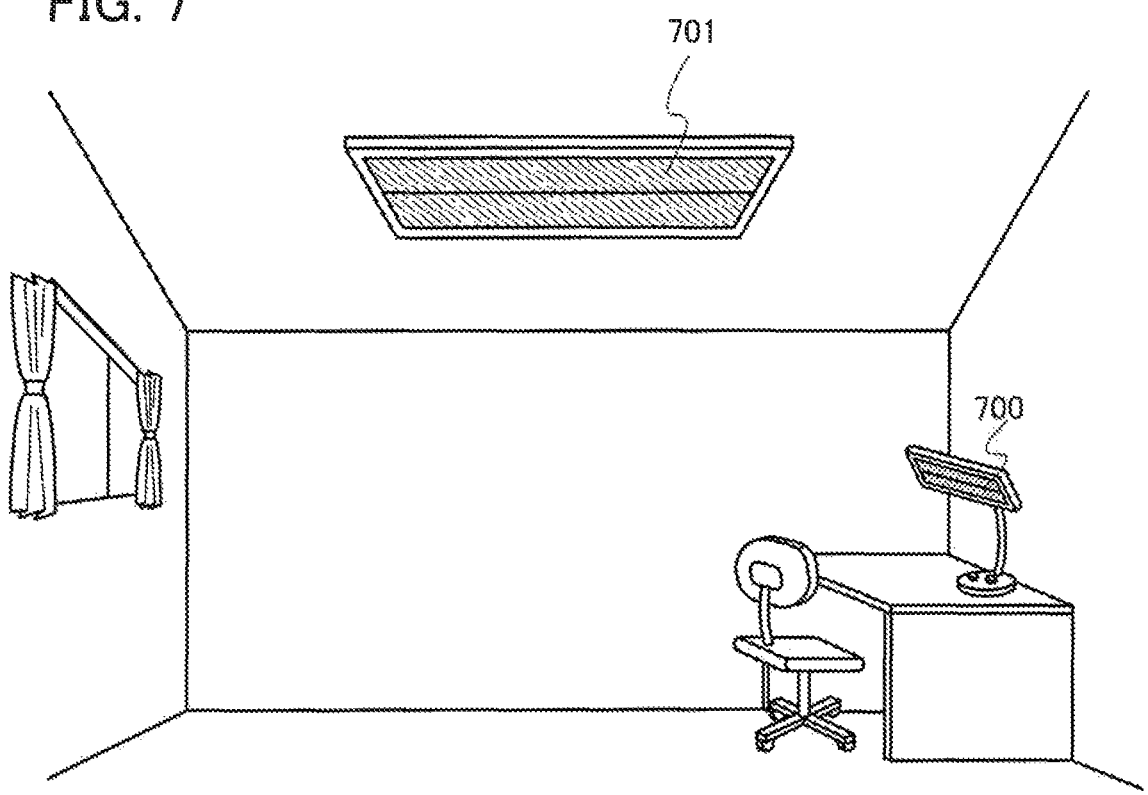
FIG. 7 illustrates lighting devices.

The light-emitting device of one embodiment of the present invention can also be used as a lighting device. FIG. 7 is an example in which the light-emitting device formed in accordance with the above embodiments is used as an indoor lighting device 701. Since the light-emitting device described in the above embodiments can be increased in area, the light-emitting device can be used as a lighting device having a large area. The light-emitting device described in the above embodiment can also be used as a desk lamp 700. Note that the lighting device includes in its category, a wall light, a lightning for an inside of a car, an emergency exit light, and the like in addition to a ceiling light and the desk lamp. Since the light-emitting device fabricated in accordance with the above embodiment includes a long-lifetime light-emitting element, the light-emitting device can be used as a long-lifetime lighting device.

Note that this embodiment can be used in appropriate combination with a structure described in another embodiment.

Example 1

In this example, an example of obtaining N,N'-bis(dibenzofuran-4-yl)-N,N'-diphenyl-pyrene-1,6-diamine (abbreviation: 1,6FrAPrn-II) represented by Structural Formula (G6-1), which is described in Embodiment 2, is described.

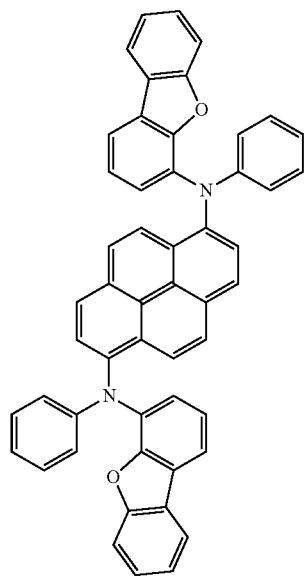

(G6-1)

Step 1: Synthesis method of N-(dibenzofuran-4-yl)-N-phenyl-amine (abbreviation: FrA-II)

First, 4.5 g (15.4 mmol) of 4-iododibenzofuran and 4.5 g (4.6 mmol) of sodium tert-butoxide were put in a 300 mL three-neck flask, and the air in the flask was replaced by nitrogen. Then, 98.0 mL of toluene, 2.8 mL (19.1 mmol) of aniline, and 0.3 mL of a 10% hexane solution of tri(tert-butyl)phosphine were added to this mixture.

The temperature of this mixture was set to 60° C., 54.1 mg (0.1 mmol) of bis(dibenzylideneacetone)palladium(0) was added, and the mixture was stirred at 80° C. for 6.5 hours. After the stirring, suction filtration was carried out through Florisil (manufactured by Wako Pure Chemical Industries, Ltd., Catalog No. 540-00135), Celite (manufactured by Wako Pure Chemical Industries, Ltd., Catalog No. 531-16855), and alumina to obtain filtrate.

The obtained filtrate was concentrated to give a solid. The given solid was purified by silica gel column chromatography (the developing solvent was hexane and toluene (hexane:toluene=5:1)). The obtained fraction was concentrated, so that 3.3 g of an objective white solid was obtained in a yield of 84%. The synthesis scheme of Step 1 is shown in (B1-1).

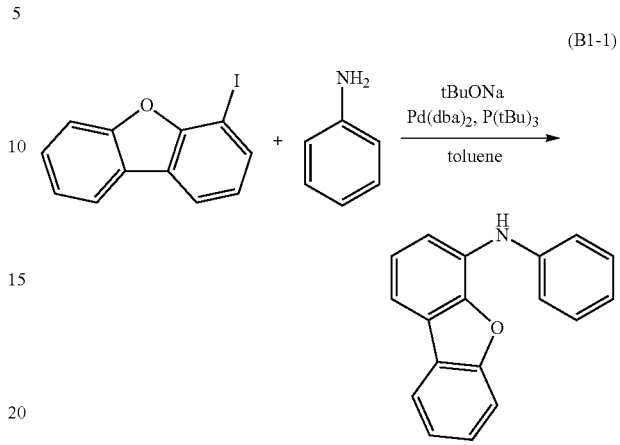

(B1-1)

By a nuclear magnetic resonance (NMR) method, this compound was confirmed to be N-(dibenzofuran-4-yl)-N-phenyl-amine (abbreviation: FrA-II), which was the objective substance.

The $^1$H-NMR data of the obtained compound are shown below.

$^1$H-NMR (CDCl$_3$, 300 MHz): δ=6.20 (s, 1H), 6.98-7.03 (m, 1H), 7.21-7.59 (m, 10H), 7.95 (d, J=7.8 Hz, 1H)

Figure 8A:
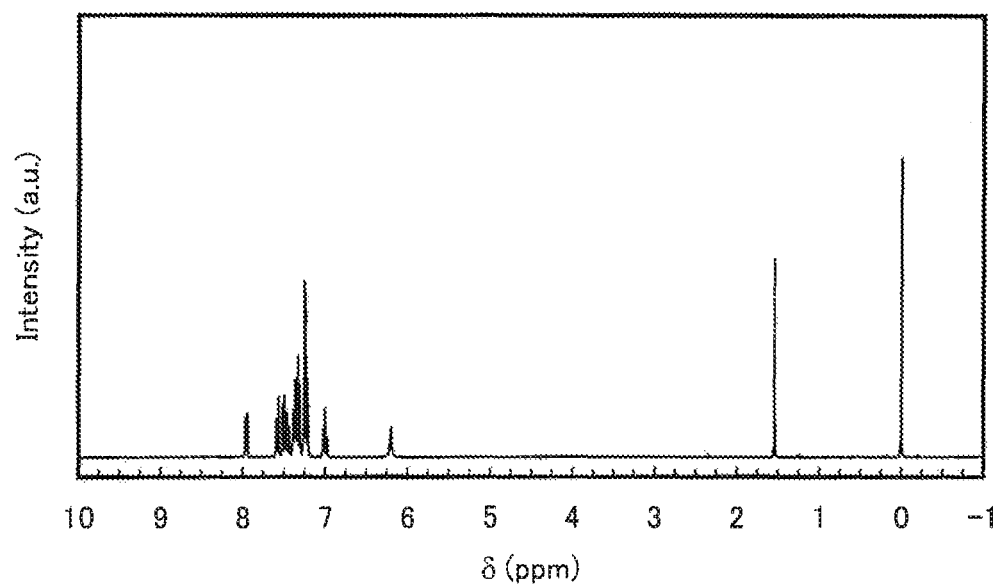
FIGS. 8A and 8B show $^1$H-NMR charts of FrA-II.
Figure 8B:
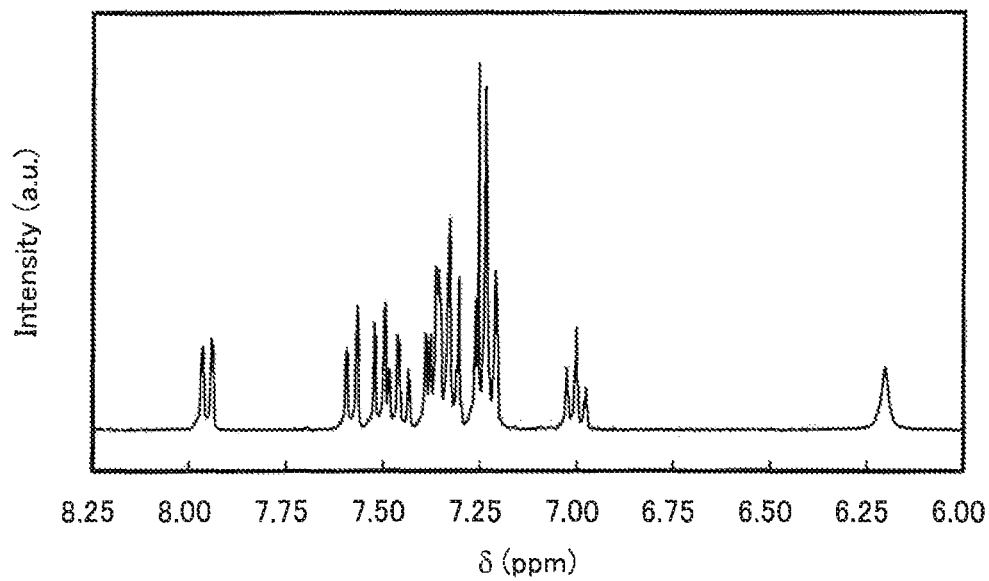

In addition, the $^1$H-NMR charts are shown in FIGS. 8A and 8B. Note that FIG. 8B is a chart showing an enlarged part of FIG. 8A in the range of 6.00 ppm to 8.25 ppm.

Step 2: Synthesis method of N,N'-bis(dibenzofuran-4-yl)-N,N'-diphenyl-pyrene-1,6-diamine (abbreviation: 1,6FrAPrn-II)

Next, 0.8 g (2.1 mmol) of 1,6-dibromopyrene, 1.1 g (4.2 mmol) of N-(dibenzofuran-4-yl)-N-phenyl-amine, and 0.6 g (6.2 mmol) of sodium tert-butoxide were put in a 50 mL three-neck flask, and the air in the flask was replaced by nitrogen. Then, 20.0 mL of toluene and 0.3 mL of a 10% hexane solution of tri(tert-butyl)phosphine were added to this mixture.

The temperature of this mixture was set to 60° C., 46.7 mg (0.1 mmol) of bis(dibenzylideneacetone)palladium(0) was added, and the mixture was stirred at 80° C. for 3.0 hours. After the stirring, suction filtration was carried out through Florisil, Celite, and alumina to obtain filtrate.

The obtained filtrate was concentrated to give a solid. The given solid was purified by silica gel column chromatography (the developing solvent was hexane and toluene (hexane:toluene=7:3)), and the obtained fraction was concentrated. The solid given by the concentration was recrystallized with chloroform and hexane, so that 0.7 g of an objective yellow solid was obtained in a yield of 45%.

Then, 0.6 g of the obtained yellow solid was sublimated and purified by a train sublimation method. The conditions for the sublimation purification were as follows: the pressure was 3.1 Pa, the argon gas flow rate was 4.0 mL/min, and the heating temperature of the yellow solid was 305° C. After the sublimation purification, 0.5 g of a yellow solid was obtained in a yield of 83%. The synthesis scheme of Step 2 is shown in (B1-2).

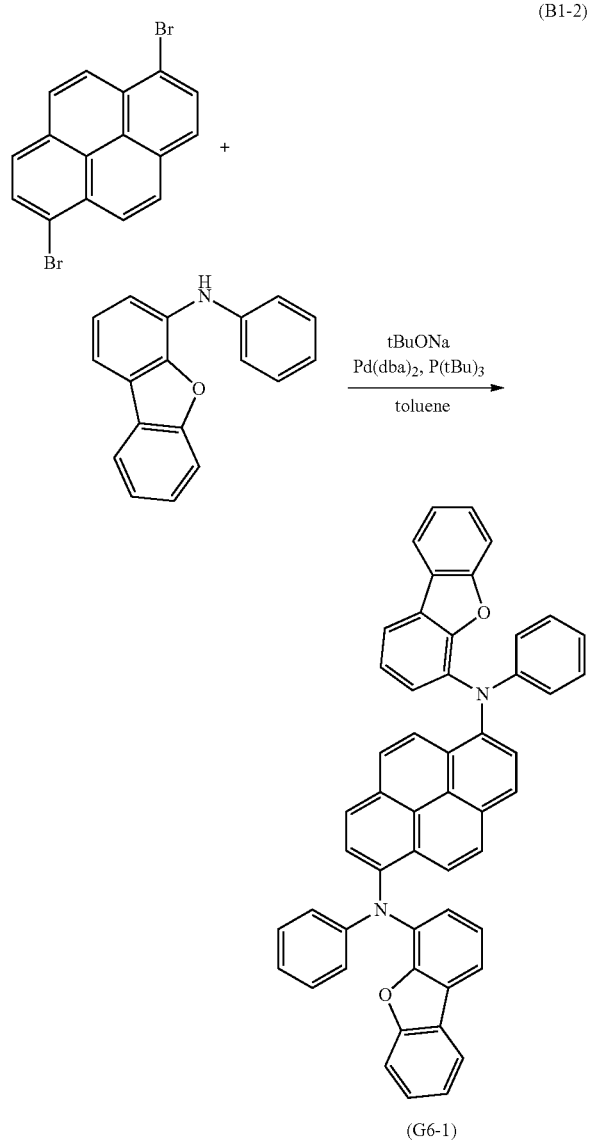

A nuclear magnetic resonance (NMR) method and a mass spectrometry identified the compound obtained in the above step as N,N'-bis(dibenzofuran-4-yl)-N,N'-diphenyl-pyrene-1,6-diamine (abbreviation: 1,6FrAPm-II), which was the objective substance.

The $^1$H-NMR data of the obtained compound are shown below.

$^1$H-NMR (CDCl$_3$, 300 MHz): δ=6.86 (d, J=7.8 Hz, 4H), 6.93 (t, J=7.2 Hz, 2H), 7.11-7.22 (m, 8H), 7.31-7.41 (m, 6H), 7.70 (d, J=6.8 Hz, 2H), 7.88-7.97 (m, 6H), 8.08 (d, J=8.4 Hz, 2H), 8.25 (d, J=9.0 Hz, 2H)

Figure 9A:
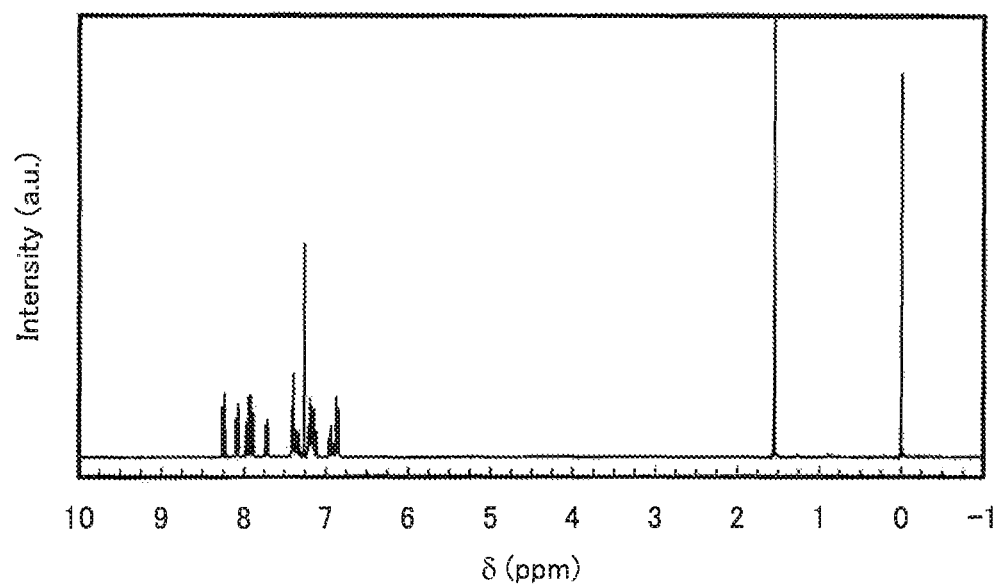
FIGS. 9A and 9B show $^1$H-NMR charts of 1,6FrAPm-II.
Figure 9B:
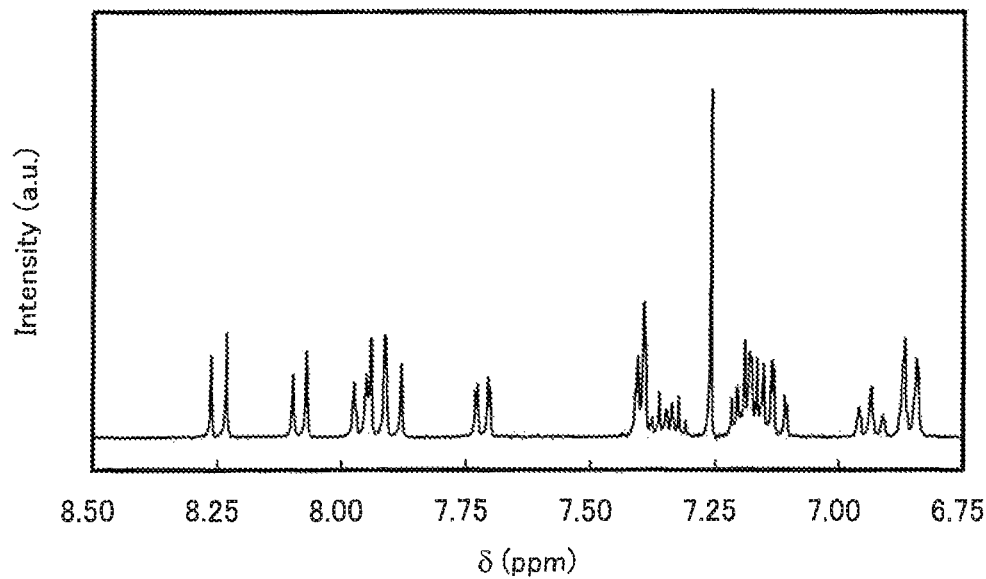

In addition, the $^1$H-NMR charts are shown in FIGS. 9A and 9B. Note that FIG. 9B is a chart showing an enlarged part of FIG. 9A in the range of 6.75 ppm to 8.50 ppm.

The measurement results of the electro spray ionization mass spectrum (ESI-MS) of the obtained compound are shown below.

MS (ESI-MS): m/z=717 (M+H)$^+$; C$_{52}$H$_{32}$N$_2$O$_2$ (716.25).

Figure 10A:
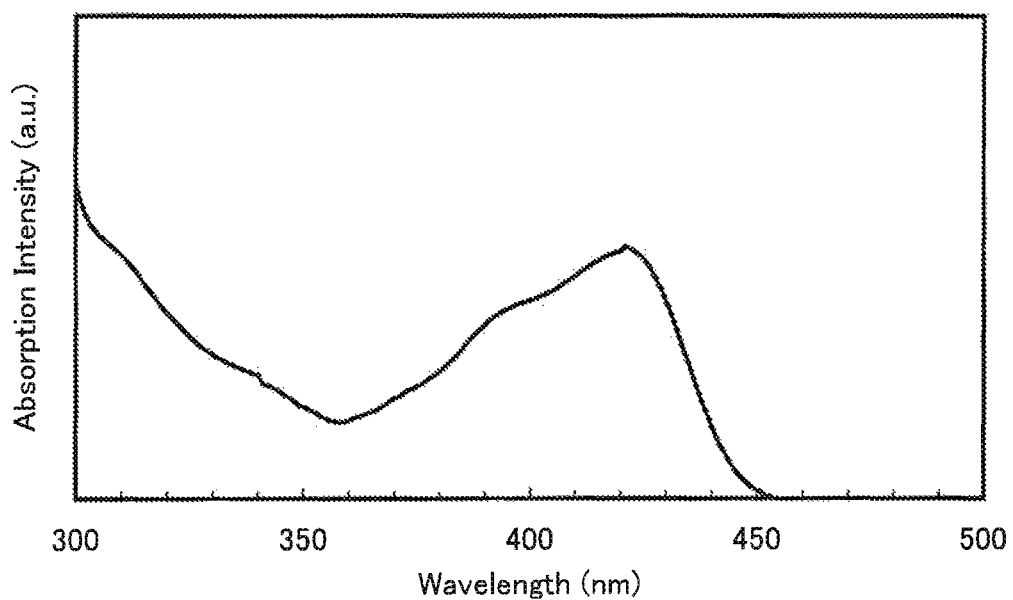
FIGS. 10A and 10B show an absorption spectrum and an emission spectrum of 1,6FrAPm-II in a toluene solution.
Figure 10B:
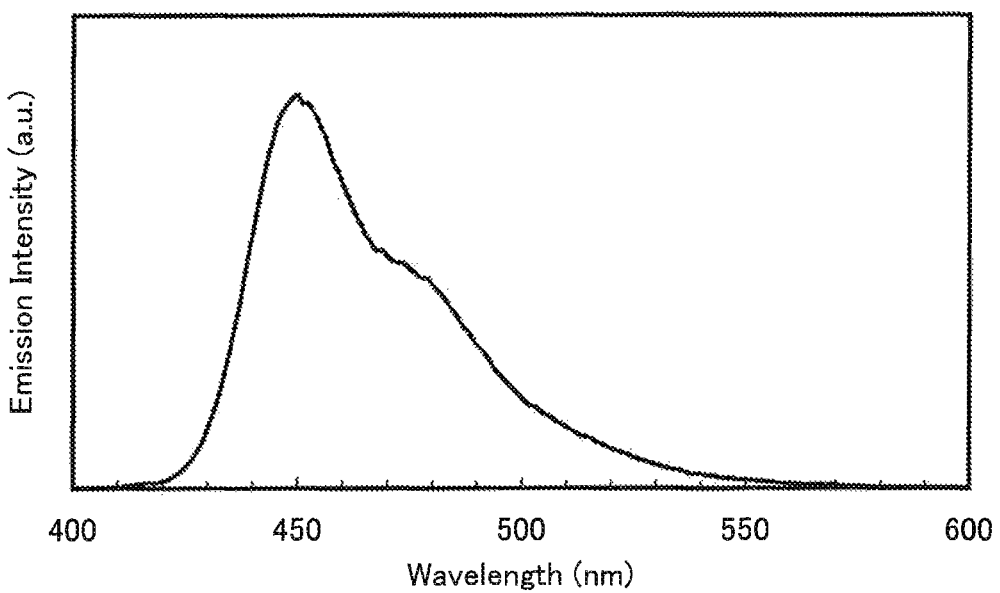
Figure 11A:
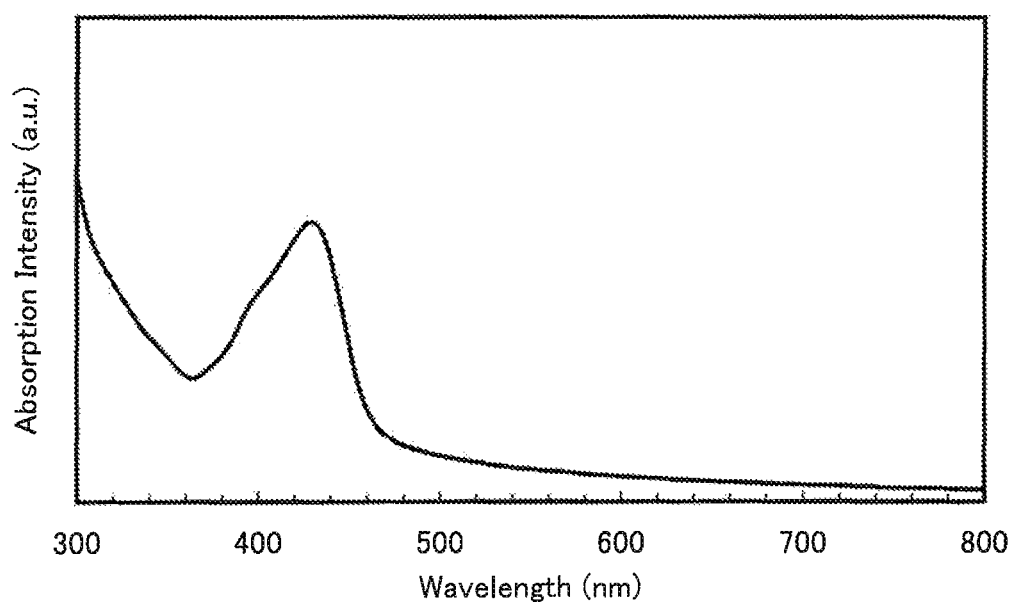
FIGS. 11A and 11B show an absorption spectrum and an emission spectrum of 1,6FrAPm-II in a thin film.
Figure 11B:
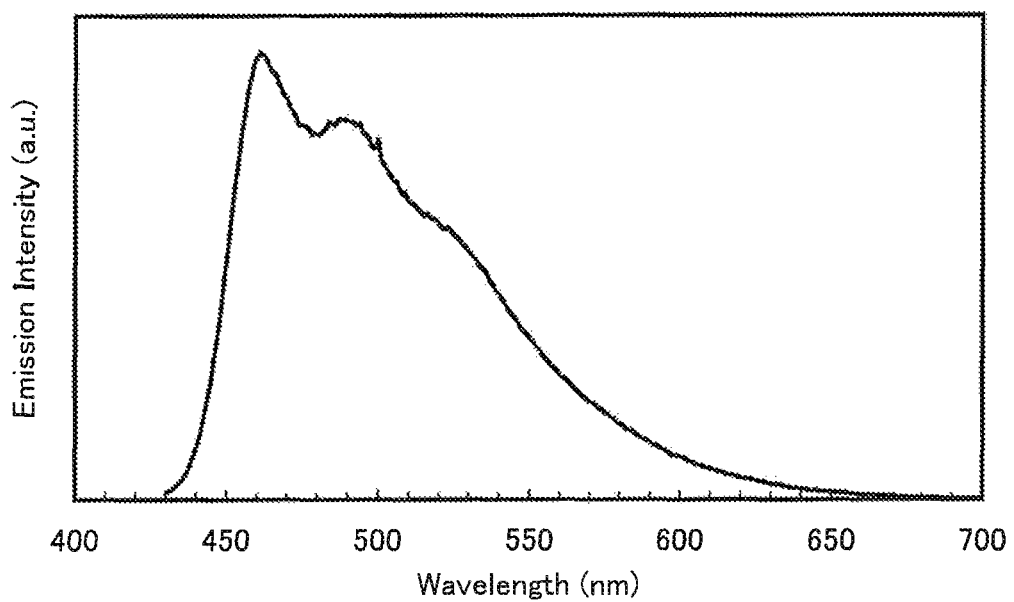

Further, an absorption spectrum of 1,6FrAPm-II in a toluene solution is shown in FIG. 10A, and an emission spectrum thereof is shown in FIG. 10B. In addition, an absorption spectrum of 1,6FrAPm-II in a thin film is shown in FIG. 11A, and an emission spectrum thereof is shown in FIG. 11B. The absorption spectra were measured using a UV-visible spectrophotometer (V-550, manufactured by JASCO Corporation). The emission spectra were measured using a fluorescence spectrophotometer (FS920, manufactured by Hamamatsu Photonics Corporation). The measurements were performed on samples obtained in such a manner that the solution was put in a quartz cell and the thin film was obtained by evaporation onto a quartz substrate. Each of the absorption spectra in FIG. 10A and FIG. 11A was obtained by subtracting a reference spectrum. The reference spectrum used for the absorption spectrum in FIG. 10A is an absorption spectrum of toluene alone in a quartz cell, and the reference spectrum used for the absorption spectrum in FIG. 11A is an absorption spectrum of a quartz substrate. Note that the horizontal axes indicate wavelength (nm) and the vertical axes indicate intensity (arbitrary unit) in FIGS. 10A and 10B and FIGS. 11A and 11B. In the case of the toluene solution, absorption was observed at approximately 421 nm, and the maximum emission wavelength was 450 nm (excitation wavelength: 370 nm). In the case of the thin film, absorption was observed at approximately 430 nm, and peaks of the emission spectrum were 461 nm and 488 nm (excitation wavelength: 428 nm).

From the results, the Stokes shift of 1,6FrAPm-II in the toluene solution is found to be as small as 29 nm.

The HOMO level and the LUMO level of 1,6FrAPm-II in the thin film were measured. The value of the HOMO level was obtained by conversion of a value of the ionization potential measured using a photoelectron spectrometer (AC-2, manufactured by Riken Keiki Co., Ltd.) in the air into a negative value. The value of the LUMO level was obtained in such a manner that the absorption edge, which was obtained from Tauc plot with an assumption of direct transition using data on the absorption spectrum of the thin film of 1,6FrAPm-II shown in FIG. 11B, was regarded as an optical energy gap and was added to the value of the HOMO level. As a result, the HOMO level of 1,6FrAPm-II was −5.57 eV, the energy gap was 2.72 eV, and the LUMO level was −2.85 eV.

Next, the oxidation-reduction characteristics were examined by cyclic voltammetry (CV) measurement. Note that an electrochemical analyzer (ALS model 600A or 600C, manufactured by BAS Inc.) was used for the measurement. Note that a method for the measurement is described in detail below.

(Calculation of Potential Energy of Reference Electrode with Respect to Vacuum Level)

First, a potential energy (eV) of the reference electrode (Ag/Ag$^+$ electrode), which was used in this example, with respect to the vacuum level was calculated. That is, the Fermi level of the Ag/Ag$^+$ electrode was calculated. It is known that the oxidation-reduction potential of ferrocene in methanol is +0.610 [V vs. SHE] with respect to the normal hydrogen electrode (Reference: Christian R. Goldsmith et al., J. Am. Chem. Soc., Vol. 124, No. 1, 83-96, 2002). On the other hand, using the reference electrode used in this example, the oxidation-reduction potential of ferrocene in methanol was calculated to be +0.11 V [vs. Ag/Ag$^+$]. Therefore, it is found that the potential energy of the reference electrode used in this example was lower than that of the normal hydrogen electrode by 0.50 [eV].

Note that it is known that the potential energy of the normal hydrogen electrode from the vacuum level is −4.44 eV (Reference: Toshihiro Ohnishi and Tamami Koyama, *Kobunshi EL Zairyou* [*High Molecular EL Material*], Kyoritsu Shuppan, pp. 64-67). From the above, the potential energy of the reference electrode with respect to the vacuum level was calculated to be −4.44−0.50=−4.94 [eV].

(CV Measurement of Objective Substance)

As for a solution used for the CV measurement, dehydrated dimethylformamide (DMF, manufactured by Sigma-Aldrich Inc., 99.8%, catalog No. 22705-6) was used as a solvent, and tetra-n-butylammonium perchlorate (n-Bu$_4$NClO$_4$, manufactured by Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. In addition, a platinum electrode (PTE platinum electrode, manufactured by BAS Inc.,) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. Note that the measurement was conducted at room temperature (20° C. to 25° C.). In addition, the scan rate at the CV measurement was set to 0.1 V/sec in all the measurement.

By using this solution, the CV measurement of the objective substance was carried out. The potential of the working electrode with respect to the reference electrode was scanned from −0.10 V to 1.50 V and then from 1.50 V to −0.10 V, whereby a distinct peak indicating oxidation was observed. The shape of the peak did not greatly change even after 100 scan cycles. As a result, 1,6FrAPm-II is found to have favorable characteristics with respect to repetition of the oxidation reduction between an oxidation state and a neutral state.

Note that in this CV measurement, the oxidation peak potential (from the neutral state to the oxidation state) $E_{pa}$ was 0.58 V. In addition, the reduction peak potential (from the oxidation side to the neutral state) $E_{pc}$ was 0.46 V. Therefore, a half-wave potential (an intermediate potential between $E_{pa}$ and $E_{pc}$, ($E_{pa}+E_{pc}$)/2 [V]) can be calculated to be 0.52 V. This shows that 1,6FrAPm-II is oxidized by an electrical energy of 0.52 [V vs. Ag/Ag$^+$]. Here, since the potential energy of the reference electrode, which was used above, with respect to the vacuum level is −4.94 [eV] as described above, the HOMO level of 1,6FrAPm-II was calculated as follows: −4.94−0.52=−5.46 [eV].

Thermogravimetry-differential thermal analysis (TG-DTA) of 1,6FrAPm-II was performed. The measurement was conducted by using a high vacuum differential type differential thermal balance (TG/DTA 2410SA, manufactured by Bruker AXS K.K.). The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 420° C., which is indicative of high heat resistance.

Example 2

In this example, an example of obtaining N,N'-bis(dibenzothiophene-4-yl)-N,N'-diphenyl-pyrene-1,6-diamine (abbreviation: 1,6ThAPm-II) represented by Structural Formula (G6-2) is described.

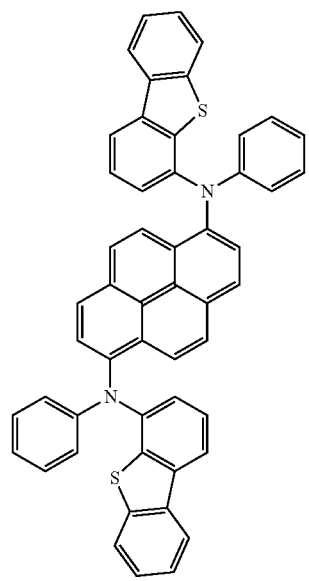

(G6-2)

Step 1: Synthesis method of N-(dibenzothiophene-4-yl)-N-phenyl-amine (abbreviation: ThA-II)

First, 4.7 g (15.3 mmol) of 4-iododibenzothiophene and 4.5 g (4.6 mmol) of sodium tert-butoxide were put in a 300 mL three-neck flask, and the air in the flask was replaced by nitrogen. Then, 98.0 mL of toluene, 2.7 mL (18.3 mmol) of aniline, and 0.3 mL of a 10% hexane solution of tri(tert-butyl)phosphine were added to this mixture.

The temperature of this mixture was set to 60° C., 69.8 mg (0.1 mmol) of bis(dibenzylideneacetone)palladium(0) was added, and the mixture was stirred at 80° C. for 14 hours. After the stirring, suction filtration was carried out through Florisil, Celite, and alumina to obtain filtrate.

The obtained filtrate was concentrated to give a solid. The given solid was purified by silica gel column chromatography (the developing solvent was hexane and toluene (hexane:toluene=4:1)). The obtained fraction was concentrated, so that 3.9 g of an objective substance was obtained in a yield of 90%. The synthesis scheme of Step 1 is shown in (B2-1).

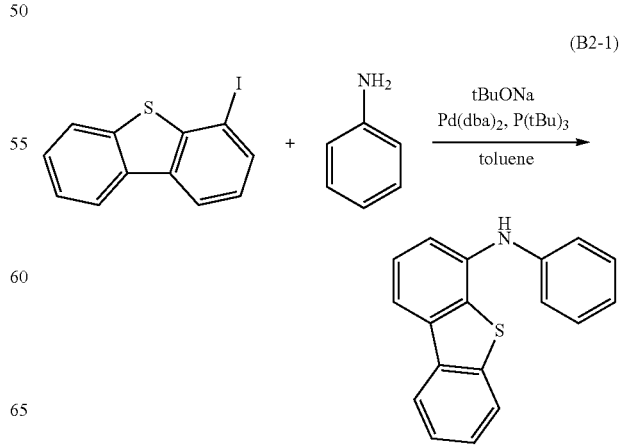

(B2-1)

By a nuclear magnetic resonance (NMR) method, the compound obtained in the above step was confirmed to be N-(dibenzothiophene-4-yl)-N-phenyl-amine (abbreviation: ThA-II).

The $^1$H-NMR data of the obtained compound are shown below.

$^1$H-NMR (CDCl$_3$, 300 MHz): δ=5.66 (s, 1H), 6.95-7.00 (m, 1H), 7.07-7.10 (m, 2H), 7.27-7.50 (m, 6H), 7.83-7.89 (m, 2H), 8.13-8.19 (m, 1H)

Figure 12A:
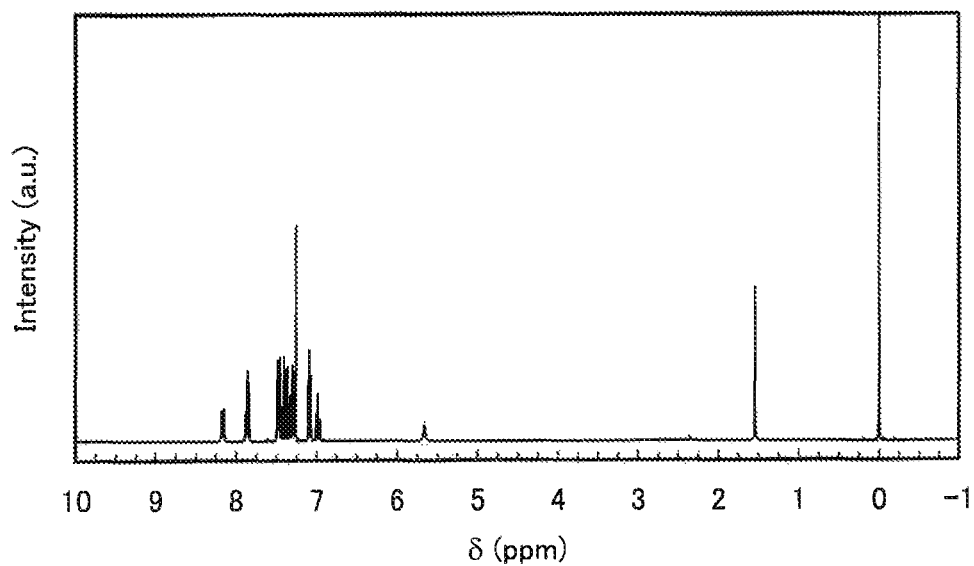
FIGS. 12A and 12B show $^1$H-NMR charts of ThA-II.
Figure 12B:
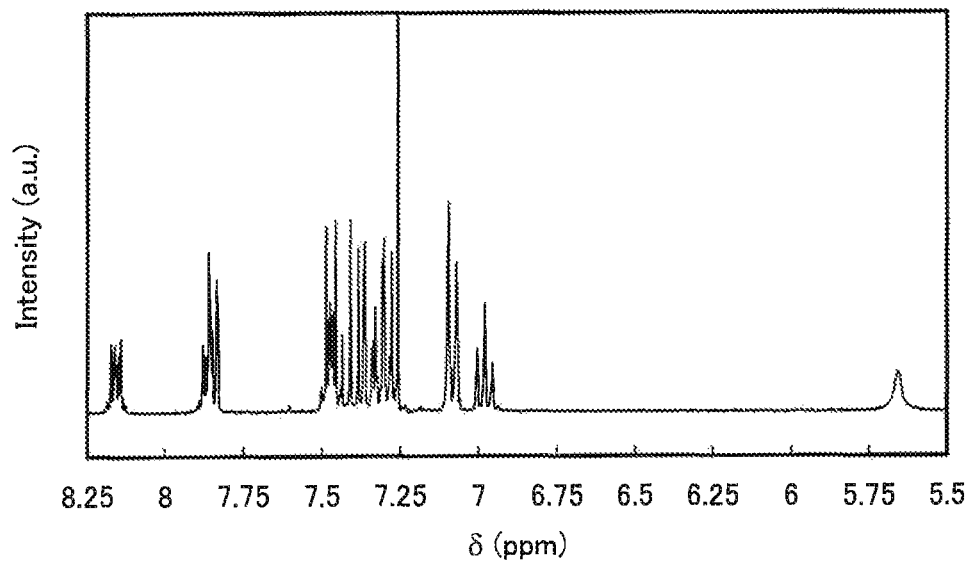

In addition, the $^1$H-NMR charts are shown in FIGS. 12A and 12B. Note that FIG. 12B is a chart showing an enlarged part of FIG. 12A in the range of 5.50 ppm to 8.25 ppm.

Step 2: Synthesis method of N,N'-bis(dibenzothiophene-4-yl)-N,N'-diphenyl-pyrene-1,6-diamine (abbreviation: 1,6ThAPm-II)

Next, 0.7 g (2.0 mmol) of 1,6-dibromopyrene, 1.1 g (4.0 mmol) of N-(dibenzothiophene-4-yl)-N-phenyl-amine, and 0.6 g (6.0 mmol) of sodium tert-butoxide were put in a 300 mL three-neck flask, and the air in the flask was replaced by nitrogen. Then, 20.0 mL of toluene and 0.3 mL of a 10% hexane solution of tri(tert-butyl)phosphine were added to this mixture.

The temperature of this mixture was set to 60° C., 40.3 mg (0.1 mmol) of bis(dibenzylideneacetone)palladium(0) was added, and the mixture was stirred at 80° C. for 3.5 hours. After the stirring, 400 mL of chloroform was added to the mixture, and suction filtration through Florisil, Celite, and alumina was carried out to obtain filtrate.

The obtained filtrate was concentrated to give a solid. The given solid was purified by silica gel column chromatography (the developing solvent was hexane and toluene (hexane:toluene=7:3)), and the obtained fraction was concentrated.

The solid given by the concentration was recrystallized with chloroform and hexane, so that 0.6 g of an objective yellow solid was obtained in a yield of 39%. Then, 0.6 g of the obtained yellow solid was sublimated and purified by a train sublimation method. The conditions for the sublimation purification were as follows: the pressure was 2.5 Pa, the argon gas flow rate was 5.0 mL/min, and the heating temperature of the yellow solid was 313° C. After the sublimation purification, 0.5 g of a yellow solid was obtained in a yield of 82%. The synthesis scheme of Step 2 is shown in (B2-2).

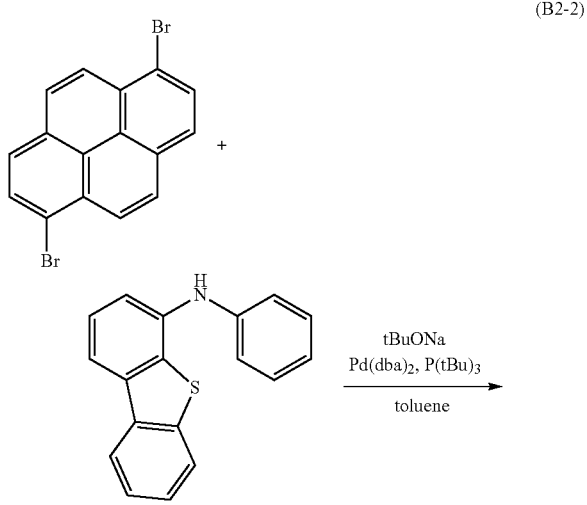

(B2-2)

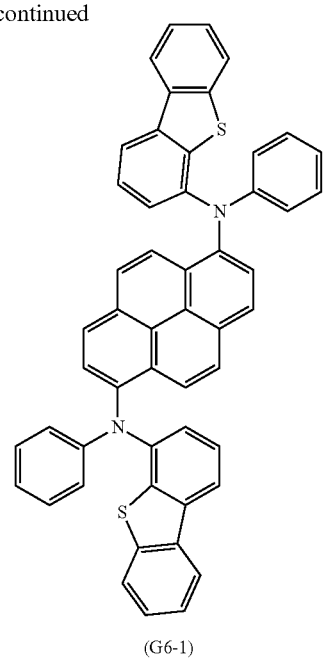

(G6-1)

A nuclear magnetic resonance (NMR) method and a mass spectrometry identified the compound obtained in the above step as N,N-bis(dibenzothiophene-4-yl)-N,N-diphenyl-pyrene-1,6-diamine (abbreviation: 1,6ThAPm-II), which was the objective substance.

The $^1$H-NMR data of the obtained compound are shown below.

$^1$H-NMR (CDCl$_3$, 300 MHz): δ=6.92-7.02 (m, 6H), 7.20-7.27 (m, 6H), 7.35-7.46 (m, 6H), 7.66-7.69 (m, 2H), 7.81 (d, J=8.4 Hz, 2H), 7.87 (d, J=9.0 Hz, 2H), 7.96 (d, J=7.8 Hz, 2H), 8.03 (d, J=8.4 Hz, 2H), 8.15-8.18 (m, 4H)

Figure 13A:
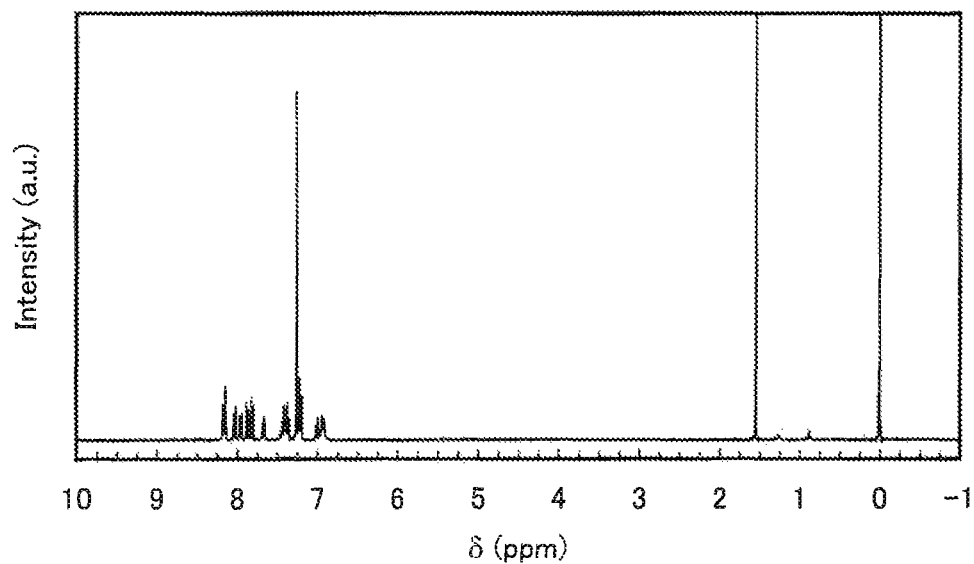
FIGS. 13A and 13B show $^1$H-NMR charts of 1,6ThAPm-II.
Figure 13B:
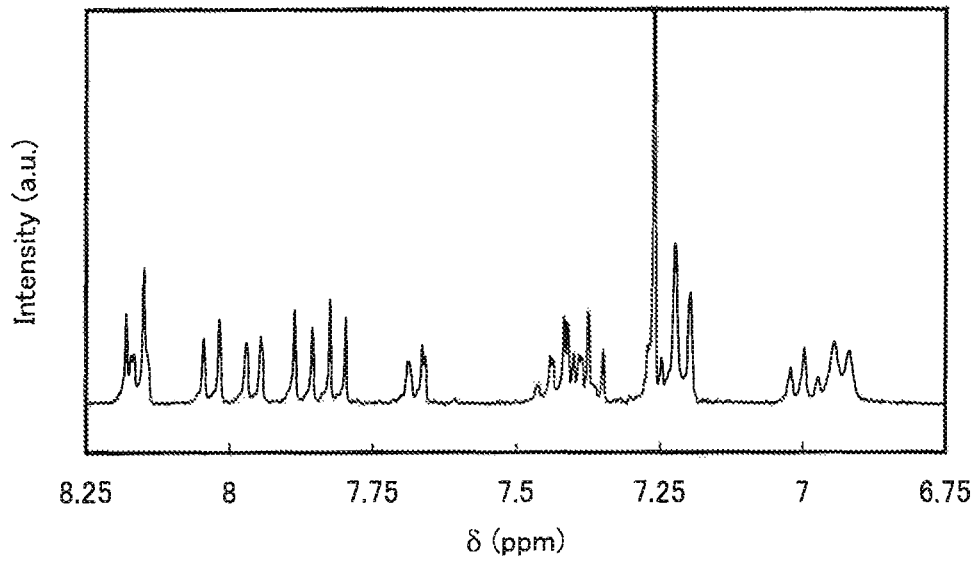

In addition, the $^1$H-NMR charts are shown in FIGS. 13A and 13B. Note that FIG. 13B is a chart showing an enlarged part of FIG. 13A in the range of 6.75 ppm to 8.25 ppm.

The measurement results of the mass spectrometry of the obtained compound are shown below.

MS (ESI-MS): m/z=748 (M+H)$^+$; C$_{52}$H$_{32}$N$_2$S$_2$ (748.2)

Figure 14A:
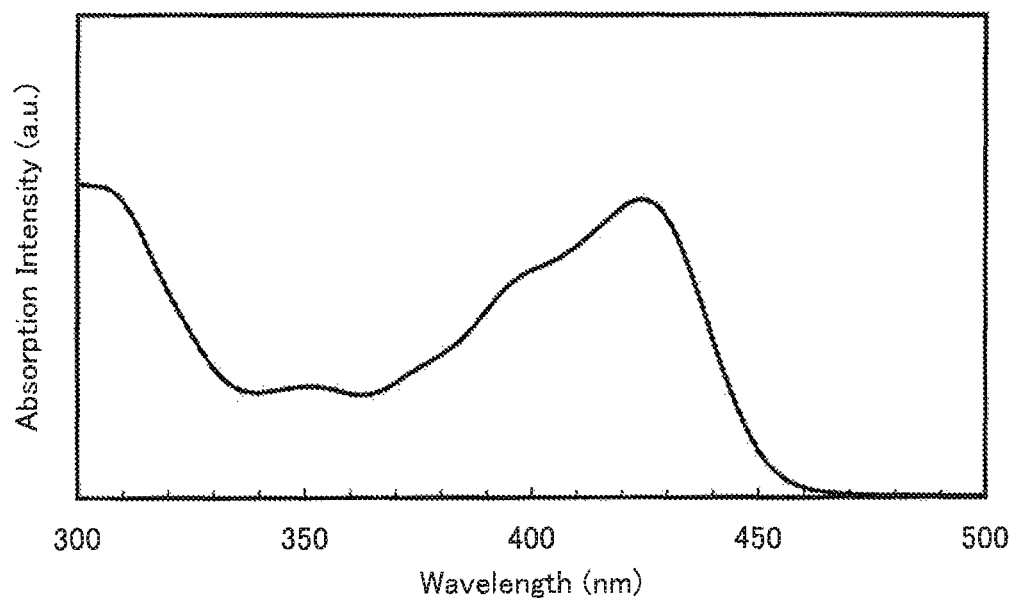
FIGS. 14A and 14B show an absorption spectrum and an emission spectrum of 1,6ThAPm-II in a toluene solution.
Figure 14B:
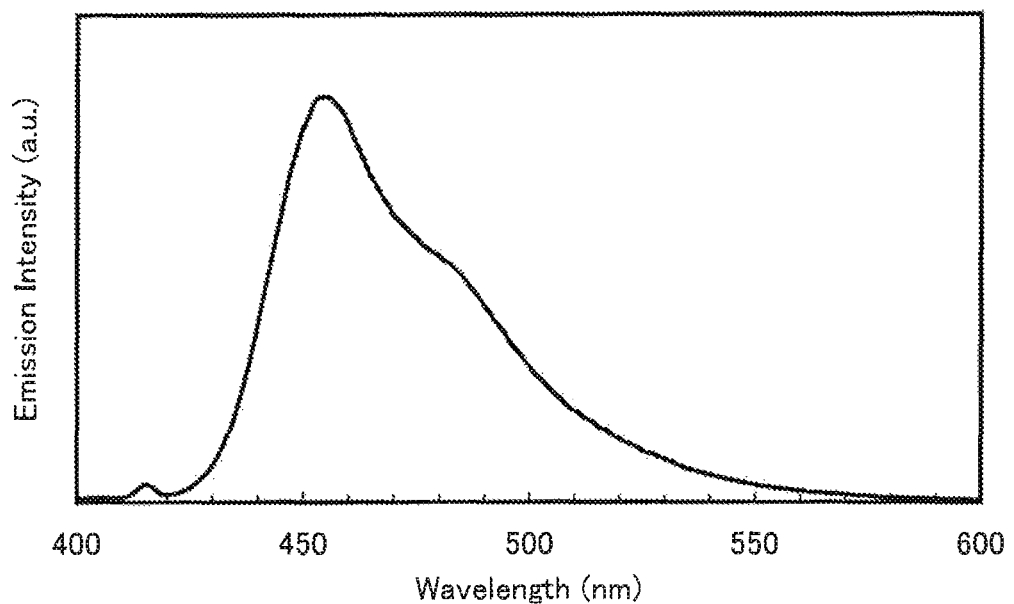
Figure 15A:
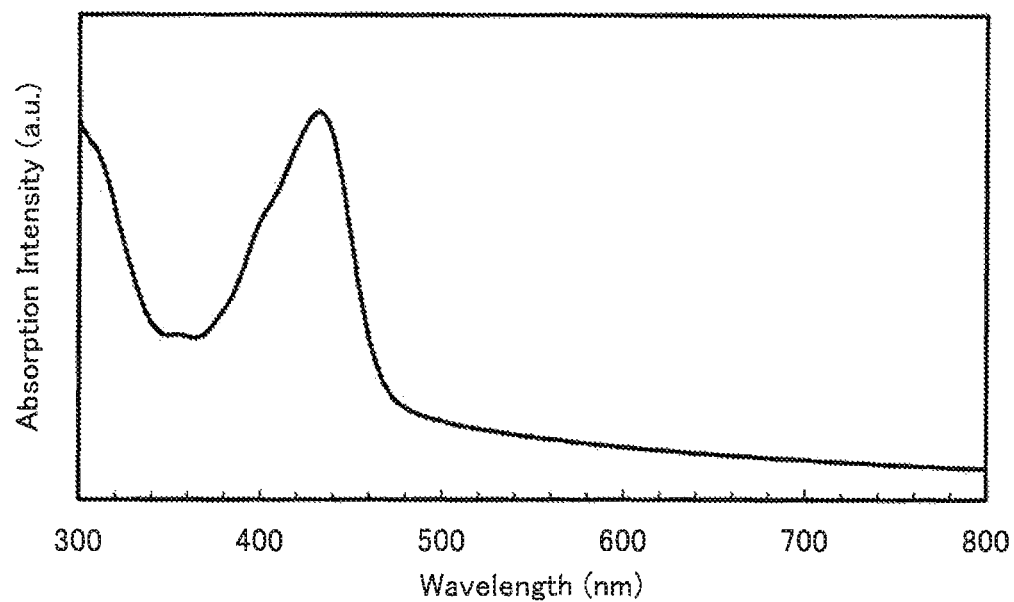
FIGS. 15A and 15B show an absorption spectrum and an emission spectrum of 1,6ThAPm-II in a thin film.
Figure 15B:
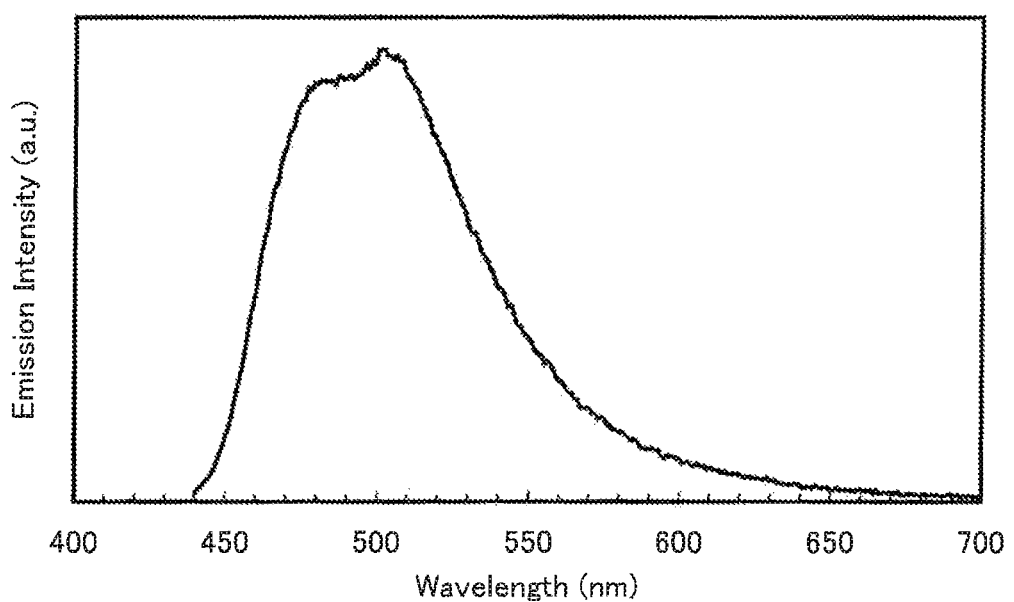

Further, an absorption spectrum of 1,6ThAPm-II in a toluene solution is shown in FIG. 14A, and an emission spectrum thereof is shown in FIG. 14B. In addition, an absorption spectrum of 1,6ThAPrn-II in a thin film is shown in FIG. 15A, and an emission spectrum thereof is shown in FIG. 15B. The measurements of the absorption spectra and the emission spectra were performed using the same device and measurement method as those in Example 1. Each of the absorption spectra in FIG. 14A and FIG. 15A was obtained by subtracting a reference spectrum, as in Example 1. Note that the horizontal axes indicate wavelength (nm) and the vertical axes indicate intensity (arbitrary unit) in FIGS. 14A and 14B and FIGS. 15A and 15B. In the case of the toluene solution, absorption was observed at approximately 424 nm, and the maximum emission wavelength was 455 nm (excitation wavelength: 370 nm). In the case of the thin film, absorption was observed at approximately 432 nm, and peaks of the emission spectrum were 483 nm and 501 nm (excitation wavelength: 438 nm).

From the results, the Stokes shift of 1,6ThAPm-II in the toluene solution is found to be as small as 31 nm.

The HOMO level and the LUMO level of 1,6ThAPm-II in the thin film were measured using the same device and measurement method as those in Example 1. As a result, the HOMO level of 1,6ThAPm-II was −5.49 eV, the energy gap was 2.69 eV, and the LUMO level was −2.80 eV.

The oxidation-reduction characteristics were examined by CV measurement, as in Example 1.

In the CV measurement in this example, the potential of the working electrode with respect to the reference electrode was scanned from −0.10 V to 0.6 V and then from 0.6 V to −0.10 V, whereby a distinct peak indicating oxidation was observed. The shape of the peak did not greatly change even after 100 scan cycles. As a result, 1,6ThAPm-II is found to have favorable characteristics with respect to repetition of the oxidation reduction between an oxidation state and a neutral state.

Note that in this CV measurement, the oxidation peak potential (from the neutral state to the oxidation state) $E_{pa}$ was 0.59 V. In addition, the reduction peak potential (from the oxidation side to the neutral state) $E_{pc}$ was 0.48 V. Therefore, a half-wave potential (an intermediate potential between $E_{pa}$ and $E_{pc}$, $(E_{pa}+E_{pc})/2$ [V]) can be calculated to be 0.54 V. This shows that 1,6ThAPm-II is oxidized by an electrical energy of 0.54 [V vs. Ag/Ag$^+$]. Here, since the potential energy of the reference electrode, which was used above, with respect to the vacuum level is −4.94 [eV] as described above, the HOMO level of 1,6ThAPm-II was calculated as follows: −4.94−0.54=−5.48 [eV].

Thermogravimetry-differential thermal analysis of 1,6ThAPm-II was performed using the same device and measurement method as those in Example 1. The relationship between weight and temperature (thermogravimetry) shows that the 5% weight loss temperature of 1,6ThAPm-II is 458° C., which is indicative of high heat resistance.

Example 3

In this example, an example of obtaining N,N'-bis(dibenzofuran-2-yl)-N,N'-diphenyl-pyrene-1,6-diamine (abbreviation: 1,6FrAPm) represented by Structural Formula (G10-1) is described.

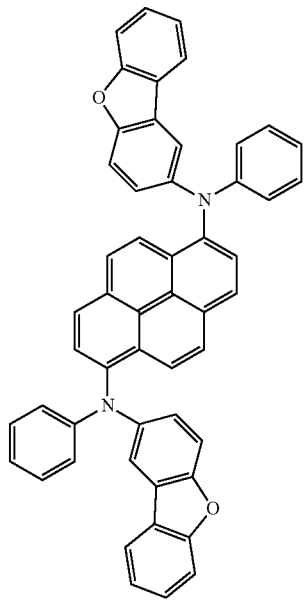

(G10-1)

First, 0.9 g (2.5 mmol) of 1,6-dibromopyrene, 1.3 g (5.0 mmol) of N-(dibenzofuran-2-yl)-N-phenyl-amine, and 0.7 g (7.4 mmol) of sodium tert-butoxide were put in a 100 mL three-neck flask, and the air in the flask was replaced by nitrogen.

Then, 25.0 mL of toluene and 0.3 mL of a 10% hexane solution of tri(tert-butyl)phosphine were added to this mixture. The temperature of this mixture was set to 80° C., 34.9 mg (0.06 mmol) of bis(dibenzylideneacetone)palladium(0) was added, and the mixture was stirred for 7 hours. After the stirring, suction filtration was carried out through Florisil, Celite, and alumina to obtain filtrate.

The obtained filtrate was concentrated to give a solid, which was then purified by silica gel column chromatography (the developing solvent was hexane and toluene (hexane:toluene=7:3)), and the obtained fraction was concentrated. The given solid was recrystallized with toluene and hexane, so that 1.3 g of an objective yellow solid was obtained in a yield of 71%.

Then, 1.2 g of the obtained yellow solid was sublimated and purified by a train sublimation method. The conditions for the sublimation purification were as follows: the pressure was 2.4 Pa, the argon gas flow rate was 5.0 mL/min, and the heating temperature of the yellow solid was 302° C. After the sublimation purification, 1.1 g of a yellow prism crystal was obtained in a yield of 90%. The synthesis scheme of the above synthesis example is shown in (C1-1).

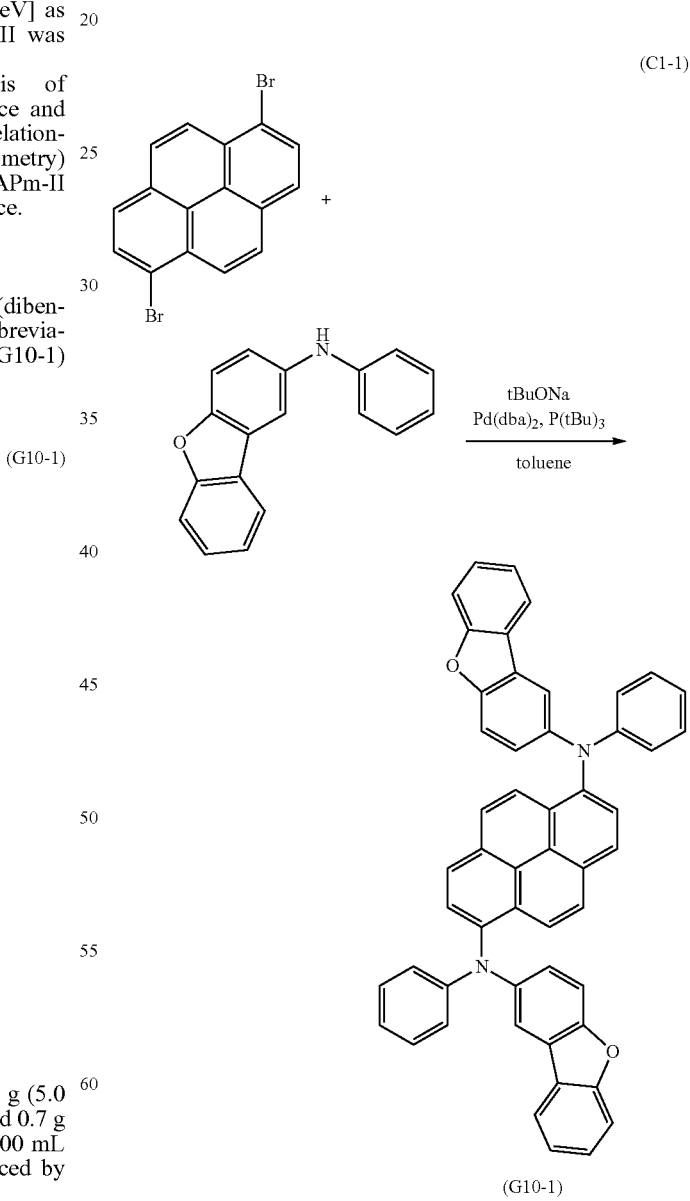

(C1-1)

A nuclear magnetic resonance (NMR) method and a mass spectrometry identified the compound obtained in the above step as N,N'-bis(dibenzofuran-2-yl)-N,N'-diphenyl-pyrene-1,6-diamine (abbreviation: 1,6FrAPm), which was the objective substance.

The ¹H-NMR data of the obtained compound are shown below.

¹H-NMR (CDCl₃, 300 MHz): δ=6.94 (t, J=6.9 Hz, 2H), 7.02 (d, J=7.8 Hz, 4H), 7.15-7.46 (m, 12H), 7.53 (d, J=8.4 Hz, 2H), 7.72-7.75 (m, 4H), 7.82-7.86 (m, 2H), 7.90-7.93 (m, 2H), 8.09-8.14 (m, 2H), 8.17-8.23 (m, 2H)

Figure 16A:
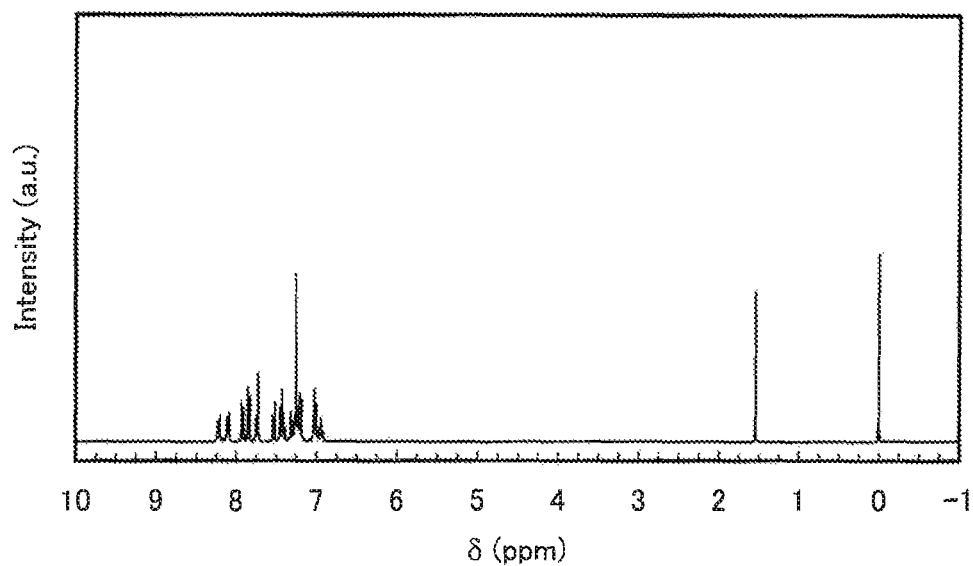
FIGS. 16A and 16B show $^1$H-NMR charts of 1,6FrAPm.
Figure 16B:
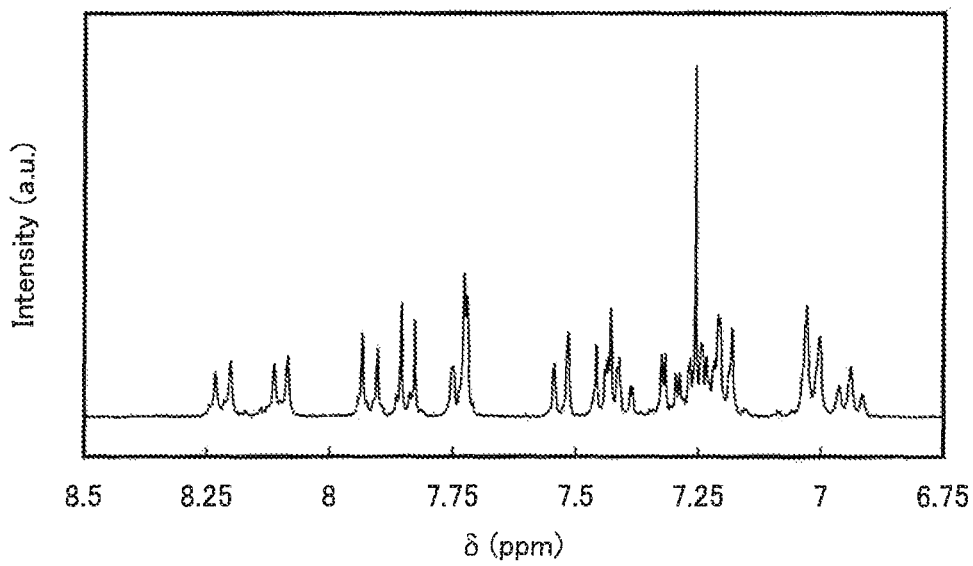

In addition, the ¹H-NMR charts are shown in FIGS. 16A and 16B. Note that FIG. 16B is a chart showing an enlarged part of FIG. 16A in the range of 6.75 ppm to 8.00 ppm.

The measurement results of the mass spectrometry of the obtained compound are shown below.

MS (ESI-MS): m/z=717 (M+H)$^+$; $C_{52}H_{32}N_2O_2$ (716.25)

Figure 17A:
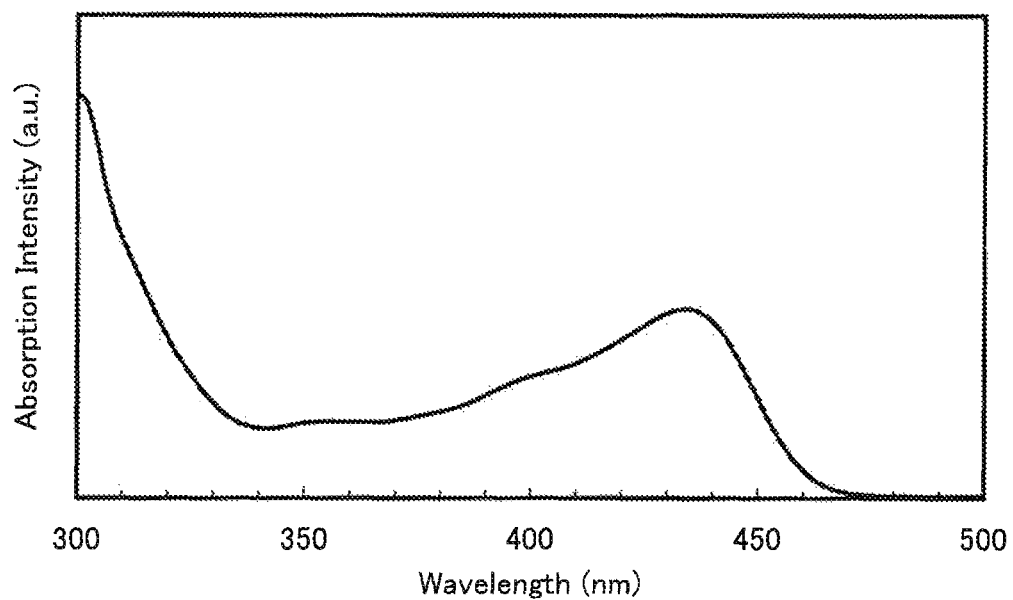
FIGS. 17A and 17B show an absorption spectrum and an emission spectrum of 1,6FrAPm in a toluene solution.
Figure 17B:
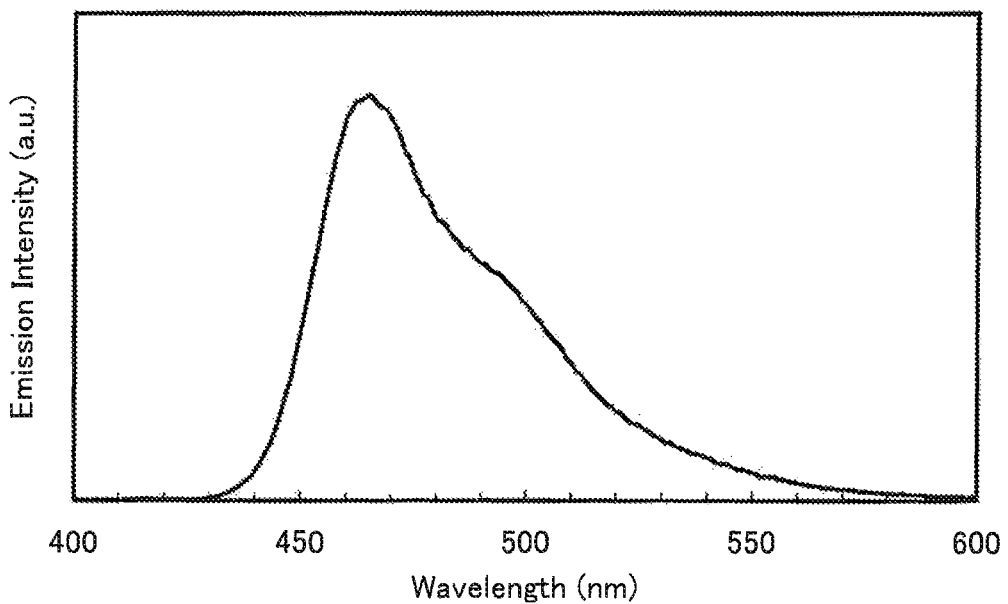
Figure 18A:
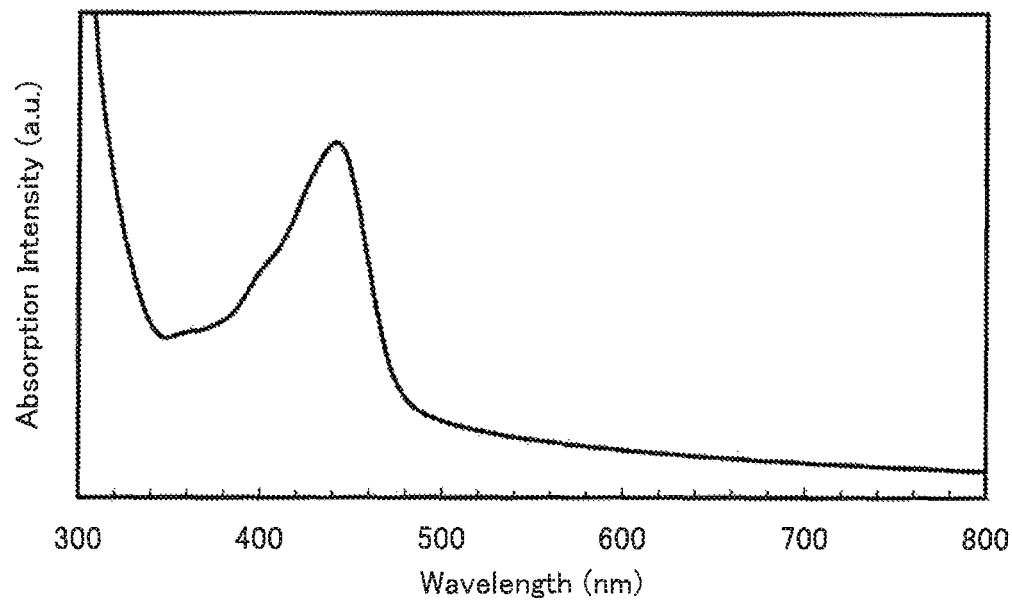
FIGS. 18A and 18B show an absorption spectrum and an emission spectrum of 1,6FrAPm in a thin film.
Figure 18B:
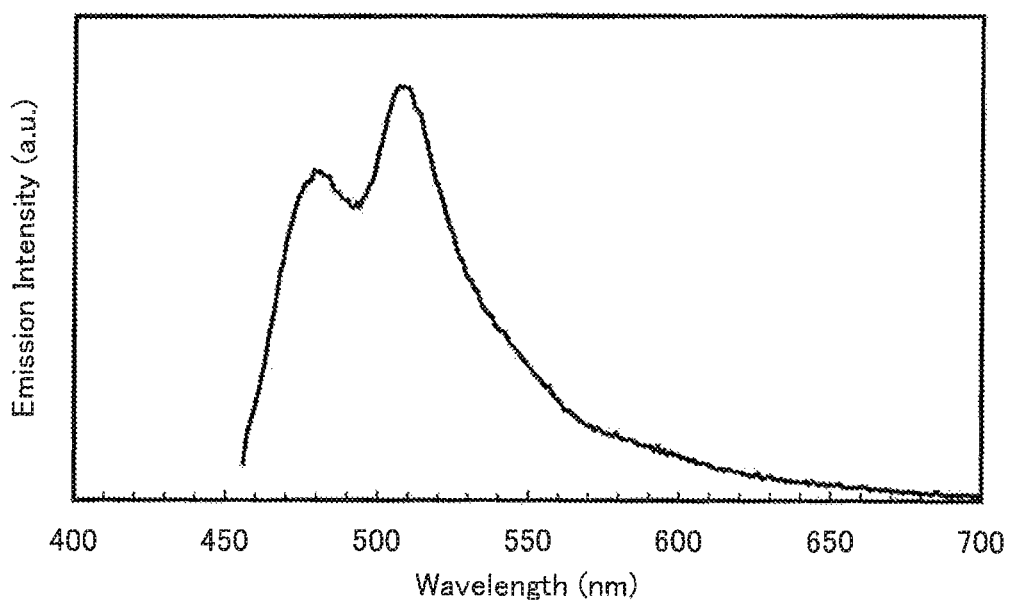

Further, an absorption spectrum of 1,6FrAPrn in a toluene solution is shown in FIG. 17A, and an emission spectrum thereof is shown in FIG. 17B. In addition, an absorption spectrum of 1,6FrAPrn in a thin film is shown in FIG. 18A, and an emission spectrum thereof is shown in FIG. 18B. The measurements of the absorption spectra and the emission spectra were performed using the same device and measurement method as those in Example 1. Each of the absorption spectra in FIG. 17A and FIG. 18A was obtained by subtracting a reference spectrum, as in Example 1. Note that the horizontal axes indicate wavelength (nm) and the vertical axes indicate intensity (arbitrary unit) in FIGS. 17A and 17B and FIGS. 18A and 18B. In the case of the toluene solution, absorption was observed at approximately 434 nm, and the maximum emission wavelength was 465 nm (excitation wavelength: 370 nm). In the case of the thin film, absorption was observed at approximately 441 nm, and peaks of the emission spectrum were 480 nm and 508 nm (excitation wavelength: 441 nm).

From the results, the Stokes shift of 1,6FrAPrn in the toluene solution is found to be as small as 31 nm.

The HOMO level and the LUMO level of 1,6FrAPm in the thin film were measured using the same device and measurement method as those in Example 1. As a result, the HOMO level of 1,6FrAPm was −5.48 eV, the energy gap was 2.64 eV, and the LUMO level was −2.84 eV.

The oxidation-reduction characteristics were examined by CV measurement, as in Example 1.

In the CV measurement in this example, the potential of the working electrode with respect to the reference electrode was scanned from −0.10 V to 0.6 V and then from 0.6 V to −0.10 V, whereby a distinct peak indicating oxidation was observed. The shape of the peak did not greatly change even after 100 scan cycles. As a result, 1,6FrAPm is found to have favorable characteristics with respect to repetition of the oxidation reduction between an oxidation state and a neutral state.

Note that in this CV measurement, the oxidation peak potential (from the neutral state to the oxidation state) $E_{pa}$ was 0.48 V. In addition, the reduction peak potential (from the oxidation side to the neutral state) $E_{pc}$ was 0.40 V. Therefore, a half-wave potential (an intermediate potential between $E_{pa}$ and $E_{pc}$, $(E_{pa}+E_{pc})/2$ [V]) can be calculated to be 0.44 V. This shows that 1,6FrAPm is oxidized by an electrical energy of 0.44 [V vs. Ag/Ag$^+$]. Here, since the potential energy of the reference electrode, which was used above, with respect to the vacuum level is −4.94 [eV] as described above, the HOMO level of 1,6FrAPm was calculated as follows: −4.94−0.44=−5.38 [eV].

Thermogravimetry-differential thermal analysis of 1,6FrAPm was performed using the same device and measurement method as those in Example 1. The relationship between weight and temperature (thermogravimetry) shows that the 5% weight loss temperature of 1,6FrAPm is 448° C., which is indicative of high heat resistance.

Example 4

In this example, an example of obtaining N,N'-bis(dibenzothiophene-2-yl)-N,N'-diphenyl-pyrene-1,6-diamine (abbreviation: 1,6ThAPm) represented by Structural Formula (G10-2) is described.

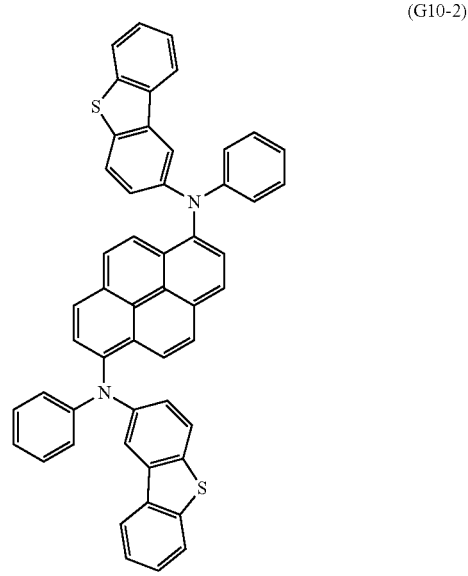 [SMILES: c1ccc(N(c2ccc3sc4ccccc4c3c2)c2ccc3ccc4c(N(c5ccccc5)c5ccc6sc7ccccc7c6c5)ccc5ccc2c3c54)cc1]

(G10-2)

First, 0.9 g (2.4 mmol) of 1,6-dibromopyrene, 1.3 g (4.8 mmol) of N-(dibenzothiophene-2-yl)-N-phenyl-amine, and 0.7 g (7.0 mmol) of sodium tert-butoxide were put in a 50 mL three-neck flask, and the air in the flask was replaced by nitrogen.

Then, 25.0 mL of toluene and 0.2 mL of a 10% hexane solution of tri(tert-butyl)phosphine were added to this mixture. The temperature of this mixture was set to 80° C., 25.7 mg (0.04 mmol) of bis(dibenzylideneacetone)palladium(0) was added, and the mixture was stirred for 2.0 hours.

After the stirring, the temperature of the mixture was set to 90° C., 26.0 mg (0.04 mmol) of bis(dibenzylideneacetone)palladium(0) was added, and the mixture was stirred for 3.5 hours. After the stirring, the temperature of the mixture was set to 80° C., 0.2 mL of a 10% hexane solution of tri(tert-butyl)phosphine was added, and the mixture was stirred for 1.0 hour. After the stirring, the temperature of this mixture was set to 85° C. and the mixture was stirred for 3.5 hours. After the stirring, suction filtration was carried out through Florisil, Celite, and alumina to obtain filtrate.

The obtained filtrate was concentrated to give a solid, which was then purified by silica gel column chromatography (the developing solvent was hexane and toluene (hexane:toluene=7:3)), and the obtained fraction was concentrated to give a yellow solid. The given solid was recrystallized with toluene and hexane, so that 0.6 g of a yellow solid was obtained in a yield of 34%.

Then, 0.6 g of the obtained yellow solid was sublimated and purified by a train sublimation method. The conditions for the sublimation purification were as follows: the pressure was 2.5 Pa, the argon gas flow rate was 5.0 mL/min, and the heating temperature of the yellow solid was 300° C. After the sublimation purification, 0.4 g of an objective yellow prism crystal was obtained in a yield of 74%. The synthesis scheme of the above synthesis example is shown in (C2-1).

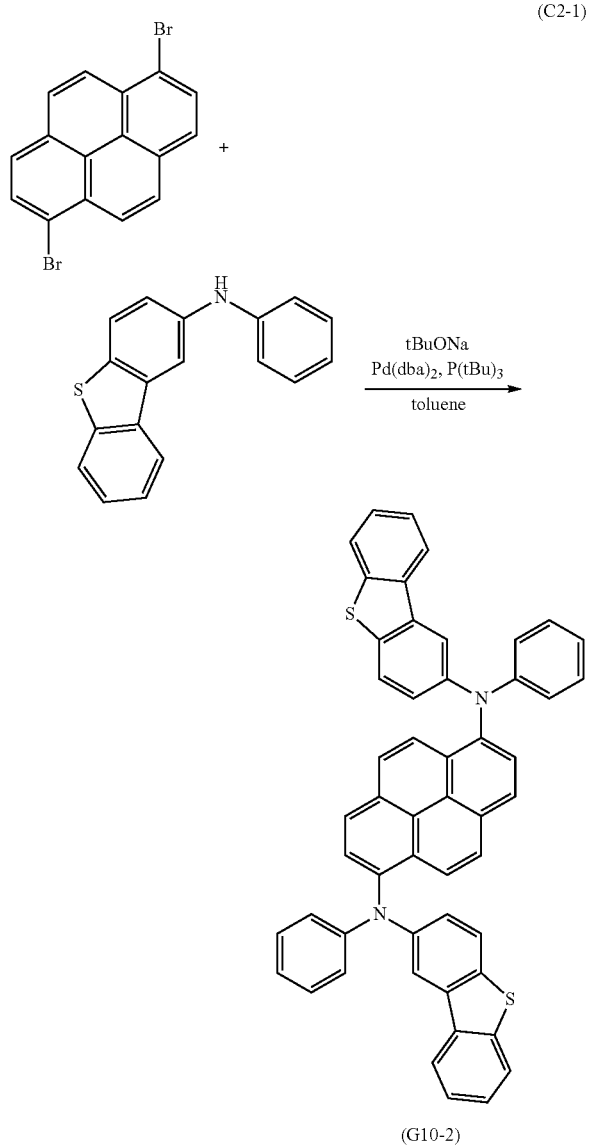

(G10-2)

A nuclear magnetic resonance (NMR) method and a mass spectrometry identified the compound obtained in the above step as N,N bis(dibenzothiophene-2-yl)-N,N-diphenyl-pyrene-1,6-diamine (abbreviation: 1,6ThAPm), which was the objective substance.

The $^1$H-NMR data of the obtained compound are shown below.

$^1$H-NMR (CDCl$_3$, 300 MHz): δ=6.95-7.00 (m, 2H), 7.08-7.11 (m, 4H), 7.02-7.42 (m, 10H), 7.68 (d, J=8.1 Hz, 2H), 7.80-7.94 (m, 10H), 8.11 (d, J=8.4 Hz, 2H), 8.21 (d, J=9.3 Hz, 2H)

Figure 19A:
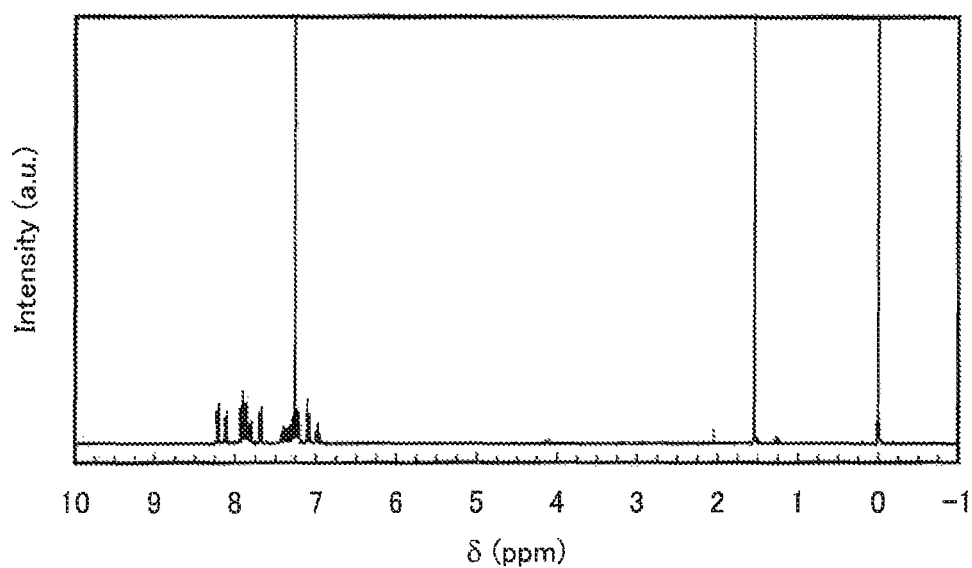
FIGS. 19A and 19B show $^1$H-NMR charts of 1,6ThAPm.
Figure 19B:
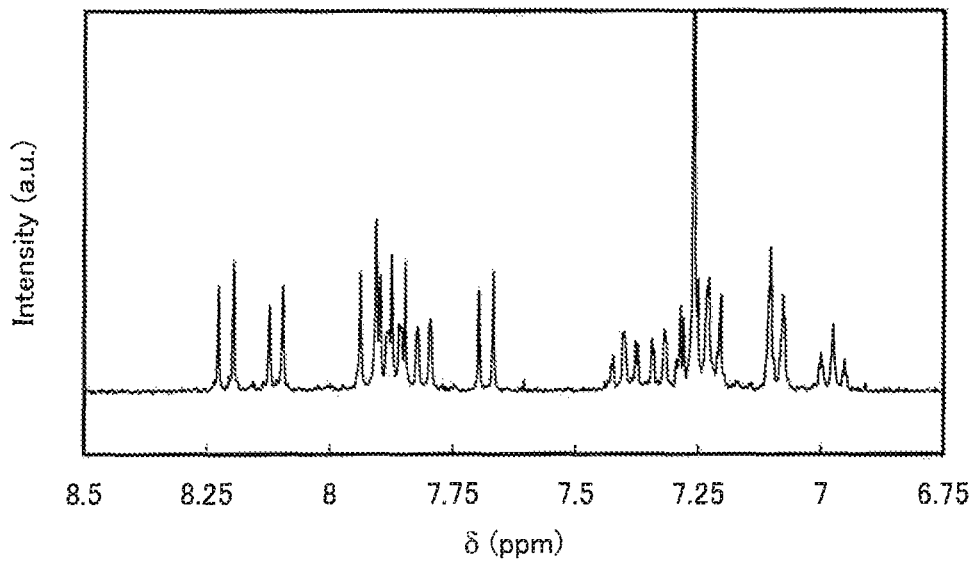

In addition, the $^1$H-NMR charts are shown in FIGS. 19A and 19B. Note that FIG. 19B is a chart showing an enlarged part of FIG. 19A in the range of 6.75 ppm to 8.50 ppm.

The measurement results of the mass spectrometry of the obtained compound are shown below.

MS (ESI-MS): m/z=749 (M+H)$^+$; C$_{52}$H$_{32}$N$_2$S$_2$ (748.2)

Figure 20A:
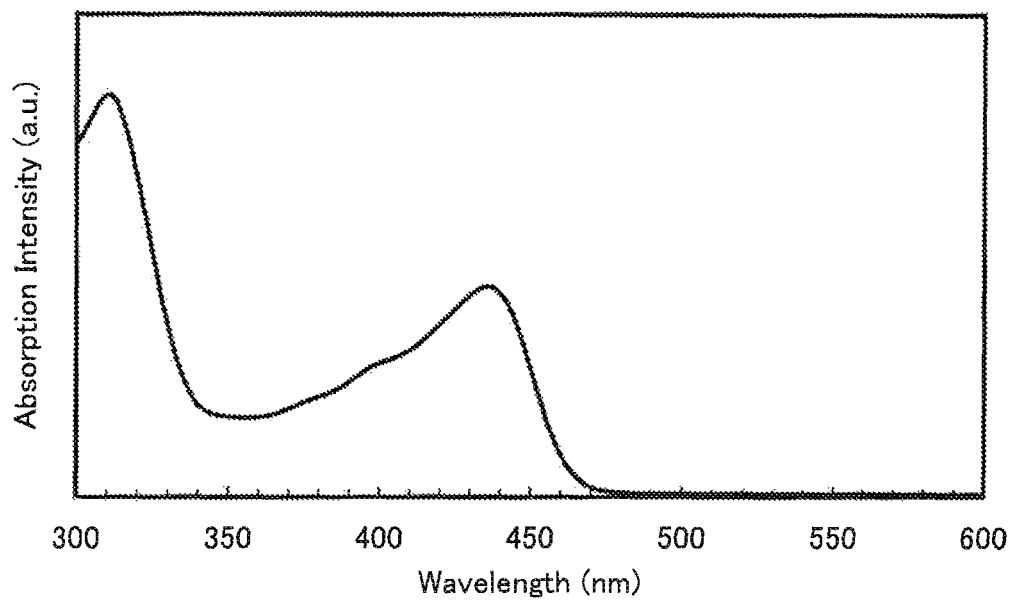
FIGS. 20A and 20B show an absorption spectrum and an emission spectrum of 1,6ThAPm in a toluene solution.
Figure 20B:
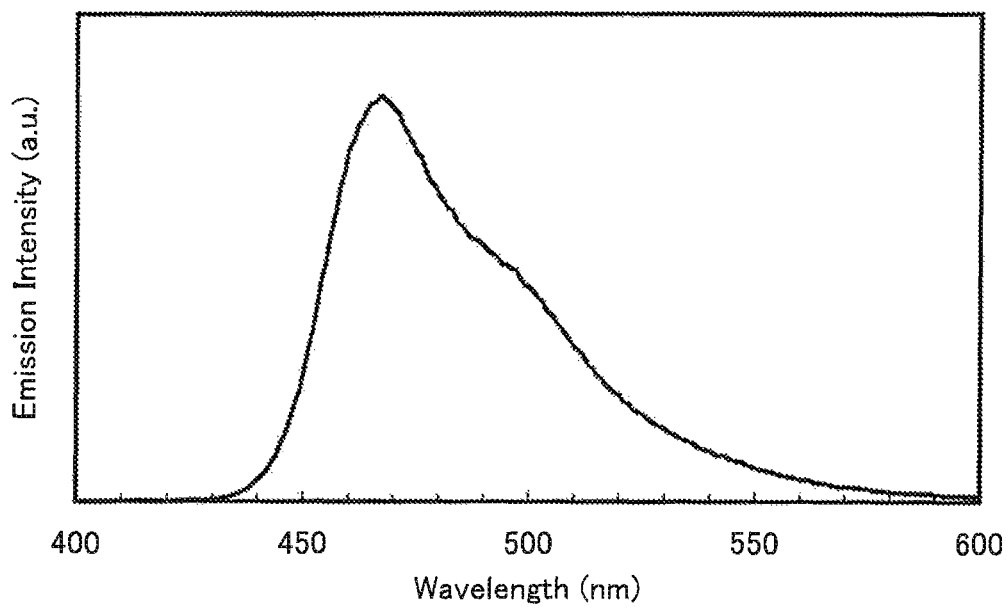
Figure 21A:
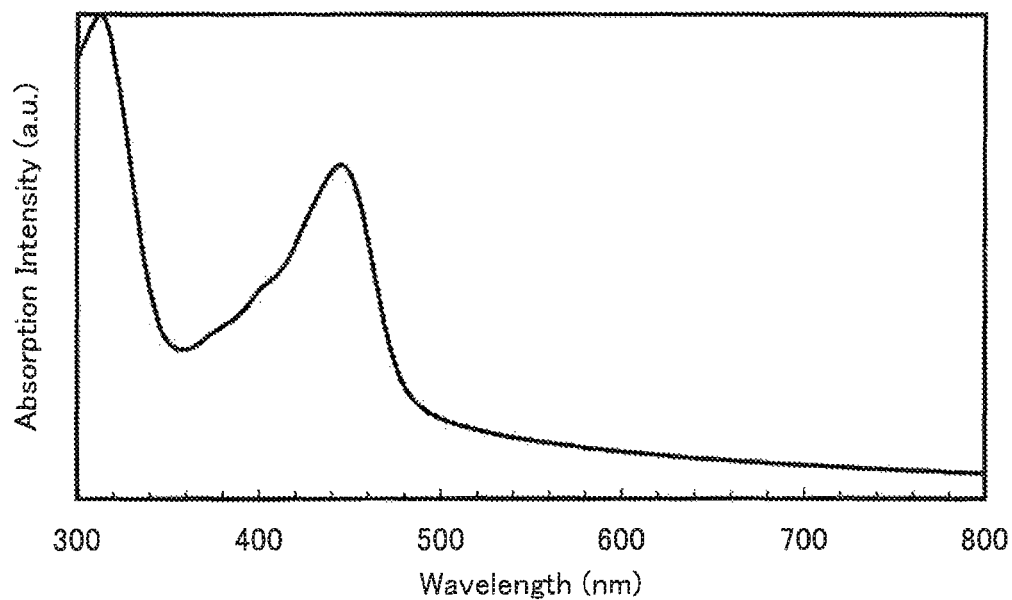
FIGS. 21A and 21B show an absorption spectrum and an emission spectrum of 1,6ThAPm in a thin film.
Figure 21B:
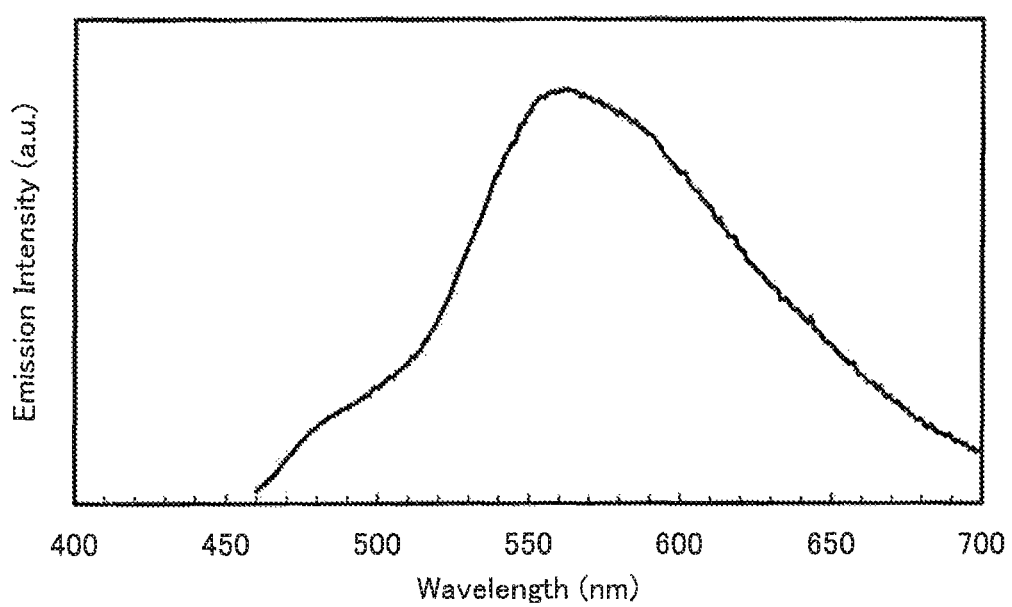

Further, an absorption spectrum of 1,6ThAPm in a toluene solution is shown in FIG. 20A, and an emission spectrum thereof is shown in FIG. 20B. In addition, an absorption spectrum of 1,6ThAPm in a thin film is shown in FIG. 21A, and an emission spectrum thereof is shown in FIG. 21B. The measurements of the absorption spectra and the emission spectra were performed using the same device and measurement method as those in Example 1. Each of the absorption spectra in FIG. 20A and FIG. 21A was obtained by subtracting a reference spectrum, as in Example 1. Note that the horizontal axes indicate wavelength (nm) and the vertical axes indicate intensity (arbitrary unit) in FIGS. 20A and 20B and FIGS. 21A and 21B. In the case of the toluene solution, absorption was observed at approximately 436 nm, and the maximum emission wavelength was 467 nm (excitation wavelength: 370 nm). In the case of the thin film, absorption was observed at approximately 445 nm, and the maximum emission wavelength was 563 nm (excitation wavelength: 445 nm).

From the results, the Stokes shift of 1,6ThAPm in the toluene solution is found to be as small as 31 nm.

The HOMO level and the LUMO level of 1,6ThAPm in the thin film were measured using the same device and measurement method as those in Example 1. As a result, the HOMO level of 1,6ThAPm was −5.48 eV, the energy gap was 2.61 eV, and the LUMO level was −2.87 eV.

The oxidation-reduction characteristics were examined by CV measurement, as in Example 1.

In the CV measurement in this example, the potential of the working electrode with respect to the reference electrode was scanned from −0.10 V to 0.6 V and then from 0.6 V to −0.10 V, whereby a distinct peak indicating oxidation was observed. The shape of the peak did not greatly change even after 100 scan cycles. As a result, 1,6ThAPm is found to have favorable characteristics with respect to repetition of the oxidation reduction between an oxidation state and a neutral state.

Note that in this CV measurement, the oxidation peak potential (from the neutral state to the oxidation state) $E_{pa}$ was 0.49 V. In addition, the reduction peak potential (from the oxidation side to the neutral state) $E_{pc}$ was 0.40 V. Therefore, a half-wave potential (an intermediate potential between $E_{pa}$ and $E_{pc}$, ($E_{pa}+E_{pc}$)/2 [V]) can be calculated to be 0.45 V. This shows that 1,6ThAPm is oxidized by an electrical energy of 0.45 [V vs. Ag/Ag$^+$]. Here, since the potential energy of the reference electrode, which was used above, with respect to the vacuum level is −4.94 [eV] as described above, the HOMO level of 1,6ThAPm was calculated as follows: −4.94−0.45=−5.39 [eV].

Thermogravimetry-differential thermal analysis of 1,6ThAPm was performed using the same device and measurement method as those in Example 1. The relationship between weight and temperature (thermogravimetry) shows that the 5% weight loss temperature of 1,6ThAPm is 468° C., which is indicative of high heat resistance.

Example 5

In this example, an example of obtaining N,N'-bis[3-(dibenzofuran-4-yl)phenyl]-N,N'-diphenyl-pyrene-1,6-diamine (abbreviation: 1,6mFrBAPm-II) represented by Structural Formula (G7-1) is described.

(G7-1)

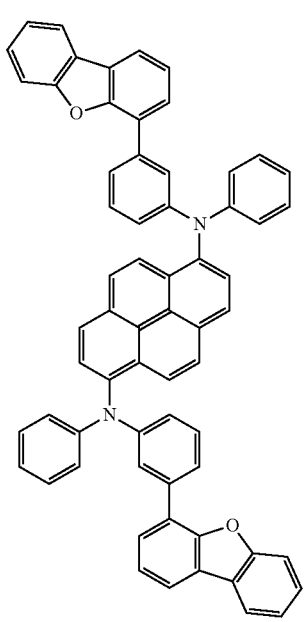

Step 1: Synthesis method of 3-(dibenzofuran-4-yl)-diphenylamine

First, 2.5 g (7.7 mmol) of 4-(3-bromophenyl)dibenzofuran and 2.1 g (21.6 mmol) of sodium tert-butoxide were put in a 200 mL three-neck flask, and the air in the flask was replaced by nitrogen.

Then, 50.0 mL of toluene, 0.7 mL (7.6 mmol) of aniline, and 0.2 mL of a 10% hexane solution of tri(tert-butyl) phosphine were added to this mixture. The temperature of this mixture was set to 65° C., 42.5 mg (0.1 mmol) of bis(dibenzylideneacetone)palladium(0) was added, and the mixture was stirred at 80° C. for 2.0 hours.

After the stirring, suction filtration was carried out through Florisil, Celite, and alumina to obtain filtrate. The obtained filtrate was concentrated to give an oily substance, which was purified by silica gel column chromatography (the developing solvent was hexane and toluene (hexane: toluene=3:2)), so that 2.4 g of an oily substance was obtained in a yield of 91%. The synthesis scheme of Step 1 is shown in (D1-1).

(D1-1)

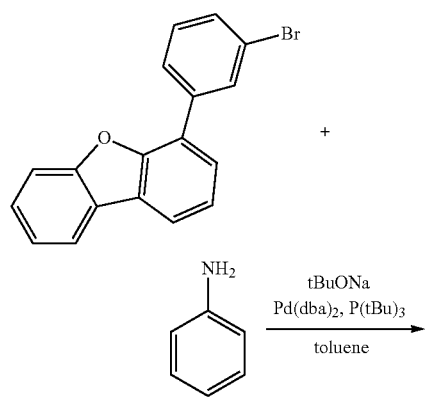

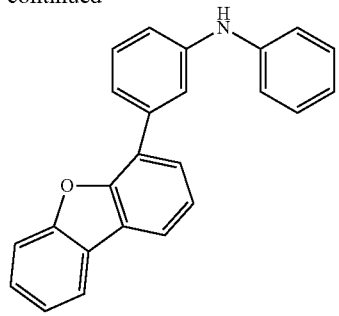

[Step 2: Synthesis method of N,N'-bis[3-(dibenzofuran-4-yl)phenyl]-N,N'-diphenyl-pyrene-1,6-diamine (abbreviation: 1,6mFrBAPm-II)]

Next, 0.6 g (1.5 mmol) of 1,6-dibromopyrene and 0.5 g (4.7 mmol) of sodium tert-butoxide were put in a 50 mL three-neck flask, and the air in the flask was replaced by nitrogen. Then, 2.2 mL of toluene, 1.0 g (3.1 mmol) of 3-(dibenzofuran-4-yl)-diphenylamine dissolved in 15.0 mL of toluene, and 0.2 mL of a 10% hexane solution of tri(tert-butyl)phosphine were added to this mixture.

The temperature of this mixture was set to 60° C., 41.2 mg (0.1 mmol) of bis(dibenzylideneacetone)palladium(0) was added, and the mixture was stirred at 80° C. for 2 hours. After the stirring, suction filtration was carried out to give a solid.

Then, 500 mL of toluene was added to the given solid, the resulting mixture was heated to 110° C., and suction filtration was carried out through Florisil, Celite, and alumina to obtain filtrate. The obtained filtrate was concentrated to give a solid. Then, 45 mL of toluene was added to the given solid and the mixture was heated.

This mixture was subjected to suction filtration, so that 0.8 g of a yellow solid was obtained in a yield of 65%. Then, 0.8 g of the obtained yellow solid was sublimated and purified by a train sublimation method. The conditions for the sublimation purification were as follows: the pressure was 2.4 Pa, the argon gas flow rate was 4.0 mL/min, and the heating temperature of the yellow solid was 305° C. After the sublimation purification, 0.6 g of a yellow solid was obtained in a yield of 73%. The synthesis scheme of Step 2 is shown in (D1-2).

(D1-2)

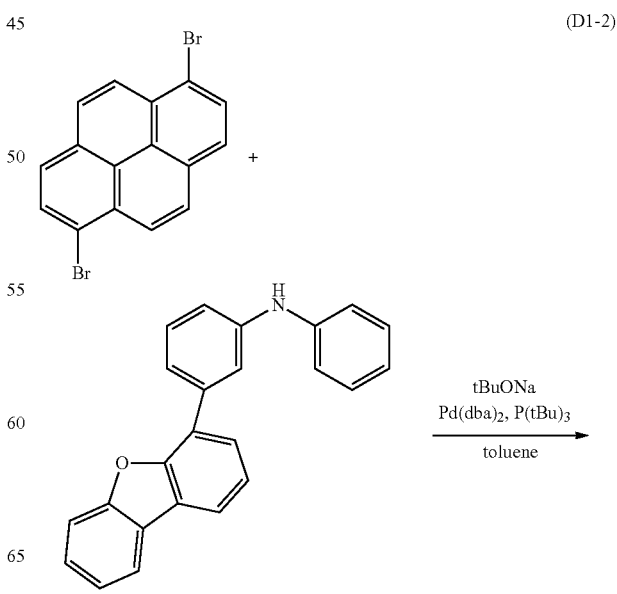

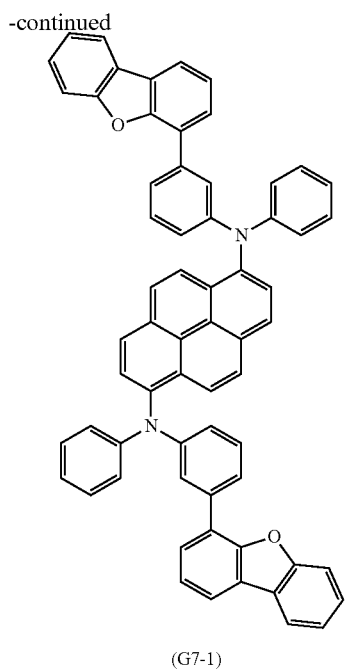

(G7-1)

A nuclear magnetic resonance (NMR) method and a mass spectrometry identified the compound obtained in the above step as N,N'-bis[3-(dibenzofuran-4-yl)phenyl]-N,N'-diphenyl-pyrene-1,6-diamine (abbreviation: 1,6mFrBAPm-II), which was the objective substance.

The $^1$H-NMR data of the obtained compound are shown below.

$^1$H-NMR (CDCl$_3$, 300 MHz): δ=6.98-7.03 (m, 2H), 7.09-7.14 (m, 4H), 7.19-7.39 (m, 16H), 7.48-7.51 (m, 4H), 7.70 (t, J=1.8 Hz, 2H), 7.82-7.87 (m, 4H), 7.92 (d, J=8.1 Hz, 2H), 7.98 (d, J=9.3 Hz, 2H), 8.15 (d, J=8.4 Hz, 2H), 8.27 (d, J=9.0 Hz, 2H)

Figure 22A:
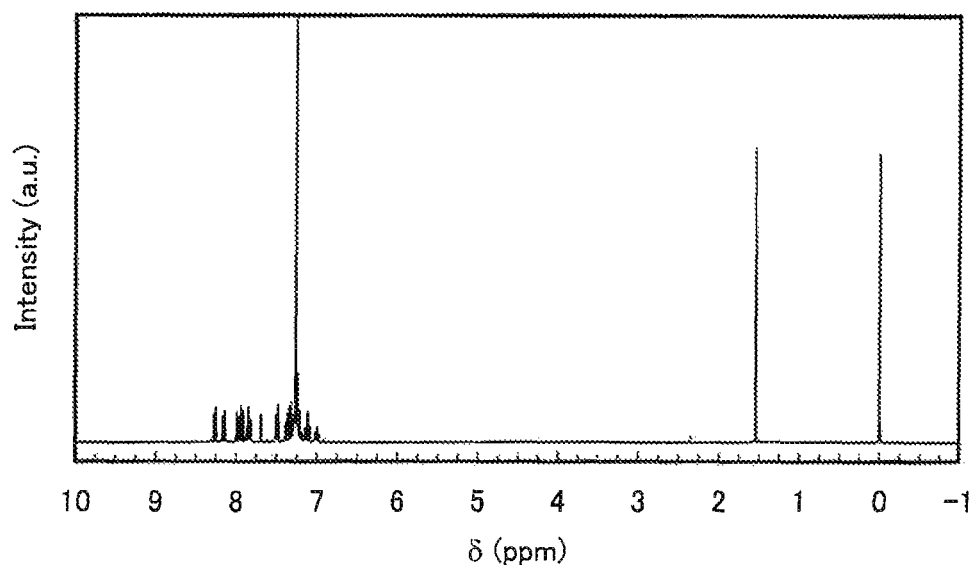
FIGS. 22A and 22B show $^1$H-NMR charts of 1,6mFrBAPm-II.
Figure 22B:
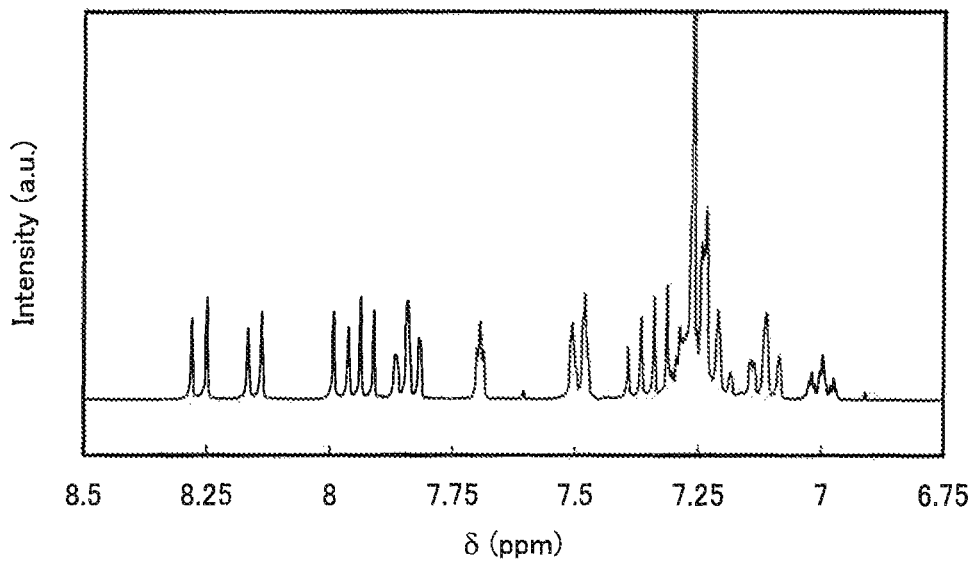

In addition, the $^1$H-NMR charts are shown in FIGS. 22A and 22B. Note that FIG. 22B is a chart showing an enlarged part of FIG. 22A in the range of 6.75 ppm to 8.50 ppm.

The measurement results of the mass spectrometry of the obtained compound are shown below.

MS (ESI-MS): m/z=869 (M+H)$^+$; C$_{64}$H$_{40}$N$_2$O$_2$ (868.31)

Figure 23A:
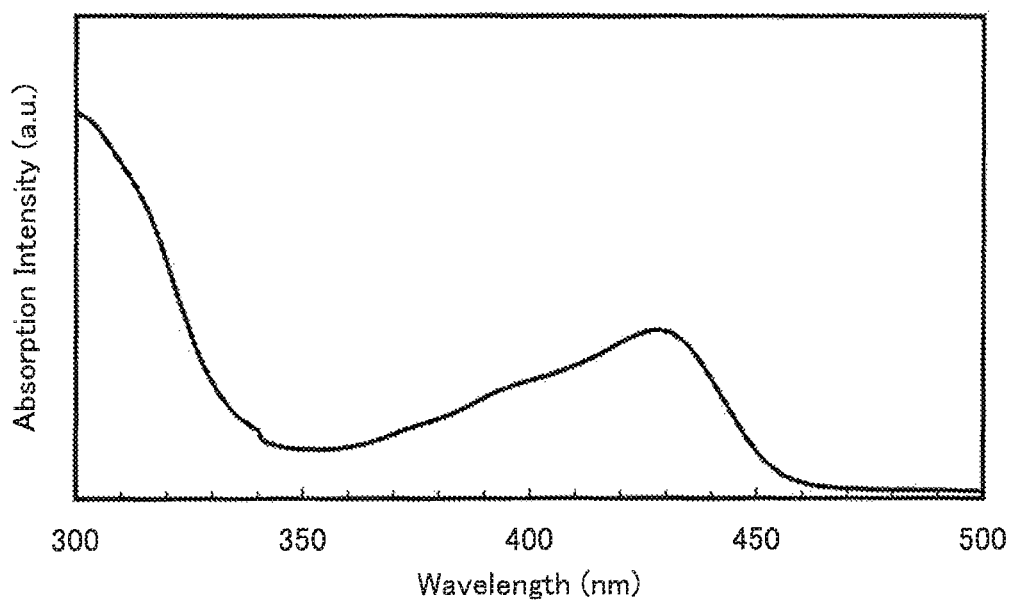
FIGS. 23A and 23B show an absorption spectrum and an emission spectrum of 1,6mFrBAPm-II in a toluene solution.
Figure 23B:
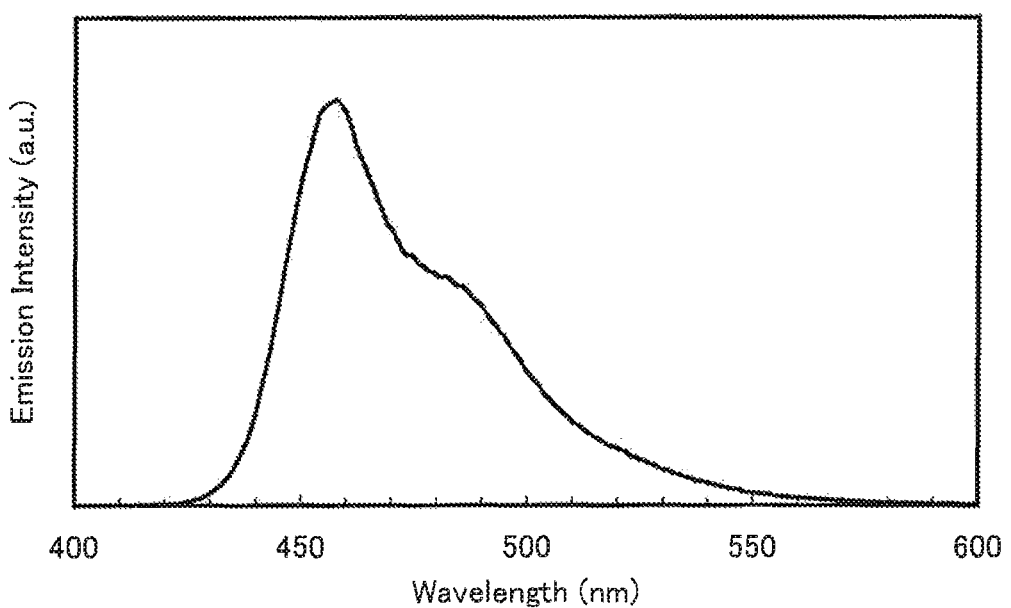
Figure 24A:
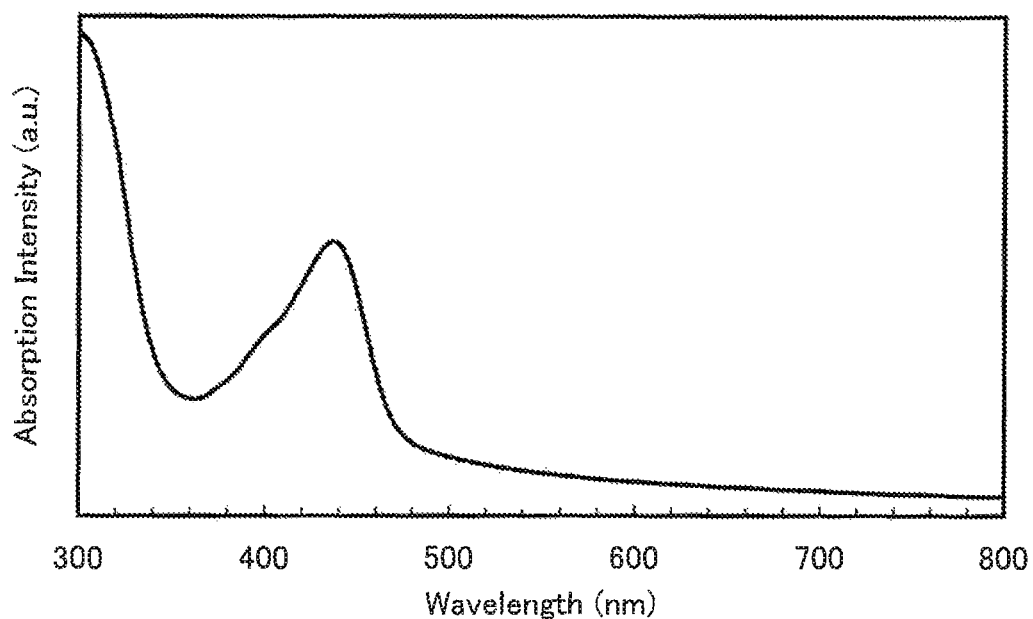
FIGS. 24A and 24B show an absorption spectrum and an emission spectrum of 1,6mFrBAPm-II in a thin film.
Figure 24B:
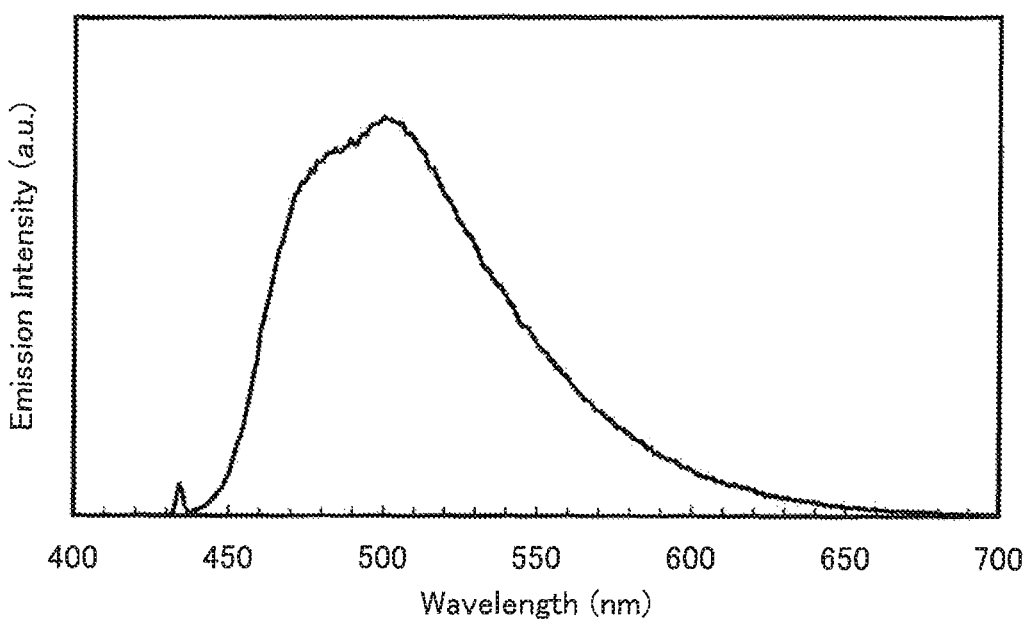

Further, an absorption spectrum of 1,6mFrBAPm-II in a toluene solution is shown in FIG. 23A, and an emission spectrum thereof is shown in FIG. 23B. In addition, an absorption spectrum of 1,6mFrBAPm-II in a thin film is shown in FIG. 24A, and an emission spectrum thereof is shown in FIG. 24B. The measurements of the absorption spectra and the emission spectra were performed using the same device and measurement method as those in Example 1. Each of the absorption spectra in FIG. 23A and FIG. 24A was obtained by subtracting a reference spectrum, as in Example 1. Note that the horizontal axes indicate wavelength (nm) and the vertical axes indicate intensity (arbitrary unit) in FIGS. 23A and 23B and FIGS. 24A and 24B. In the case of the toluene solution, absorption was observed at approximately 428 nm, and the maximum emission wavelength was 458 nm (excitation wavelength: 370 nm). In the case of the thin film, absorption was observed at approximately 437 nm, and peaks of the emission spectrum were 484 nm and 501 nm (excitation wavelength: 434 nm).

From the results, the Stokes shift of 1,6mFrBAPm-II in the toluene solution is found to be as small as 30 nm.

The HOMO level and the LUMO level of 1,6mFrBAPm-II in the thin film were measured using the same device and measurement method as those in Example 1. As a result, the HOMO level of 1,6mFrBAPm-II was −5.51 eV, the energy gap was 2.67 eV, and the LUMO level was −2.84 eV.

The oxidation-reduction characteristics were examined by CV measurement, as in Example 1.

In the CV measurement in this example, the potential of the working electrode with respect to the reference electrode was scanned from −0.10 V to 0.6 V and then from 0.6 V to −0.10 V, whereby a distinct peak indicating oxidation was observed. The shape of the peak did not greatly change even after 100 scan cycles. As a result, 1,6mFrBAPm-II is found to have favorable characteristics with respect to repetition of the oxidation reduction between an oxidation state and a neutral state.

Note that in this CV measurement, the oxidation peak potential (from the neutral state to the oxidation state) $E_{pa}$ was 0.52 V. In addition, the reduction peak potential (from the oxidation side to the neutral state) $E_{pc}$ was 0.45 V. Therefore, a half-wave potential (an intermediate potential between $E_{pa}$ and $E_{pc}$, $(E_{pa}+E_{pc})/2$ [V]) can be calculated to be 0.49 V. This shows that 1,6mFrBAPm-II is oxidized by an electrical energy of 0.49 [V vs. Ag/Ag$^+$]. Here, since the potential energy of the reference electrode, which was used above, with respect to the vacuum level is −4.94 [eV] as described above, the HOMO level of 1,6mFrBAPm-II was calculated as follows: −4.94−0.49=−5.43 [eV].

Thermogravimetry-differential thermal analysis of 1,6mFrBAPm-II was performed using the same device and measurement method as those in Example 1. The relationship between weight and temperature (thermogravimetry) shows that the 5% weight loss temperature of 1,6mFrBAPm-II is 500° C. or higher, which is indicative of high heat resistance.

Example 6

In this example, an example of obtaining N,N-bis[3-(dibenzothiophene-4-yl)phenyl]-N,N'-diphenyl-pyrene-1,6-diarylamine (abbreviation: 1,6mThBAPm-II) represented by Structural Formula (G7-2) is described.

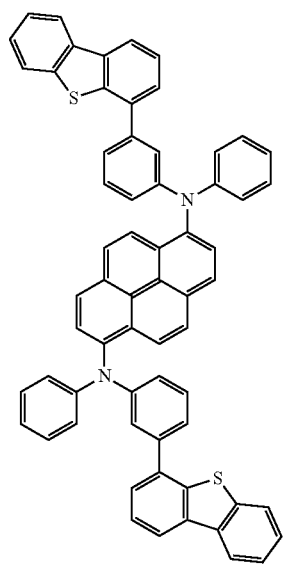

(G7-2)

Step 1: Synthesis method of 3-(dibenzothiophene-4-yl)-diphenylamine

First, 2.4 g (7.1 mmol) of 4-(3-bromophenyl)dibenzothiophene and 2.0 g (20.9 mmol) of sodium tert-butoxide were put in a 200 mL three-neck flask, and the air in the flask was replaced by nitrogen.

Then, 50.0 mL of toluene, 0.7 mL (7.6 mmol) of aniline, and 0.2 mL of a 10% hexane solution of tri(tert-butyl)phosphine were added to this mixture. The temperature of this mixture was set to 60° C., 42.7 mg (0.1 mmol) of bis(dibenzylideneacetone)palladium(0) was added, and the mixture was stirred at 80° C. for 5.0 hours.

After the stirring, suction filtration was carried out through Florisil, Celite, and alumina to obtain filtrate. The obtained filtrate was concentrated to give an oily substance, which was purified by silica gel column chromatography (the developing solvent was hexane and toluene (hexane:toluene=2:1)), so that 2.4 g of an objective substance was obtained in a yield of 95%. The synthesis scheme of Step 1 is shown in (D2-1).

stirring, 18.5 mg (0.03 mmol) of bis(dibenzylideneacetone)palladium(0) was added, and the mixture was stirred for 1.0 hour.

After the stirring, 600 mL of toluene was added, and suction filtration was carried out through Florisil, Celite, and alumina to obtain filtrate. The obtained filtrate was concentrated to give a solid.

Then, 75 mL of toluene was added to the given solid and the mixture was heated. This mixture was subjected to suction filtration, so that a yellow solid was obtained. Then, 0.6 g of the obtained yellow solid was sublimated and purified by a train sublimation method. The conditions for the sublimation purification were as follows: the pressure was 2.3 Pa, the argon gas flow rate was 6.0 mL/min, and the heating temperature of the yellow solid was 308° C. After the sublimation purification, 0.5 g of a yellow solid was obtained in a yield of 77%. The synthesis scheme of Step 2 is shown in (D2-2).

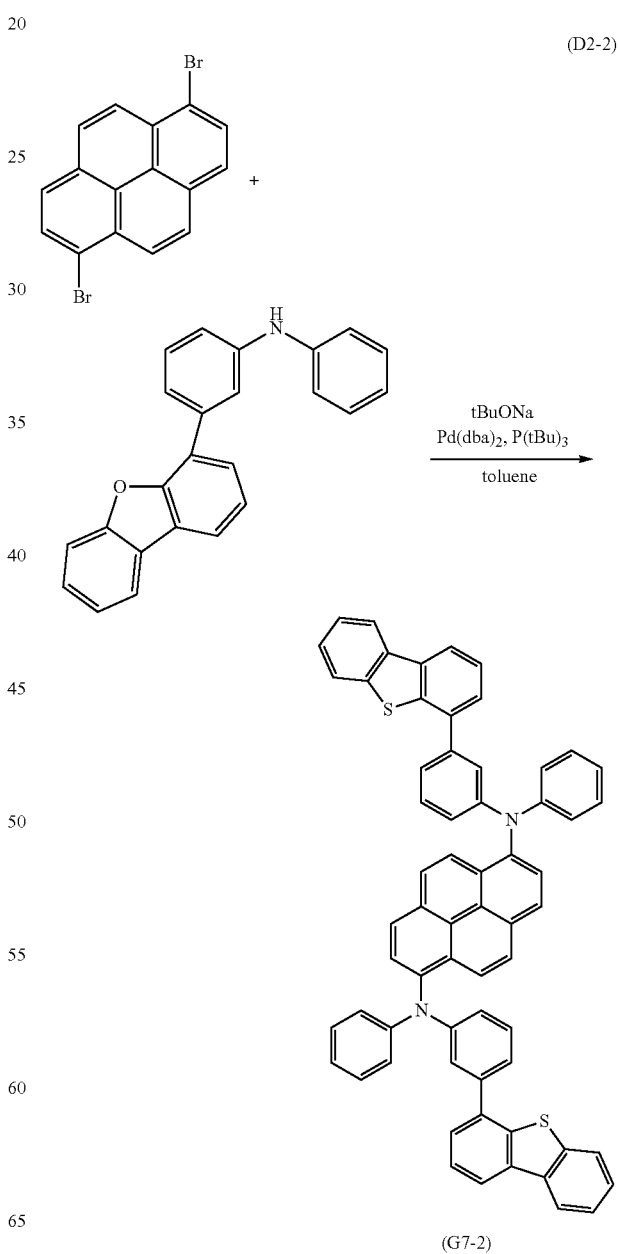

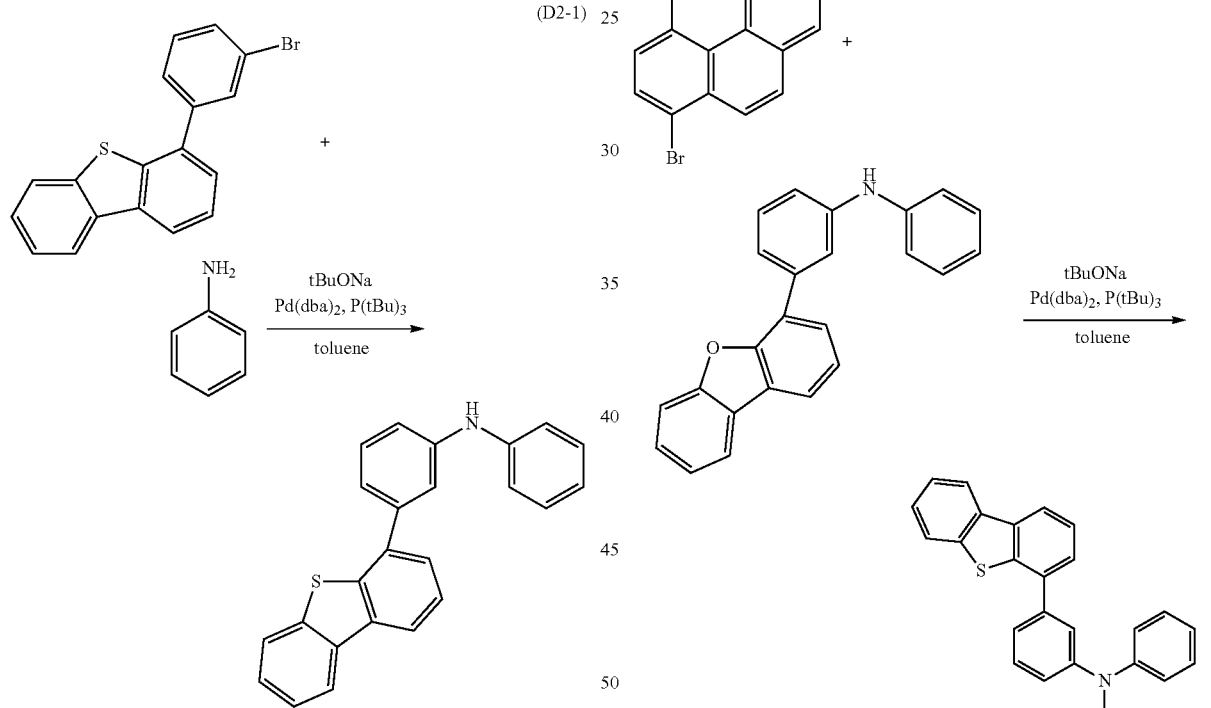

[Step 2: Synthesis method of N,N'-bis[3-(dibenzothiophene-4-yl)phenyl]-N,N'-diphenyl-pyrene-1,6-diamine (abbreviation: 1,6mThBAPm-II)]

Next, 0.6 g (1.7 mmol) of 1,6-dibromopyrene and 0.5 g (5.2 mmol) of sodium tert-butoxide were put in a 50 mL three-neck flask, and the air in the flask was replaced by nitrogen. Then, 2.0 mL of toluene, 1.2 g (3.3 mmol) of 3-(dibenzothiophene-4-yl)-diphenylamine dissolved in 15.0 mL of toluene, and 0.2 mL of a 10% hexane solution of tri(tert-butyl)phosphine were added to this mixture.

The temperature of this mixture was set to 80° C., 17.2 mg (0.03 mmol) of bis(dibenzylideneacetone)palladium(0) was added, and the mixture was stirred for 1.0 hour. After the A nuclear magnetic resonance (NMR) method and a mass spectrometry identified the compound obtained in the above step as N,N'-bis[3-(dibenzothiophene-4-yl)phenyl]-N,N'-diphenyl-pyrene-1,6-diamine (abbreviation: 1,6mThBAPm-II).

The ¹H-NMR data of the obtained compound are shown below.

¹H-NMR (CDCl₃, 300 MHz): δ=7.00-7.44 (m, 28H), 7.90-7.97 (m, 6H), 8.00 (d, J=9.3 Hz, 2H), 8.17 (d, J=8.4 Hz, 2H), 8.27 (d, J=9.3 Hz, 2H)

Figure 25A:
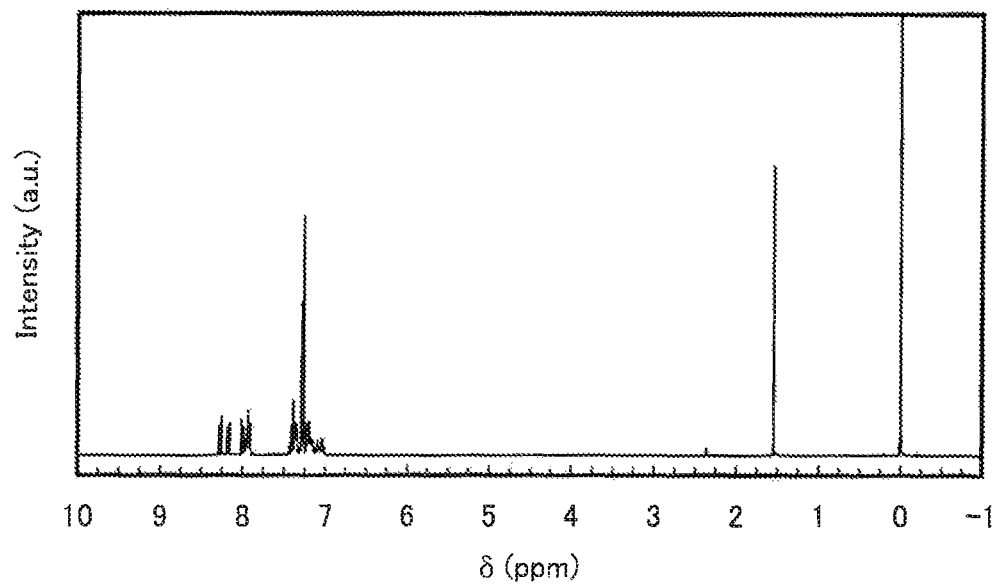
FIGS. 25A and 25B show $^1$H-NMR charts of 1,6mTh-BAPm-II.
Figure 25B:
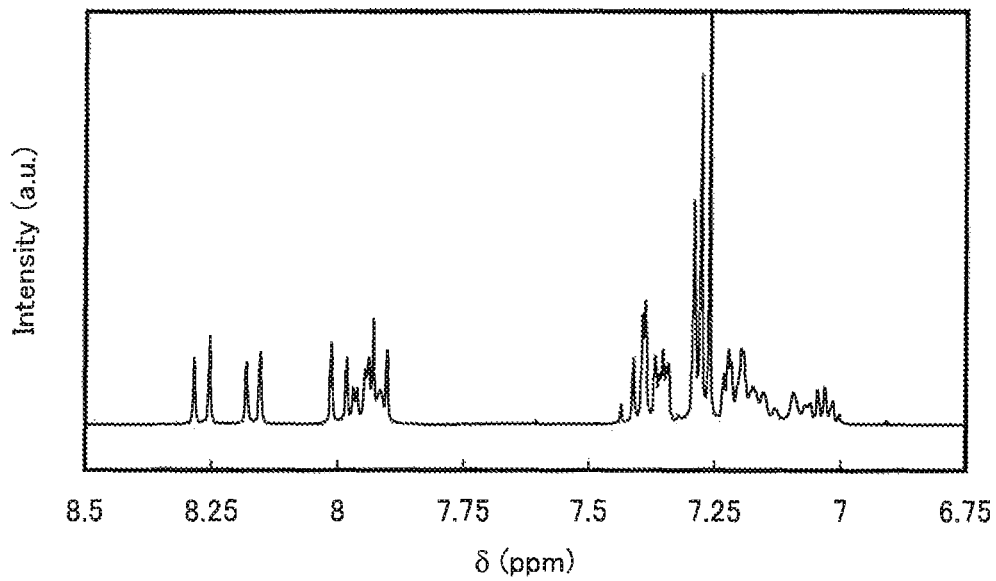

In addition, the ¹H-NMR charts are shown in FIGS. 25A and 25B. Note that FIG. 25B is a chart showing an enlarged part of FIG. 25A in the range of 6.75 ppm to 8.50 ppm.

The measurement results of the mass spectrometry of the obtained compound are shown below.

MS (ESI-MS): m/z=901 (M+H)⁺; $C_{64}H_{40}N_2S_2$ (900.26)

Figure 26A:
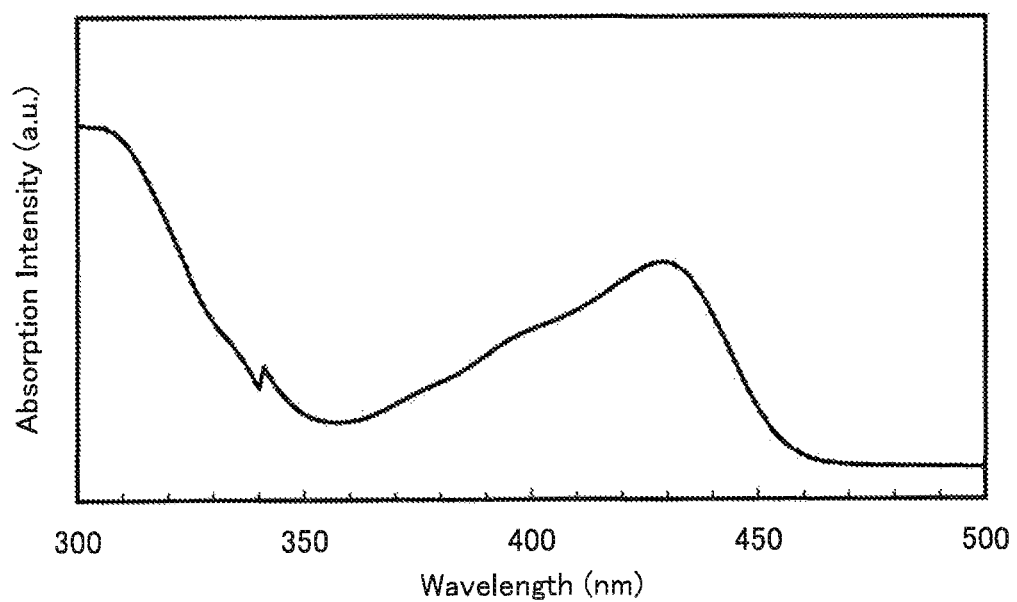
FIGS. 26A and 26B show an absorption spectrum and an emission spectrum of 1,6mThBAPm-II in a toluene solution.
Figure 26B:
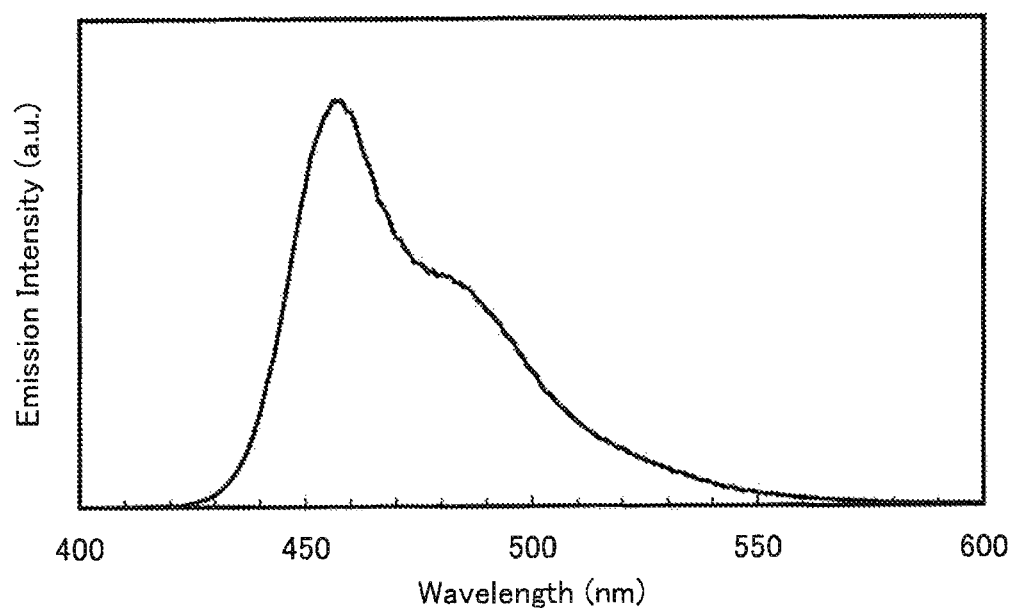
Figure 27A:
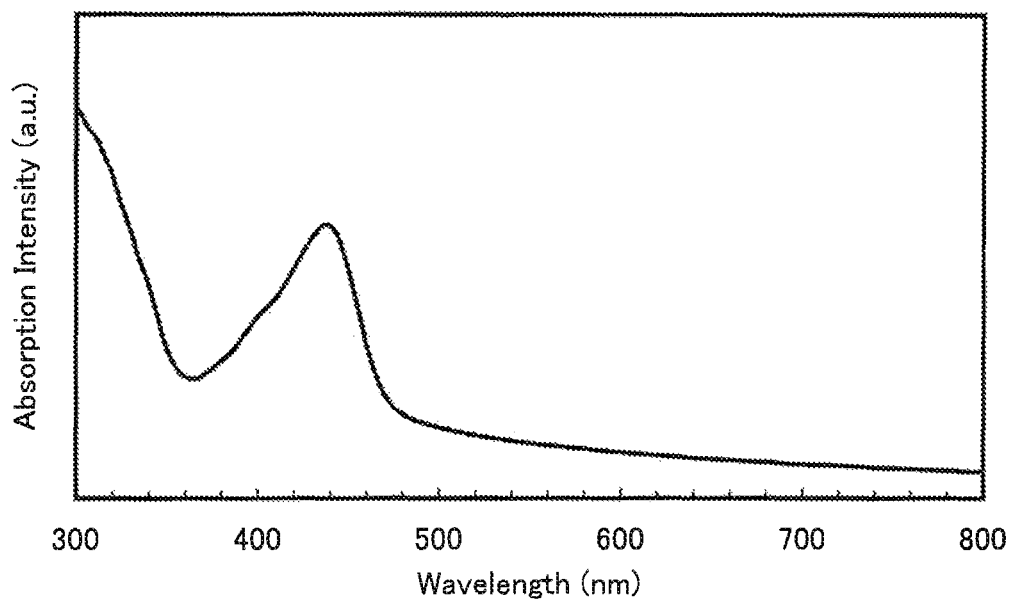
FIGS. 27A and 27B show an absorption spectrum and an emission spectrum of 1,6mThBAPm-II in a thin film.
Figure 27B:
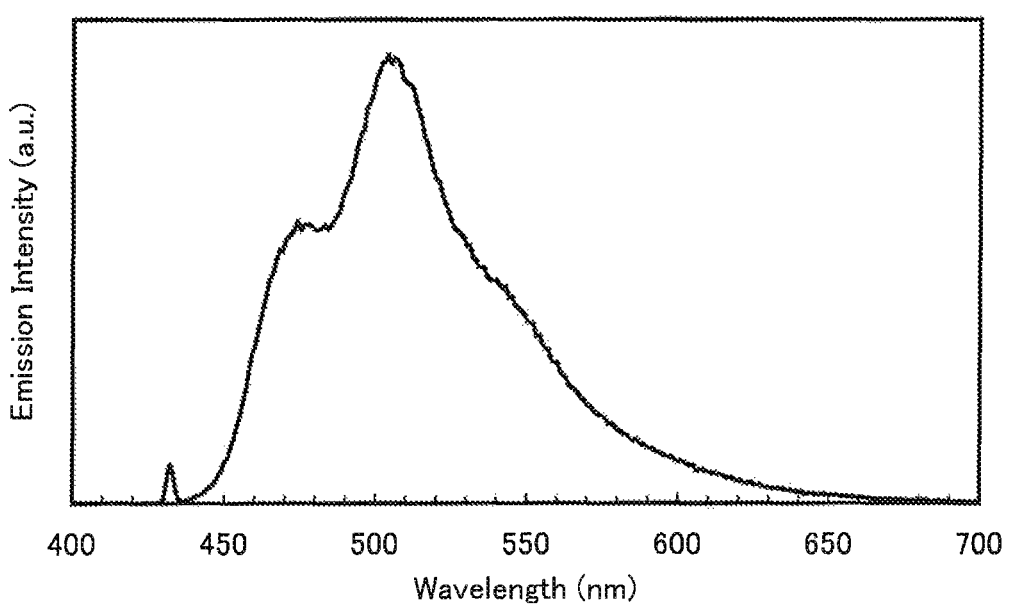

Further, an absorption spectrum of 1,6mThBAPm-II in a toluene solution is shown in FIG. 26A, and an emission spectrum thereof is shown in FIG. 26B. In addition, an absorption spectrum of 1,6mThBAPm-II in a thin film is shown in FIG. 27A, and an emission spectrum thereof is shown in FIG. 27B. The measurements of the absorption spectra and the emission spectra were performed using the same device and measurement method as those in Example 1. Each of the absorption spectra in FIG. 26A and FIG. 27A was obtained by subtracting a reference spectrum, as in Example 1. Note that the horizontal axes indicate wavelength (nm) and the vertical axes indicate intensity (arbitrary unit) in FIGS. 26A and 26B and FIGS. 27A and 27B. In the case of the toluene solution, absorption was observed at approximately 429 nm, and the maximum emission wavelength was 457 nm (excitation wavelength: 370 nm). In the case of the thin film, absorption was observed at approximately 438 nm, and peaks of the emission spectrum were 475 nm and 504 nm (excitation wavelength: 432 nm).

From the results, the Stokes shift of 1,6mThBAPm-II in the toluene solution is found to be as small as 28 nm.

The HOMO level and the LUMO level of 1,6mThBAPm-II in the thin film were measured using the same device and measurement method as those in Example 1. As a result, the HOMO level of 1,6mThBAPm-II was −5.51 eV, the energy gap was 2.66 eV, and the LUMO level was −2.85 eV.

The oxidation-reduction characteristics were examined by CV measurement, as in Example 1.

In the CV measurement in this example, the potential of the working electrode with respect to the reference electrode was scanned from −0.10 V to 0.6 V and then from 0.6 V to −0.10 V, whereby a distinct peak indicating oxidation was observed. The shape of the peak did not greatly change even after 100 scan cycles. As a result, 1,6mThBAPm-II is found to have favorable characteristics with respect to repetition of the oxidation reduction between an oxidation state and a neutral state.

Note that in this CV measurement, the oxidation peak potential (from the neutral state to the oxidation state) $E_{pa}$ was 0.53 V. In addition, the reduction peak potential (from the oxidation side to the neutral state) $E_{pc}$ was 0.45 V. Therefore, a half-wave potential (an intermediate potential between $E_{pa}$ and $E_{pc}$, $(E_{pa}+E_{pc})/2$ [V]) can be calculated to be 0.49 V. This shows that 1,6mThBAPm-II is oxidized by an electrical energy of 0.49 [V vs. Ag/Ag⁺]. Here, since the potential energy of the reference electrode, which was used above, with respect to the vacuum level is −4.94 [eV] as described above, the HOMO level of 1,6mThBAPm-II was calculated as follows: −4.94−0.49=−5.43 [eV].

Thermogravimetry-differential thermal analysis of 1,6mThBAPm-II was performed using the same device and measurement method as those in Example 1. The relationship between weight and temperature (thermogravimetry) shows that the 5% weight loss temperature of 1,6mTh-BAPm-II is 500° C. or higher, which is indicative of high heat resistance.

Example 7

In this example, an example of obtaining N,N'-bis[4-(dibenzofuran-4-yl)phenyl]-N,N'-diphenyl-pyrene-1,6-diarylamine (abbreviation: 1,6FrBAPm-II) represented by Structural Formula (G8-1) is described.

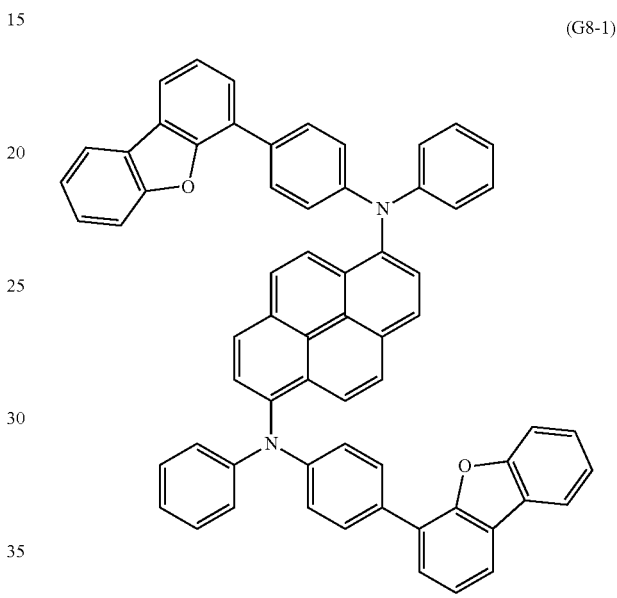

(G8-1)

Step 1: Synthesis method of 4-(dibenzofuran-4-yl)-diphenylamine

First, 1.8 g (7.5 mmol) of 4-bromodiphenylamine, and 1.6 g (7.5 mmol) of (dibenzofuran-4-yl)boronic acid, and 0.1 g (0.4 mmol) of tris(2-methylphenyl)phosphine were put in a 100 mL three-neck flask, and the air in the flask was replaced by nitrogen.

Then, 30.0 mL of toluene, 9.3 mL of ethanol, and 7.5 mL of an aqueous solution of potassium carbonate (2 mol/L) were added to this mixture, and the mixture was stirred to be degassed while the pressure in the flask was reduced.

After the degassing, the temperature of the mixture was set to 60° C., and 41.2 mg (0.2 mmol) of palladium(II) acetate was added. The temperature of this mixture was set to 80° C., followed by reflux at 80° C. for 3.0 hours. After the reflux, toluene and water were added to the mixture, an organic layer and an aqueous layer were separated, and the aqueous layer was extracted three times with ethyl acetate. This extract and the organic layer were together washed with a saturated aqueous sodium chloride solution.

This extract and the organic layer were dried with magnesium sulfate. The obtained mixture was subjected to gravity filtration, so that magnesium sulfate was removed, and the obtained filtrate was concentrated to give a solid. The given solid was purified by silica gel column chromatography (the developing solvent was hexane and toluene (hexane:toluene=3:7). The obtained fraction was concentrated, so that 2.1 g of an objective white solid was obtained in a yield of 83%. The synthesis scheme of Step 1 is shown in (E1-1).

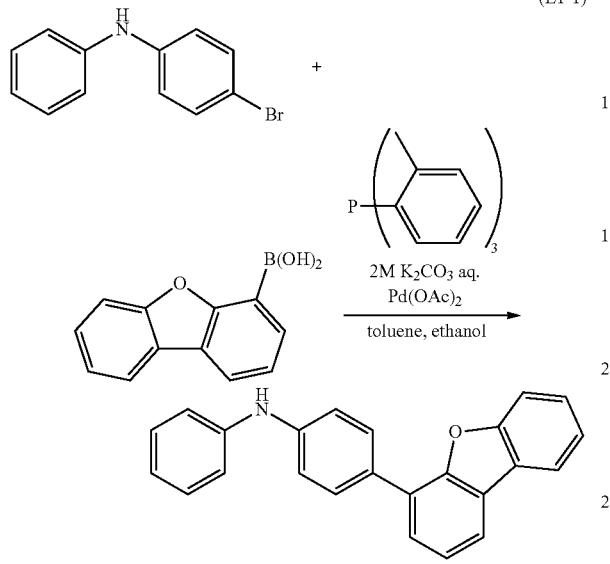

The measurement results of the mass spectrometry of the obtained compound are shown below.

MS (ESI-MS): m/z=336 (M+H)$^+$; $C_{24}H_{17}NO$ (335.13)

[Step 2: Synthesis method of N,N'-bis[4-(dibenzofuran-4-yl)phenyl]-N,N'-diphenyl-pyrene-1,6-diamine (abbreviation: 1,6FrBAPm-II)]

Next, 0.6 g (1.7 mmol) of 1,6-dibromopyrene, 1.2 g (3.4 mmol) of 4-(dibenzofuran-4-yl)-diphenylamine, and 0.5 g (5.2 mmol) of sodium tert-butoxide were put in a 50 mL three-neck flask, and the air in the flask was replaced by nitrogen. Then, 17.0 mL of toluene and 0.3 mL of a 10% hexane solution of tri(tert-butyl)phosphine were added to this mixture.

The temperature of this mixture was set to 80° C., 33.4 mg (0.1 mmol) of bis(dibenzylideneacetone)palladium(0) was added, and the mixture was stirred at 80° C. for 4.0 hours. After the stirring, suction filtration was carried out through Florisil, Celite, and alumina to obtain filtrate. The obtained filtrate was concentrated to give a solid.

The given solid was purified by silica gel column chromatography (the developing solvent was hexane and toluene (hexane:toluene=7:3)), and the obtained fraction was concentrated. The solid given by the concentration was washed with chloroform and hexane, so that 1.0 g of a yellow solid was obtained in a yield of 66%.

Then, 1.0 g of the obtained yellow solid was sublimated and purified by a train sublimation method. The conditions for the sublimation purification were as follows: the pressure was 2.6 Pa, the argon gas flow rate was 5.0 mL/min, and the heating temperature of the yellow solid was 370° C. After the sublimation purification, 0.8 g of a yellow solid was obtained in a yield of 86%. The synthesis scheme of Step 2 is shown in (E1-2).

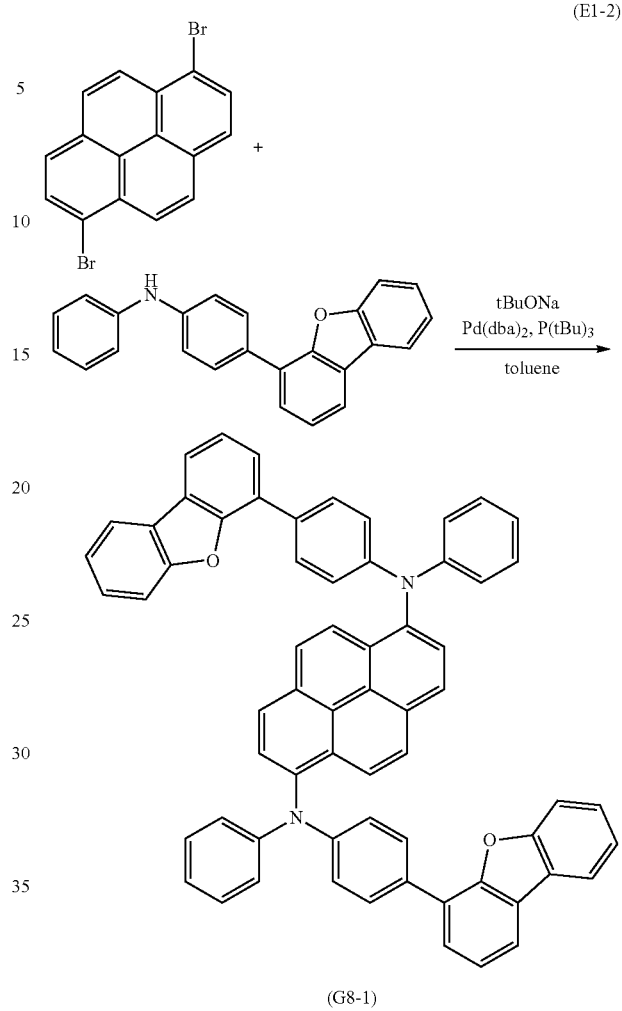

A nuclear magnetic resonance (NMR) method and a mass spectrometry identified the compound obtained in the above step as N,N'-bis[4-(dibenzofuran-4-yl)phenyl]-N,N'-diphenyl-pyrene-1,6-diamine (abbreviation: 1,6FrBAPm-II).

The $^1$H-NMR data of the obtained compound are shown below.

$^1$H-NMR (CDCl$_3$, 300 MHz): δ=7.02 (t, J=6.9 Hz, 2H), 7.20-7.48 (m, 18H), 7.56 (d, J=7.8 Hz, 4H), 7.81 (d, J=8.7 Hz, 4H), 7.88-8.01 (m, 8H), 8.17 (d, J=8.4 Hz, 2H), 8.23 (d, J=9.3 Hz, 2H)

Figure 28A:
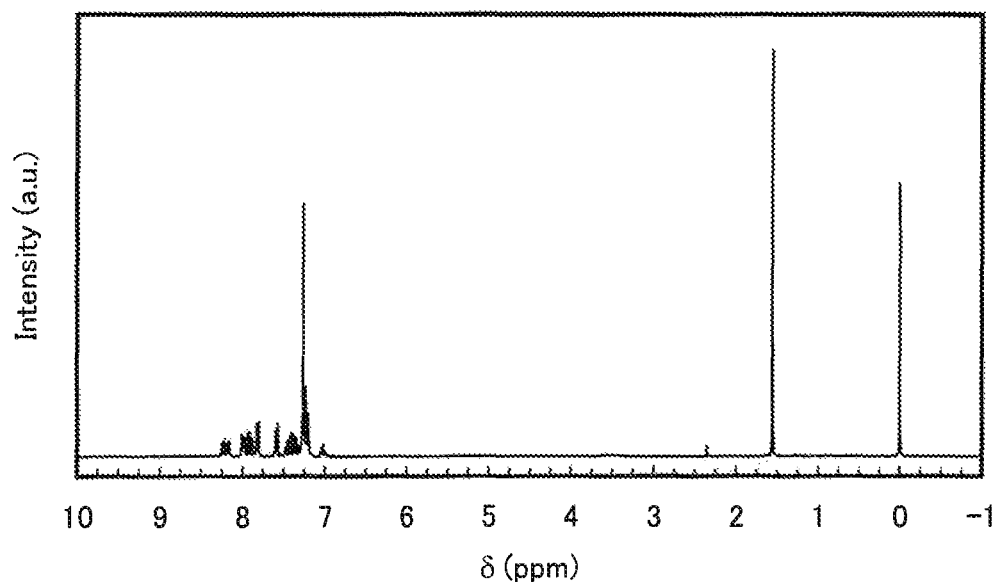
FIGS. 28A and 28B show $^1$H-NMR charts of 1,6Fr-BAPm-II.
Figure 28B:
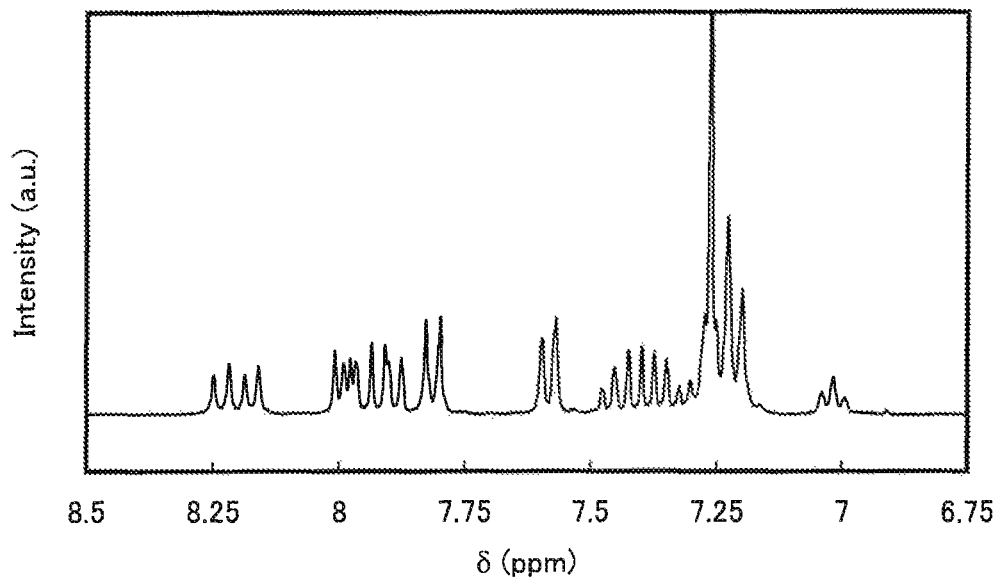

In addition, the $^1$H-NMR charts are shown in FIGS. 28A and 28B. Note that FIG. 28B is a chart showing an enlarged part of FIG. 28A in the range of 6.75 ppm to 8.50 ppm.

The measurement results of the mass spectrometry of the obtained compound are shown below.

MS (ESI-MS): m/z=869 (M+H)$^+$; $C_{64}H_{40}N_2O_2$ (868.31)

Figure 29A:
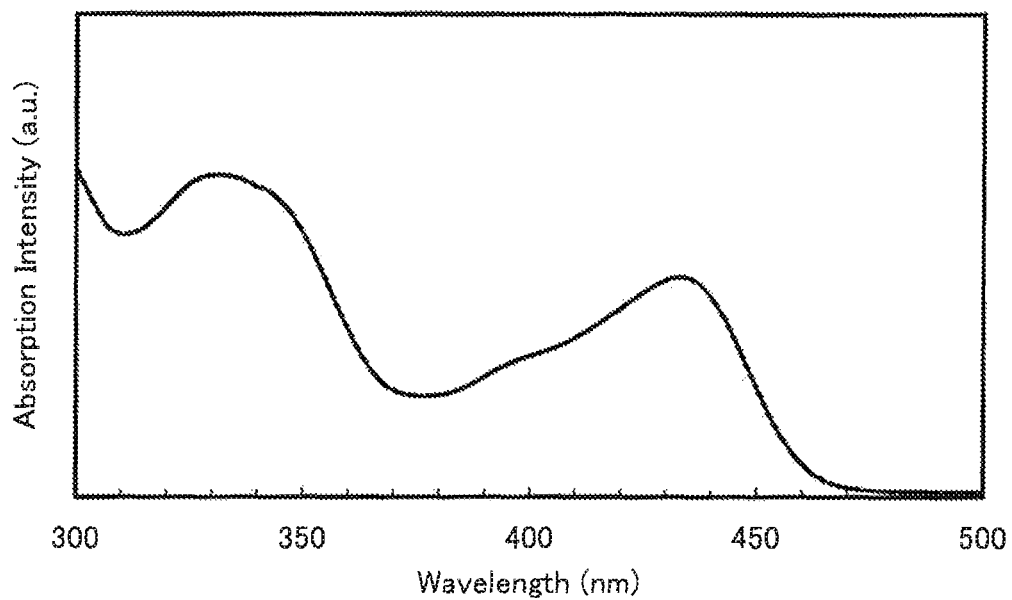
FIGS. 29A and 29B show an absorption spectrum and an emission spectrum of 1,6FrBAPm-II in a toluene solution.
Figure 29B:
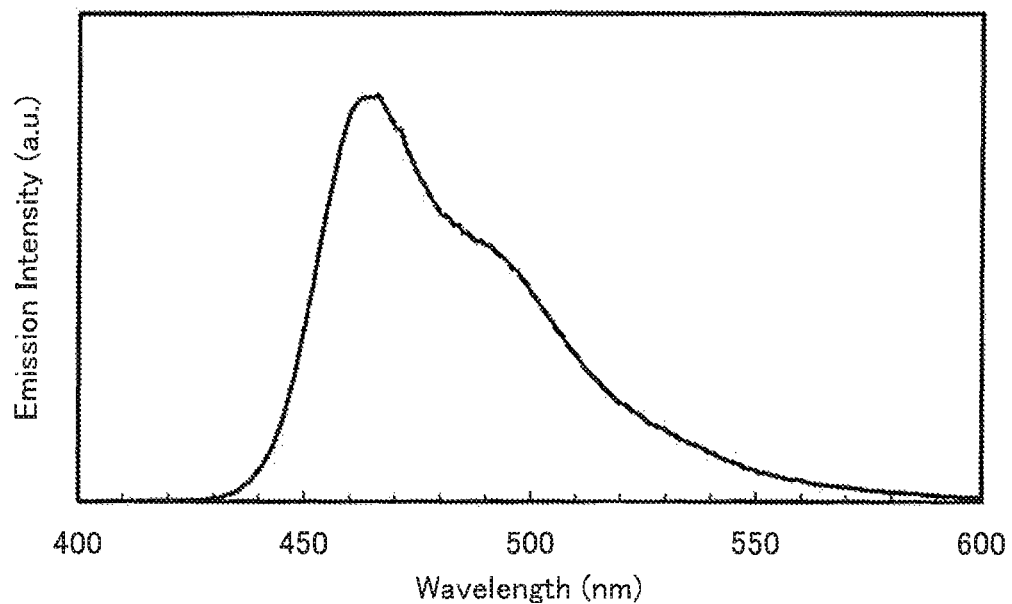
Figure 30A:
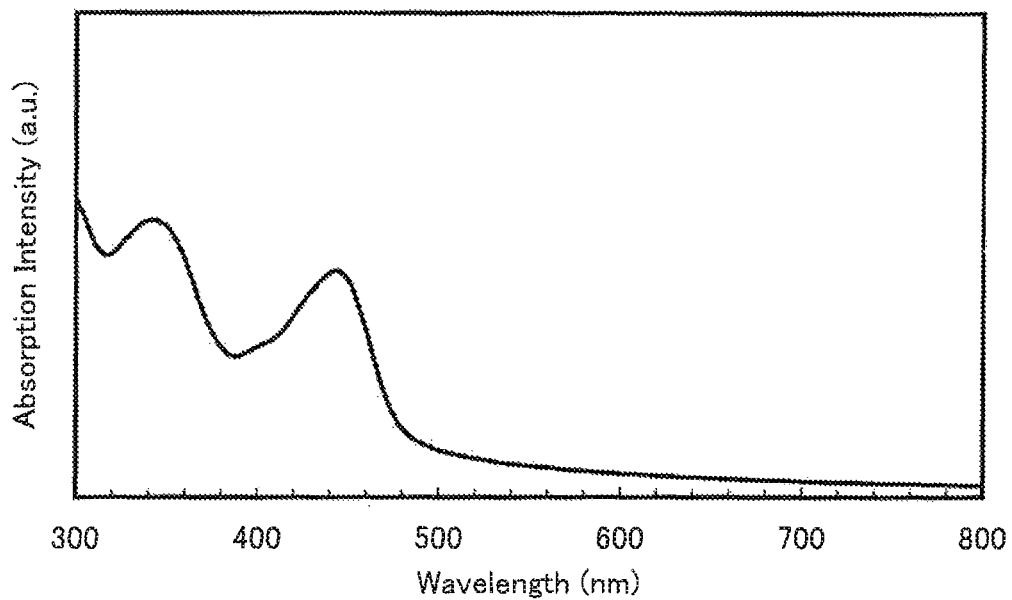
FIGS. 30A and 30B show an absorption spectrum and an emission spectrum of 1,6FrBAPm-II in a thin film.
Figure 30B:
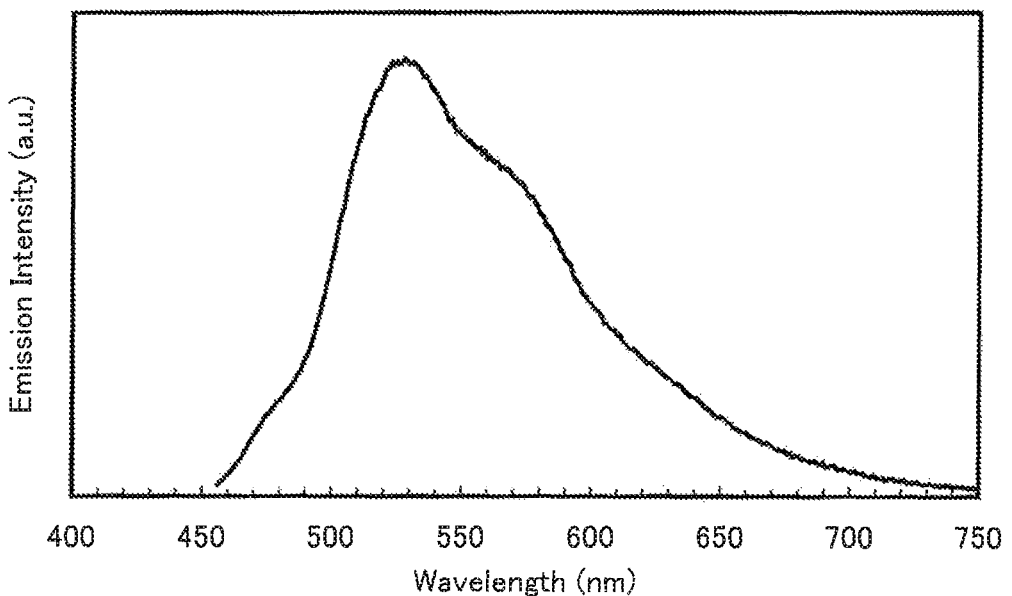

Further, an absorption spectrum of 1,6FrBAPm-II in a toluene solution is shown in FIG. 29A, and an emission spectrum thereof is shown in FIG. 29B. In addition, an absorption spectrum of 1,6FrBAPm-II in a thin film is shown in FIG. 30A, and an emission spectrum thereof is shown in FIG. 30B. The measurements of the absorption spectra and the emission spectra were performed using the same device and measurement method as those in Example 1. Each of the absorption spectra in FIG. 29A and FIG. 30A was obtained by subtracting a reference spectrum, as in Example 1. Note that the horizontal axes indicate wavelength (nm) and the vertical axes indicate intensity (arbitrary unit) in FIGS. 29A and 29B and FIGS. 30A and 30B. In the case of the toluene solution, absorption was observed at approximately 433 nm, and the maximum emission wavelength was 464 nm (excitation wavelength: 370 nm). In the case of the thin film, absorption was observed at approximately 443 nm, and the maximum emission wavelength was 528 nm (excitation wavelength: 441 nm).

From the results, the Stokes shift of 1,6FrBAPm-II in the toluene solution is found to be as small as 31 nm.

The HOMO level and the LUMO level of 1,6FrBAPm-II in the thin film were measured using the same device and measurement method as those in Example 1. As a result, the HOMO level of 1,6FrBAPm-II was −5.49 eV, the energy gap was 2.62 eV, and the LUMO level was −2.87 eV.

The oxidation-reduction characteristics were examined by CV measurement, as in Example 1.

In the CV measurement in this example, the potential of the working electrode with respect to the reference electrode was scanned from −0.10 V to 0.6 V and then from 0.6 V to −0.10 V, whereby a distinct peak indicating oxidation was observed. The shape of the peak did not greatly change even after 100 scan cycles. As a result, 1,6FrBAPm-II is found to have favorable characteristics with respect to repetition of the oxidation reduction between an oxidation state and a neutral state.

Note that in this CV measurement, the oxidation peak potential (from the neutral state to the oxidation state) $E_{pa}$ was 0.52 V. In addition, the reduction peak potential (from the oxidation side to the neutral state) $E_{pc}$ was 0.43 V. Therefore, a half-wave potential (an intermediate potential between $E_{pa}$ and $E_{pc}$, $(E_{pa}+E_{pc})/2$ [V]) can be calculated to be 0.48 V. This shows that 1,6FrBAPm-II is oxidized by an electrical energy of 0.48 [V vs. Ag/Ag$^+$]. Here, since the potential energy of the reference electrode, which was used above, with respect to the vacuum level is −4.94 [eV] as described above, the HOMO level of 1,6FrBAPm-II was calculated as follows: −4.94−0.48=−5.42 [eV].

Thermogravimetry-differential thermal analysis of 1,6FrBAPm-II was performed using the same device and measurement method as those in Example 1. The relationship between weight and temperature (thermogravimetry) shows that the 5% weight loss temperature of 1,6FrBAPm-II is 500° C. or higher, which is indicative of high heat resistance.

Example 8

In this example, a method for manufacturing light-emitting elements using the aromatic amine derivatives described in Embodiment 2 as light-emitting materials, and measurement results of their element characteristics are described. Specifically, Light-emitting Element 1, Light-emitting Element 2, Light-emitting Element 3, and Light-emitting Element 4 are described which were formed using N,N'-bis(dibenzofuran-4-yl)-N,N'-diphenyl-pyrene-1,6-diamine (abbreviation: 1,6FrAPm-II) represented by Structural Formula (G6-1), N,N'-bis(dibenzothiophene-4-yl)-N,N'-diphenyl-pyrene-1,6-diamine (abbreviation: 1,6ThAPm-II) represented by Structural Formula (G6-2), N,N'-bis(dibenzofuran-2-yl)-N,N'-diphenyl-pyrene-1,6-diamine (abbreviation: 1,6FrAPm) represented by Structural Formula (G10-1), and N,N'-bis(dibenzothiophene-2-yl)-N,N'-diphenyl-pyrene-1,6-diamine (abbreviation: 1,6ThAPm) represented by Structural Formula (G10-2), respectively.

Figure 31:
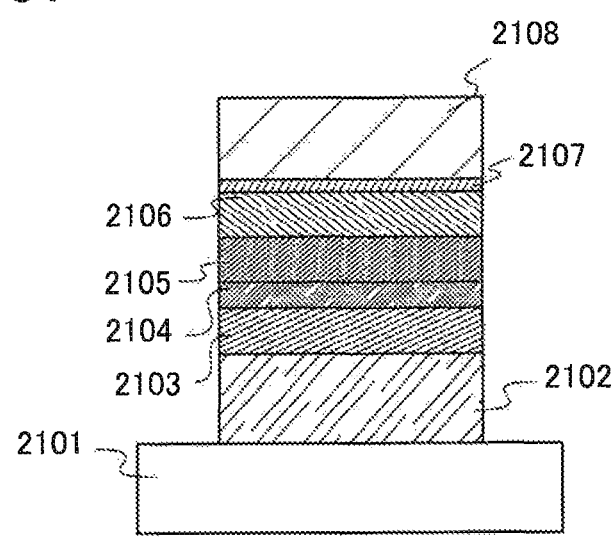
FIG. 31 illustrates a light-emitting element in Examples 8 and 9.

A method for manufacturing Light-emitting Elements 1 to 4 is described below with reference to FIG. 31. In addition, structural formulae of organic compounds used in this example are shown below.

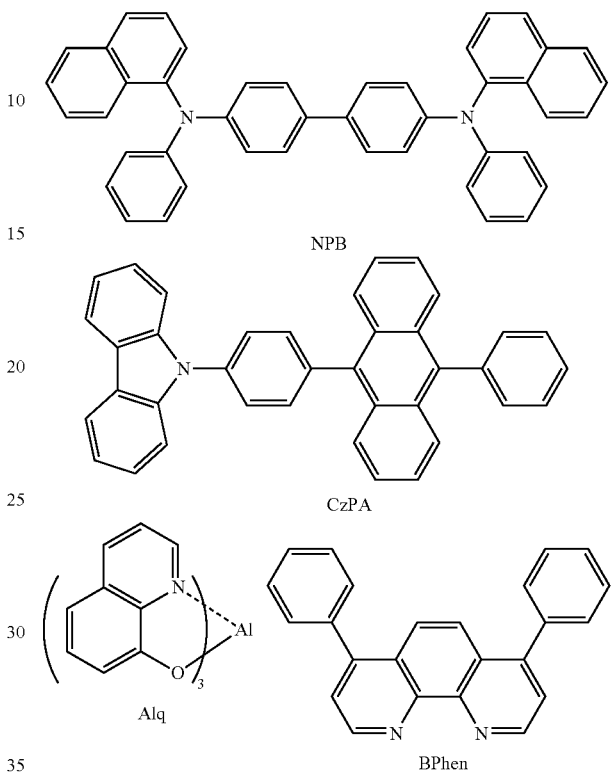

NPB

CzPA

Alq

BPhen (Light-Emitting Element 1)

First, on a substrate 2101 which is a glass substrate, an anode 2102 was formed. A 110-nm-thick indium oxide-tin oxide film containing silicon oxide was formed first by a sputtering method, and then the film formed was processed such that the electrode area was 2 mm×2 mm.

Next, an EL layer having a stack of plural layers was formed over the anode 2102. In this example, the EL layer includes a hole-injection layer 2103, a hole-transport layer 2104, a light-emitting layer 2105, an electron-transport layer 2106, and an electron-injection layer 2107, which are sequentially stacked.

In this example, the substrate 2101 on which the anode 2102 was formed was fixed to a substrate holder provided in a vacuum evaporation apparatus. When the substrate 2101 was fixed to the substrate holder, the side on which the anode 2102 was formed faced downward. The pressure in the vacuum evaporation apparatus was reduced to about 10$^{-4}$ Pa. Then, on the anode 2102, 4,4'-bis[N-(1-naphthyl)-N-phenylamino]biphenyl (abbreviation: NPB) and molybdenum(VI) oxide were deposited as the hole-injection layer 2103 by a co-evaporation method. The thickness of the hole-injection layer 2103 formed was 50 nm, and the evaporation rate was adjusted such that the weight ratio of NPB to molybdenum(VI) oxide was 4:1 (=NPB: molybdenum oxide). Note that the co-evaporation method is an evaporation method in which evaporation is carried out from a plurality of evaporation sources at the same time in one treatment chamber.

Next, on the hole-injection layer 2103, a 10-nm-thick hole-transport layer 2104 was formed by an evaporation method using resistance heating. Note that NPB was used for the hole-transport layer 2104.

Next, on the hole-transport layer 2104, 9-[4-(10-phenyl-9-anthryl)phenyl]-9H-carbazole (abbreviation: CzPA) and N,N'-bis(dibenzofuran-4-yl)-N,N'-diphenyl-pyrene-1,6-diamine (abbreviation: 1,6FrAPm-II) were deposited as the light-emitting layer 2105 by a co-evaporation method. The thickness of the light-emitting layer 2105 was 30 nm, and the evaporation rate was adjusted such that the weight ratio of CzPA to 1,6FrAPm-II was 1:0.05 (=CzPA:1,6FrAPm-II).

Next, tris(8-quinolinolato)aluminum (abbreviation: Alq) was deposited on the light-emitting layer 2105, and bathophenanthroline (abbreviation: BPhen) was deposited on the Alq, by an evaporation method using resistance heating to form the electron-transport layer 2106. Note that in the electron-transport layer 2106, the thickness of the Alq layer was 10 nm, and the thickness of the BPhen layer was 15 nm.

Next, on the electron-transport layer 2106, lithium fluoride (LiF) was deposited to a thickness of 1 nm as the electron-injection layer 2107. Note that the electron-injection layer 2107 was formed by an evaporation method using resistance heating.

Lastly, on the electron-injection layer 2107, a cathode 2108 was formed by an evaporation method using resistance heating, so that Light-emitting Element 1 of this example was fabricated. Note that aluminum was deposited to a thickness of 200 nm as the cathode 2108.

(Light-Emitting Element 2)

Light-emitting Element 2 was fabricated in a manner similar to that of Light-emitting Element 1 except for the light-emitting layer 2105. In Light-emitting Element 2, 9-[4-(10-phenyl-9-anthryl)phenyl]-9H-carbazole (abbreviation: CzPA) and N,N'-bis(dibenzothiophene-4-yl)-N,N'-diphenyl-pyrene-1,6-diamine (abbreviation: 1,6ThAPm-II) were deposited as the light-emitting layer 2105 by a co-evaporation method. The thickness of the light-emitting layer 2105 was 30 nm, and the evaporation rate was adjusted such that the weight ratio of CzPA to 1,6ThAPm-II was 1:0.05 (=CzPA:1,6ThAPm-II).

Thus, Light-emitting Element 2 of this example was fabricated.

(Light-Emitting Element 3)

Light-emitting Element 3 was fabricated in a manner similar to that of Light-emitting Element 1 except for the light-emitting layer 2105. In Light-emitting Element 3, 9-[4-(10-phenyl-9-anthryl)phenyl]-9H-carbazole (abbreviation: CzPA) and N,N'-bis(dibenzofuran-2-yl)-N,N'-diphenyl-pyrene-1,6-diamine (abbreviation: 1,6FrAPm) were deposited as the light-emitting layer 2105 by a co-evaporation method. The thickness of the light-emitting layer 2105 was 30 nm, and the evaporation rate was adjusted such that the weight ratio of CzPA to 1,6FrAPm was 1:0.01 (=CzPA:1,6FrAPm).

Thus, Light-emitting Element 3 of this example was fabricated.

(Light-Emitting Element 4)

Light-emitting Element 4 was fabricated in a manner similar to that of Light-emitting Element 1 except for the light-emitting layer 2105. In Light-emitting Element 4, 9-[4-(10-phenyl-9-anthryl)phenyl]-9H-carbazole (abbreviation: CzPA) and N,N'-bis(dibenzothiophene-2-yl)-N,N'-diphenyl-pyrene-1,6-diamine (abbreviation: 1,6ThAPm) were deposited as the light-emitting layer 2105 by a co-evaporation method. In was 30 nm, and the evaporation rate was adjusted such that the weight ratio of CzPA to 1,6ThAPm was 1:0.01 (=CzPA:1,6ThAPm).

Thus, Light-emitting Element 4 of this example was fabricated.

Table 1 shows element structures of Light-emitting Elements 1 to 4 fabricated in this example. In Table 1, the mixture ratios are all represented in weight ratios.

TABLE 1

| | Anode 2102 | Hole-injection Layer 2103 | Hole-transport Layer 2104 | Light-emitting Layer 2105 |
|---|---|---|---|---|
| Light-emitting Element 1 | ITSO 110 nm | NPB:MoO$_x$ (=4:1) 50 nm | NPB 10 nm | CzPA:1, 6FrAPrn-II (=1:0.05) 30 nm |
| Light-emitting Element 2 | ITSO 110 nm | NPB:MoO$_x$ (=4:1) 50 nm | NPB 10 nm | CzPA:1, 6ThAPrn-II (=1:0.05) 30 nm |
| Light-emitting Element 3 | ITSO 110 nm | NPB:MoO$_x$ (=4:1) 50 nm | NPB 10 nm | CzPA:1, 6FrAPrn (=1:0.01) 30 nm |
| Light-emitting Element 4 | ITSO 110 nm | NPB:MoO$_x$ (=4:1) 50 nm | NPB 10 nm | CzPA:1, 6ThAPrn (=1:0.01) 30 nm |

| | Electron-transport Layer 2106 | Electron-injection Layer 2107 | Cathode 2108 |
|---|---|---|---|
| Light-emitting Element 1 | Alq 10 nm | BPhen 15 nm | LiF 1 nm | Al 200 nm |
| Light-emitting Element 2 | Alq 10 nm | BPhen 15 nm | LiF 1 nm | Al 200 nm |
| Light-emitting Element 3 | Alq 10 nm | BPhen 15 nm | LiF 1 nm | Al 200 nm |
| Light-emitting Element 4 | Alq 10 nm | BPhen 15 nm | LiF 1 nm | Al 200 nm |

The mixture ratios are all represented in weight ratios.

Light-emitting Elements 1 to 4 thus obtained were sealed in a glove box under a nitrogen atmosphere without being exposed to the air. Then, the operation characteristics of Light-emitting Elements 1 to 4 were measured. Note that the measurement was carried out at room temperature (in an atmosphere kept at 25° C.).

Figure 32:
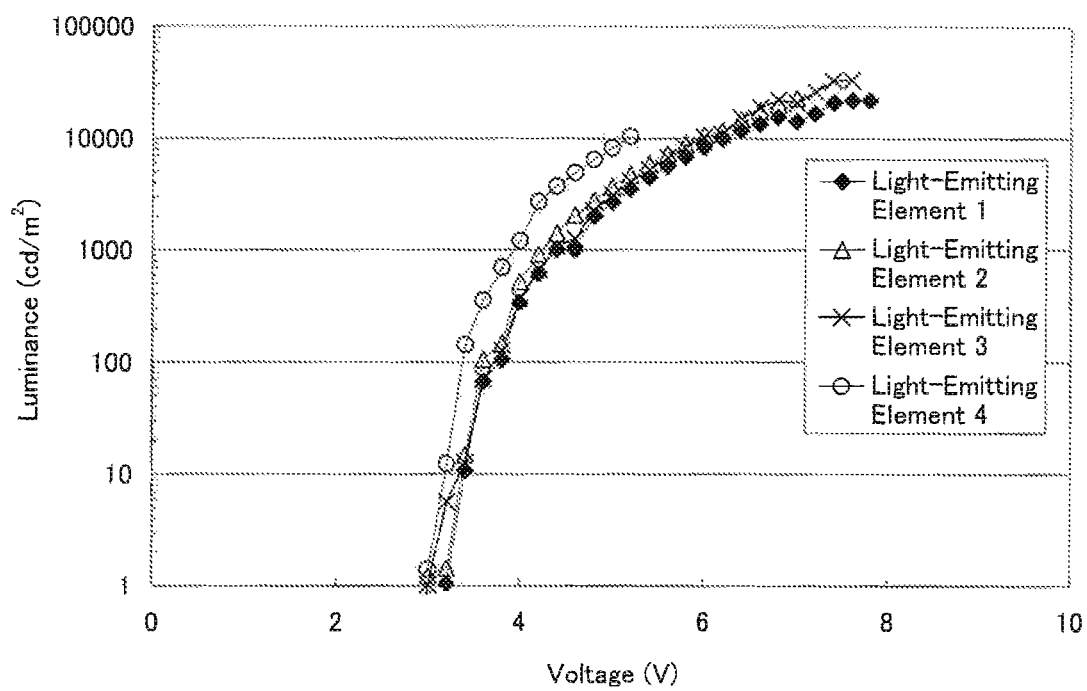
FIG. 32 shows characteristics of Light-emitting Element 1 to Light-emitting Element 4.
Figure 33:
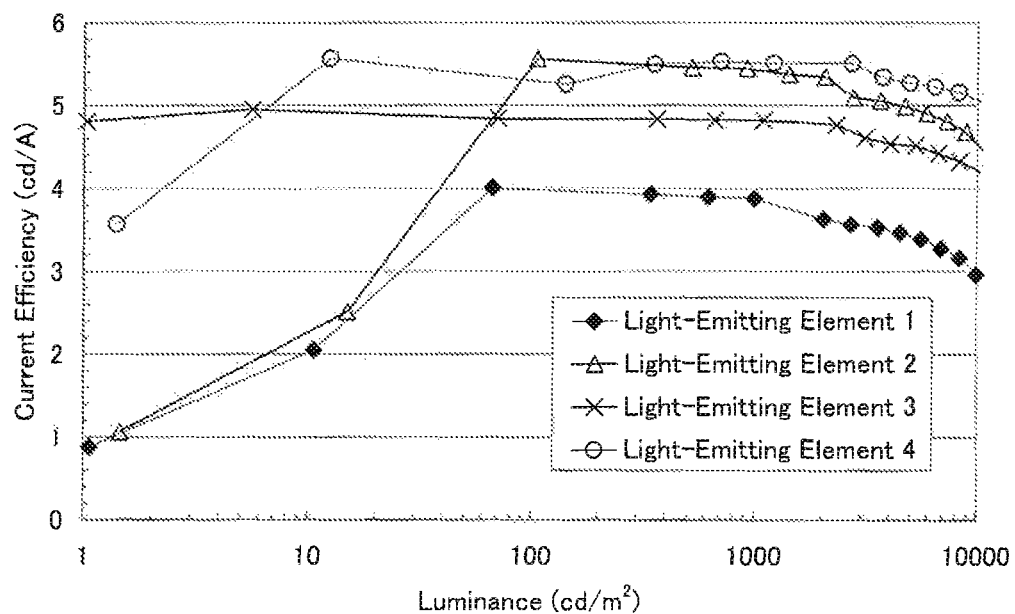
FIG. 33 shows characteristics of Light-emitting Element 1 to Light-emitting Element 4.

FIG. 32 shows voltage vs. luminance characteristics of Light-emitting Elements 1 to 4 and FIG. 33 shows luminance vs. current efficiency characteristics thereof. In FIG. 32, the vertical axis represents luminance (cd/m$^2$), and the horizontal axis represents voltage (V). In FIG. 33, the vertical axis represents current efficiency (cd/A), and the horizontal axis represents luminance (cd/m$^2$). Further, Table 2 shows the chromaticity of Light-emitting Elements 1 to 4 at around 1000 cd/m$^2$.

TABLE 2

| | Chromaticity (x, y) |
|---|---|
| Light-emitting Element 1 | (0.15, 0.13) |
| Light-emitting Element 2 | (0.15, 0.19) |
| Light-emitting Element 3 | (0.15, 0.19) |
| Light-emitting Element 4 | (0.15, 0.21) |

Figure 34:
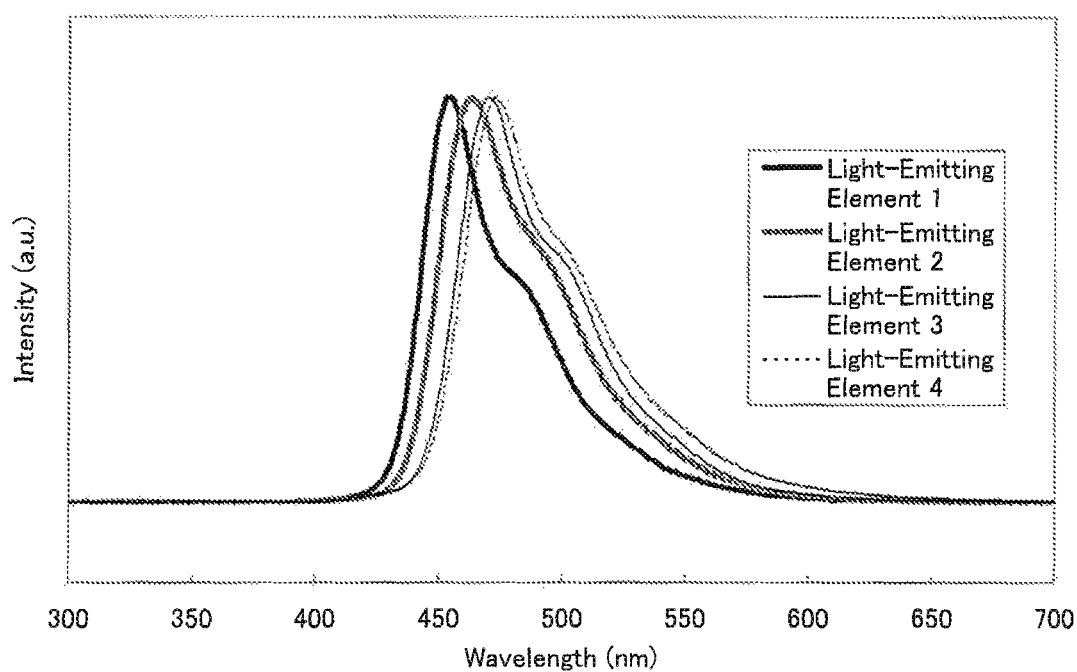
FIG. 34 shows characteristics of Light-emitting Element 1 to Light-emitting Element 4.

FIG. 34 shows emission spectra of Light-emitting Elements 1 to 4.

From Table 2 and FIG. 34, it is found that each of Light-emitting Elements 1 to 4 emits favorable blue light. In particular, Light-emitting Element 1 is found to emit blue light with the highest color purity because the y-coordinate of the chromaticity of Light-emitting Element 1 at approximately 1000 cd/m² is the smallest and the peak of the emission spectrum of Light-emitting Element 1 is around 454 nm, which is the shortest wavelength.

Figure 35:
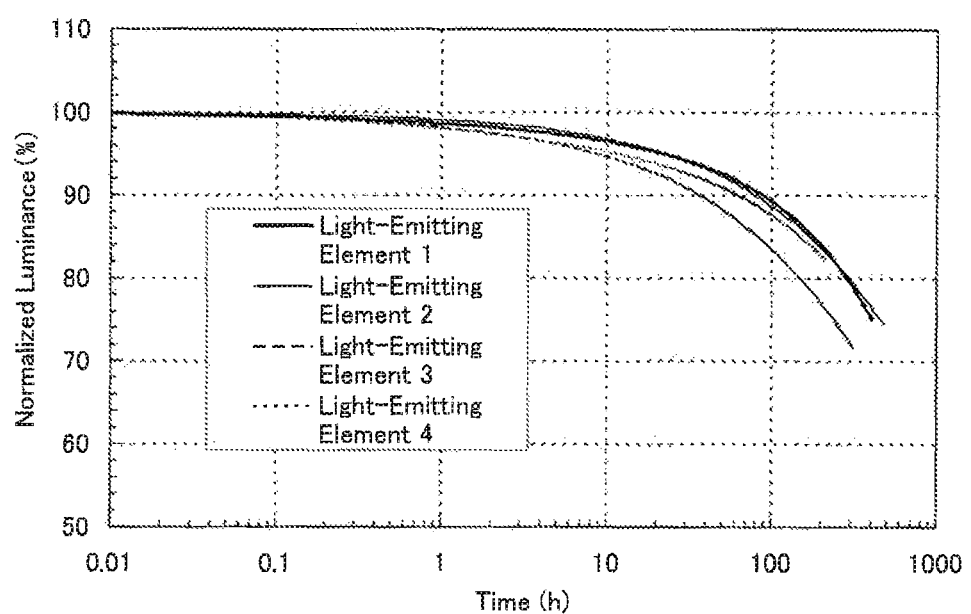
FIG. 35 shows characteristics of Light-emitting Element 1 to Light-emitting Element 4.

In addition, reliability tests of Light-emitting Elements 1 to 4 were conducted. In the reliability tests, the initial luminance was set at 1000 cd/m², these elements were operated at a constant current density, and the luminance was measured every time a predetermined period of time passed. The results obtained by the reliability tests are shown in FIG. 35. In FIG. 35, the horizontal axis represents current flow time (hour) and the vertical axis represents percentage of luminance to the initial luminance at each time, that is, normalized luminance (%).

From FIG. 35, it is found that each of the Light-emitting Elements 1 to 4 has a normalized luminance of 80% or higher after 100-hour-operation, and thus is a long-lifetime light-emitting element.

As described above, it is found that Light-emitting Elements 1 to 4 of this example can be blue light-emitting elements with a long lifetime and high color purity, and in particular, Light-emitting Element 1 can be a blue light-emitting element with the highest color purity.

Example 9

In this example, a method for manufacturing light-emitting elements using the aromatic amine derivatives described in Embodiment 3 as light-emitting materials, and measurement results of their element characteristics are described. Specifically, Light-emitting Element 5 was formed using N,N'-bis[3-(dibenzofuran-4-yl)phenyl]-N,N'-diphenyl-pyrene-1,6-diamine (abbreviation: 1,6mFrBAPm-II) represented by Structural Formula (G7-1) as a light-emitting material. In addition, Light-emitting Element 6 was formed using N,N-bis[3-(dibenzothiophene-4-yl)phenyl]-N,N'-diphenyl-pyrene-1,6-diamine (abbreviation: 1,6mTh-BAPm-II) represented by Structural Formula (G7-2) as a light-emitting material. Further, Light-emitting Element 7 was formed using N,N'-bis[4-(dibenzofuran-4-yl)phenyl]-N,N'-diphenyl-pyrene-1,6-diamine (abbreviation: 1,6Fr-BAPm-II) represented by Structural Formula (G8-1) as a light-emitting material.

In element structures of Light-emitting Element 5 and Light-emitting Element 6, the anode 2102, the electron-transport layer 2106, the element-injection layer 2107, and the cathode 2108 are the same as those in Light-emitting Element 1 to Light-emitting Element 4 described in Example 8; however, the light-emitting layer 2105, the hole-injection layer 2103, and the hole-transport layer 2104 are different from those in Light-emitting Element 1 to Light-emitting Element 4 described in Example 8. In addition, in element structures of Light-emitting Element 7, the anode 2102, the hole-injection layer 2103, the hole-transport layer 2104, the electron-transport layer 2106, the element-injection layer 2107, and the cathode 2108 are the same as those in Light-emitting Element 1 to Light-emitting Element 4 described in Example 8; however, the light-emitting layer 2105 is different from that in Light-emitting Element 1 to Light-emitting Element 4 described in Example 8. A structural formula of an organic compound additionally used in this example is shown below.

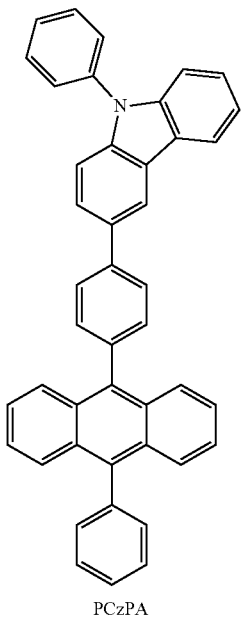 [SMILES: c1ccc(-c2c3ccccc3c(-c3ccc(-c4ccc5c(c4)c4ccccc4n5-c4ccccc4)cc3)c3ccccc23)cc1]

PCzPA (Light-Emitting Element 5)

On the substrate 2101, the anode 2102 was formed in a manner similar to that in Example 8. Next, on the anode 2102, 9-phenyl-3-[4-(10-phenyl-9-anthryl)phenyl]-9H-carbazole (abbreviation: PCzPA) and molybdenum(VI) oxide were deposited as the hole-injection layer 2103 of Light-emitting Element 5 by the co-evaporation method described in Example 8. The thickness of the hole-injection layer 2103 formed was 50 nm, and the evaporation rate was adjusted such that the weight ratio of PCzPA to molybdenum(VI) oxide was 4:2 (=PCzPA: molybdenum oxide).

Next, on the hole-injection layer 2103, the hole-transport layer 2104 with a thickness of 10 nm was formed by an evaporation method using resistance heating. Note that PCzPA was used for the hole-transport layer 2104.

In Light-emitting Element 5, on the hole-transport layer 2104, 9-[4-(10-phenyl-9-anthryl)phenyl]-9H-carbazole (abbreviation: CzPA) and N,N'-bis[3-(dibenzofuran-4-yl)phenyl]-N,N'-diphenyl-pyrene-1,6-diamine (abbreviation: 1,6mFrBAPm-II) were deposited as the light-emitting layer 2105 by the co-evaporation method that is described in Example 8. The thickness of the light-emitting layer 2105 was 30 nm, and the evaporation rate was adjusted such that the weight ratio of CzPA to 1,6mFrBAPm-II was 1:0.05 (=CzPA: 1,6mFrBAPm-II).

The electron-transport layer 2106, the electron-injection layer 2107, and the cathode 2108 were formed in a manner similar to that in Example 8, so that Light-emitting Element 5 of this example was fabricated.

(Light-Emitting Element 6)

On the substrate 2101, the anode 2102 was formed in a manner similar to that in Example 8.

Next, the hole-injection layer 2103 and the hole-transport layer 2104 of Light-emitting Element 6 were formed in a manner similar to that of Light-emitting Element 5. Next, 9-[4-(10-phenyl-9-anthryl)phenyl]-9H-carbazole (abbreviation: CzPA) and N,N-bis[3-(dibenzothiophene-4-yl)phenyl]-N,N'-diphenyl-pyrene-1,6-diamine (abbreviation: 1,6mTh-BAPm-II) were deposited as the light-emitting layer 2105 of Light-emitting Element 6 by the co-evaporation method that is described in Example 8. The thickness of the light-emitting layer 2105 was 30 nm, and the evaporation rate was adjusted such that the weight ratio of CzPA to 1,6mTh-BAPm-II was 1:0.05 (=CzPA:1,6mThBAPm-II).

Then, the electron-transport layer 2106, the electron-injection layer 2107, and the cathode 2108 were formed in a manner similar to that of Light-emitting Element 1 to Light-emitting Element 4 in Example 8, so that Light-emitting Element 6 of this example was fabricated.

(Light-Emitting Element 7) On the substrate 2101, the anode 2102, the hole-injection layer 2103, and the hole-transport layer 2104 were formed in a manner similar to that in Example 8.

Next, 9-[4-(10-phenyl-9-anthryl)phenyl]-9H-carbazole (abbreviation: CzPA) and N,N'-bis[4-(dibenzofuran-4-yl)phenyl]-N,N-diphenyl-pyrene-1,6-diamine (abbreviation: 1,6FrBAPm-II) were deposited as the light-emitting layer 2105 of Light-emitting Element 7 by the co-evaporation method that is described in Example 8. The thickness of the light-emitting layer 2105 was 30 nm, and the evaporation rate was adjusted such that the weight ratio of CzPA to 1,6FrBAPm-II was 1:0.05 (=CzPA:1,6FrBAPm-II).

Then, the electron-transport layer 2106, the electron-injection layer 2107, and the cathode 2108 were formed in a manner similar to that of Light-emitting Element 1 to Light-emitting Element 4 in Example 8, so that Light-emitting Element 7 of this example was fabricated.

Table 3 shows element structures of Light-emitting Elements 5 to 7 fabricated in this example. In Table 3, the mixture ratios are all represented in weight ratios.

TABLE 3

| | Anode 2102 | Hole-injection Layer 2103 | Hole-transport Layer 2104 | Light-emitting Layer 2105 |
|---|---|---|---|---|
| Light-emitting Element 5 | ITSO 110 nm | PCzPA:MoO$_x$ (=4:2) 50 nm | PCzPA 10 nm | CzPA:1, 6mThBAPrn-II (=1:0.05) 30 nm |
| Light-emitting Element 6 | ITSO 110 nm | PCzPA:MoO$_x$ (=4:2) 50 nm | PCzPA 10 nm | CzPA:1, 6mThBAPrn-II (=1:0.05) 30 nm |
| Light-emitting Element 7 | ITSO 110 nm | NPB:MoO$_x$ (=4:1) 50 nm | NPB 10 nm | CzPA:1, 6FrBAPrn-II (=1:0.05) 30 nm |

| | Electron-transport Layer 2106 | Electron-injection Layer 2107 | Cathode 2108 |
|---|---|---|---|
| Light-emitting Element 5 | Alq 10 nm | BPhen 15 nm | LiF 1 nm | Al 200 nm |
| Light-emitting Element 6 | Alq 10 nm | BPhen 15 nm | LiF 1 nm | Al 200 nm |
| Light-emitting Element 7 | Alq 10 nm | BPhen 15 nm | LiF 1 nm | Al 200 nm |

The mixture ratios are all represented in weight ratios.

Light-emitting Element 5 to Light-emitting Element 7 thus obtained were sealed in a glove box under a nitrogen atmosphere without being exposed to the air. Then, the operation characteristics of Light-emitting Element 5 to Light-emitting Element 7 were measured. Note that the measurement was carried out at room temperature (in an atmosphere kept at 25° C.).

Figure 36:
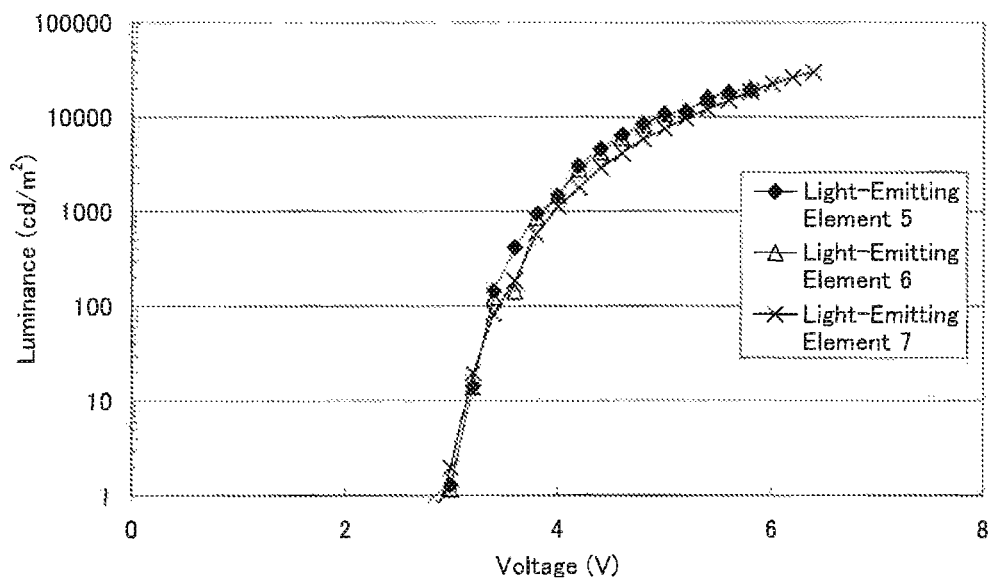
FIG. 36 shows characteristics of Light-emitting Element 5 to Light-emitting Element 7.
Figure 37:
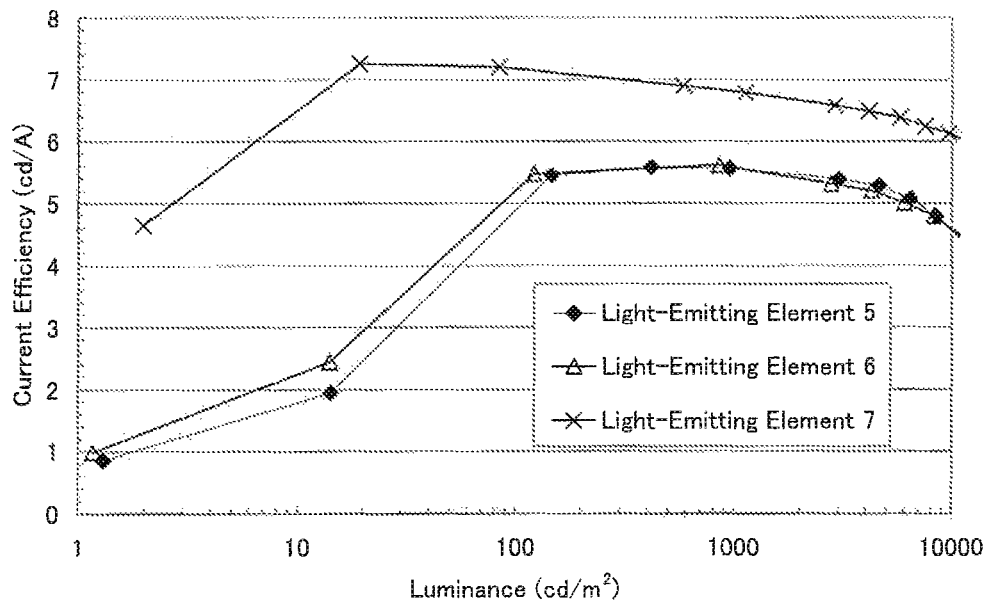
FIG. 37 shows characteristics of Light-emitting Element 5 to Light-emitting Element 7.

FIG. 36 shows voltage vs. luminance characteristics of Light-emitting Element 5 to Light-emitting Element 7 and FIG. 37 shows luminance vs. current efficiency characteristics thereof. In FIG. 36, the vertical axis represents luminance (cd/m$^2$), and the horizontal axis represents voltage (V). In FIG. 37, the vertical axis represents current efficiency (cd/A), and the horizontal axis represents luminance (cd/m$^2$). Further, Table 4 shows the chromaticity of Light-emitting Element 5 to Light-emitting Element 7 at around 1000 cd/m$^2$. [Table 4]

TABLE 4

| | Chromaticity (x, y) |
|---|---|
| Light-emitting Element 5 | (0.14, 0.16) |
| Light-emitting Element 6 | (0.14, 0.17) |
| Light-emitting Element 7 | (0.16, 0.27) |

Figure 38:
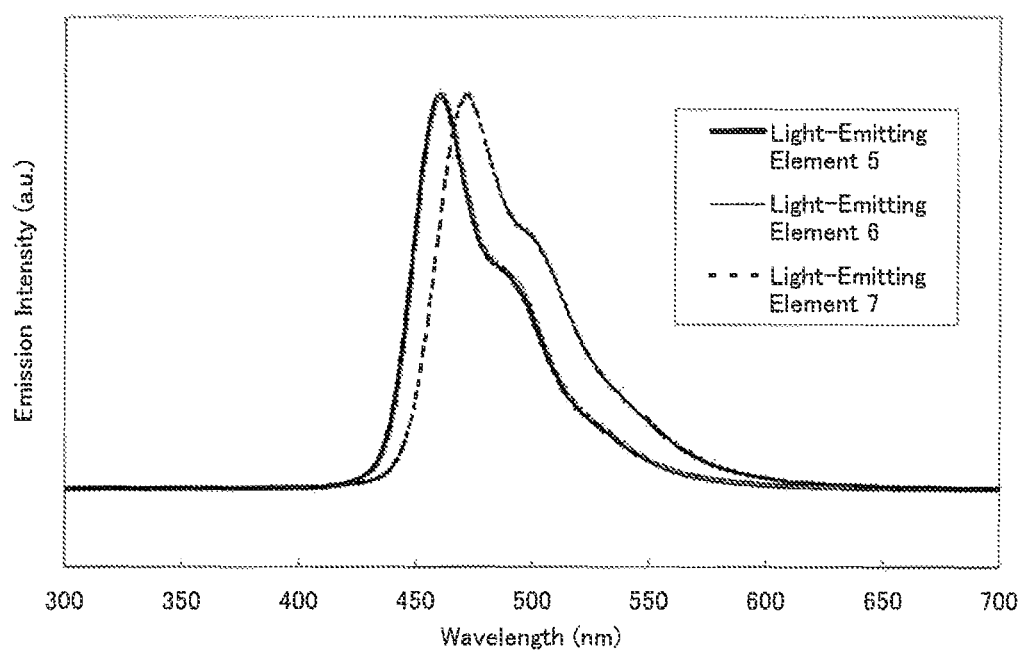
FIG. 38 shows characteristics of Light-emitting Element 5 to Light-emitting Element 7.

FIG. 38 shows emission spectra of Light-emitting Element 5 to Light-emitting Element 7.

A great difference was not formed in luminance to voltage among Light-emitting Element 5 to Light-emitting Element 7. In addition, from Table 4 and FIG. 38, it is found that each of Light-emitting Element 5 to Light-emitting Element 7 emits favorable blue light. Light-emitting Element 5 and Light-emitting Element 6 can emit blue light with high color purity because the peaks of the emission spectra of Light-emitting Element 5 and Light-emitting Element 6 are closer to 460 nm, which is on a shorter wavelength side than the peak of the emission spectrum of Light-emitting Element 7.

Figure 39:
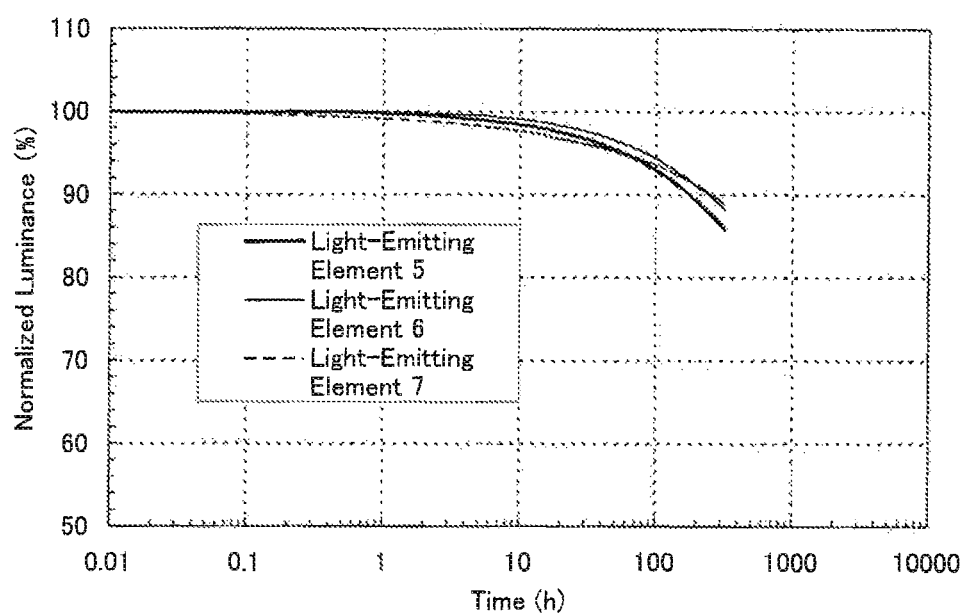
FIG. 39 shows characteristics of Light-emitting Element 5 to Light-emitting Element 7.

In addition, reliability tests of Light-emitting Element 5 to Light-emitting Element 7 were conducted. In the reliability tests, the initial luminance was set at 1000 cd/m$^2$, these elements were operated at a constant current density, and the luminance was measured every time a predetermined period of time passed. The results obtained by the reliability tests are shown in FIG. 39. In FIG. 39, the horizontal axis represents current flow time (hour) and the vertical axis represents percentage of luminance to the initial luminance at each time, that is, normalized luminance (%).

From FIG. 39, it is found that each of the Light-emitting Element 5 to Light-emitting Element 7 has a normalized luminance of 90% or higher after 100-hour-operation, and thus is a long-lifetime light-emitting element.

As described above, it is found that Light-emitting Element 5 to Light-emitting Element 7 of this example can be blue light-emitting elements with a long lifetime and high color purity.

This application is based on Japanese Patent Application serial no. 2010-090941 filed with Japan Patent Office on Apr. 9, 2010, the entire contents of which are hereby incorporated by reference.

What is claimed is:

1. A light-emitting element comprising:
an anode;
a first EL layer over the anode, the first EL layer comprising:
a first layer comprising a first aromatic amine compound;
a second layer comprising a second aromatic amine compound over the first layer;
a third layer comprising a carbazole compound or a third aromatic amine compound over the second layer;
a blue light-emitting layer comprising a light-emitting compound and a host material over the third layer; and a fourth layer comprising a first heterocyclic compound over the blue light-emitting layer;

an intermediate layer comprising a second heterocyclic compound and an electron donor over the first EL layer;

a second EL layer over the intermediate layer; and a cathode over the second EL layer, wherein a difference between a HOMO level of the third layer and a HOMO level of the blue light-emitting layer is less than or equal to 0.2 eV, wherein a difference between a LUMO level of the blue light-emitting layer and a LUMO level of the fourth layer is less than or equal to 0.2 eV, wherein the light-emitting compound is represented by Formula (G1),

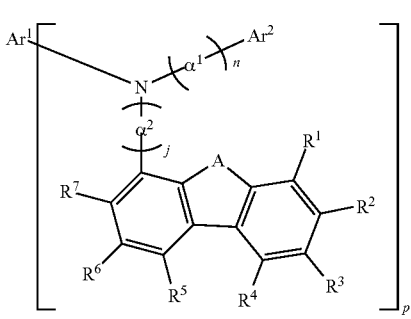

(G1)

wherein A represents oxygen or sulfur, wherein $R^1$ to $R^7$ individually represent any of a hydrogen atom, an alkyl group having 1 to 6 carbon atoms, a substituted or unsubstituted phenyl group, and a substituted or unsubstituted biphenyl group, wherein $\alpha^1$ and $\alpha^2$ individually represent a substituted or unsubstituted phenylene group, wherein $Ar^1$ represents a substituted or unsubstituted condensed aromatic hydrocarbon having 14 to 18 carbon atoms included in a ring, wherein $Ar^2$ represents a substituted or unsubstituted aryl group having 6 to 13 carbon atoms included in a ring, wherein j and n are individually 0 or 1, wherein p is 1 or 2, and wherein the light-emitting element emits white light.

2. The light-emitting element according to claim 1, wherein $Ar^1$ in Formula (G1) is Formula (Ar1-1) or (Ar1-2),

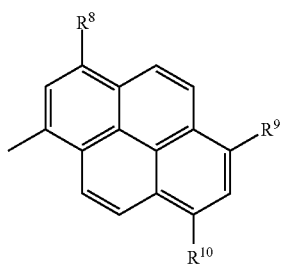

(Ar1-1)

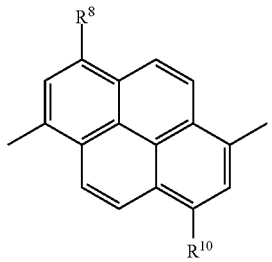

(Ar1-2)

wherein $R^8$ to $R^{10}$ individually represent any of a hydrogen atom, an alkyl group having 1 to 6 carbon atoms, a substituted or unsubstituted phenyl group, and a substituted or unsubstituted biphenyl group, wherein p is 1 when $Ar^1$ in Formula (G1) is Formula (Ar1-1), and wherein p is 2 when $Ar^1$ in Formula (G1) is Formula (Ar1-2).

3. The light-emitting element according to claim 2, wherein A is oxygen.

4. The light-emitting element according to claim 1, wherein the light-emitting element includes a plurality of light-emitting layers.

5. The light-emitting element according to claim 4, wherein the host material comprises a plurality of substances in which the light-emitting compound is dispersed.

6. The light-emitting element according to claim 4, wherein the light-emitting element comprises a light-emitting layer having a relationship of complementary colors with the blue light-emitting layer.

7. The light-emitting element according to claim 4, wherein the blue light-emitting layer comprises the light-emitting compound at a concentration of lower than or equal to 10% in terms of mass ratio.

8. The light-emitting element according to claim 1, wherein A is oxygen.

9. A light-emitting element comprising:
an anode;
a first EL layer over the anode, the first EL layer comprising:
a first layer comprising a first aromatic amine compound;
a second layer comprising a second aromatic amine compound over the first layer;
a third layer comprising a carbazole compound or a third aromatic amine compound over the second layer;
a blue light-emitting layer comprising a light-emitting compound and a host material over the third layer; and
a fourth layer comprising a first heterocyclic compound over the blue light-emitting layer;
an intermediate layer comprising a second heterocyclic compound and a metal over the first EL layer, wherein the metal is an alkali metal, an alkaline-earth metal, a rare-earth metal, or a metal that belongs to Group 13 of the periodic table;
a second EL layer over the intermediate layer; and
a cathode over the second EL layer,
wherein a difference between a HOMO level of the third layer and a HOMO level of the blue light-emitting layer is less than or equal to 0.2 eV,
wherein a difference between a LUMO level of the blue light-emitting layer and a LUMO level of the fourth layer is less than or equal to 0.2 eV,
wherein the light-emitting compound is represented by Formula (G3),

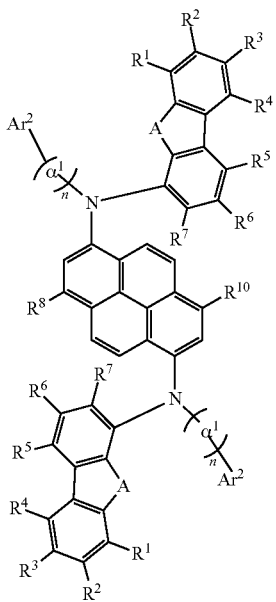

(G3)

wherein A represents oxygen or sulfur,
wherein $R^1$ to $R^7$, $R^8$, and $R^{10}$ individually represent any of a hydrogen atom, an alkyl group having 1 to 6 carbon atoms, a substituted or unsubstituted phenyl group, and a substituted or unsubstituted biphenyl group, wherein $\alpha^1$ represents a substituted or unsubstituted phenylene group,
wherein $Ar^2$ represents a substituted or unsubstituted aryl group having 6 to 13 carbon atoms included in a ring,
wherein n is 0 or 1, and
wherein the light-emitting element emits white light.

10. The light-emitting element according to claim 9, wherein the light-emitting element comprises a plurality of light-emitting layers, and
wherein the plurality of light-emitting layers comprises the blue light-emitting layer.

11. The light-emitting element according to claim 10, wherein the host material comprises a plurality substances in which the light-emitting compound is dispersed.

12. The light-emitting element according to claim 10, wherein the light-emitting element comprises a light-emitting layer having a relationship of complementary colors with the blue light-emitting layer.

13. The light-emitting element according to claim 10, wherein the blue light-emitting layer comprises the light-emitting compound at a concentration of lower than or equal to 10% in terms of mass ratio.

14. The light-emitting element according to claim 9, wherein A is oxygen.

* * * * *